(12) United States Patent
Yen et al.

(10) Patent No.: US 11,236,075 B2
(45) Date of Patent: Feb. 1, 2022

(54) ORGANIC COMPOUND AND ORGANIC ELECTROLUMINESCENCE DEVICE USING THE SAME

(71) Applicants: Feng-Wen Yen, Taipei (TW); Li-Chieh Chuang, Nantou (TW)

(72) Inventors: Feng-Wen Yen, Taipei (TW); Li-Chieh Chuang, Nantou (TW)

(73) Assignee: LUMINESCENCE TECHNOLOGY CORP., Hsin-Chu (TW)

( * ) Notice: Subject to any disclaimer, the term of this patent is extended or adjusted under 35 U.S.C. 154(b) by 481 days.

(21) Appl. No.: 16/221,626

(22) Filed: Dec. 17, 2018

(65) Prior Publication Data
US 2020/0190065 A1   Jun. 18, 2020

(51) Int. Cl.
| | |
|---|---|
| *H01L 51/50* | (2006.01) |
| *C07D 405/04* | (2006.01) |
| *C07D 405/14* | (2006.01) |
| *C07D 409/04* | (2006.01) |
| *C07D 409/14* | (2006.01) |
| *C07D 401/14* | (2006.01) |
| *C07D 403/04* | (2006.01) |
| *H01L 51/00* | (2006.01) |

(52) U.S. Cl.
CPC ......... *C07D 405/04* (2013.01); *C07D 401/14* (2013.01); *C07D 403/04* (2013.01);
(Continued)

(58) Field of Classification Search
None
See application file for complete search history.

(56) References Cited

U.S. PATENT DOCUMENTS 9,172,046 B1 * 10/2015 Kim ......................... C09B 1/00
10,056,561 B2   8/2018 Yen
(Continued)

FOREIGN PATENT DOCUMENTS

CN         107827808      *  3/2018   ........... C07D 209/80
WO   WO-2018070641 A2 *  4/2018   ........... C07D 307/77

OTHER PUBLICATIONS

Machine translation of CN-107827808, tanslation generated Jan. 2021, 18 pages. (Year: 2021).*

*Primary Examiner* — Robert S Loewe

(57) ABSTRACT

The present invention discloses an organic compound and an organic electroluminescence device using the organic compound as an emitting host material, an electron transfer material or a hole blocking material in the light emitting layer of the organic electroluminescence device. The organic compound may be for increasing a half-life or current efficiency of the organic electroluminescence device, and may be for lowering a driving voltage or power consumption of the organic electroluminescence device.

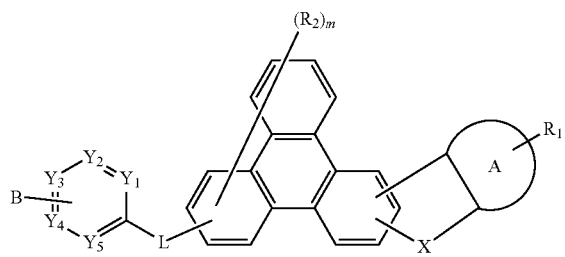

The same definition as described in the present invention.

17 Claims, 1 Drawing Sheet

(52) U.S. Cl.
CPC ......... *C07D 405/14* (2013.01); *C07D 409/04* (2013.01); *C07D 409/14* (2013.01); *H01L 51/0067* (2013.01); *H01L 51/0072* (2013.01); *H01L 51/0073* (2013.01); *H01L 51/0074* (2013.01); *H01L 51/0094* (2013.01); *H01L 51/5012* (2013.01); *H01L 51/5096* (2013.01); *H01L 51/5072* (2013.01)

(56) References Cited

U.S. PATENT DOCUMENTS

| | | | |
|---|---|---|---|
| 2013/0048975 A1* | 2/2013 | Hong | C07D 409/10 |
| | | | 257/40 |
| 2014/0231754 A1* | 8/2014 | Yen | C07D 333/22 |
| | | | 257/40 |
| 2016/0072073 A1* | 3/2016 | Lee | C07D 409/14 |
| | | | 257/40 |
| 2016/0133844 A1* | 5/2016 | Kim | H01L 51/0054 |
| | | | 257/40 |
| 2016/0133853 A1* | 5/2016 | Cho | H01L 51/0059 |
| | | | 257/40 |
| 2016/0141512 A1* | 5/2016 | Jung | H01L 51/0072 |
| | | | 257/40 |
| 2016/0204345 A1* | 7/2016 | Yen | H01L 51/0056 |
| | | | 257/40 |
| 2016/0240783 A1 | 8/2016 | Yen et al. | |
| 2017/0012211 A1* | 1/2017 | Cho | H01L 51/0072 |
| 2018/0155325 A1* | 6/2018 | Lee | H01L 51/0067 |
| 2019/0229275 A1* | 7/2019 | Lee | C07D 307/77 |
| 2020/0111971 A1* | 4/2020 | Yen | H01L 51/0054 |

\* cited by examiner

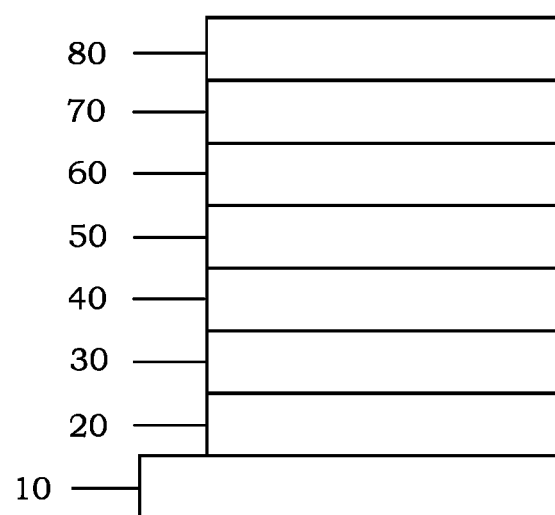

ORGANIC COMPOUND AND ORGANIC ELECTROLUMINESCENCE DEVICE USING THE SAME

FIELD OF INVENTION

The present invention relates to an organic compound and, more particularly, to an organic electroluminescence device using the organic compound.

BACKGROUND OF THE INVENTION

An organic electroluminescence (organic EL) device is an organic light-emitting diode (OLED) in which the light emitting layer is a film made from organic compounds, which emits light in response to the electric current. The light emitting layer containing the organic compound is sandwiched between two electrodes. The organic EL device is applied to flat panel displays due to its high illumination, low weight, ultra-thin profile, self-illumination without back light, low power consumption, wide viewing angle, high contrast, simple fabrication methods and rapid response time.

Typically, the organic EL device is composed of organic material layers sandwiched between two electrodes. The organic material layers include, e.g., hole injection layer, hole transporting layer, emitting layer, electron transporting layer, and electron injection layer. The basic mechanism of organic EL involves the injection, transport, and recombination of carriers as well as exciton formation for emitting light. When an external voltage is applied across the organic EL device, electrons and holes are injected from the cathode and the anode, respectively. Electrons will be injected from the cathode into a LUMO (lowest unoccupied molecular orbital) and holes will be injected from the anode into a HOMO (highest occupied molecular orbital). Subsequently, the electrons recombine with holes in the light emitting layer to form excitons, which then deactivate to emit light. When luminescent molecules absorb energy to achieve an excited state, the exciton may either be in a singlet state or a triplet state, depending on how the spins of the electrons and holes have been combined. It is well known that the excitons formed under electrical excitation typically include 25% singlet excitons and 75% triplet excitons. In the fluorescence materials, however, the electrically generated energy in the 75% triplet excitons will be dissipated as heat for decay from the triplet state is spin forbidden. Therefore, a fluorescent electroluminescence device has only 25% internal quantum efficiency, which leads to the theoretically highest external quantum efficiency (EQE) of only 5% due to only ~20% of the light out-coupling efficiency of the device. In contrast to fluorescent electroluminescence devices, phosphorescent organic EL devices make use of spin-orbit interactions to facilitate intersystem crossing between singlet and triplet states, thus obtaining emission from both singlet and triplet states and the internal quantum efficiency of electroluminescence devices from 25% to 100%.

However, there is still a need for improvement in the case of use of those organic materials in an organic EL device of some displays, for example, in relation to the half-life, current efficiency or driving voltage of the organic EL device.

SUMMARY OF THE INVENTION

Accordingly, an object of the present invention is to provide an organic compound, which can be used as an emitting host material, an electron transfer material, or a hole blocking material in an organic EL device to improve the half-life, current efficiency, driving voltage or power consumption of the device.

Another object of the invention is to provide an organic compound and an organic EL device using the same. The organic compound of the device may be a material for increasing the half-life of the device, for lowering the driving voltage of the device, or for increasing the current efficiency of the device.

According to the present invention, an organic compound which can be used in organic EL devices is disclosed. The organic compound is represented by the following formula (1):

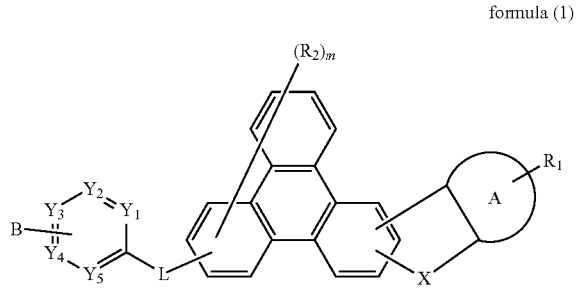

formula (1)

wherein X represents a divalent bridge selected from the group consisting of O, S, Se, $NR_3$ and $SiR_4R_5$; m represents an integer of 0 to 8; ring A represents a phenyl group or a fused ring hydrocarbon unit with two to four rings; L represents a single bond, a substituted or unsubstituted divalent arylene group having 6 to 30 ring carbon atoms, or a substituted or unsubstituted divalent heteroarylene group having 6 to 30 ring carbon atoms. $R_1$ to $R_5$ are independently selected from the group consisting of a hydrogen atom, a substituted or unsubstituted alkyl group having 1 to 20 carbon atoms, a substituted or unsubstituted aryl group having 6 to 30 carbon atoms, a substituted or unsubstituted aralkyl group having 6 to 30 carbon atoms and a substituted or unsubstituted heteroaryl group having 3 to 30 carbon atoms. $Y_1$ to $Y_5$ independently represent a nitrogen atom or $CR_6$. $R_6$ represents a hydrogen atom, a substituted or unsubstituted phenylene group having 6 to 30 ring carbon atoms, or a bond linked to B. B may be represented by the following formula (2):

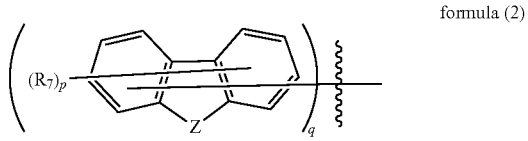

formula (2)

wherein q may represent an integer of 0, 1, 2, or 3; p represents an integer of 0 to 7; Z represents O, S, or $NR_8$. $R_8$ represents a hydrogen atom, a substituted or unsubstituted phenyl group, a substituted or unsubstituted carbazole group, or a bond linked to formula (1). $R_7$ has the same definition as $R_1$.

The present invention further discloses an organic EL device. The organic EL device comprises a pair of electrodes composed of a cathode and an anode, and a light emitting layer between the pair of electrodes. The light emitting layer, which may be an emitting layer, a hole blocking layer or an electron transport layer, may comprise the organic compound of the present invention.

BRIEF DESCRIPTION OF THE DRAWINGS

The FIGURE is a schematic view showing an organic EL device according to an embodiment of the present invention.

DESCRIPTION OF THE PREFERRED EMBODIMENTS

What probed into the invention is the organic compound and organic EL device using the organic compound. Detailed descriptions of the production, structure and elements will be provided as follows such that the invention can be fully understood. Obviously, the application of the invention is not confined to specific details familiar to those skilled in the art. On the other hand, the common elements and procedures that are known to everyone are not described in details to avoid unnecessary limits of the invention. Some preferred embodiments of the present invention will now be described in greater detail as follows. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

In one embodiment of the present invention, an organic compound which can be used as a host material of a light emitting layer in an organic EL device is disclosed. The organic compound may be represented by the following formula (1):

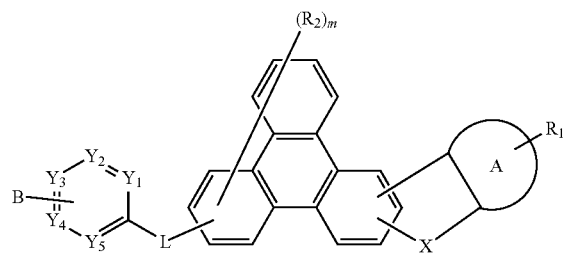

formula (1)

wherein X represents a divalent bridge selected from the group consisting of O, S, Se, $NR_3$ and $SiR_4R_5$; m represents an integer of 0 to 8. Ring A may represent a phenyl group. Ring A may also represent a fused ring hydrocarbon unit with, for example, two, three or four rings. L may represent a single bond.

L may also represent a substituted or unsubstituted divalent arylene group having 6 to 30 ring carbon atoms. Preferably, L may represent a divalent arylene group having 6 to 18 ring carbon atoms. More preferably, L may represent a divalent arylene group having 6 to 12 ring carbon atoms. L may further represent a substituted or unsubstituted divalent heteroarylene group having 6 to 30 ring carbon atoms. Preferably, L may represent a divalent heteroarylene group having 6 to 18 ring carbon atoms. More preferably, L may represent a divalent arylene group having 6 to 12 ring carbon atoms.

Each of $R_1$ to $R_5$ may be a hydrogen atom, or a substituted or unsubstituted alkyl group having 1 to 20 carbon atoms, preferably 1 to 12 carbon atoms, and more preferably 1 to 8 atoms. Each of $R_1$ to $R_5$ may also be a substituted or unsubstituted aryl group having 6 to 30 carbon atoms, preferably 6 to 18 carbon atoms and more preferably 6 to 12 carbon atoms. Alternatively, each of $R_1$ to $R_5$ may a be a substituted or unsubstituted aralkyl group having 6 to 30 carbon atoms, preferably 6 to 18 carbon atoms and more preferably 6 to 12 carbon atoms. Furthermore, each of $R_1$ to $R_5$ may also be a substituted or unsubstituted heteroaryl group having 3 to 30 carbon atoms, preferably 3 to 18 carbon atoms, and more preferably 3 to 12 carbon atoms. In some embodiments, $R_2$ may be a methyl group, a butyl group or a hexyl group, wherein the methyl group is preferable. $Y_1$ to $Y_5$ may independently represent a nitrogen atom or $CR_6$. $R_6$ may represent a hydrogen atom, a substituted or unsubstituted phenylene group having 6 to 30 ring carbon atoms, preferably 6 to 18 carbon atoms, and more preferably 6 to 12 carbon atoms. $R_6$ may also represent a bond linked to B. In some embodiments, m may preferably be 0, 1 or 2, more preferably be 0 or 2, and most preferably be 0.

B may be represented by the following formula (2):

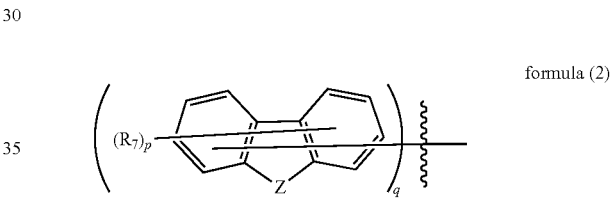

formula (2)

wherein q may be an integer of 0, 1, 2 or 3; p may be an integer of 0 to 7. Z may be O, S, or $NR_8$. $R_8$ may be a hydrogen atom, a substituted or unsubstituted phenyl group, a substituted or unsubstituted carbazole group, or a bond linked to formula (1). $R_7$ may have the same definition as $R_1$.

When q is an integer of 1, Z may be O or S, ring A may be a phenyl group, L may be a single bond, and at least one of $Y_1$ to $Y_5$ represents a nitrogen atom. In some embodiments, two or three of $Y_1$ to $Y_5$ independently represent a nitrogen atom.

In some embodiments, the organic compound may also be represented by one of the following formula (3) to (5):

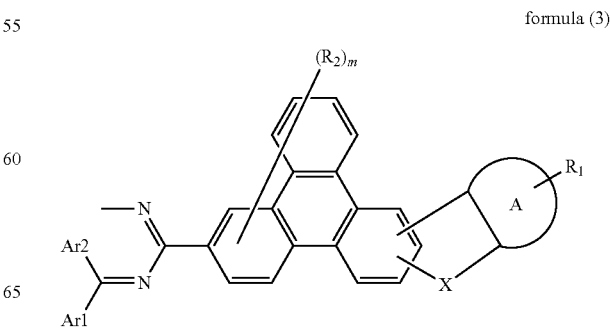

formula (3)

-continued formula (4)

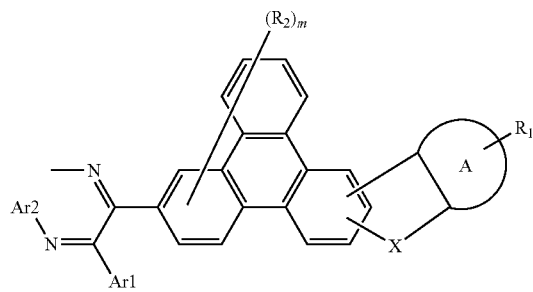

formula (5)

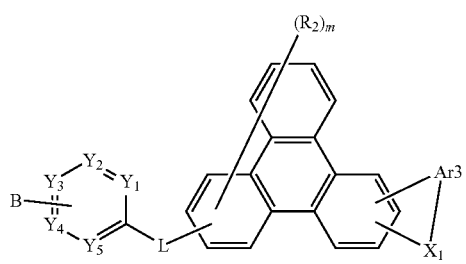

wherein Ar1 may represent a phenyl group. Ar2 may represent a phenyl group or a fused ring hydrocarbon unit with two rings. Ar3 may represent a phenyl group or a fused ring hydrocarbon unit with two, three or four rings. $X_1$ may be O or S.

The organic compound represented by the formula (3) may also be represented by the following formula (6):

formula (6)

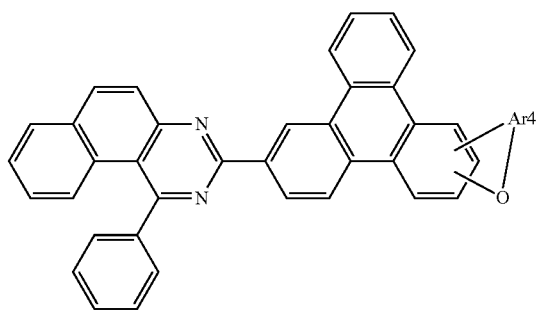

wherein Ar4 represents a phenyl group or a fused ring hydrocarbon unit with two, three or four rings.

In some embodiments, Ar4 may represent a phenyl group or a fused ring hydrocarbon unit with four rings.

The organic compound represented by the formula (3) may also be represented by the following formula (7):

formula (7)

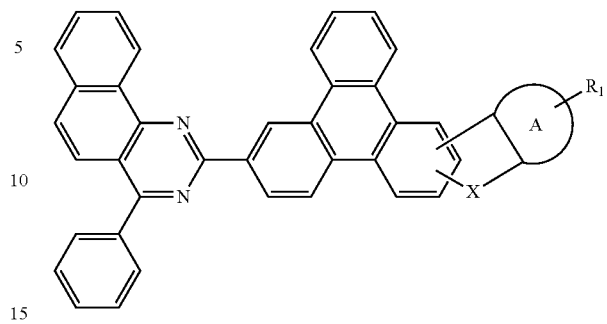

wherein X may represent a divalent bridge selected from the group consisting of O, S and $NR_3$. Ring A may represent a phenyl group. $R_1$ may be a hydrogen atom or an aryl group.

The organic compound may also be represented by the following formula (8):

formula (8)

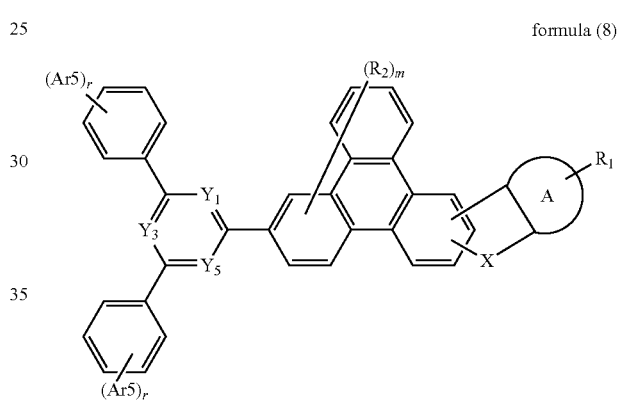

wherein Ar5 each represents a substituted or unsubstituted phenyl group; r may represent an integer of 0, 1 or 2. $Y_1$ and $Y_5$ may be the same. Each of $Y_1$ and $Y_5$ represents a nitrogen atom or $CR_6$. $Y_3$ may represent a nitrogen atom or $CR_6$.

In some embodiments, the organic compound may be represented by the following formula (9):

formula (9)

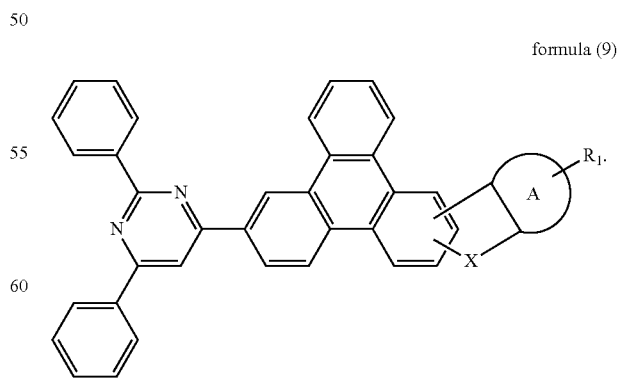

In some embodiments, the organic compound may also be represented by the following formula (10):

formula (10)

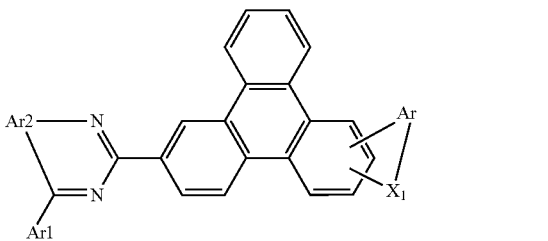

wherein Ar and Ar1 may independently represent a phenyl group. Ar2 may represent a phenyl group or a fused ring hydrocarbon unit with two rings. $X_1$ may be O or S.

In some embodiments, the organic compound may be represented by the following formula (11):

formula (11)

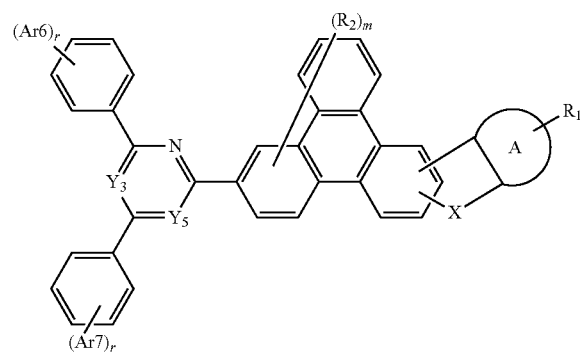

wherein Ar6 and Ar7 may independently represent a nitrogen-substituted or unsubstituted phenyl group; r may represent an integer of 0 to 1; and m may represent an integer of 0 to 1. $Y_3$ and $Y_5$ may independently represent a nitrogen atom or $CR_6$. X may represent a divalent bridge selected from the group consisting of O, S, Se, $NR_3$ and $SiR_4R_5$. $R_4$ and $R_5$ may independently represent a nitrogen-substituted or unsubstituted phenyl group. $R_6$ may represent a hydrogen atom.

In another embodiment of the present invention, an organic EL device is disclosed. The organic EL device comprises a pair of electrodes composed of a cathode and an anode, and a light emitting layer between the pair of electrodes. The light emitting layer, which may be an emitting layer, a hole blocking layer or an electron transport layer, may comprise the organic compound represented by formulas (1), (2), (3), (4), (5), (6), (7), (8), (9), (10) or (11).

In some embodiments, the organic compound of the light emitting layer may be an emitting material, and preferable an emitting host material. The emitting material is capable of increasing a half-life or current efficiency of the organic EL device, or lowering a driving voltage of the organic EL device. For example, the light emitting layer comprising the organic compound as an emitting host material may increase a half-life of the organic EL device to be more than about 730 hours, or even up to be about 780 hours. The organic compound may be represented by formula (10).

In some embodiments, the organic compound of the light emitting layer may be an electron transfer material (ETM, i.e., a material for ETL). The material for ETL may lower the driving voltage of the organic EL device to be less than about 5.1 V. Moreover, the material for ETL may lower the driving voltage of the organic EL device to be about 3.4 V to about 4.6 V. On the other hand, the material for ETL may increase the current efficiency of the organic EL device to be more than about 18 V. Moreover, the material for ETL may increase the current efficiency of the organic EL device to be about 23 cd/A to about 33 cd/A. In some examples, the material for ETL may increase the half-life of the organic EL device to be more than about 450 hours. Preferably, the material for ETL may increase the half-life of the organic EL device to be about 470 hours to about 560 hours.

When non-obviousness of the present invention is evaluated, the technical solution of the invention cannot be required to produce an advantageous technical effect in any situation and in all aspects. Such requirement does not comply with non-obviousness-related provisions of a patent law.

One person having ordinary skill in the art of the present application, in actual use, may select a material of a compound to take advantage of one kind of luminescent data (for example, to emit a specific color of light). In the same art of the present application, however, it is not always necessary for the present invention to take advantage of other kinds of luminescent data such as a driving voltage, a current efficiency or a half-life of the device.

When the non-obviousness of the present application is evaluated, it shall not be required to take advantage of all kinds of luminescent data. As long as the present invention takes advantage of one kind of luminescent data, such as a lower driving voltage, a higher current efficiency or a longer half-life, the device of the present invention shall be regarded as producing an advantageous luminescent effect. It shall not be required to have a general improvement of all kinds of luminescent data of the compound in any case. Moreover, the present invention shall be considered as a whole. The technical effect brought by the whole technical solution should not be negated, even if some luminescent data of the compound are not good, or one luminescent data is not good for some kinds of color of light or for the application of some kinds of host.

A compound of the present application, as a material, shall not be required to improve all kinds of luminesce data, for all kinds of color of light, in the case of application of all kinds of host. As long as one kind of luminesce data, such as a current efficiency or a half-life of a specific color of light, is improved in the case of a specific host, the present invention shall be regarded as producing an advantageous technical effect. The advantageous technical effect is non-obvious enough to be a prominent substantive feature, so that the corresponding technical solution of the present invention involves an inventive step.

In some embodiments, the organic compound of the light emitting layer may be a hole blocking material (HBM, i.e., a material for HBL). The material for HBL may lower the driving voltage of the organic EL device to be about 4.4 V to about 4.9 V. On the other hand, the material for HBL may increase the current efficiency of the organic EL device to be 20 cd/A to about 26 cd/A. The material for HBL may increase the half-life of the organic EL device to be about 370 hours to about 390 hours.

In a further embodiment of the present invention, the organic EL device is a lighting panel. In other embodiment of the present invention, the organic EL device is a backlight panel.

In some embodiments, L is selected from the group consisting of the following formulas:

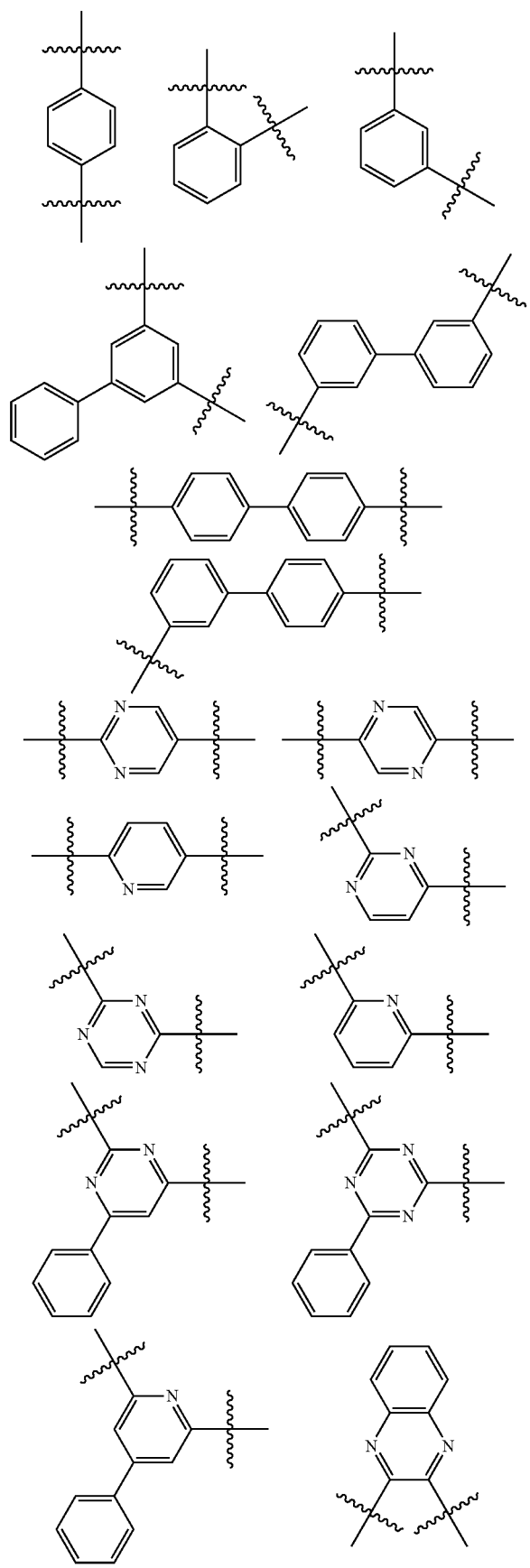
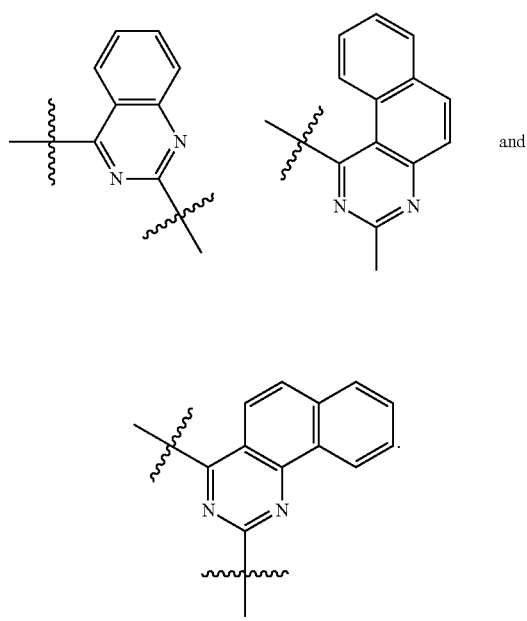
Ring A of the organic compound may be selected from the group consisting of a naphthyl group, an anthracenyl group, a phenanthrenyl group, a pyrenyl group, a chrysenyl group and a triphenylene group.
Preferably, the organic compound may be represented by one of the following compounds:
Compound 1
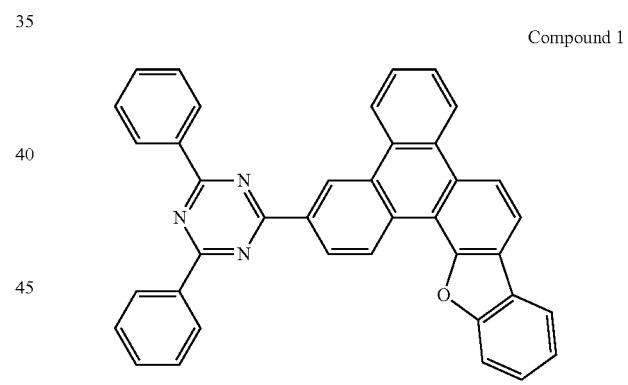
Compound 2
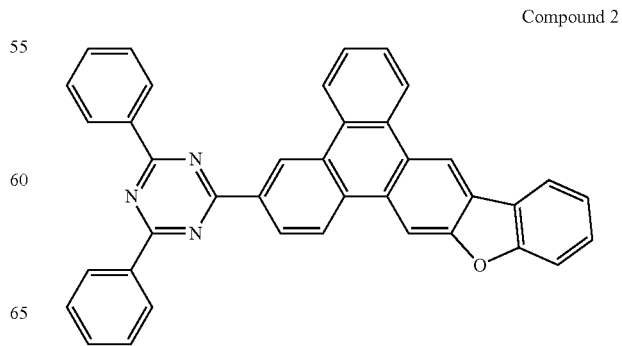

Compound 3
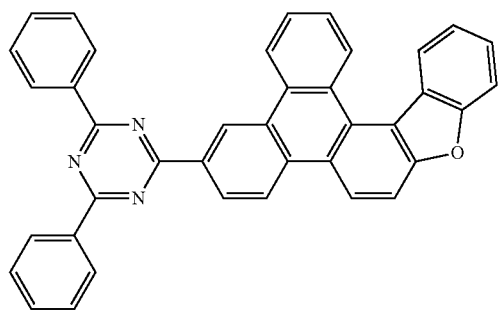
Compound 7
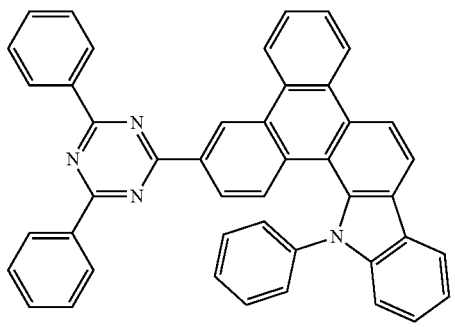
Compound 4
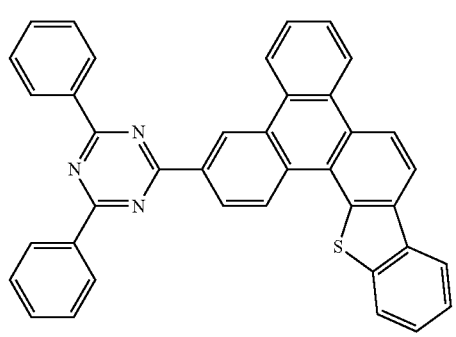
Compound 8
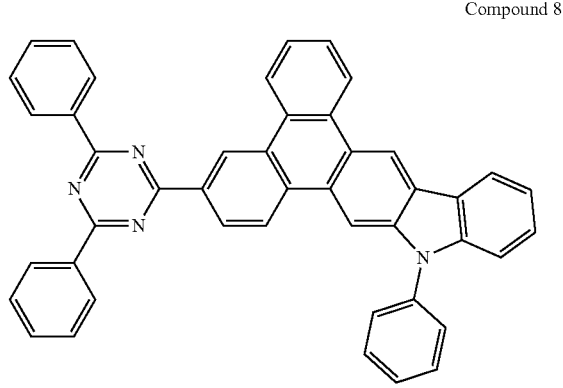
Compound 5
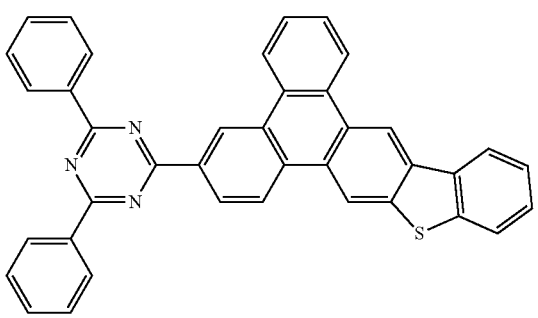
Compound 9
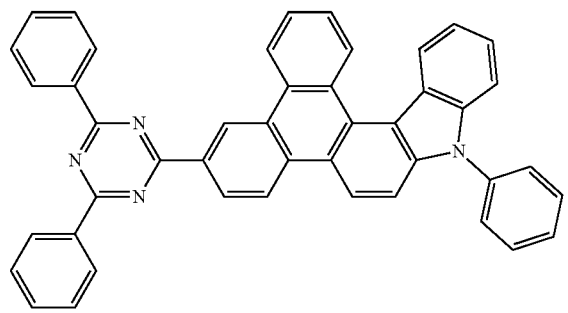
Compound 6
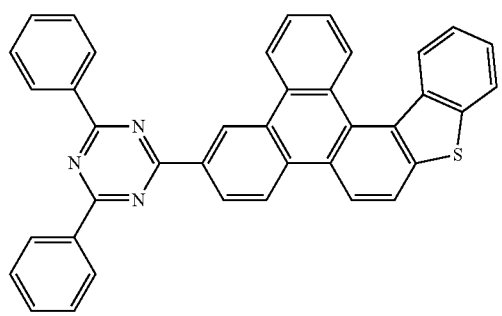
Compound 10
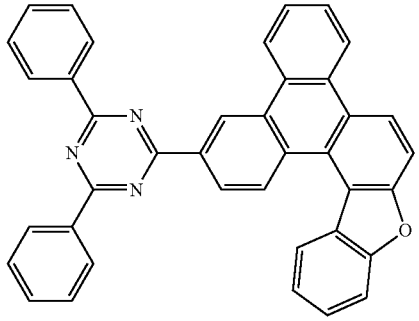

Compound 11
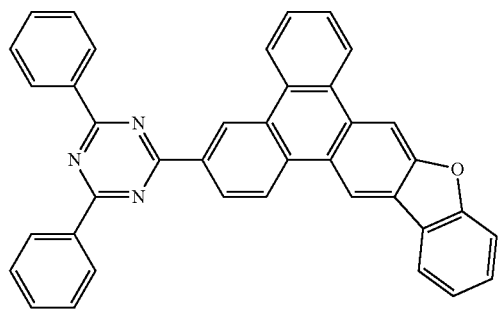
Compound 15
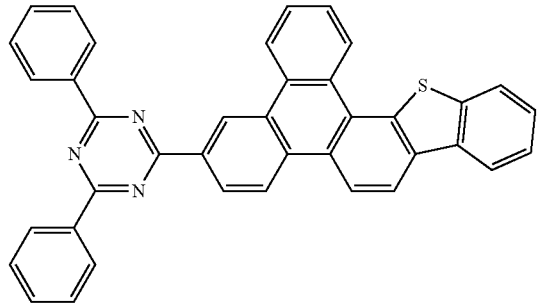
Compound 12
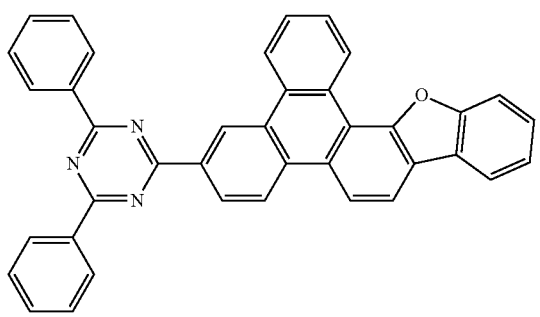
Compound 16
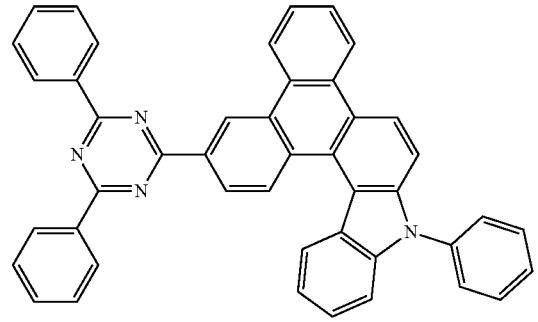
Compound 13
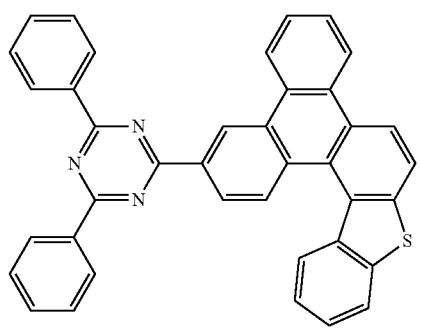
Compound 17
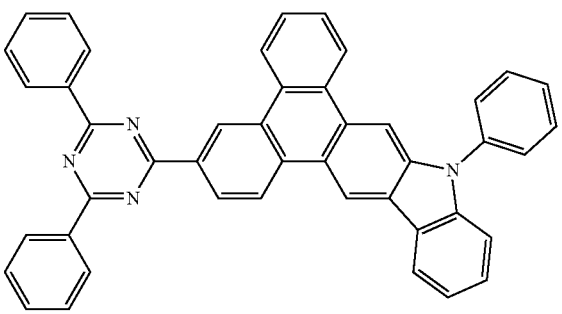
Compound 14
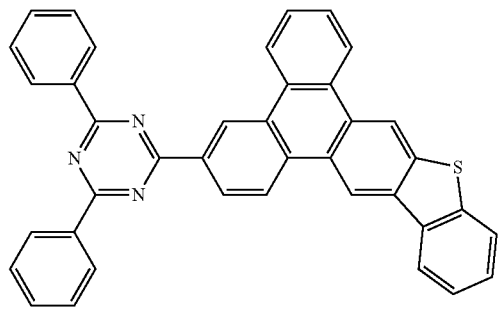
Compound 18
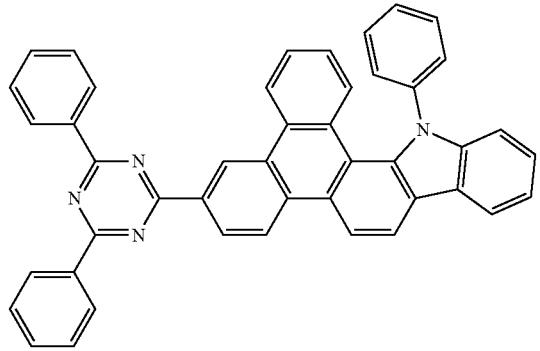

Compound 19
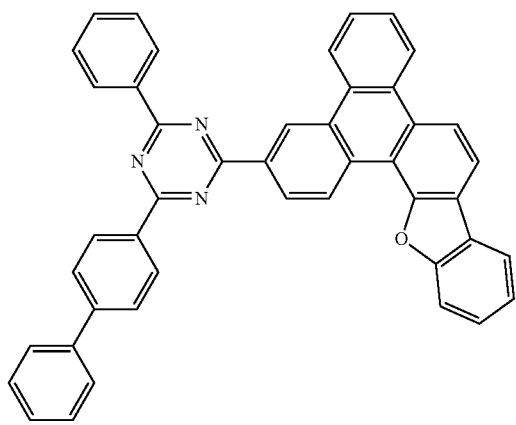
Compound 22
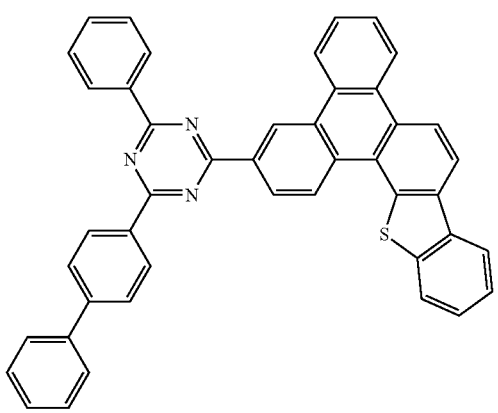
Compound 20
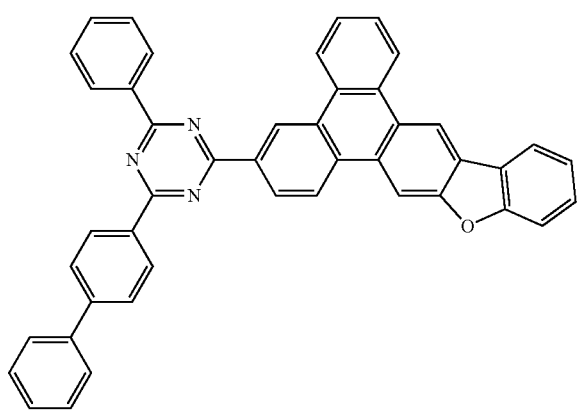
Compound 23
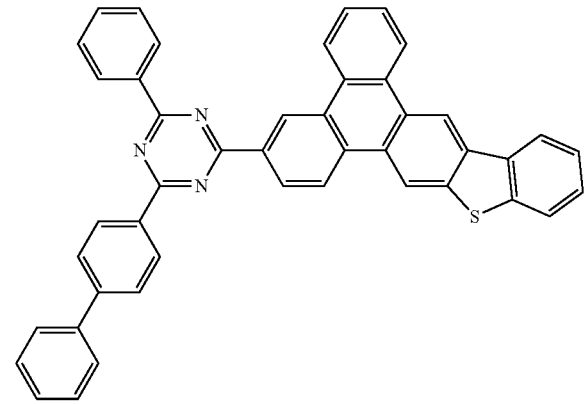
Compound 21
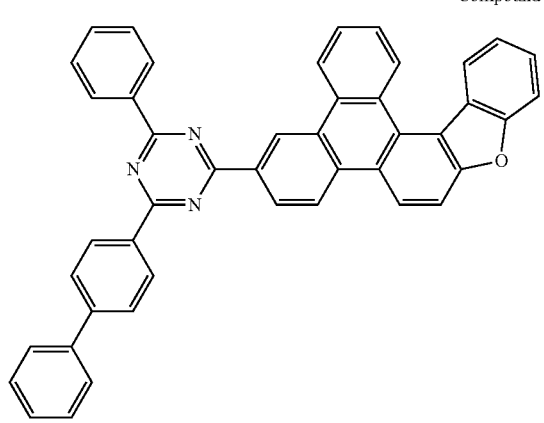
Compound 24
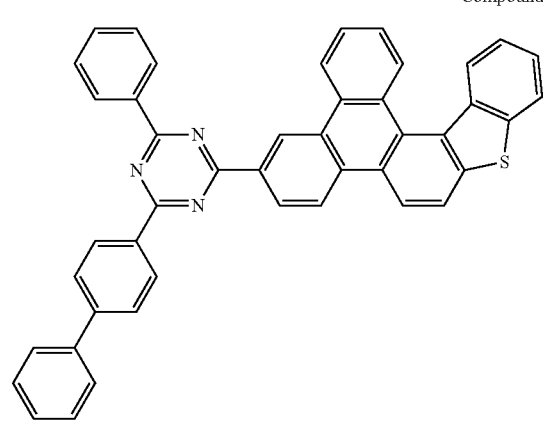

Compound 25
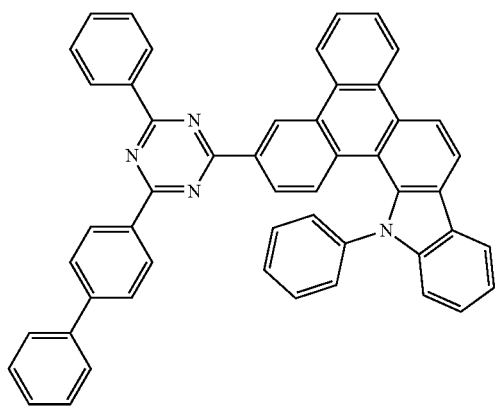
Compound 26
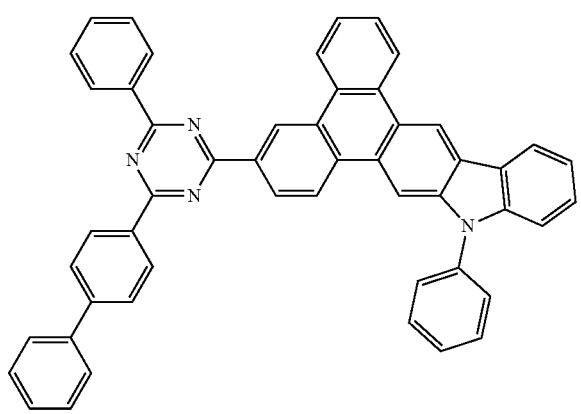
Compound 27
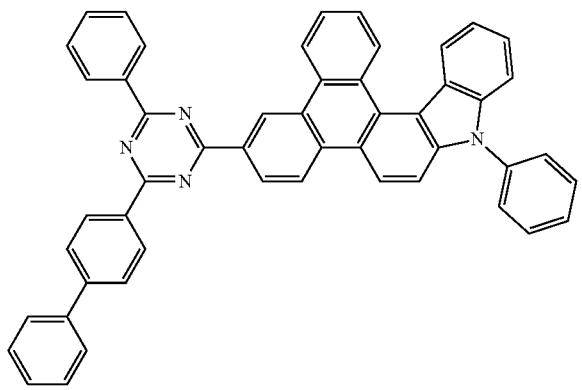
Compound 28
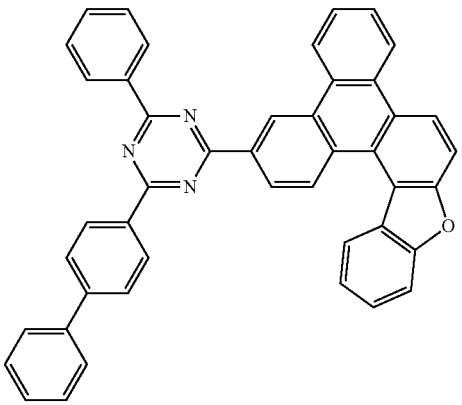
Compound 29
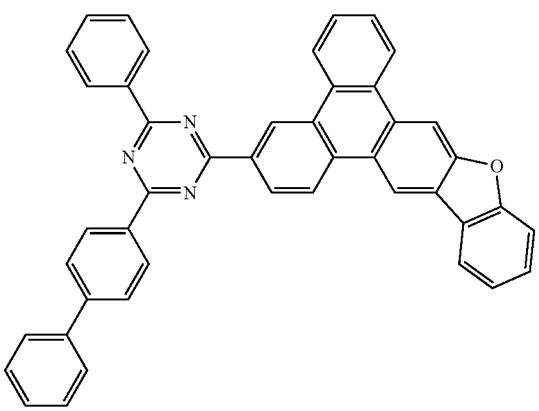
Compound 30
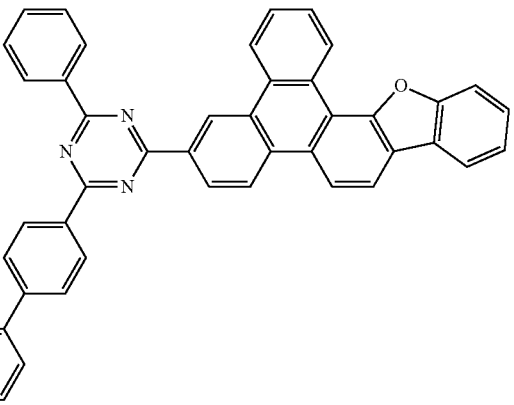

Compound 31
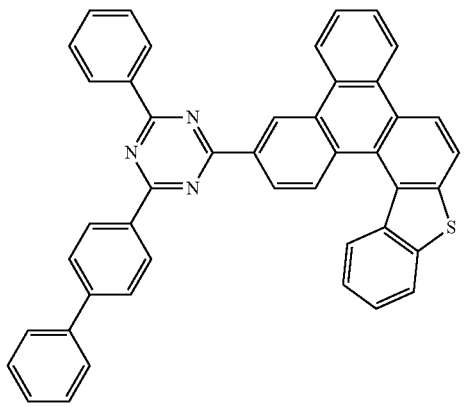
Compound 32
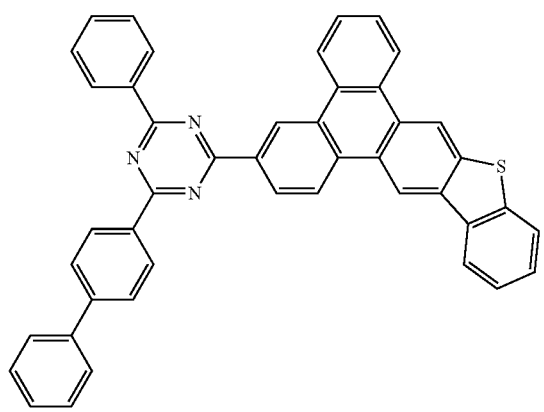
Compound 33
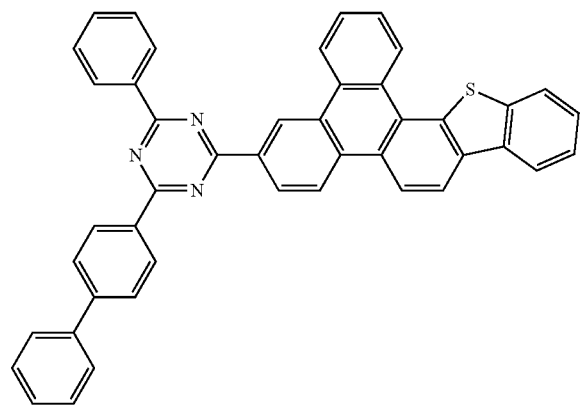
Compound 34
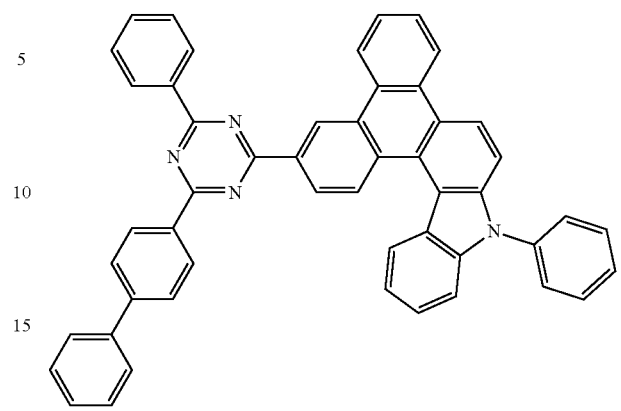
Compound 35
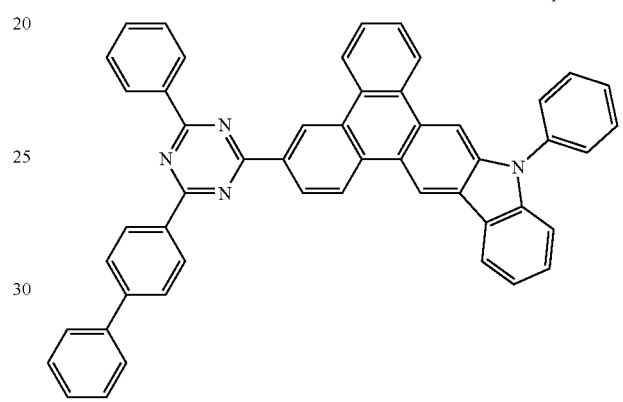
Compound 36
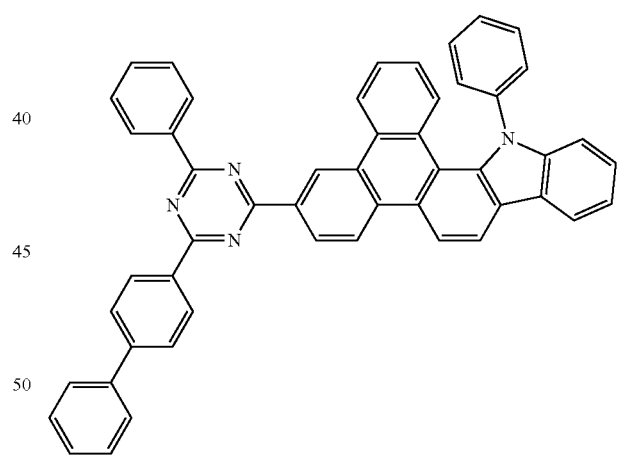
Compound 37
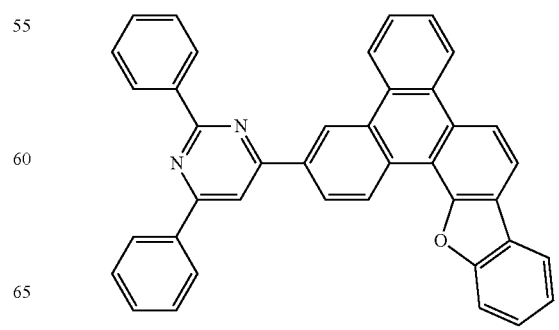

-continued
Compound 38
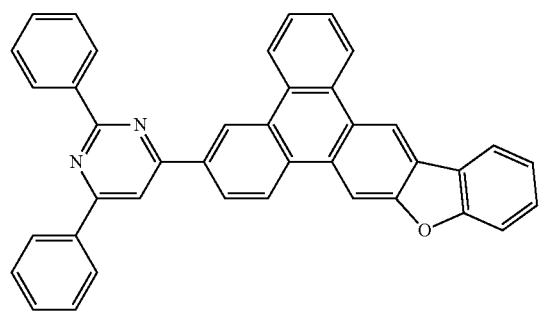
Compound 39
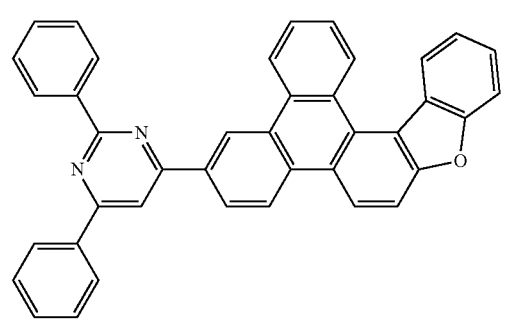
Compound 40
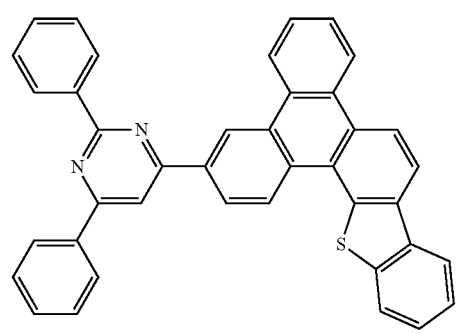
Compound 41
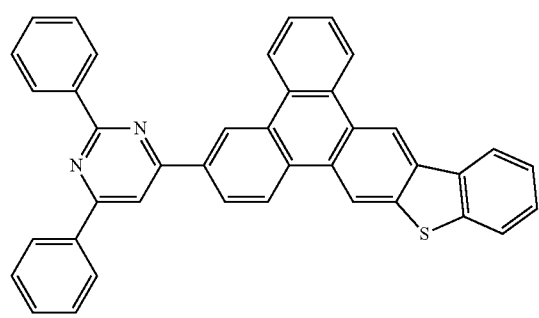
Compound 42
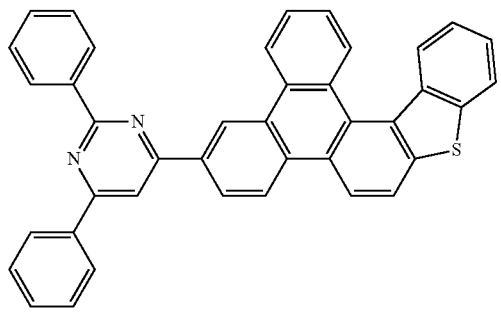
Compound 43
Compound 44
Compound 45
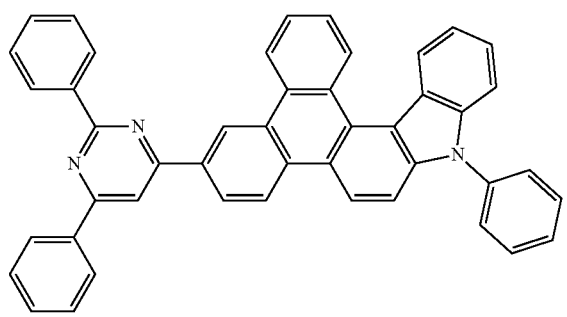

Compound 46
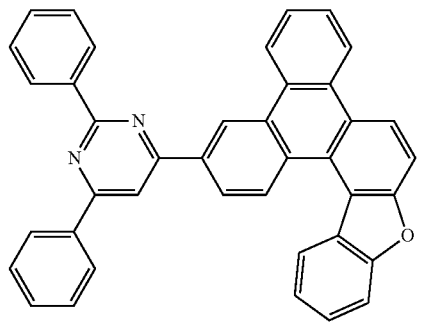
Compound 47
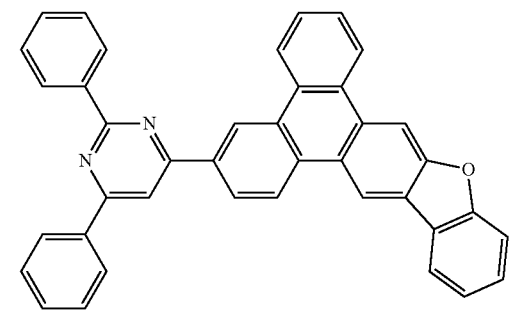
Compound 48
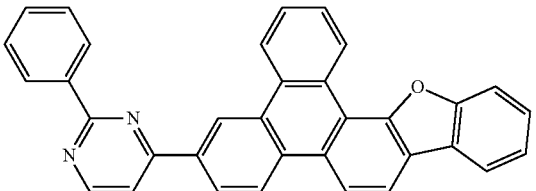
Compound 49
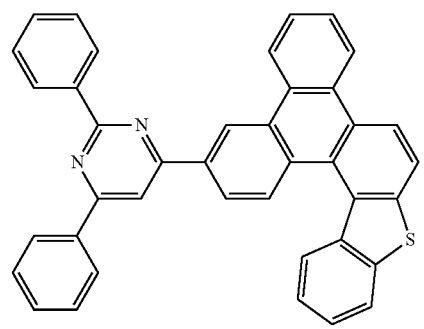
Compound 50
Compound 51
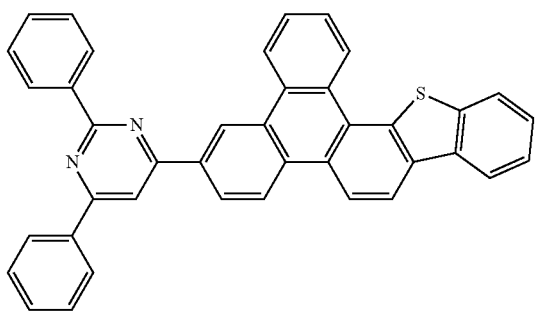
Compound 52
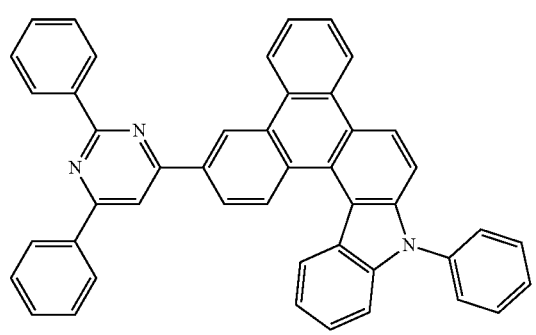
Compound 53
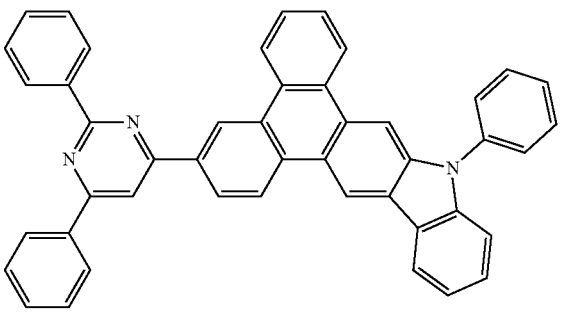
Compound 54
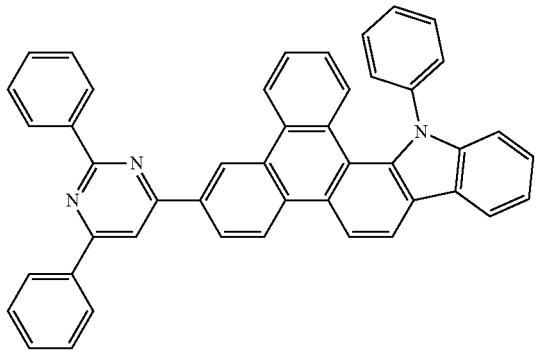

Compound 55
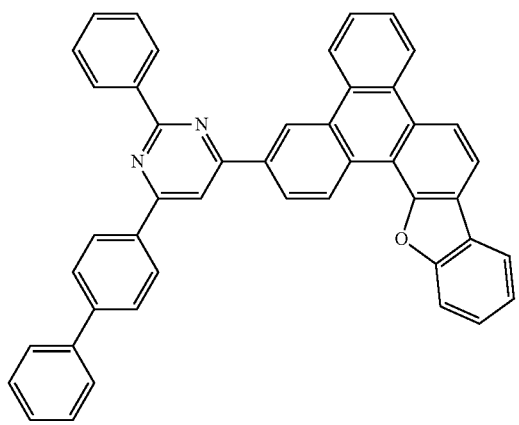
Compound 56
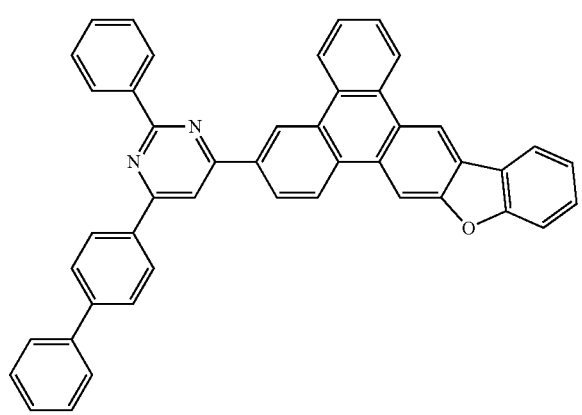
Compound 57
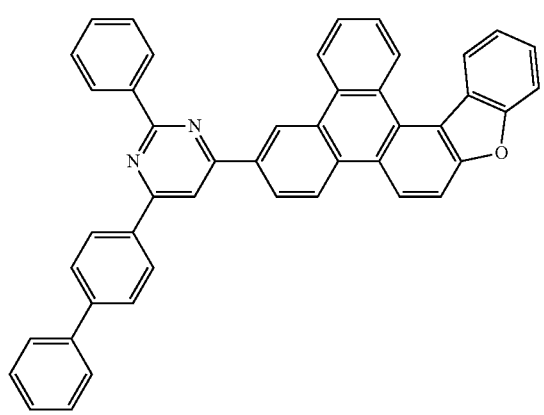
Compound 58
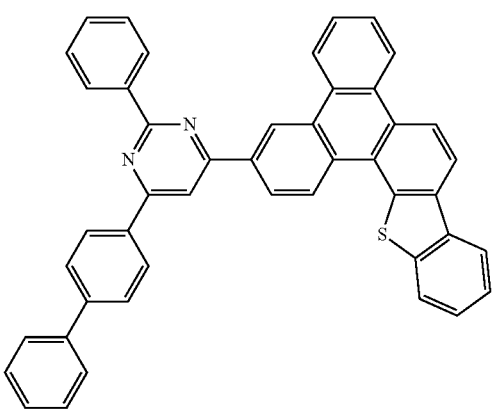
Compound 59
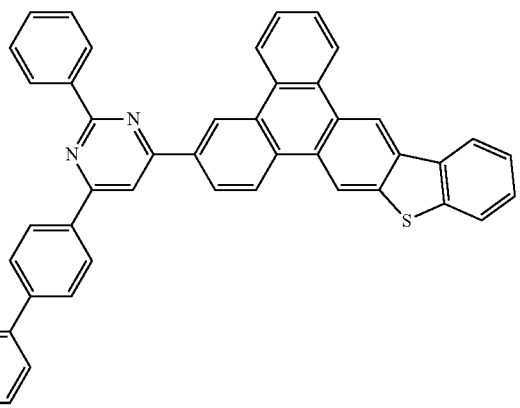
Compound 60
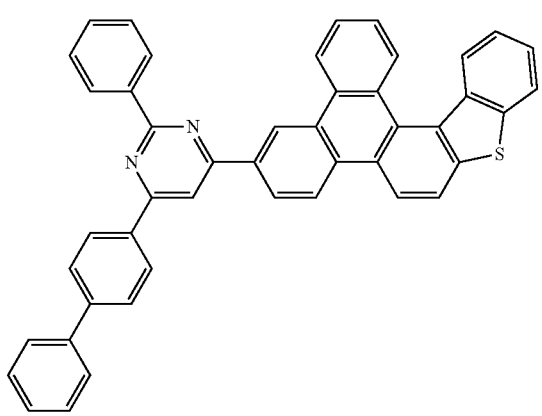

Compound 61
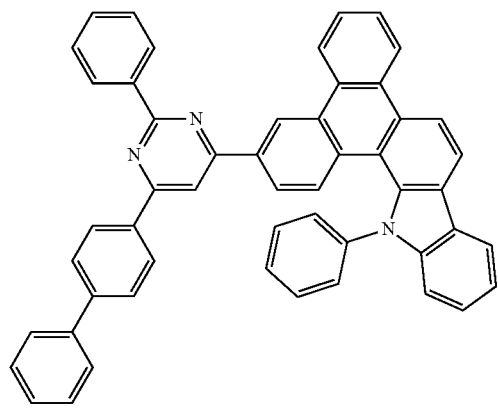
Compound 64
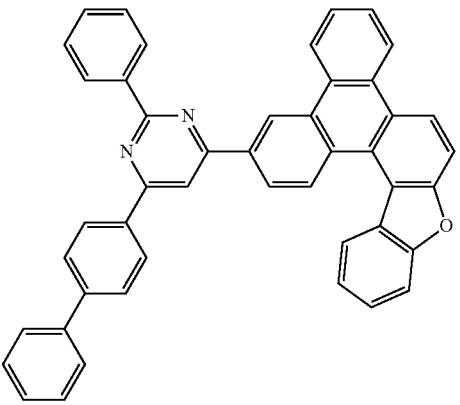
Compound 62
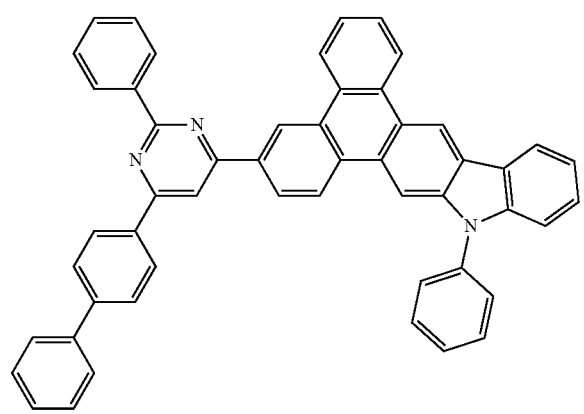
Compound 65
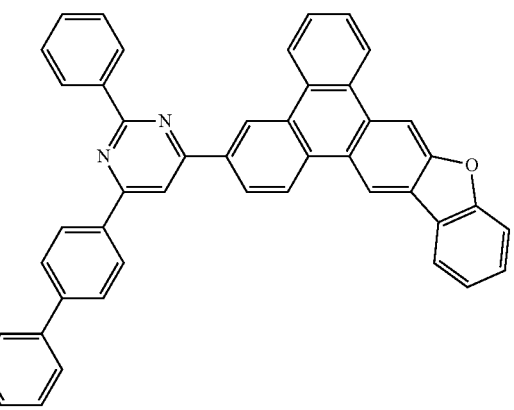
Compound 63
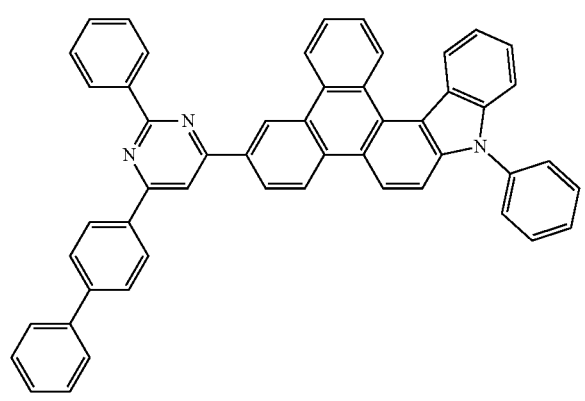
Compound 66
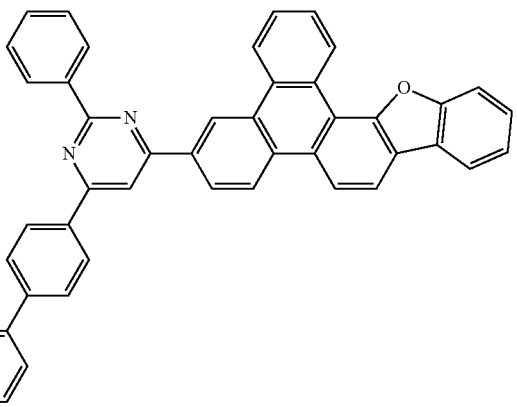

Compound 67
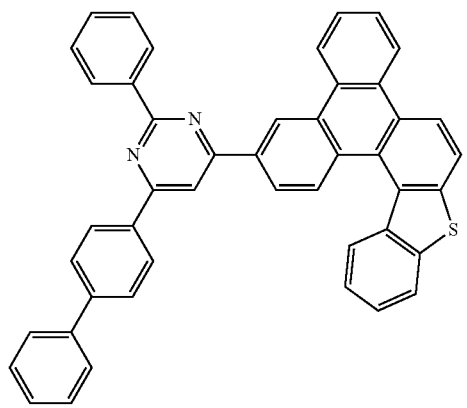
Compound 68
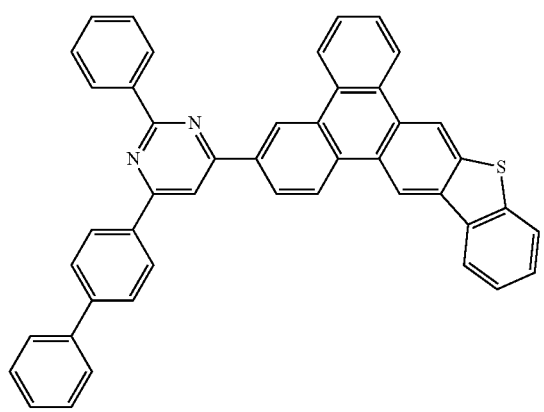
Compound 69
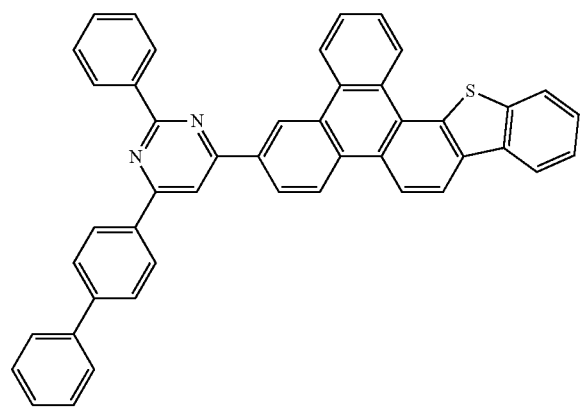
Compound 70
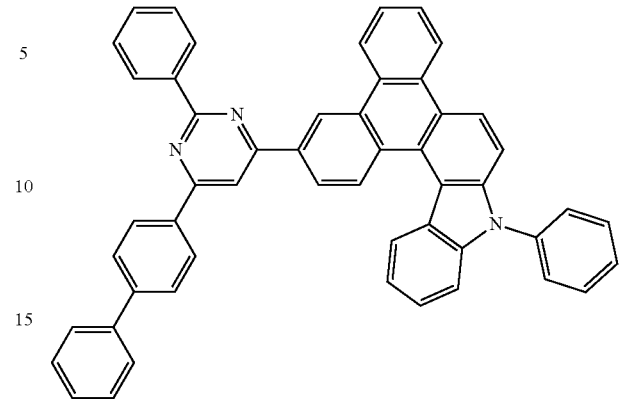
Compound 71
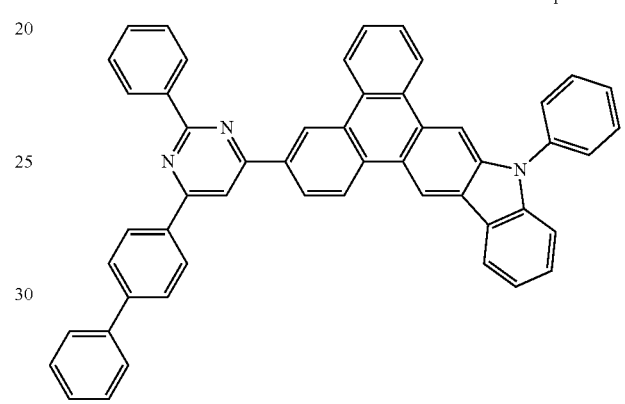
Compound 72
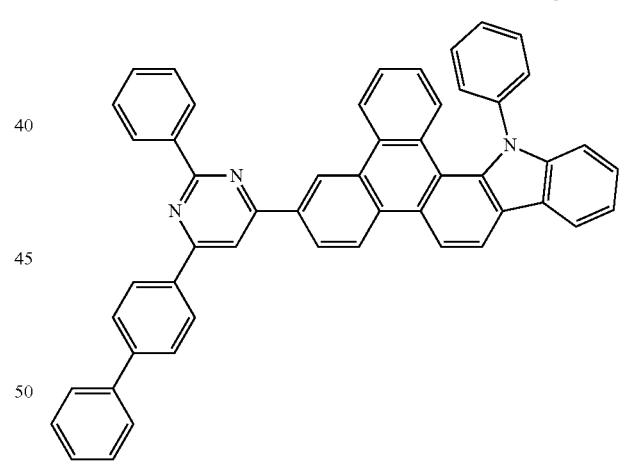
Compound 73
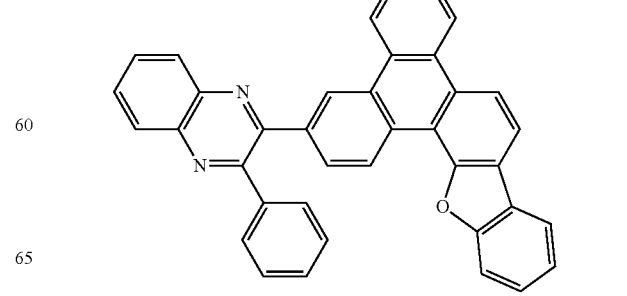

Compound 74
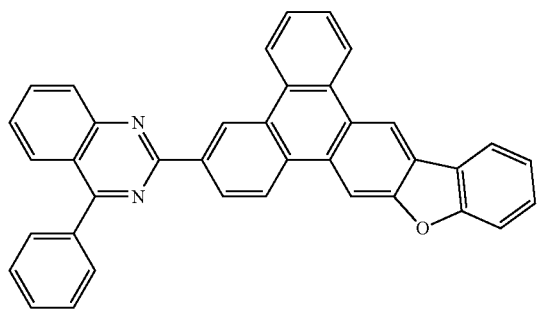
Compound 75
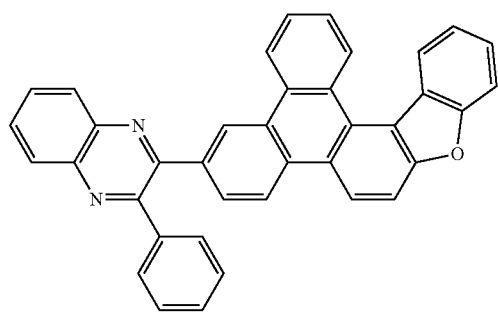
Compound 76
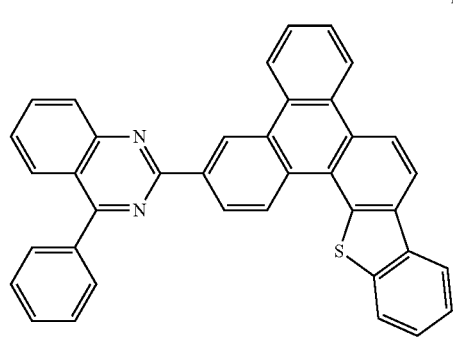
Compound 77
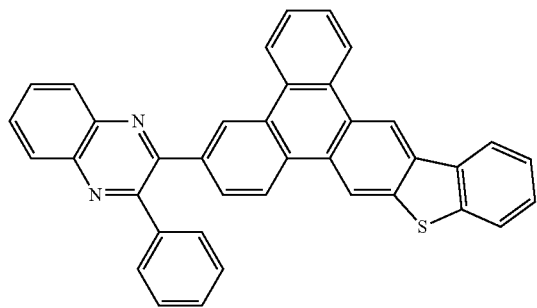
Compound 78
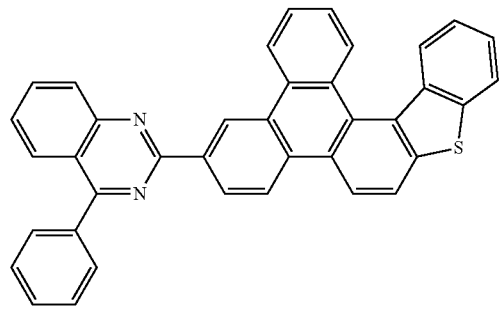
Compound 79
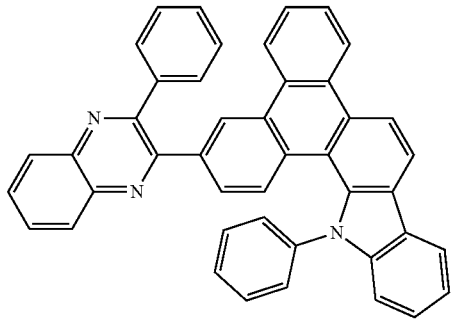
Compound 80
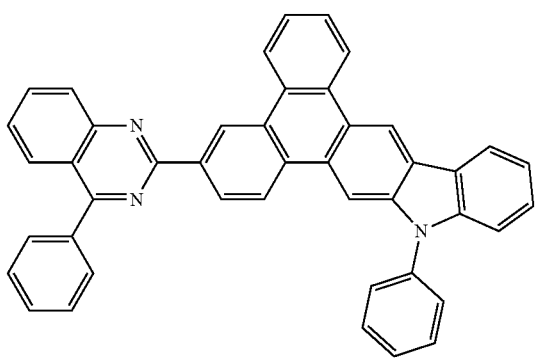
Compound 81
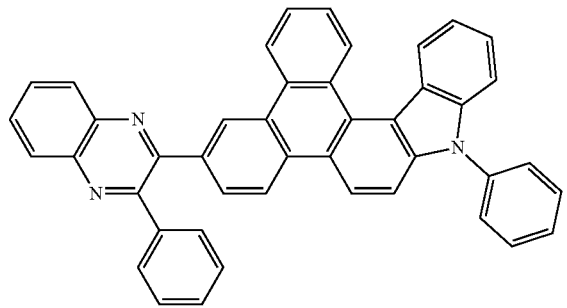

Compound 82
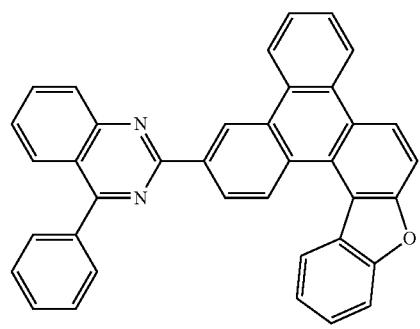
Compound 83
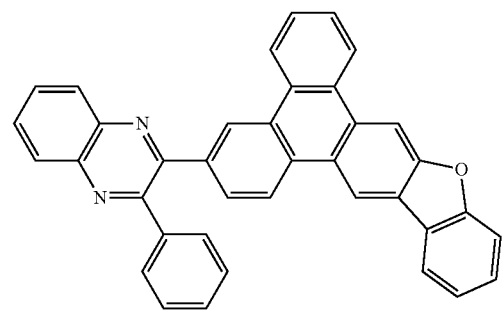
Compound 84
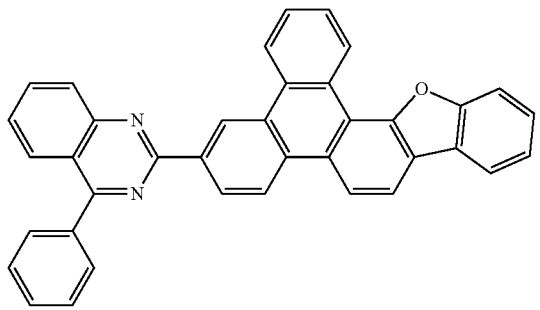
Compound 85
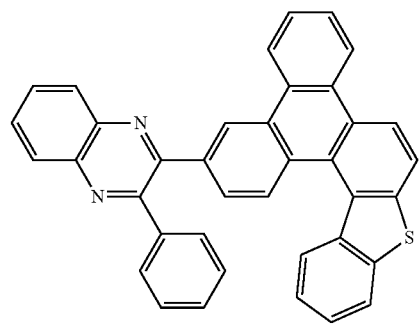
Compound 86
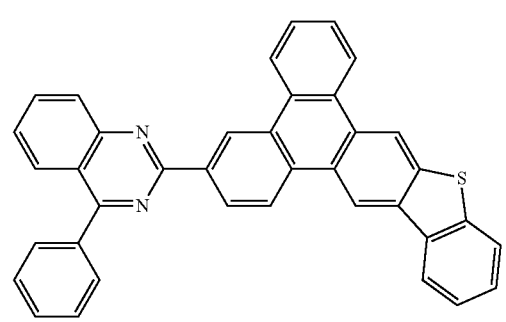
Compound 87
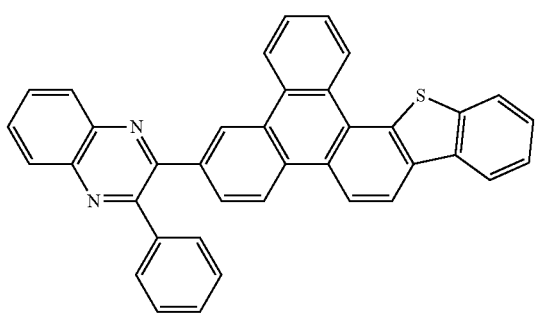
Compound 88
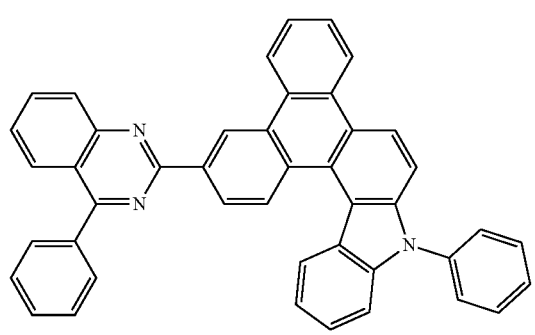
Compound 89
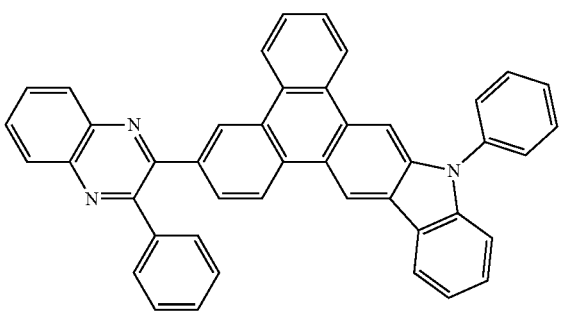
Compound 90
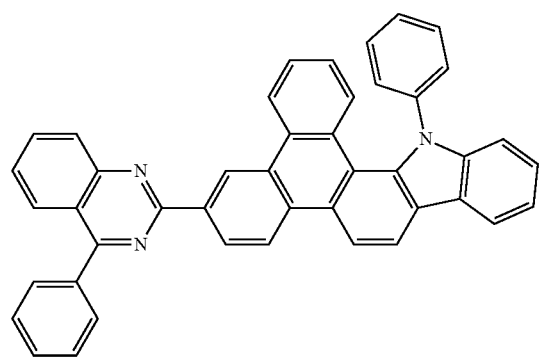

Compound 91
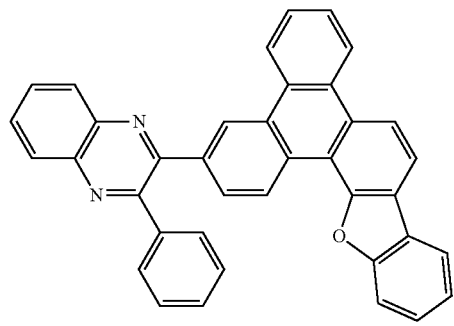
Compound 92
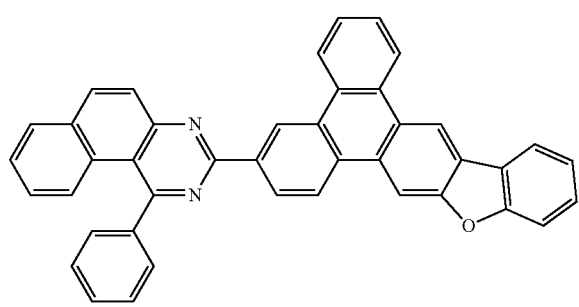
Compound 93
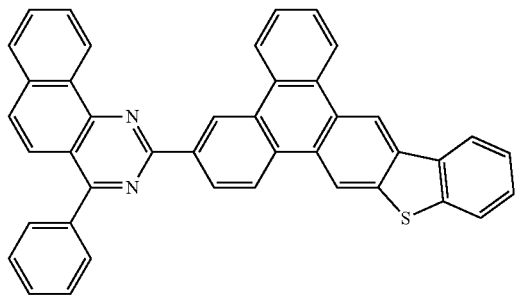
Compound 94
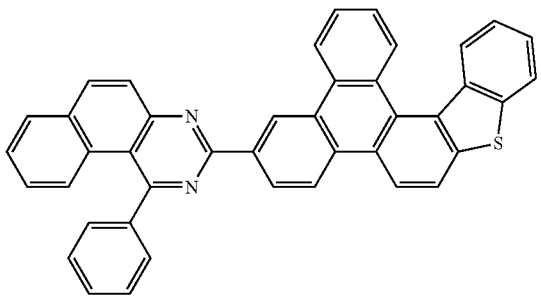
Compound 95
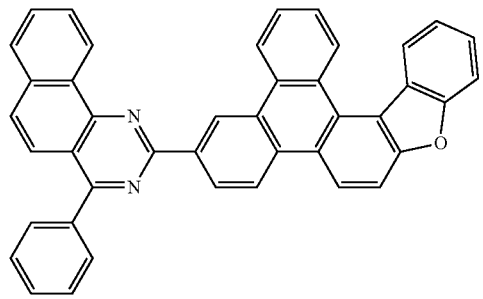
Compound 96
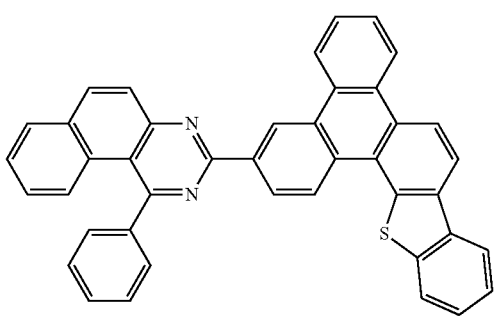
Compound 97
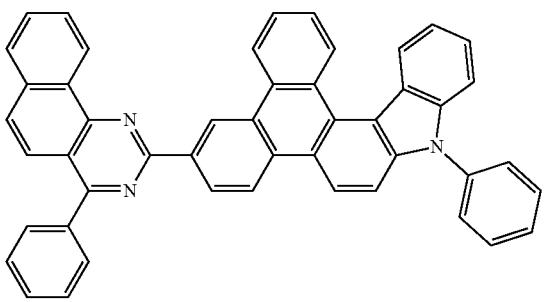
Compound 98
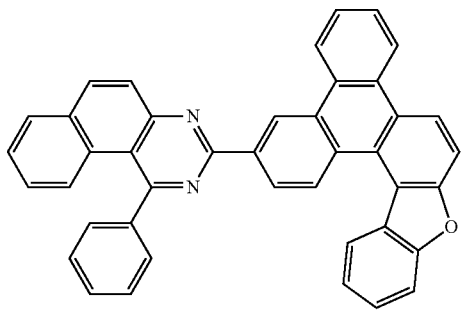
Compound 99
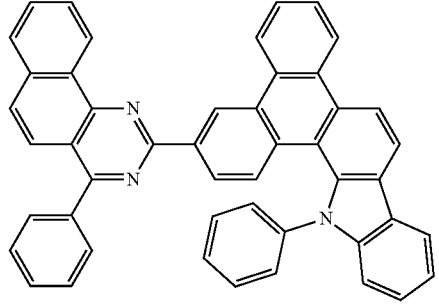

Compound 100
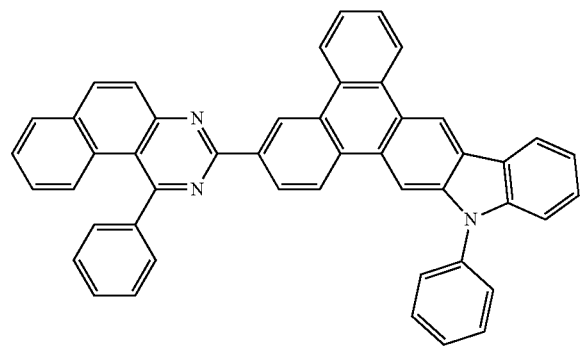
Compound 101
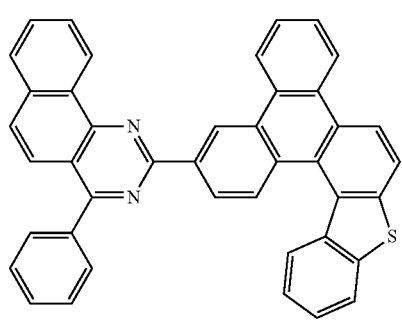
Compound 102
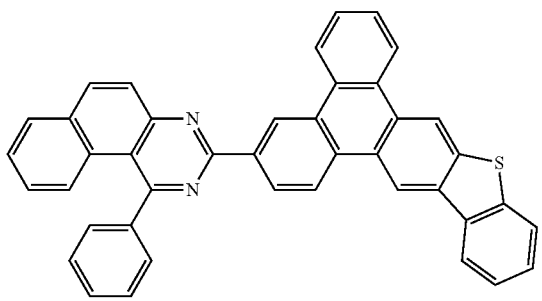
Compound 103
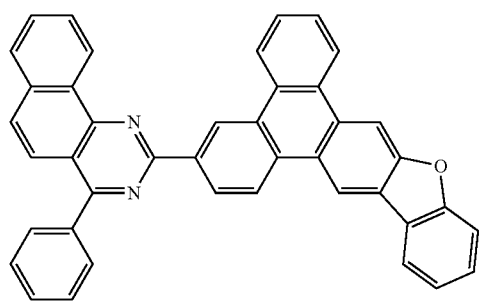
Compound 104
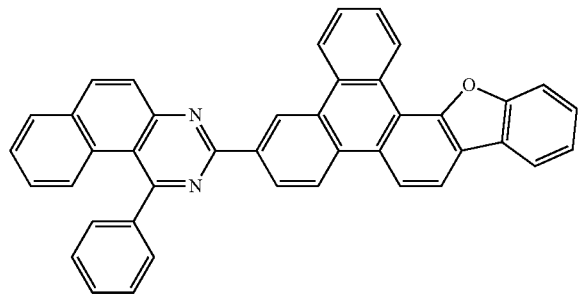
Compound 105
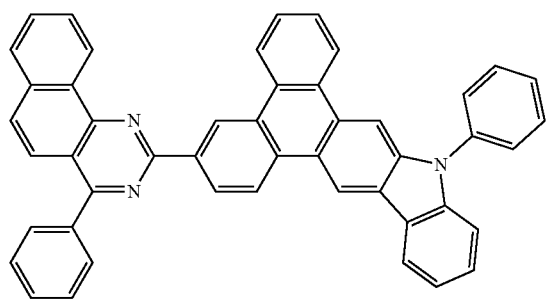
Compound 106
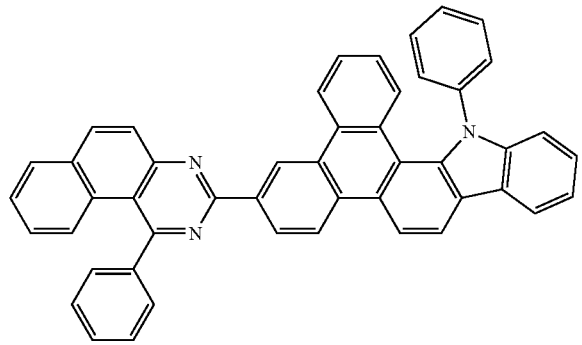
Compound 107
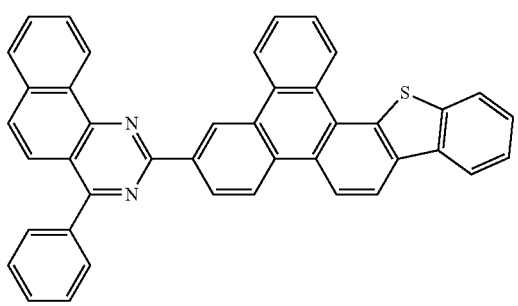

Compound 108
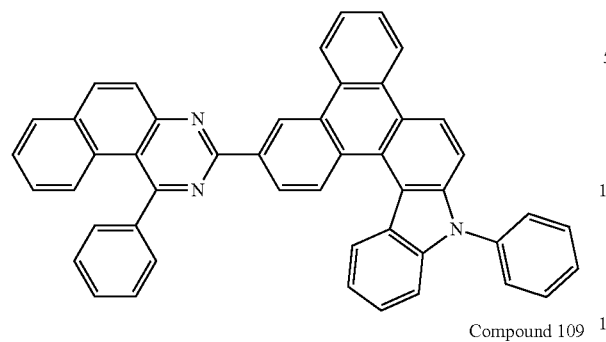
Compound 109
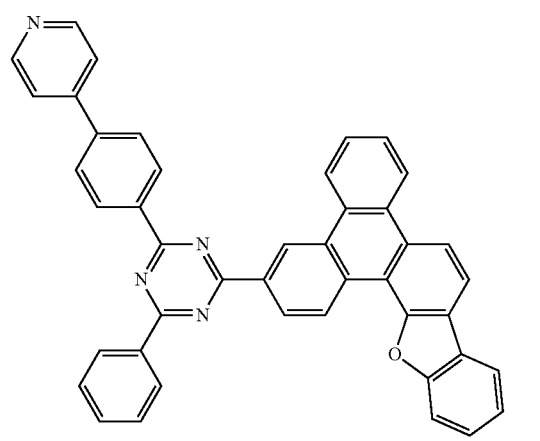
Compound 110
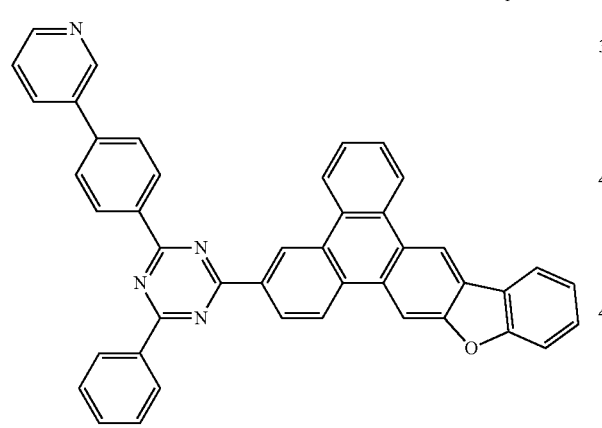
Compound 112
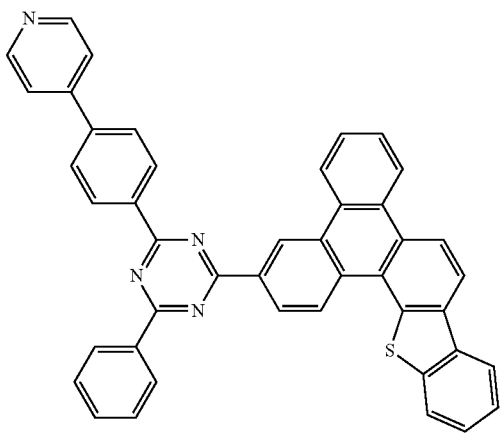
Compound 113
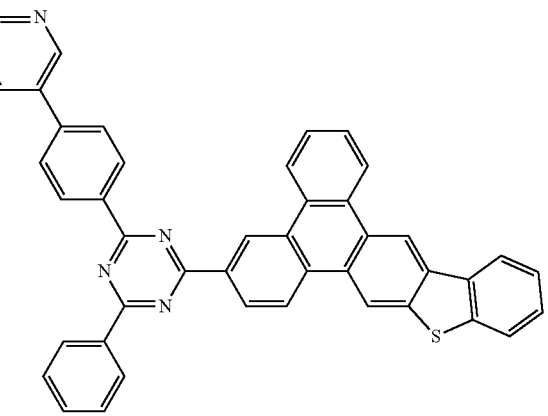
Compound 114
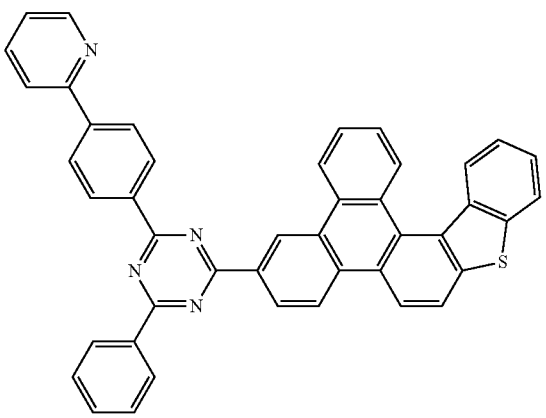

Compound 115
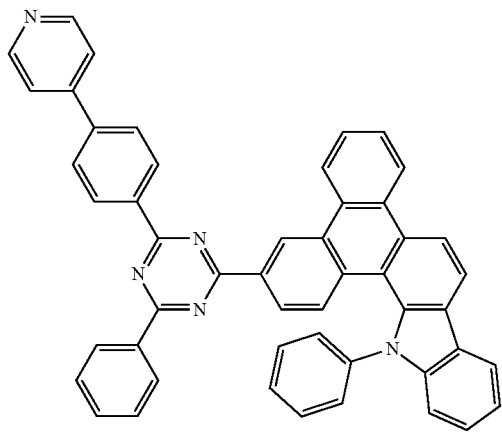
Compound 118
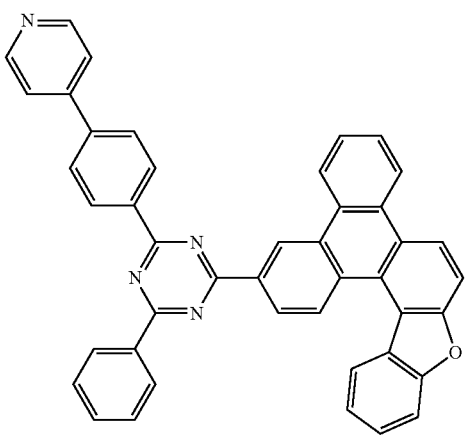
Compound 116
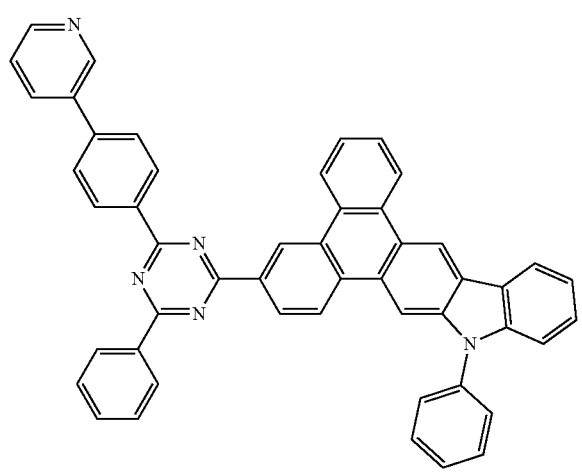
Compound 119
Compound 117
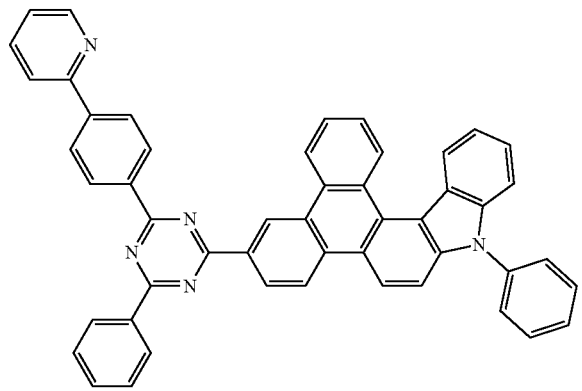
Compound 120
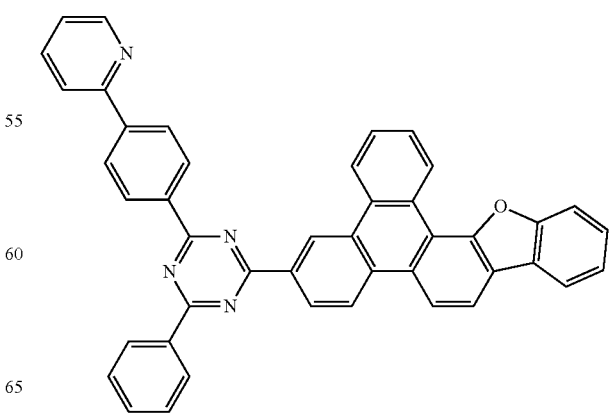

Compound 121
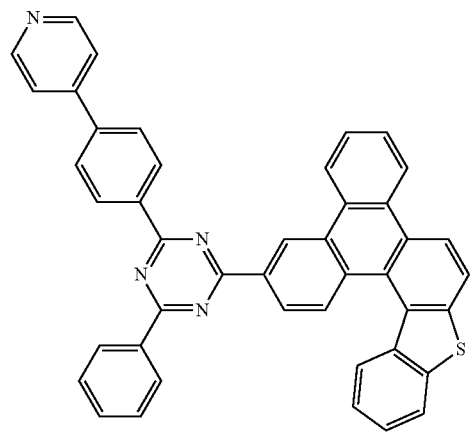
Compound 124
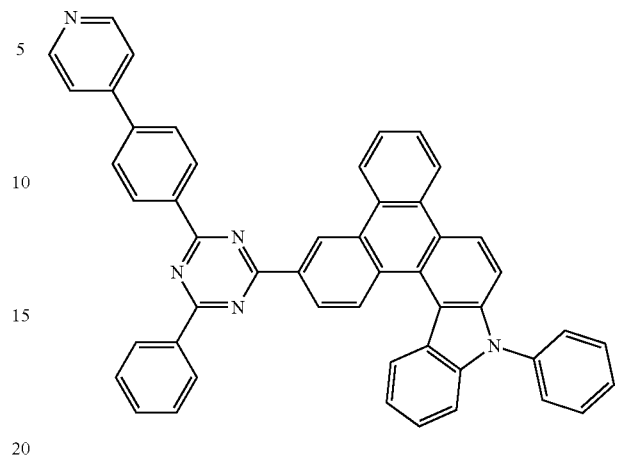
Compound 122
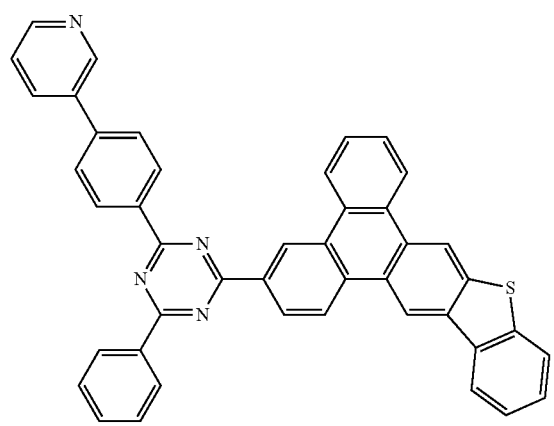
Compound 125
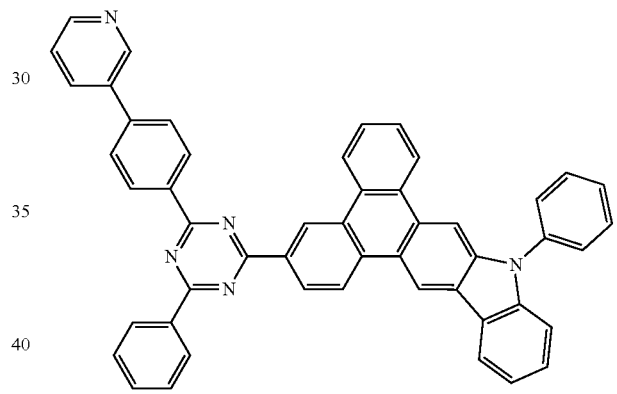
Compound 123
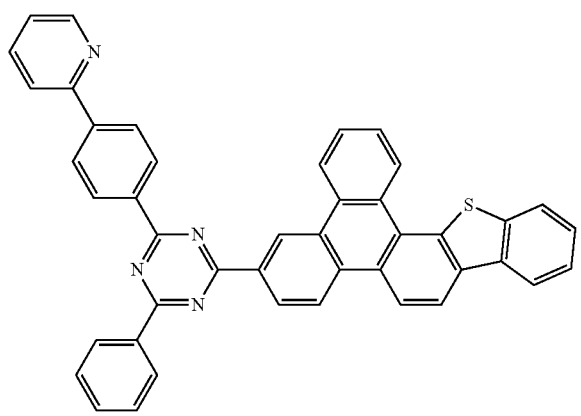
Compound 126
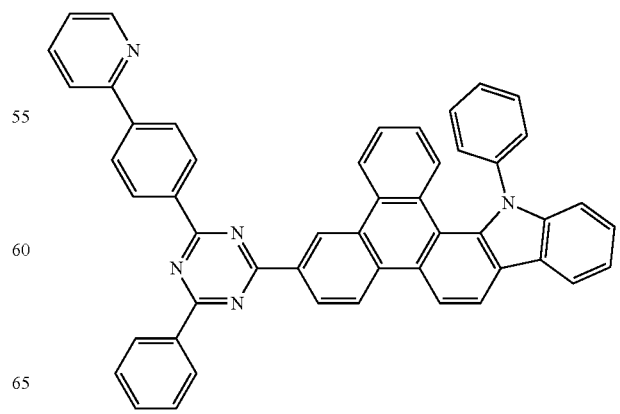

Compound 127
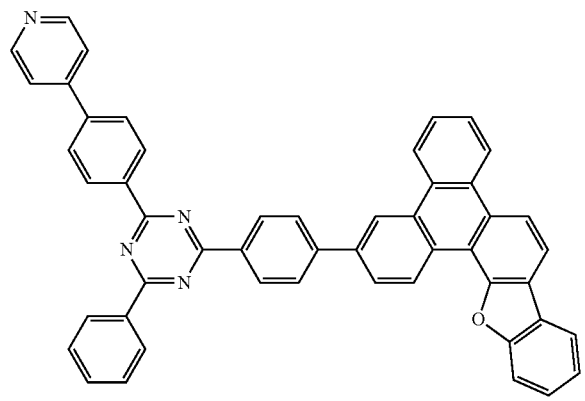
Compound 128
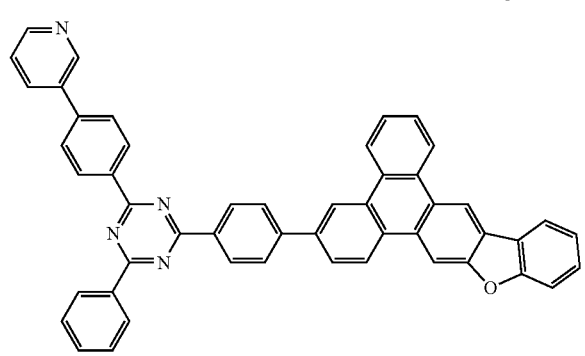
Compound 129
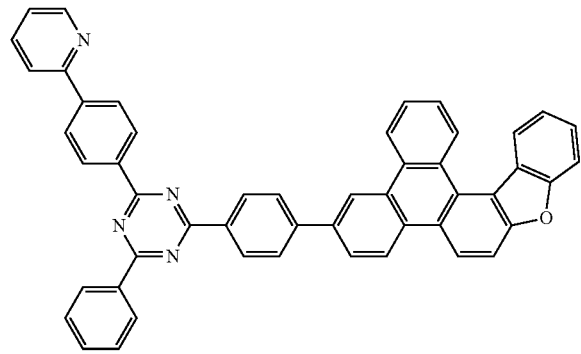
Compound 130
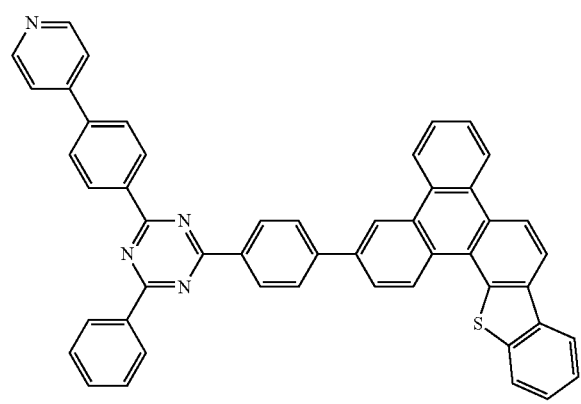
Compound 131
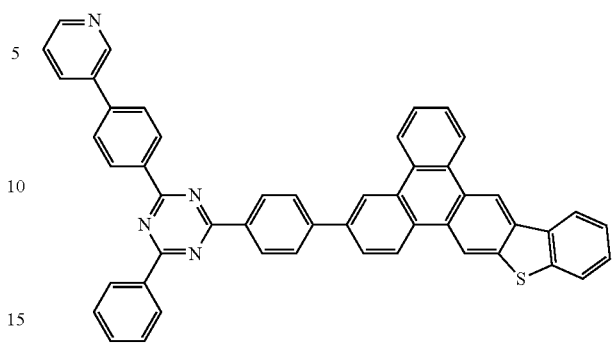
Compound 132
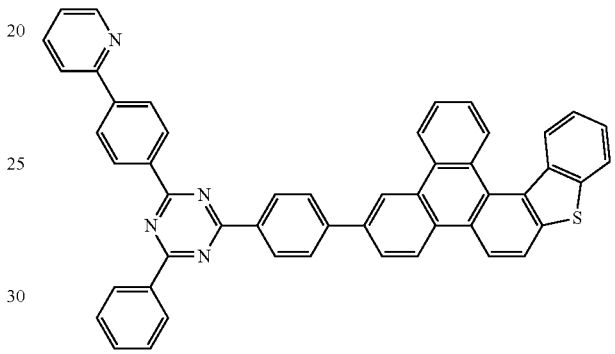
Compound 133
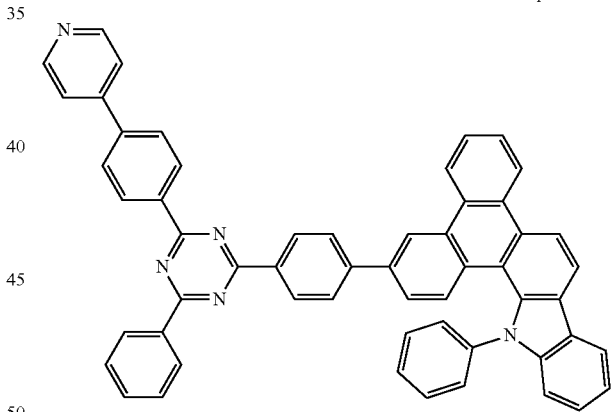
Compound 134
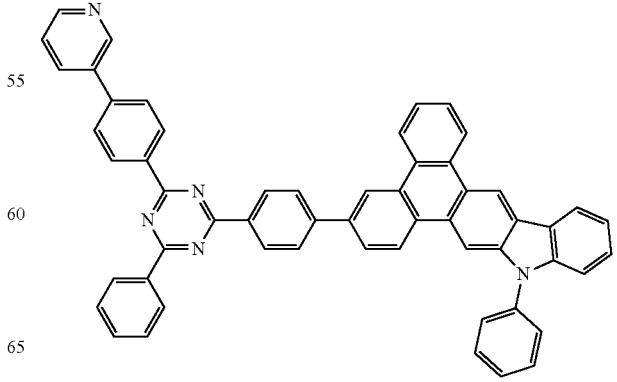

Compound 135
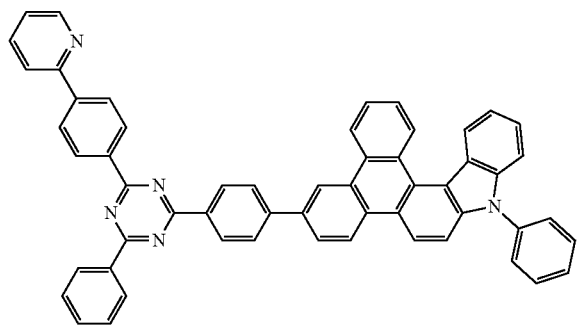
Compound 136
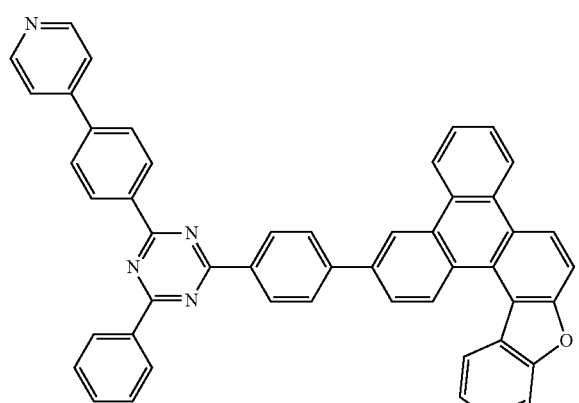
Compound 137
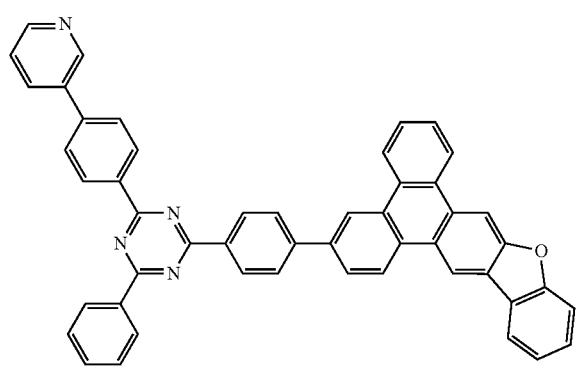
Compound 138
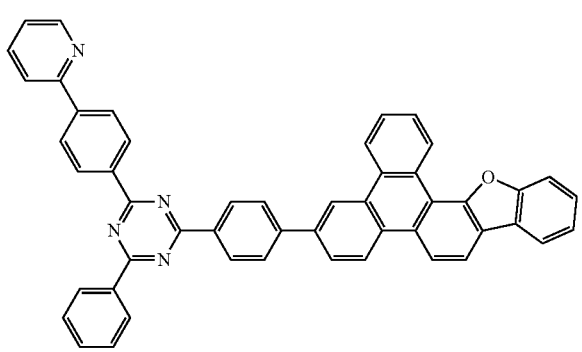
Compound 139
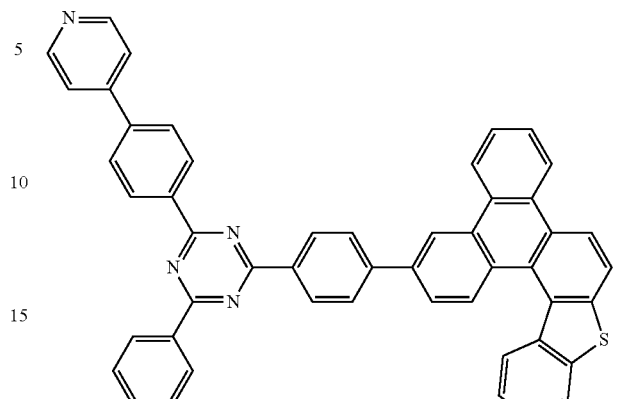
Compound 140
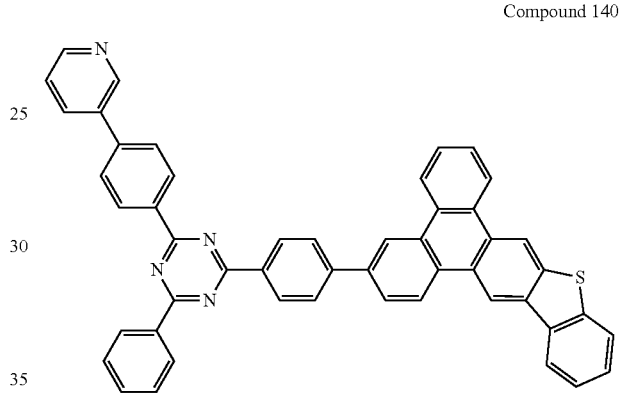
Compound 141
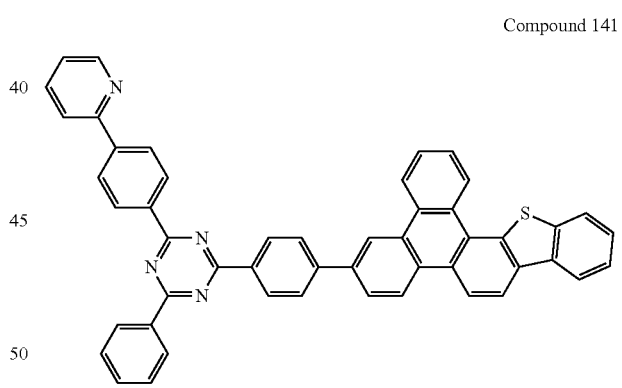
Compound 142
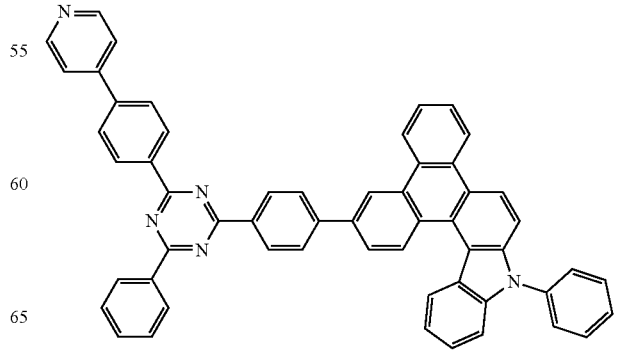

Compound 143
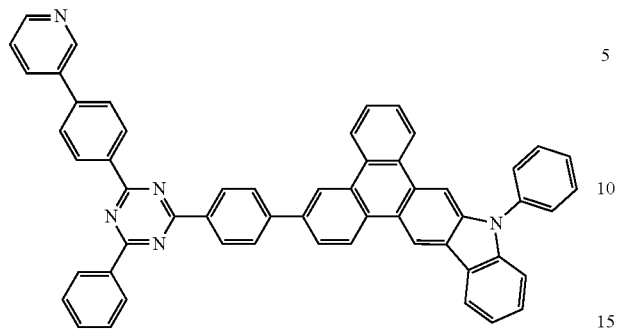
Compound 144
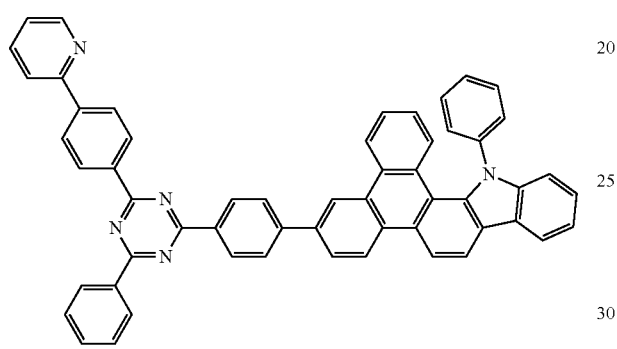
Compound 145
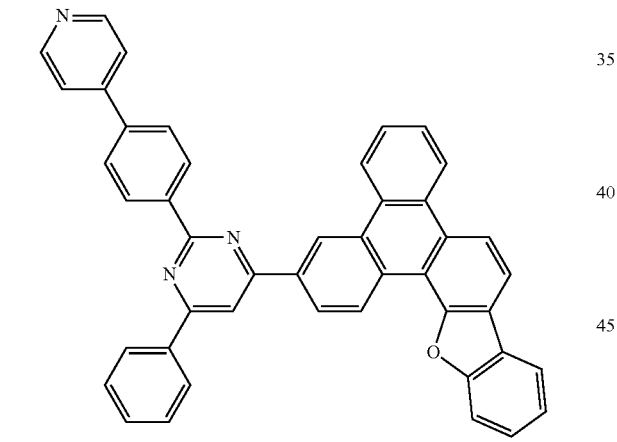
Compound 146
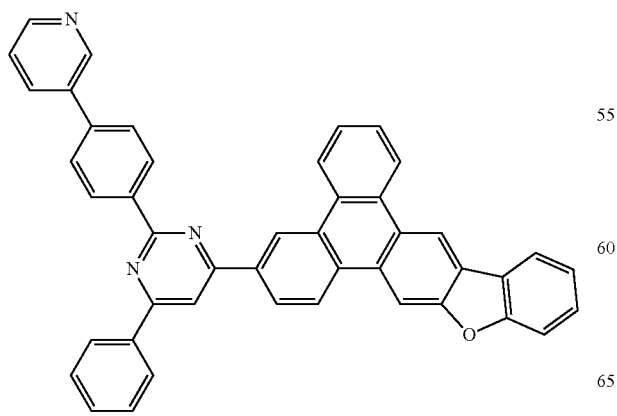
Compound 147
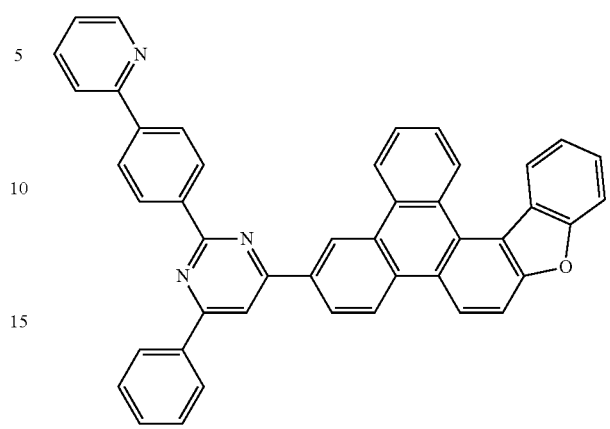
Compound 148
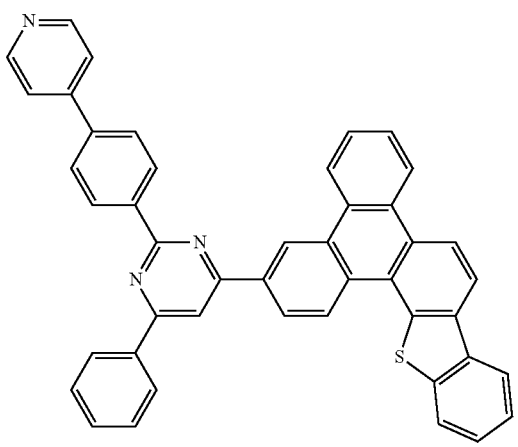
Compound 149
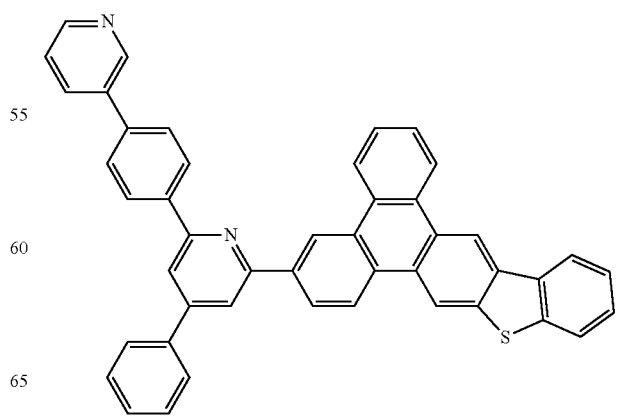

Compound 150
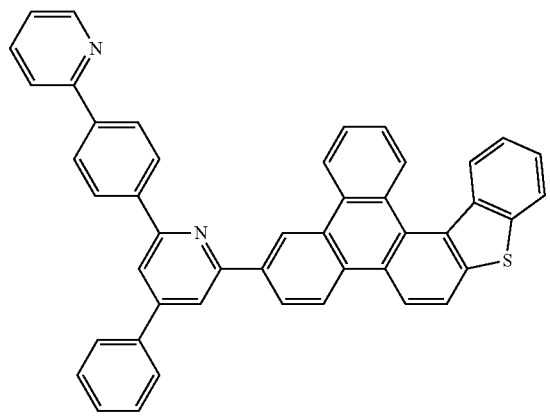
Compound 153
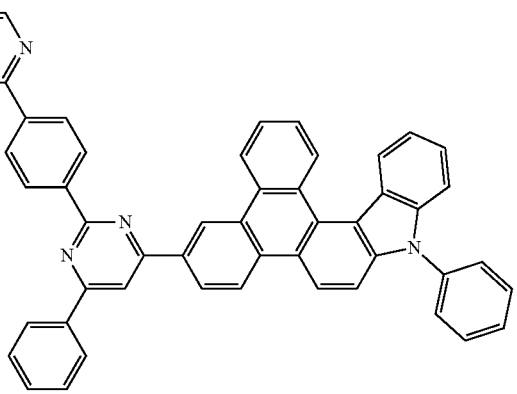
Compound 151
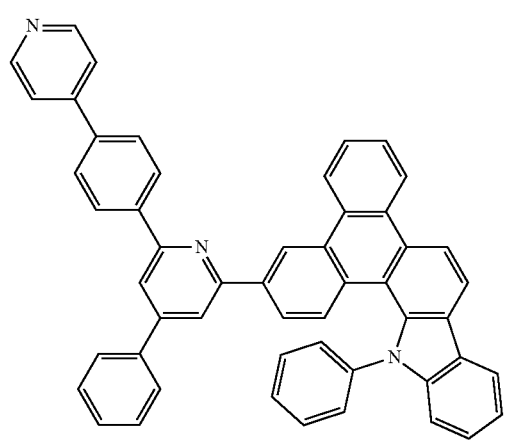
Compound 154
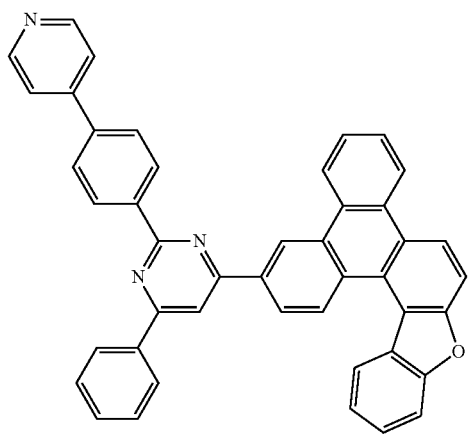
Compound 152
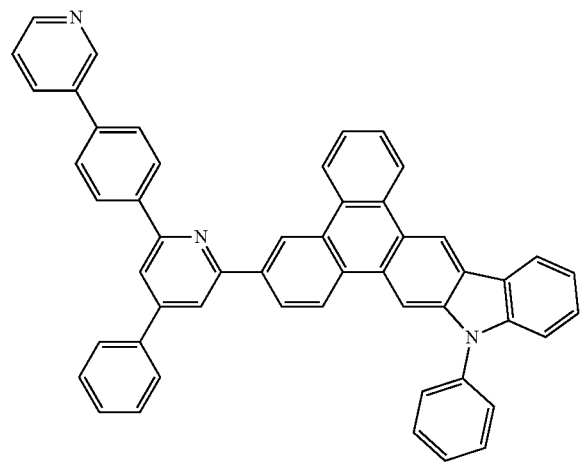
Compound 155
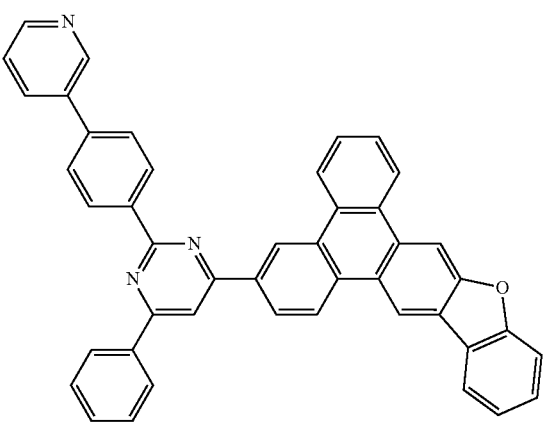

-continued
Compound 156
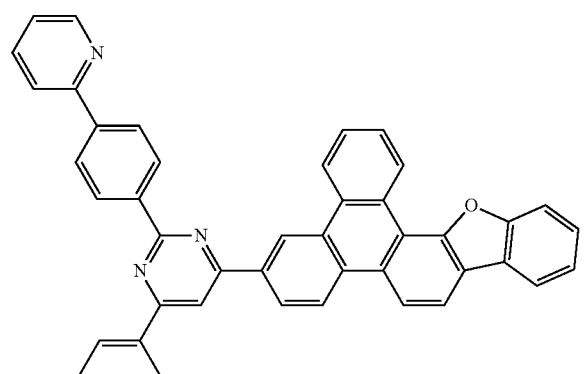
Compound 157
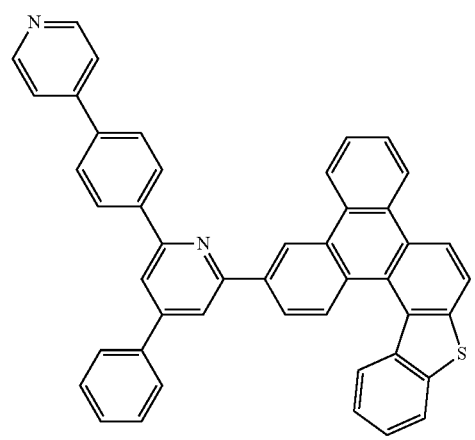
Compound 158
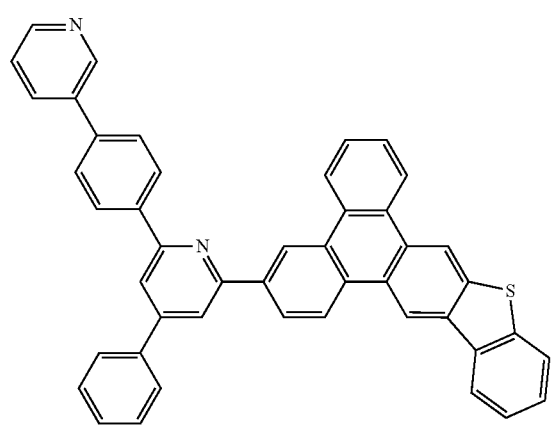
-continued
Compound 159
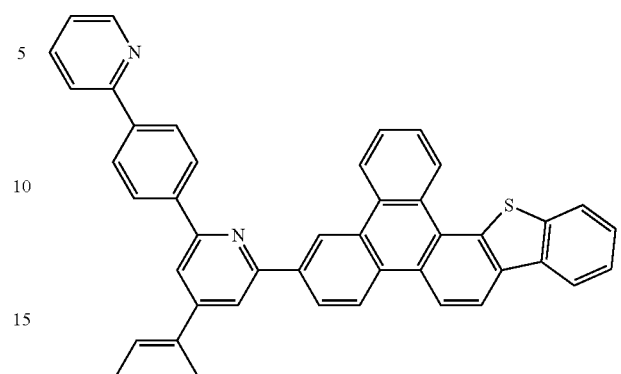
Compound 160
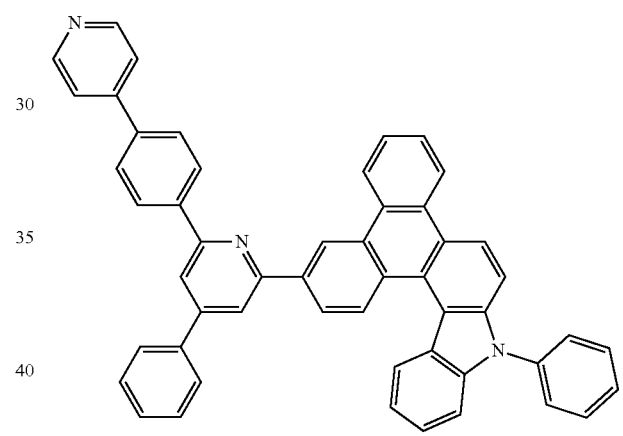
Compound 161
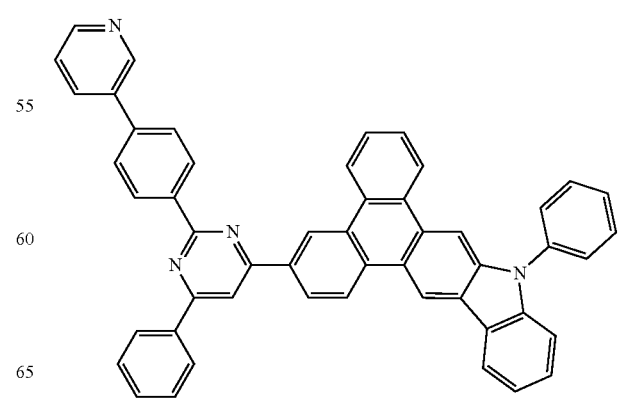

Compound 162
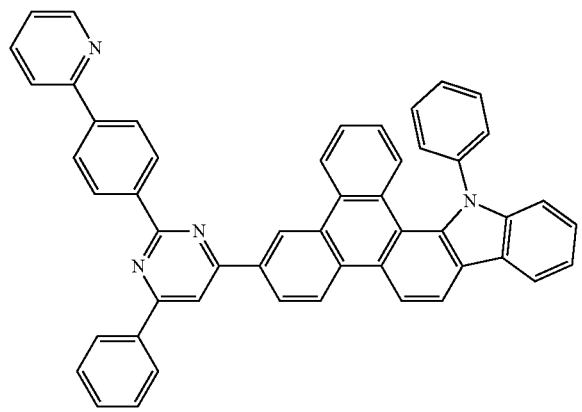
Compound 163
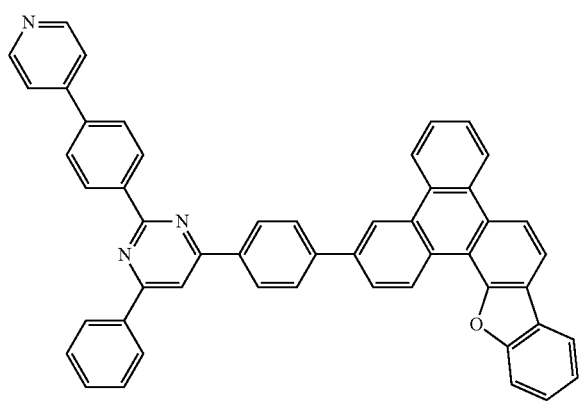
Compound 164
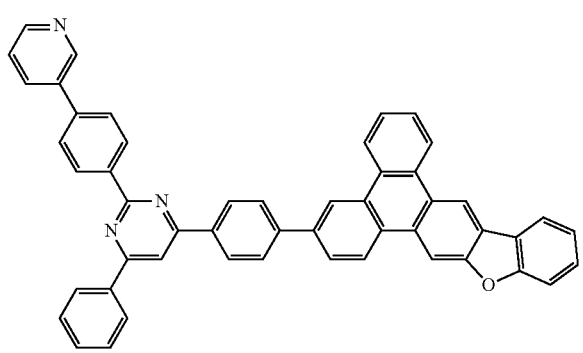
Compound 165
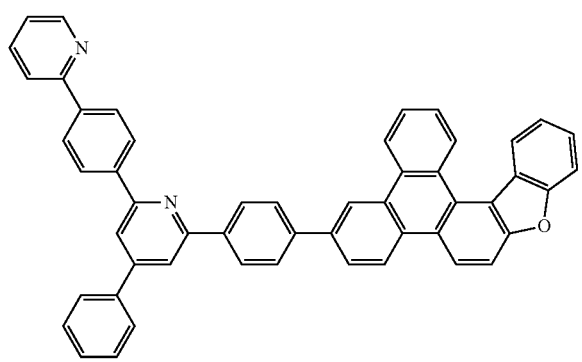
Compound 166
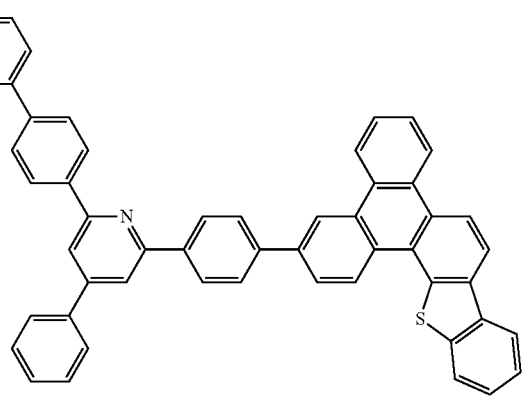
Compound 167
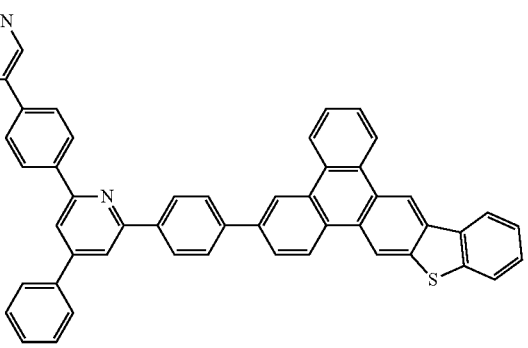
Compound 168
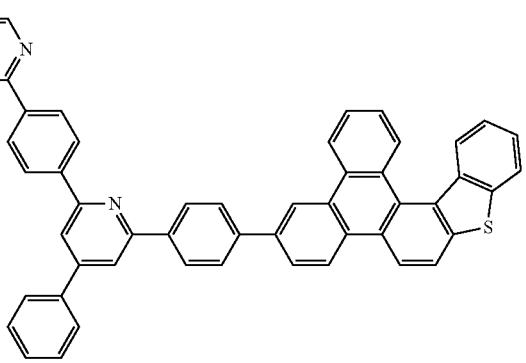

Compound 169
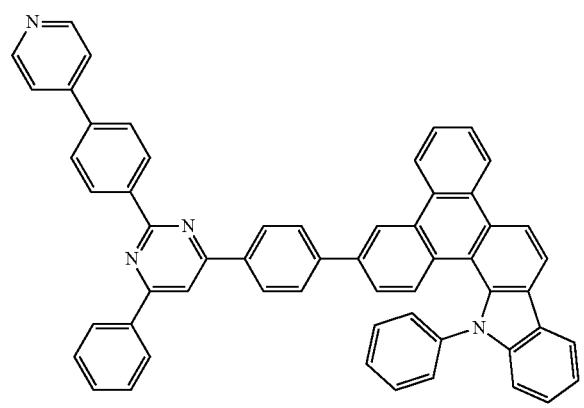
Compound 171
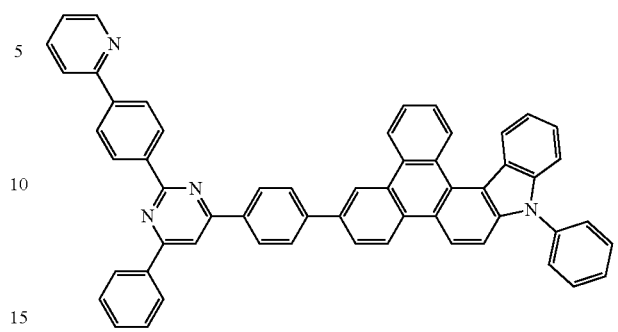
Compound 170
Compound 172
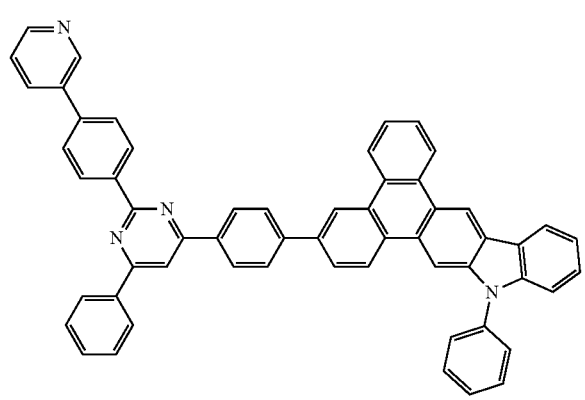
Compound 173
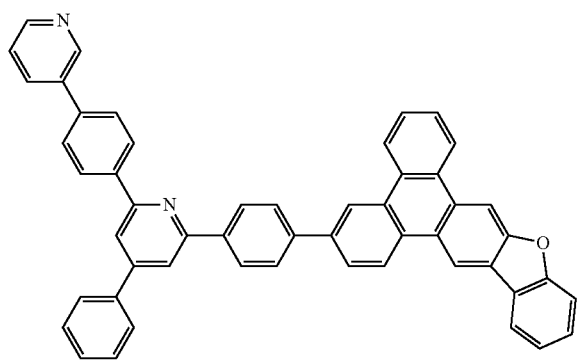
Compound 174
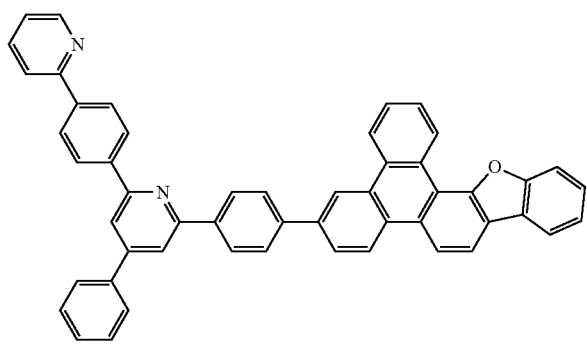

-continued
Compound 175
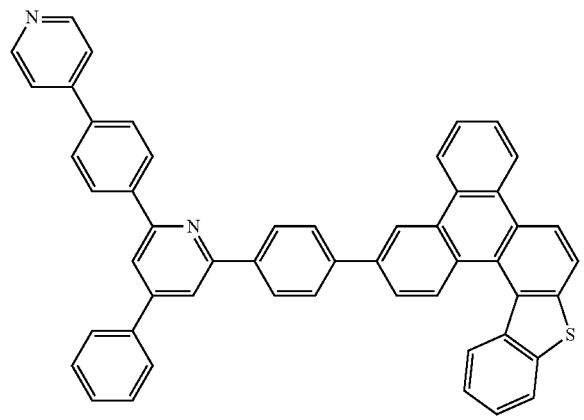
Compound 176
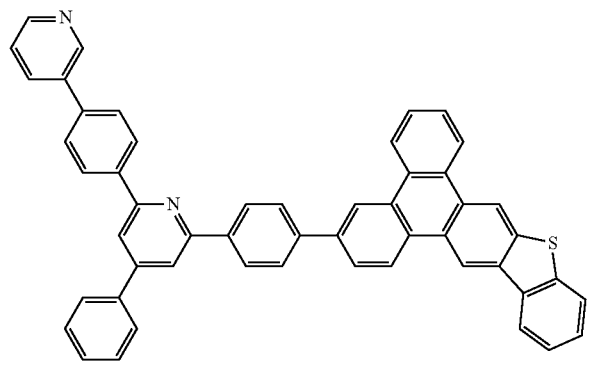
Compound 177
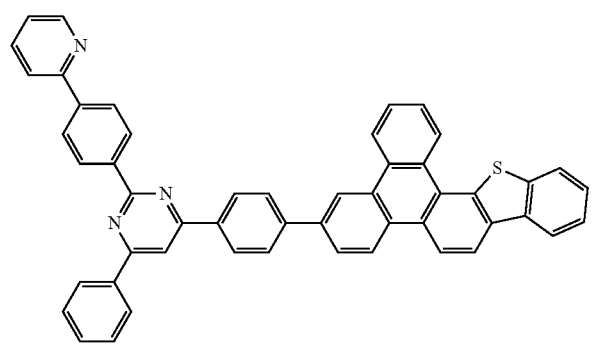
Compound 178
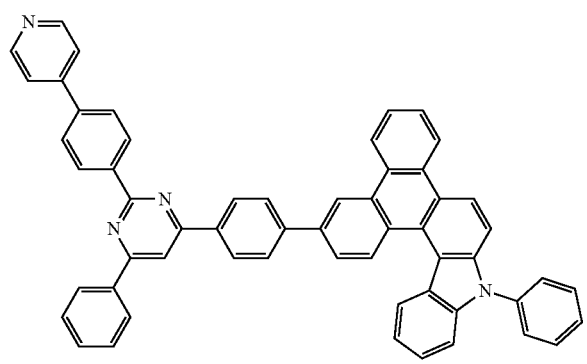
Compound 179
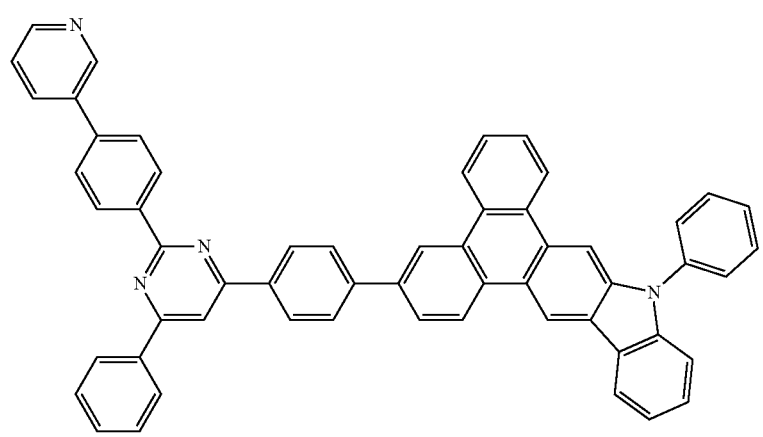

Compound 180
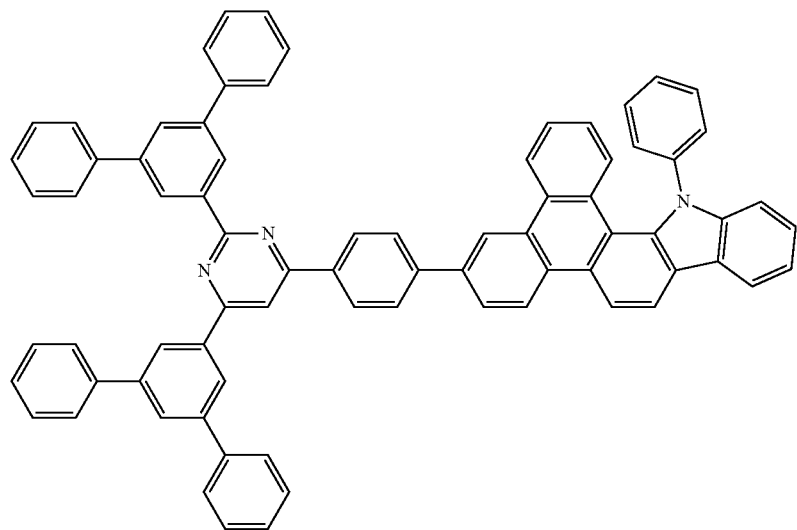
Compound 181
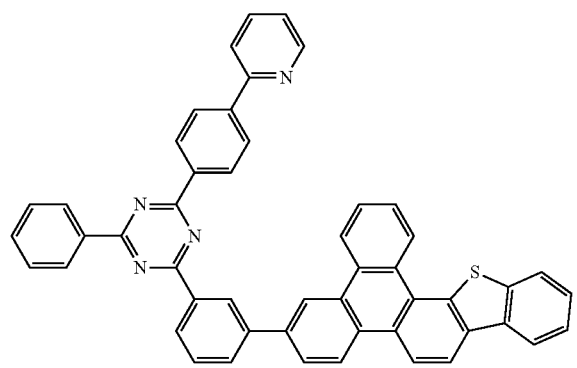
Compound 182
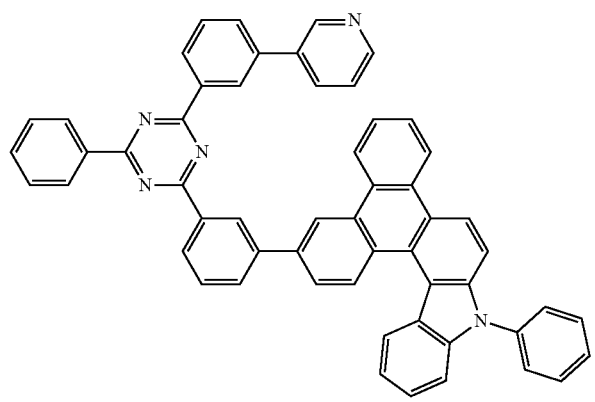
Compound 183
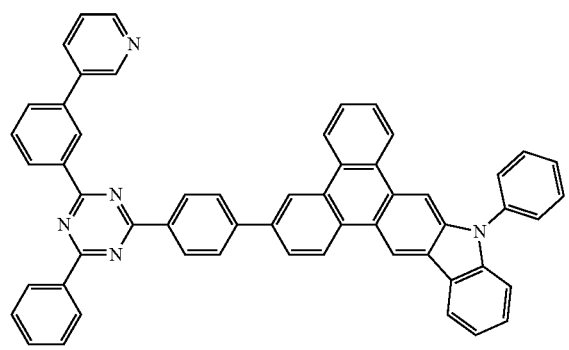
Compound 184
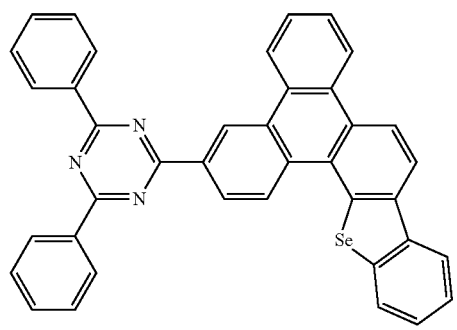

-continued
Compound 185
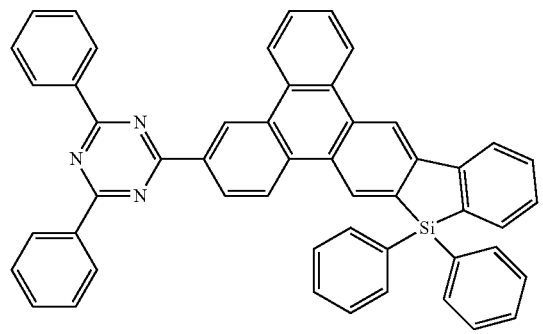
Compound 186
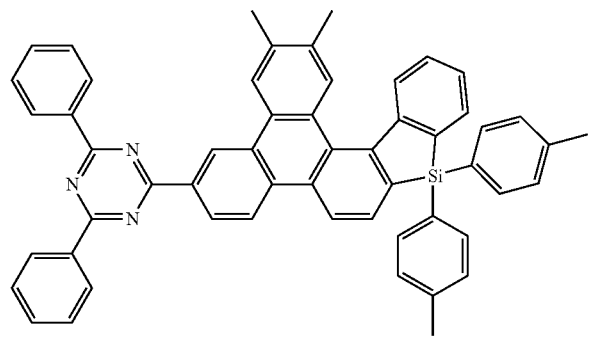
Compound 187
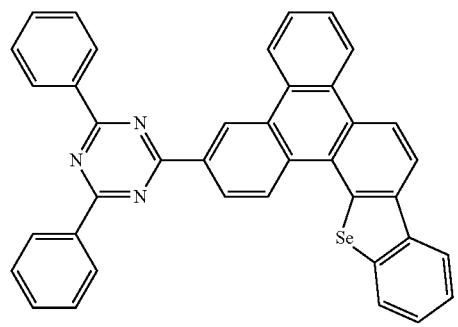
Compound 188
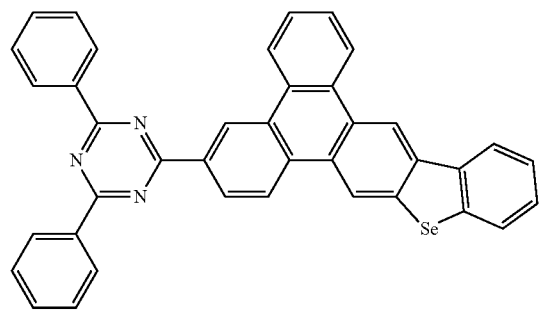
Compound 189
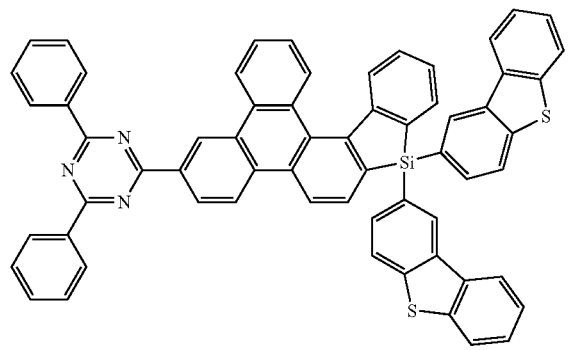
Compound 190
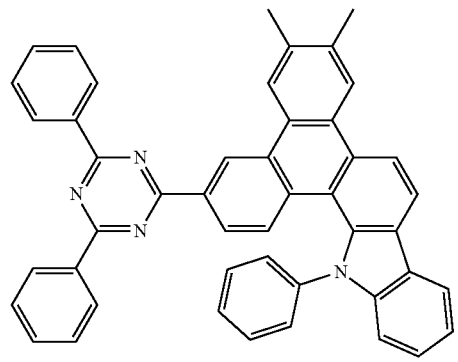
Compound 191
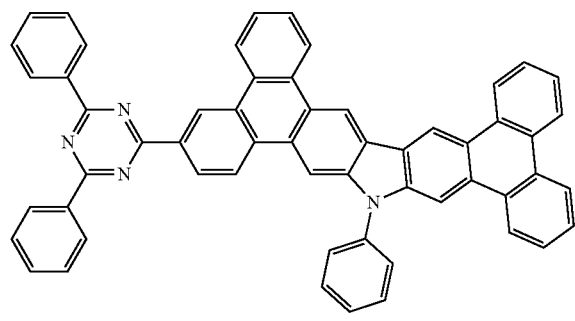
Compound 192
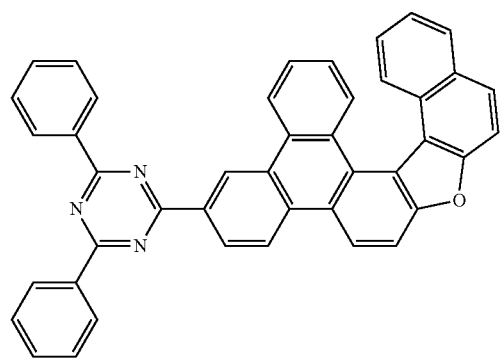

Compound 193
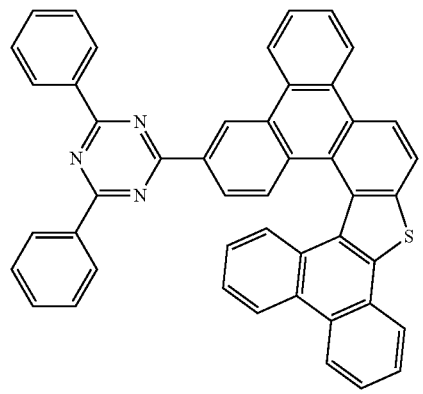
Compound 194
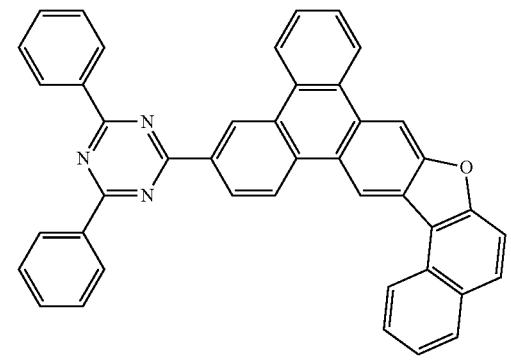
Compound 195
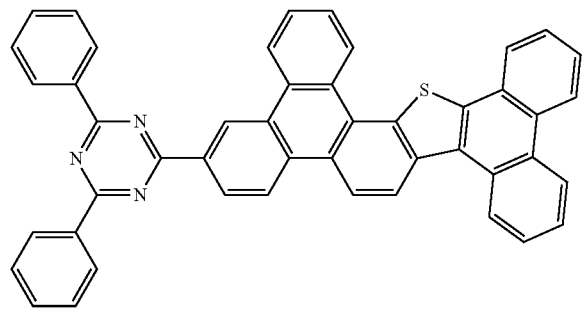
Compound 196
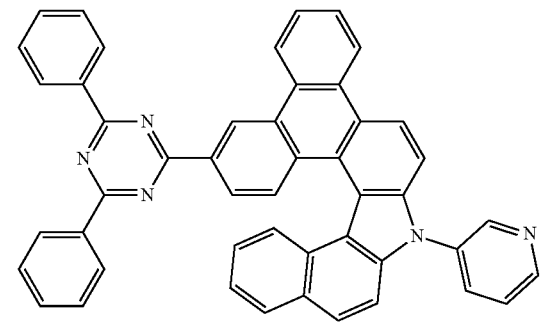
Compound 197
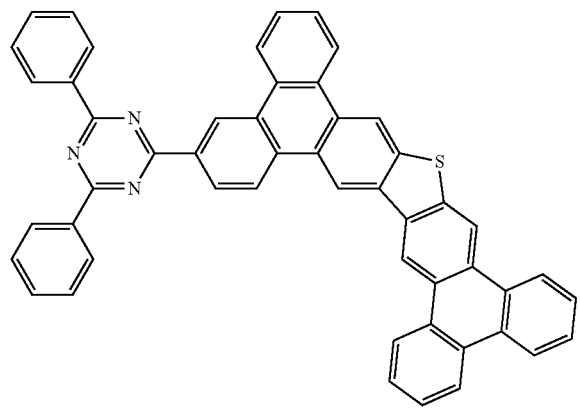
Compound 198
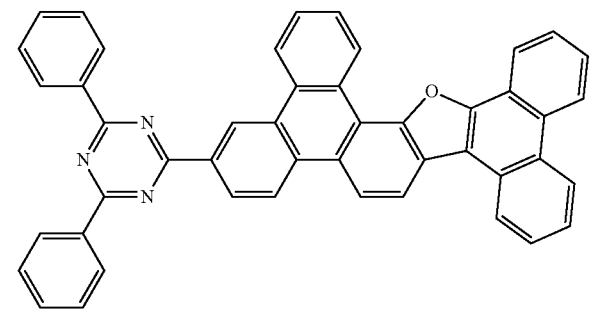
Compound 199
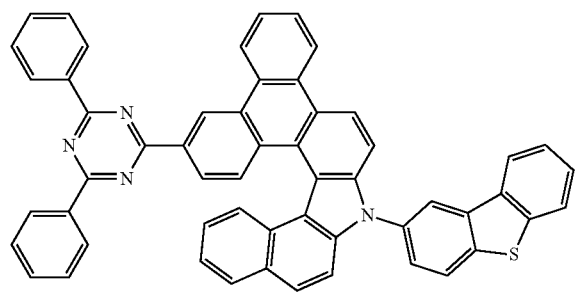
Compound 200
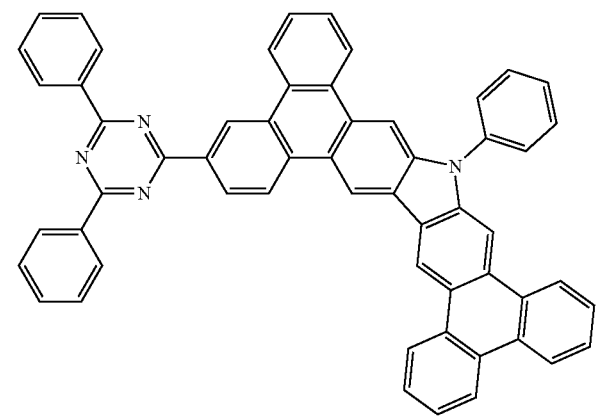

-continued
Compound 201
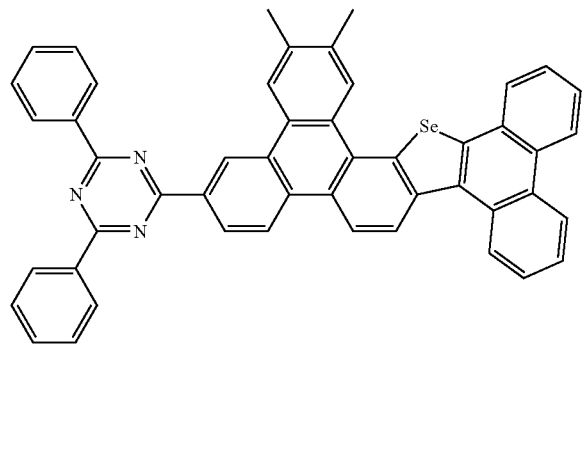
Compound 202
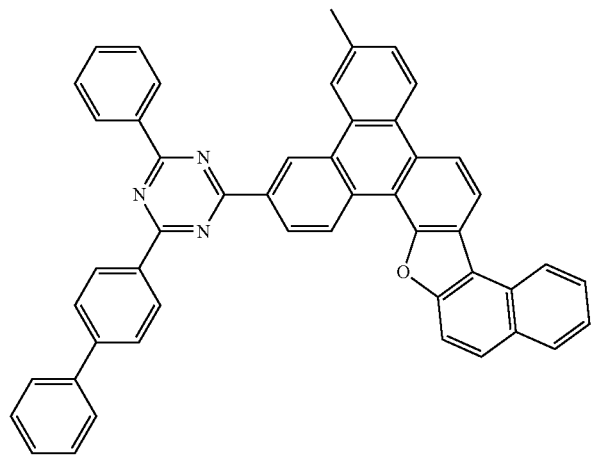
Compound 203
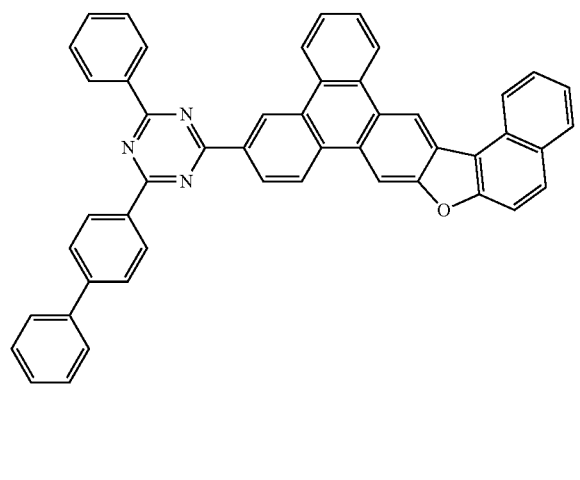
Compound 204
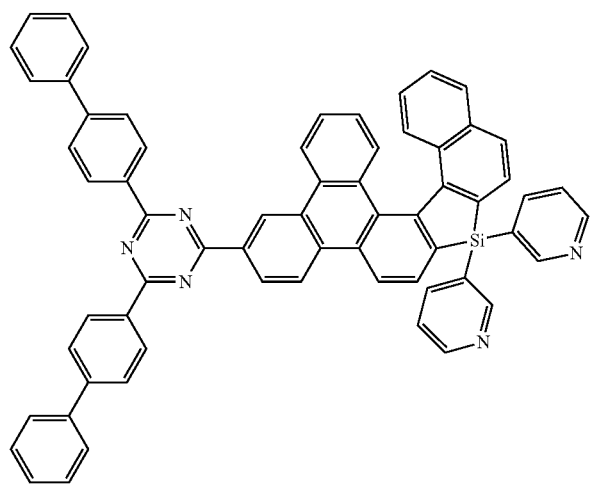
Compound 205
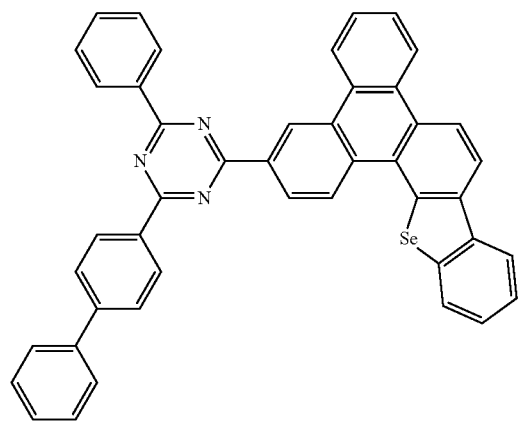
Compound 206
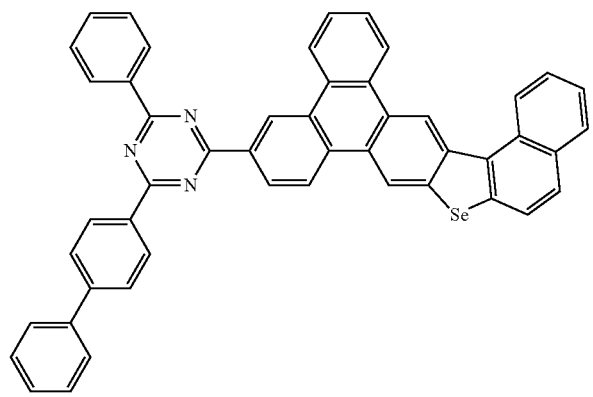

-continued
Compound 207
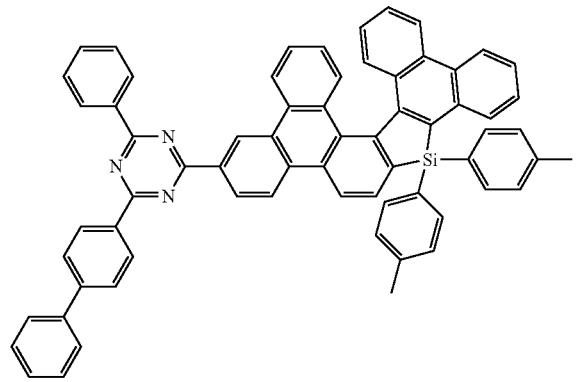
Compound 208
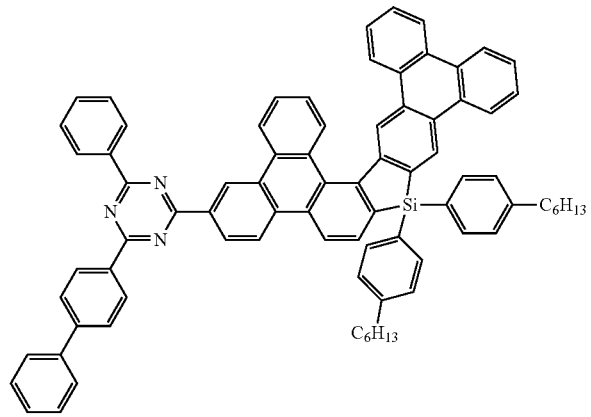
Compound 209
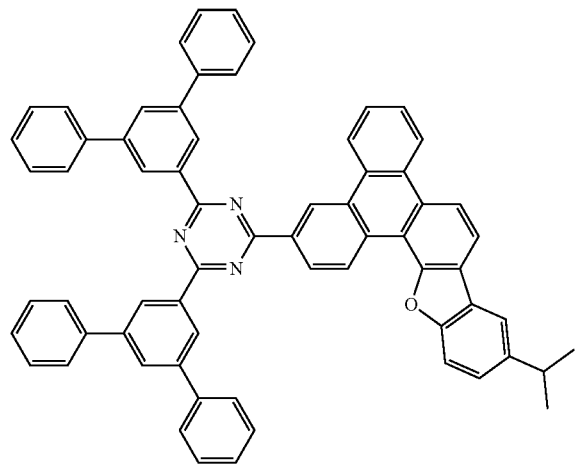
Compound 210
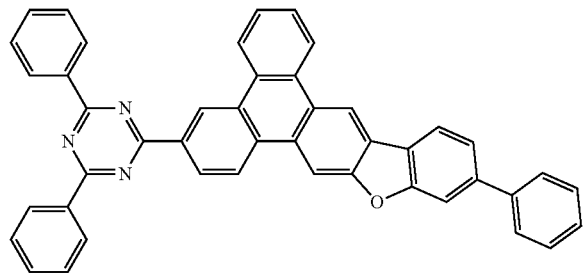
Compound 211
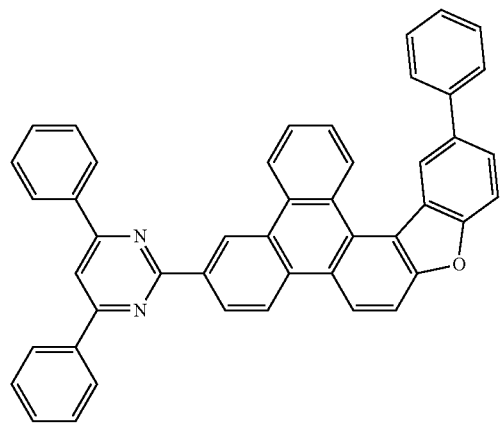
Compound 212
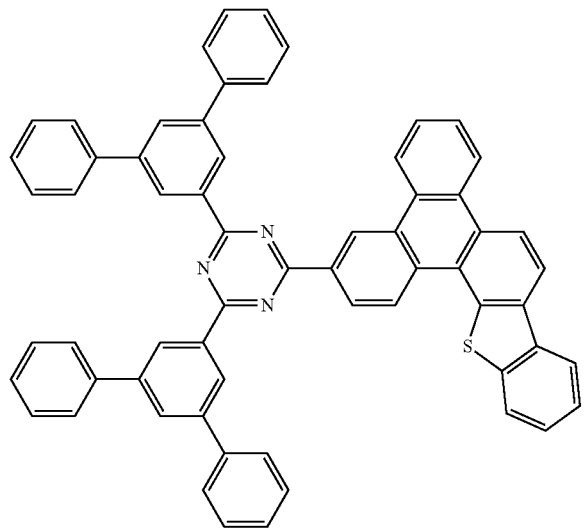

-continued
Compound 213
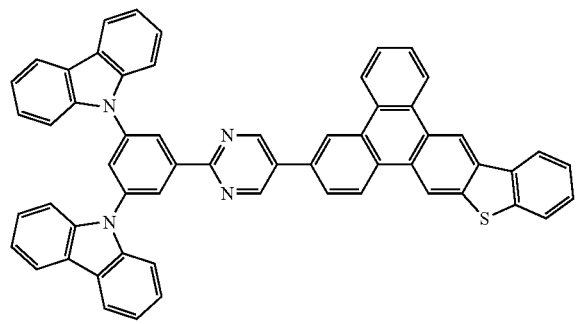
Compound 214
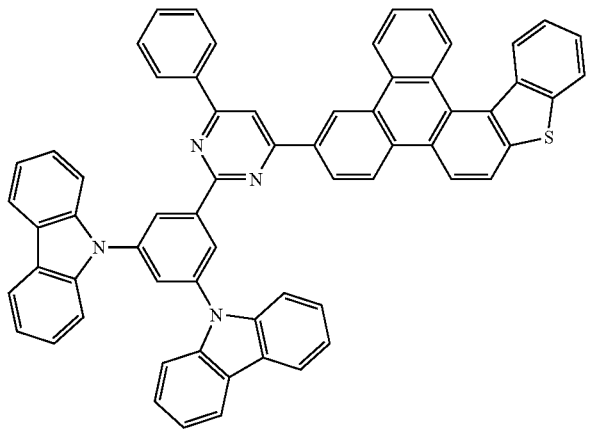
Compound 215
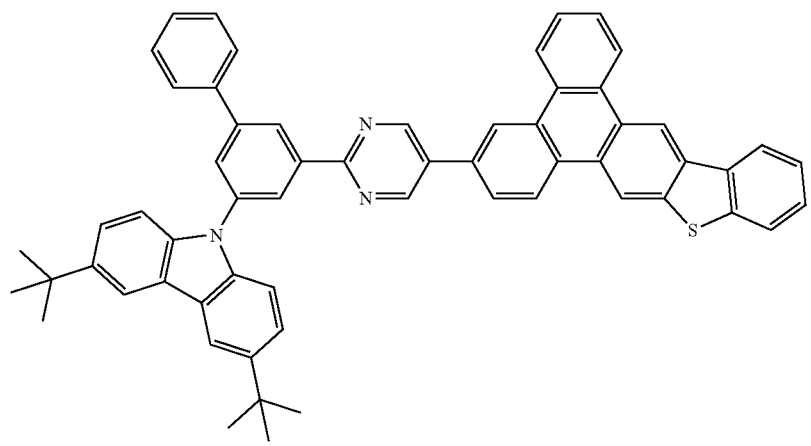
Compound 216
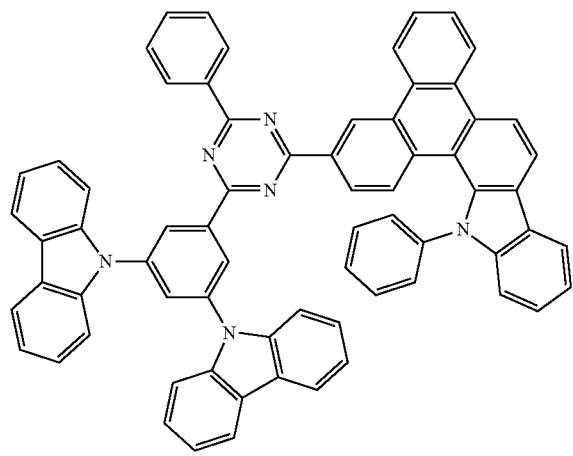
Compound 217
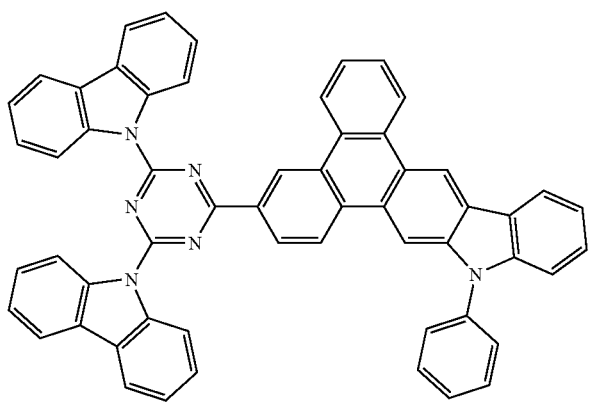

-continued
Compound 218
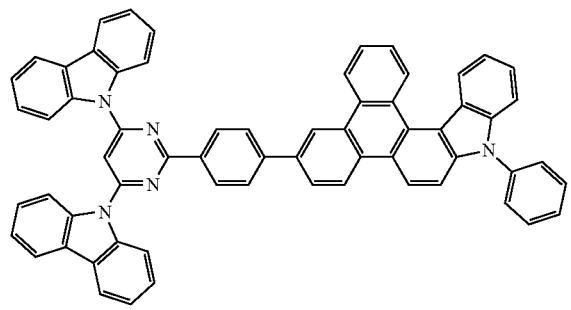
Compound 219
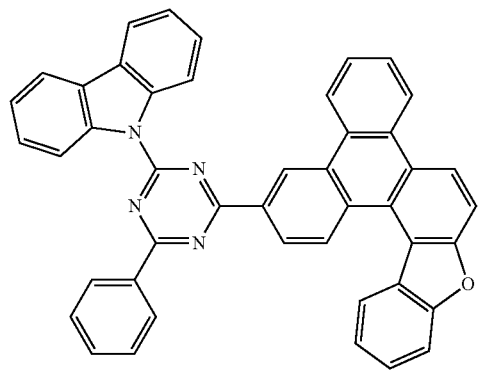
Compound 220
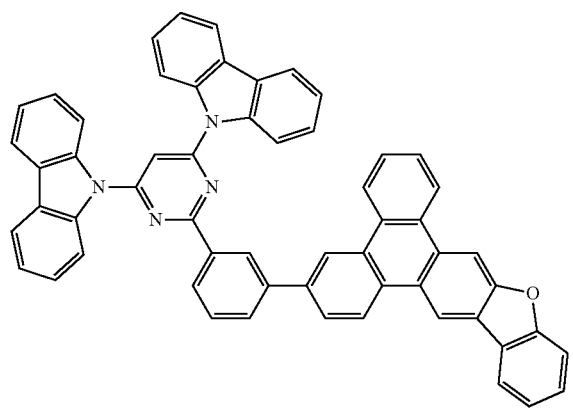
Compound 221
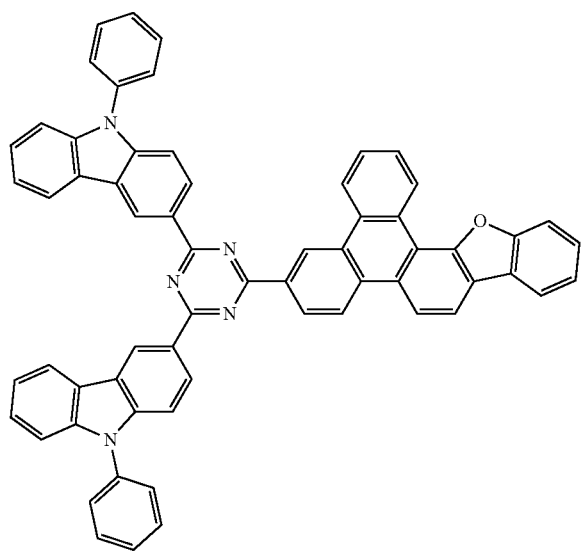
Compound 222
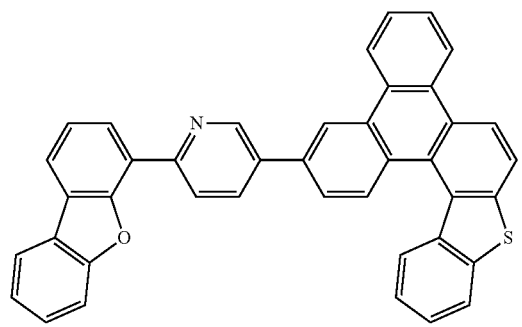
Compound 223
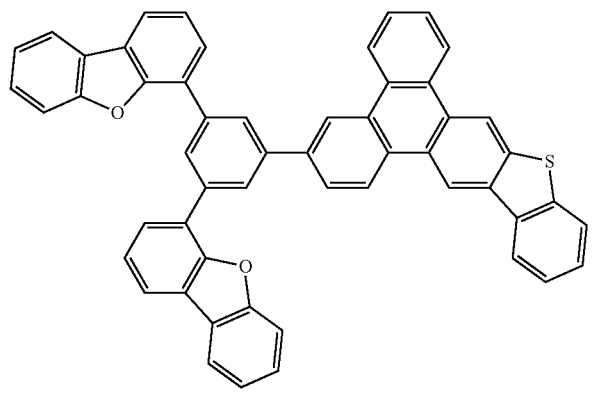

-continued
Compound 224
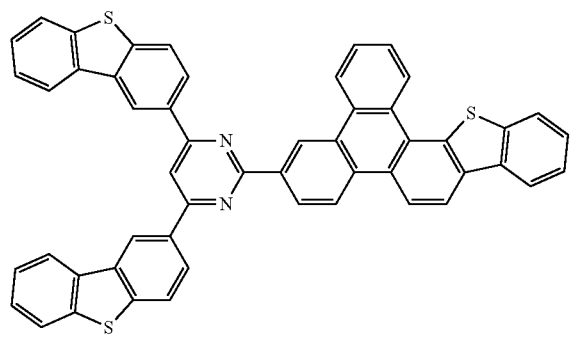
Compound 225
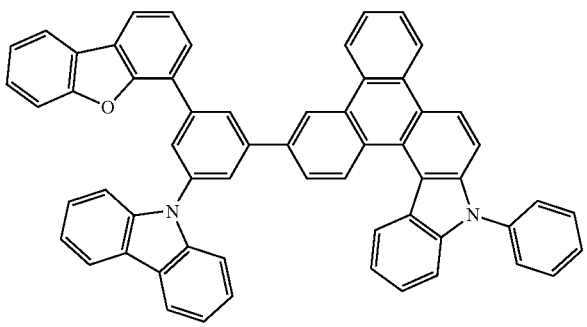
Compound 226
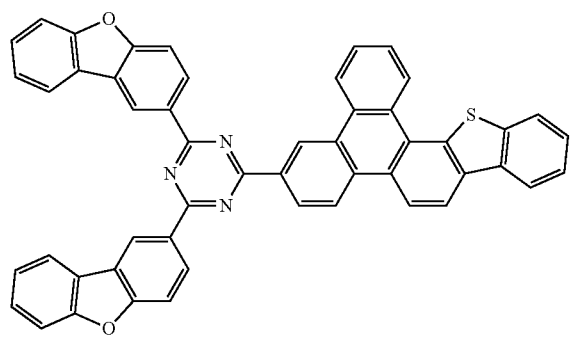
Compound 227
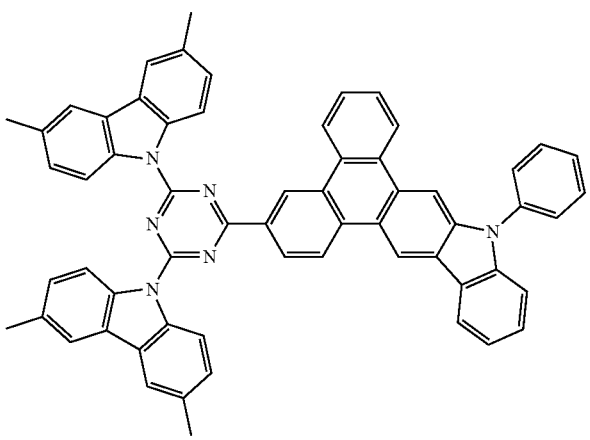
Compound 228
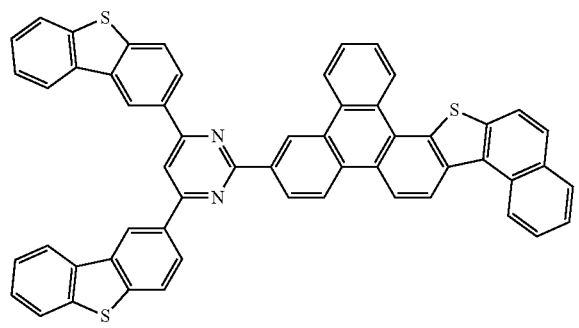
Compound 229
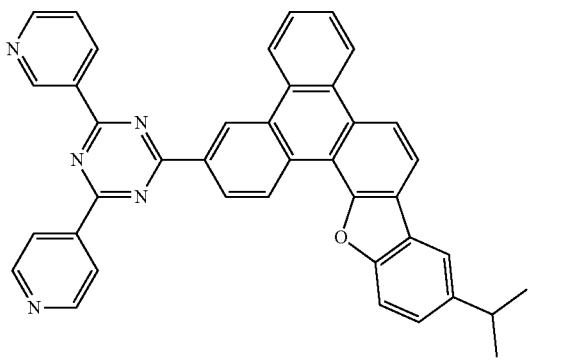
Compound 230
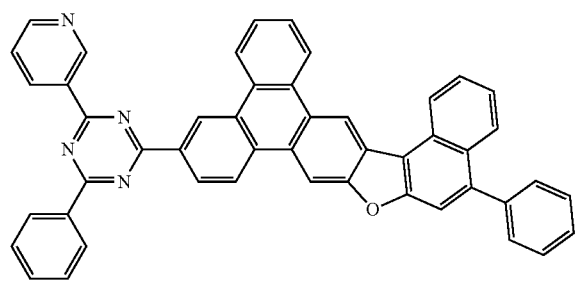
Compound 231
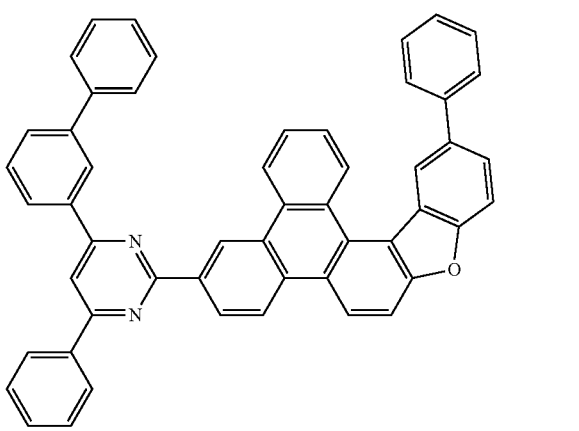

-continued
Compound 232
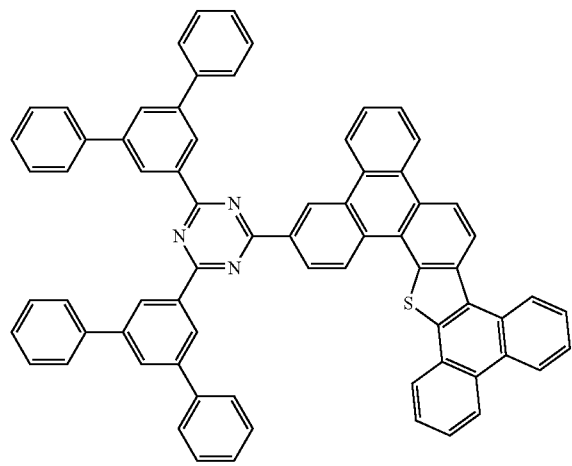
Compound 233
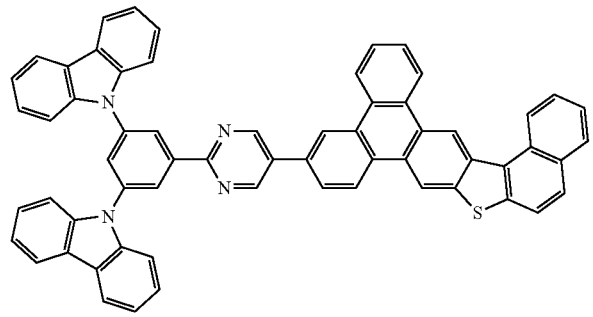
Compound 234
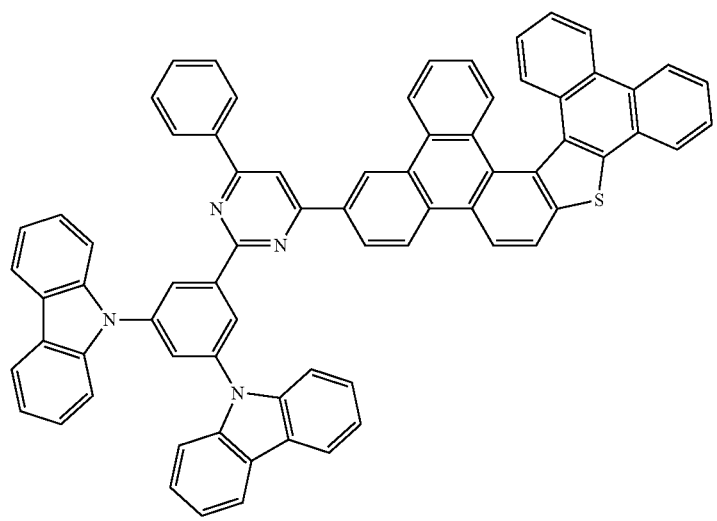
Compound 235
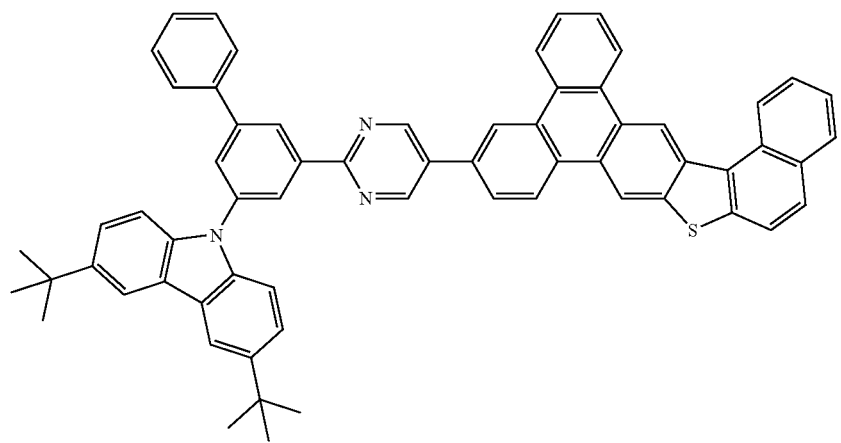

-continued
Compound 236
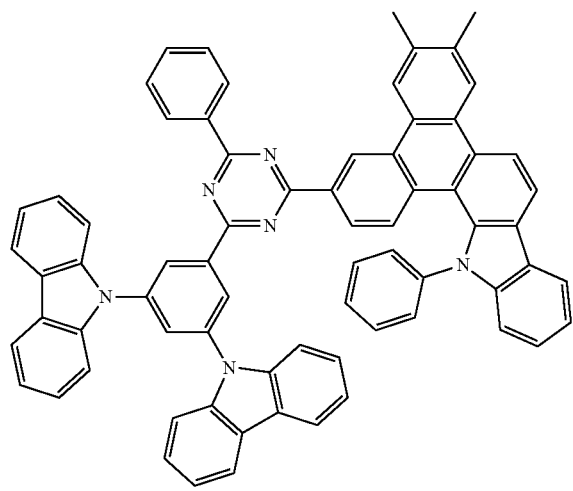
Compound 237
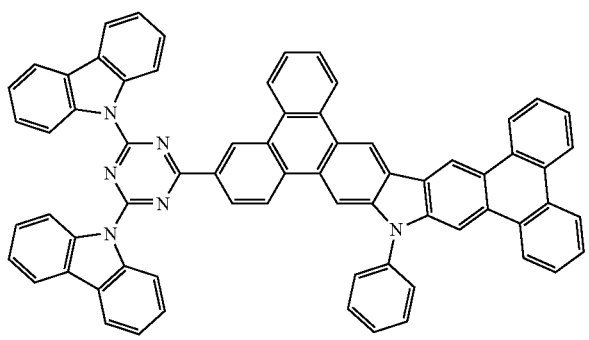
Compound 238
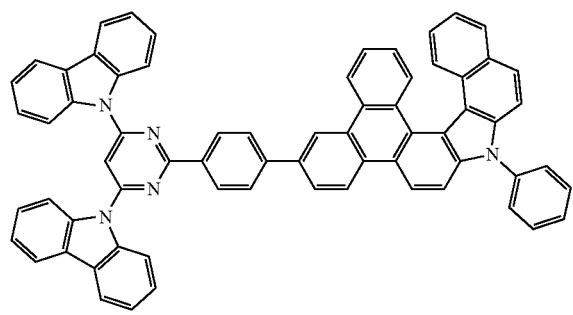
Compound 239
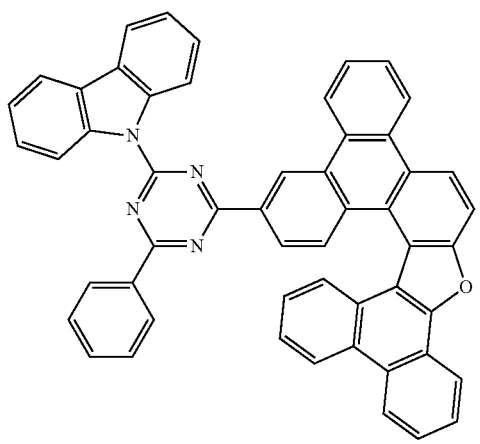
Compound 240
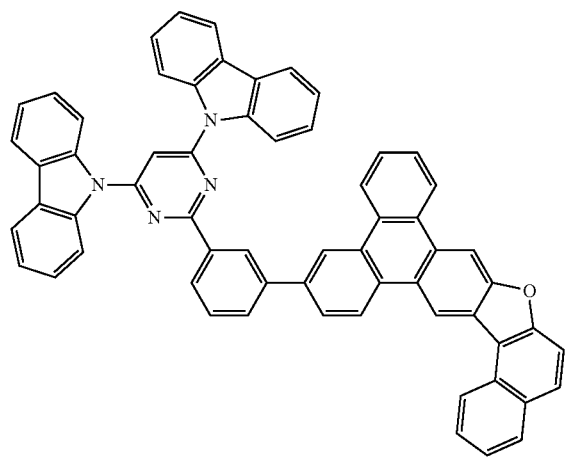
Compound 241
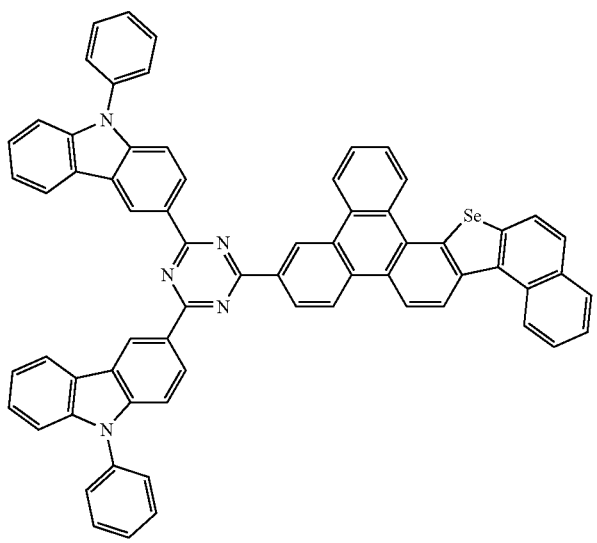

-continued
Compound 242
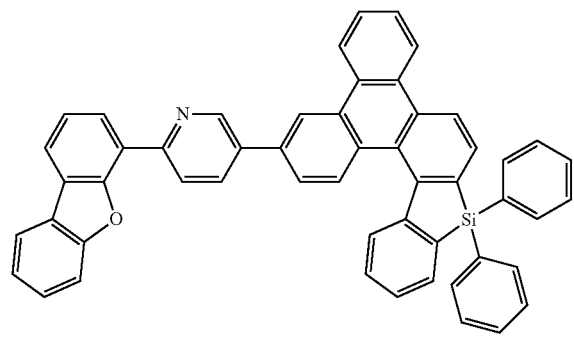
Compound 243
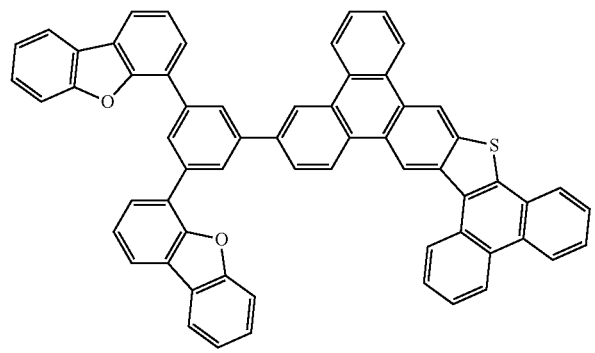
Compound 244
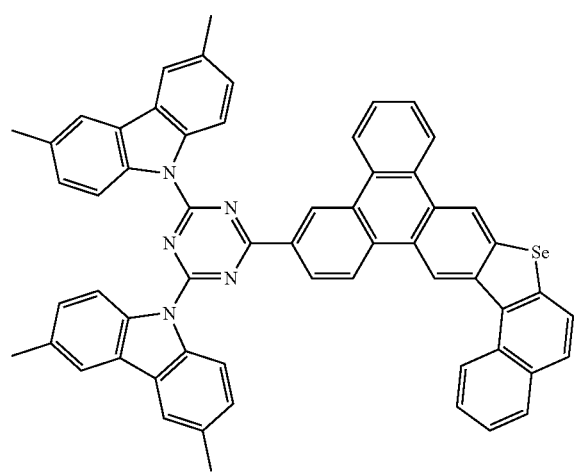
Compound 245
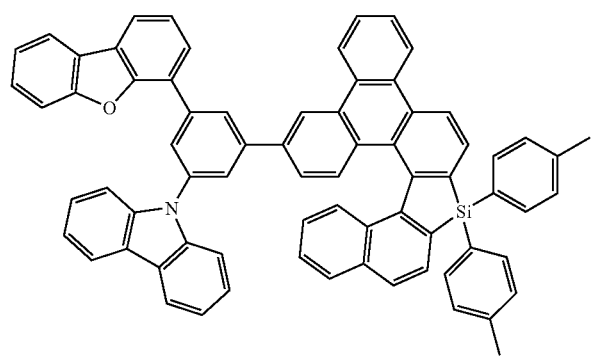
Compound 246
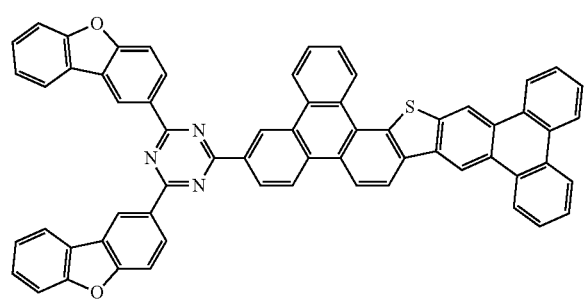
Compound 247
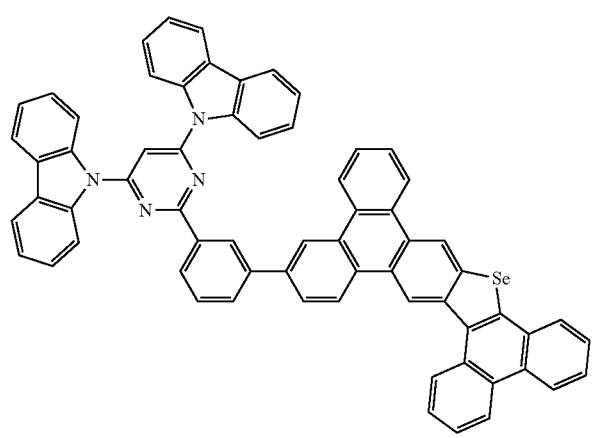

Compound 248
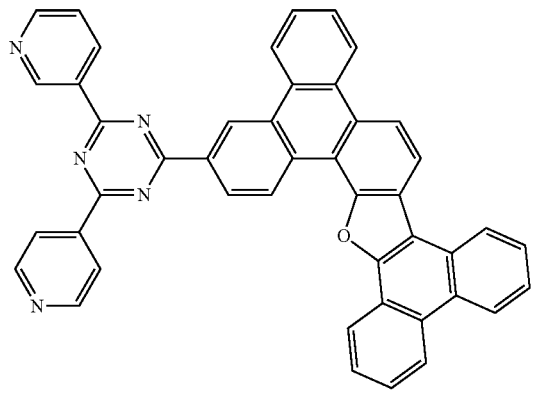
Compound 249
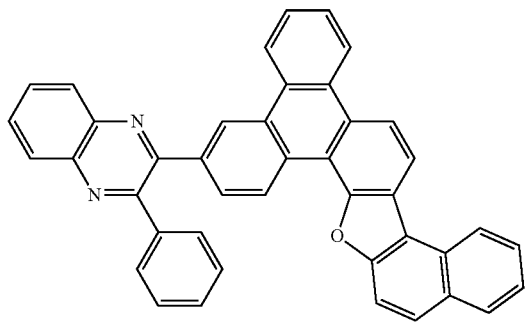
Compound 250
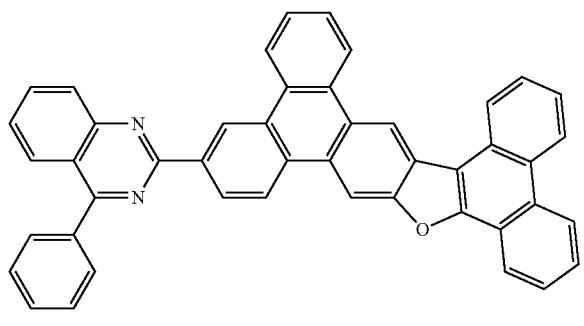
Compound 251
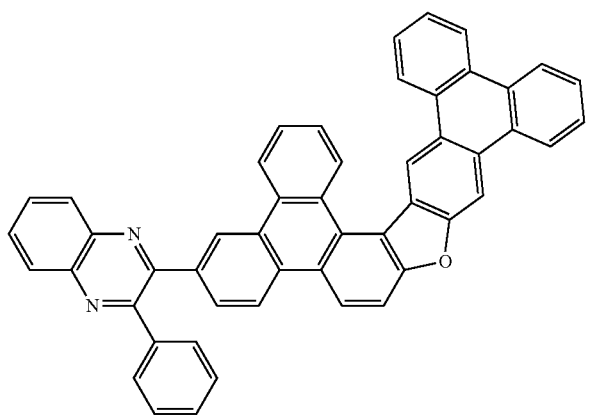
Compound 252
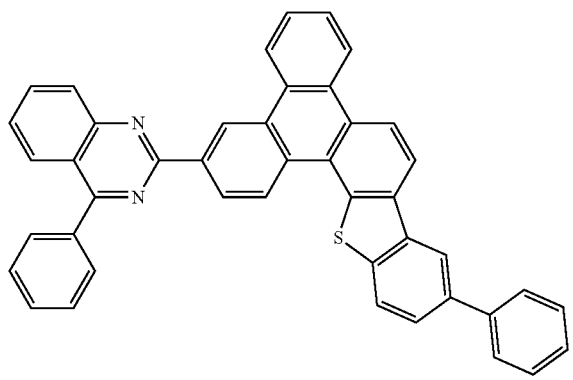
Compound 253
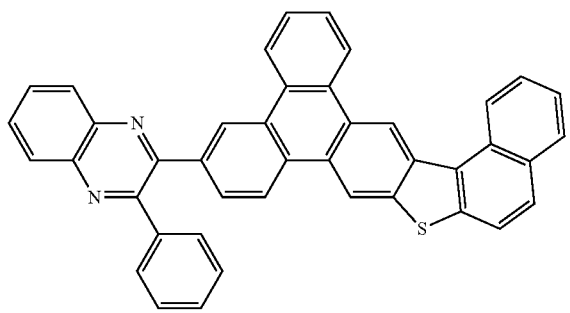
Compound 254
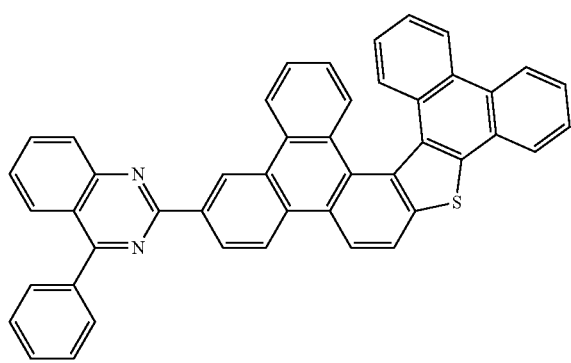
Compound 255
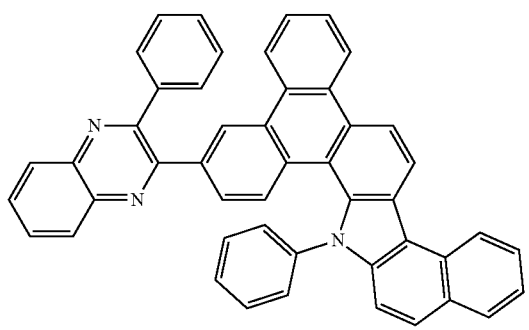

-continued
Compound 256
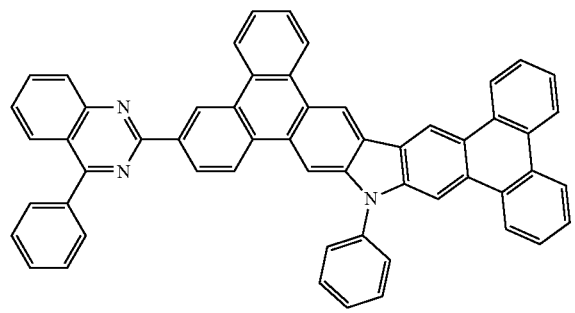
Compound 257
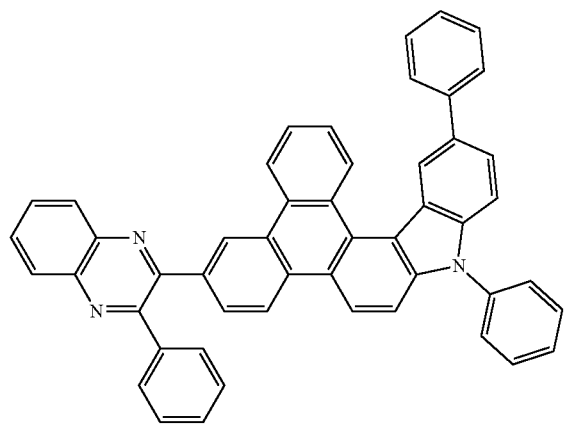
Compound 258
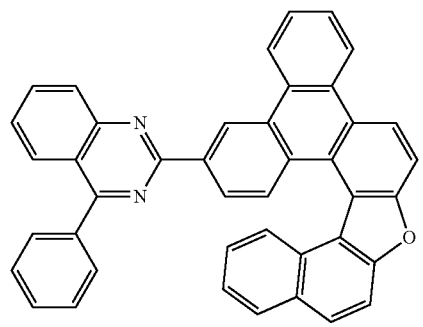
Compound 259
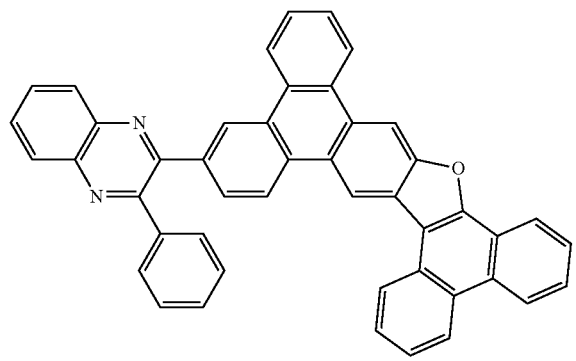
Compound 260
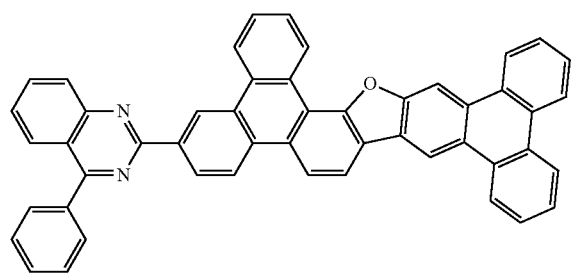
Compound 261
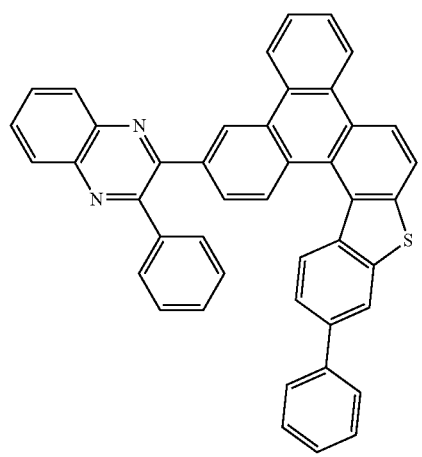

-continued
Compound 262
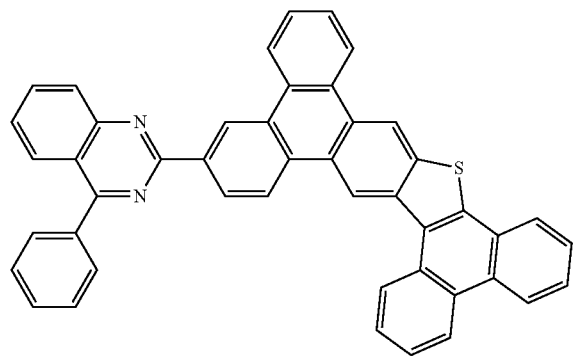
Compound 263
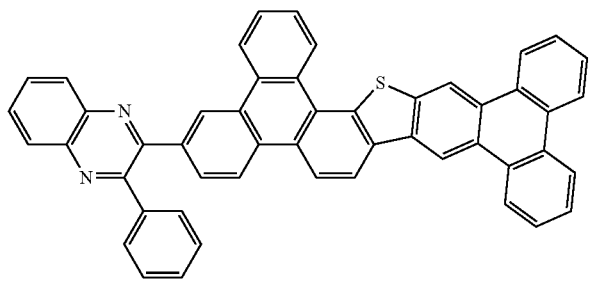
Compound 264
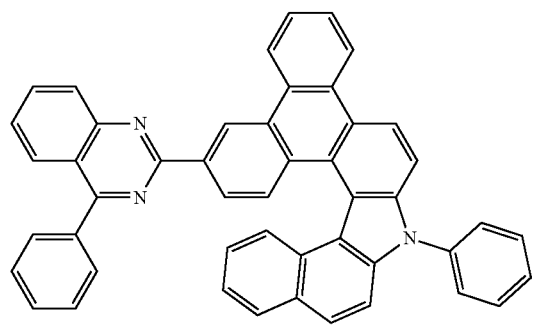
Compound 265
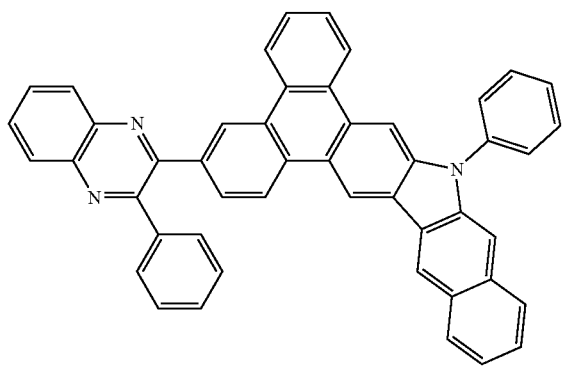
Compound 266
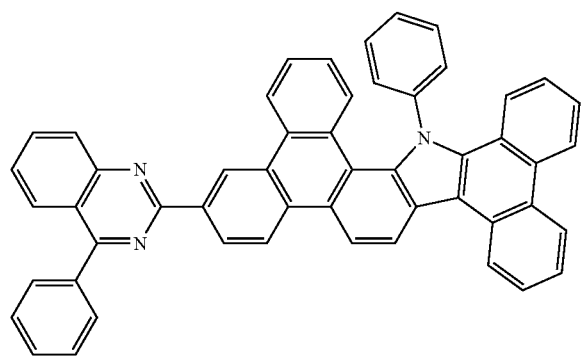
Compound 267
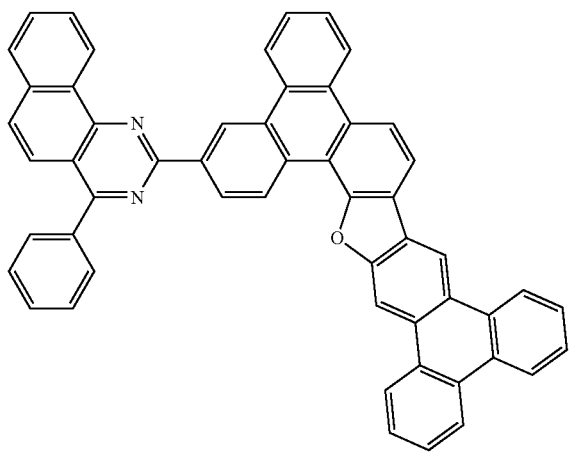
Compound 268
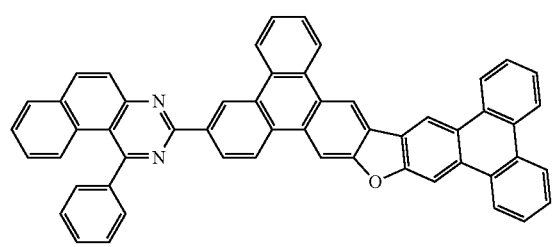
Compound 269
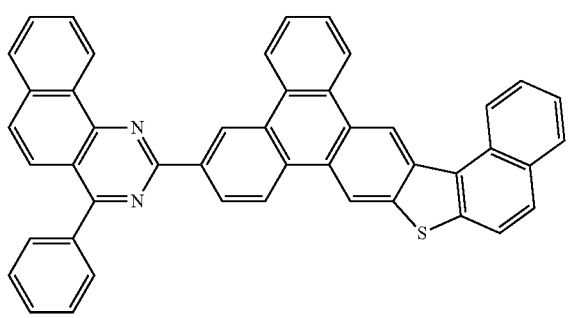

-continued
Compound 270
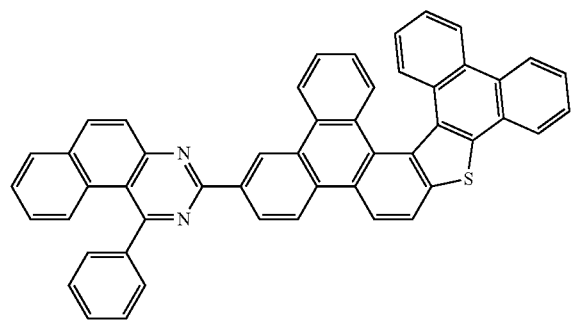
Compound 271
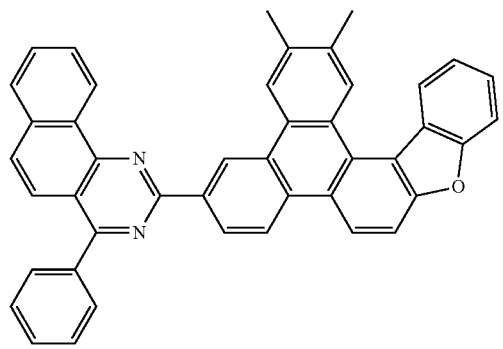
Compound 272
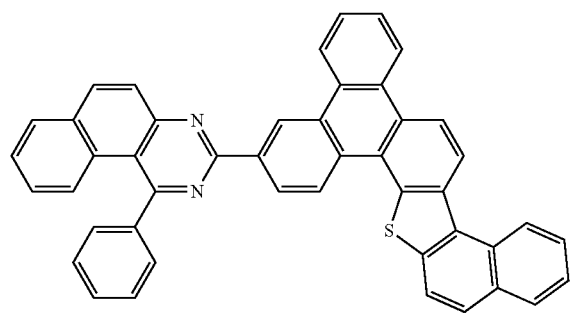
Compound 273
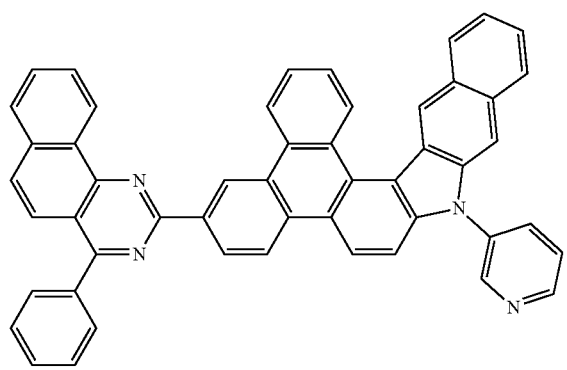
Compound 274
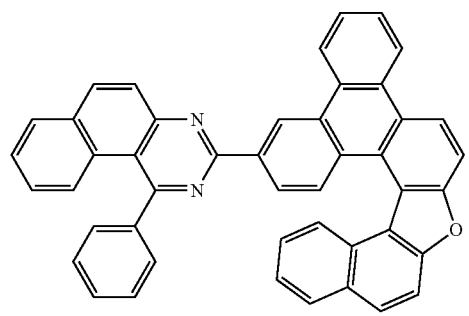
Compound 275
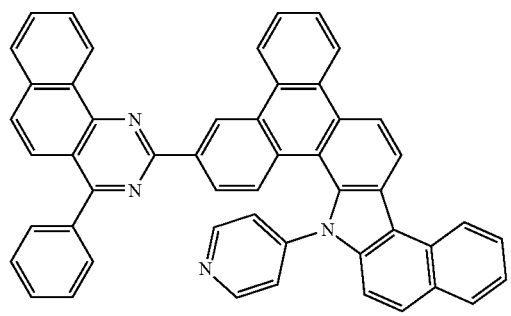
Compound 276
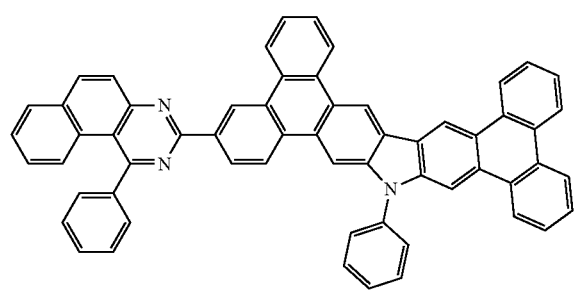
Compound 277
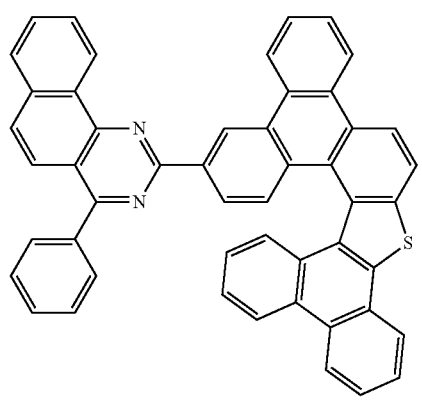

-continued
Compound 278
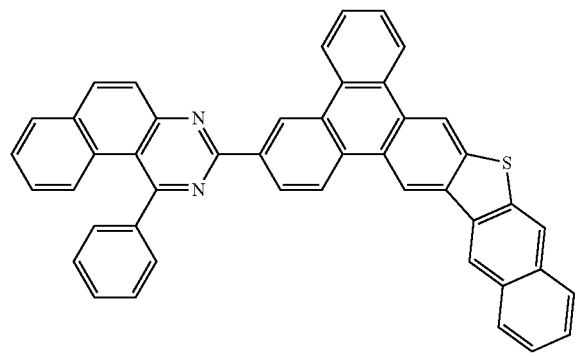
Compound 279
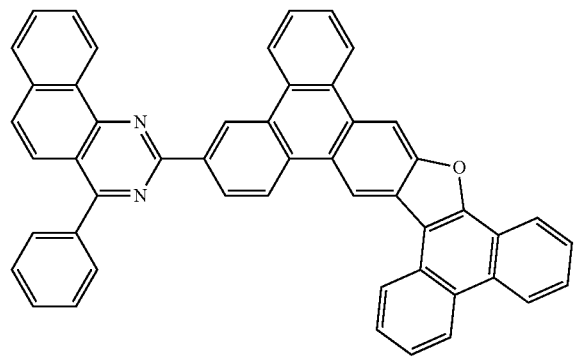
Compound 280
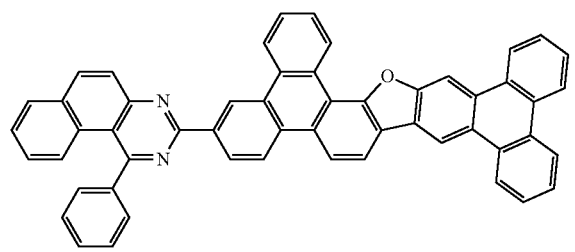
Compound 281
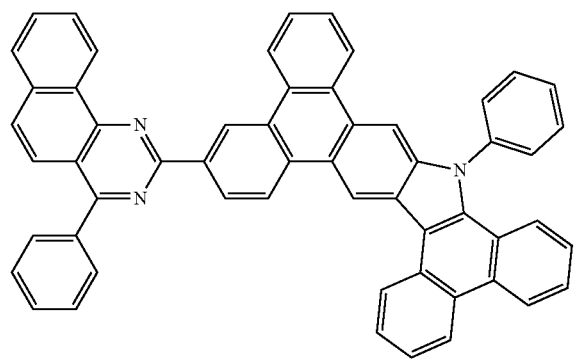
Compound 282
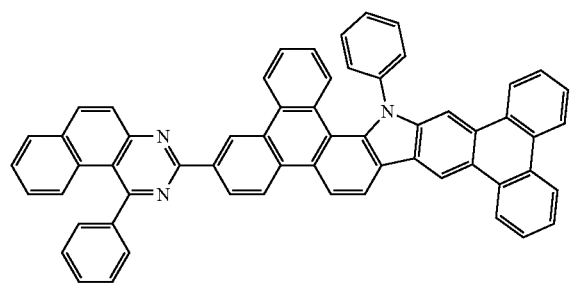
Compound 283
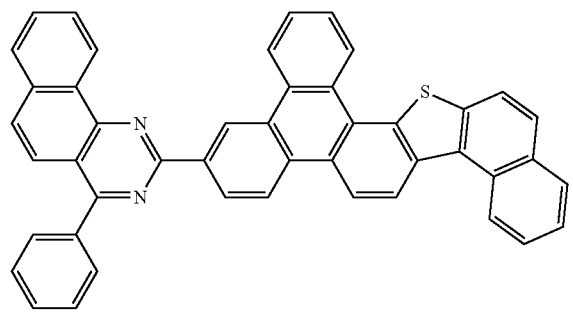
Compound 284
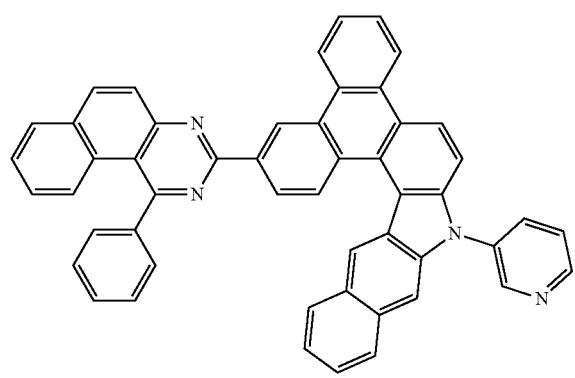
Compound 285
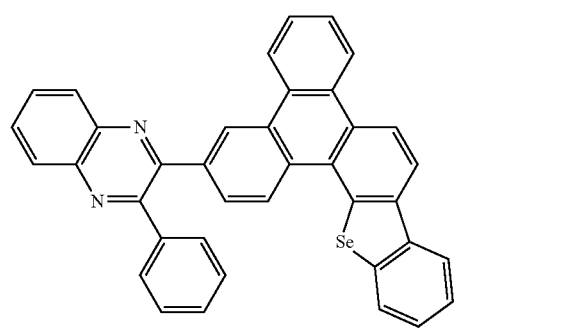

-continued
Compound 286
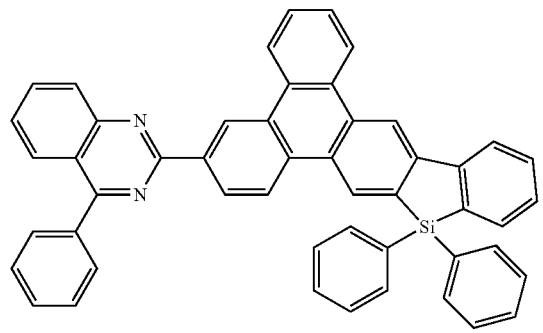
Compound 287
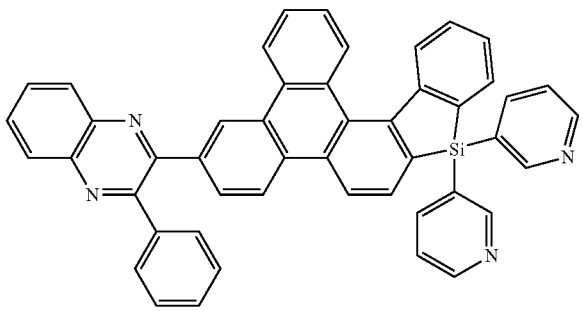
Compound 288
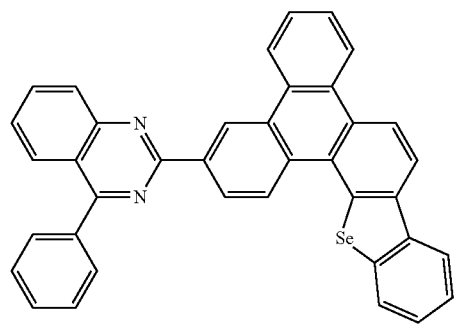
Compound 289
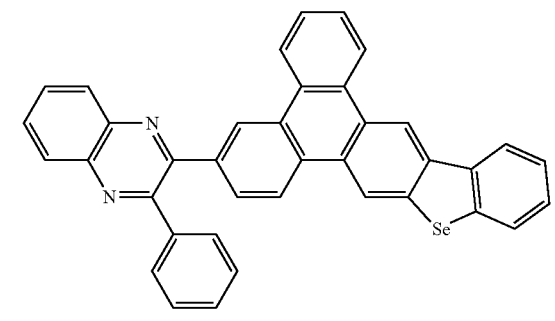
Compound 290
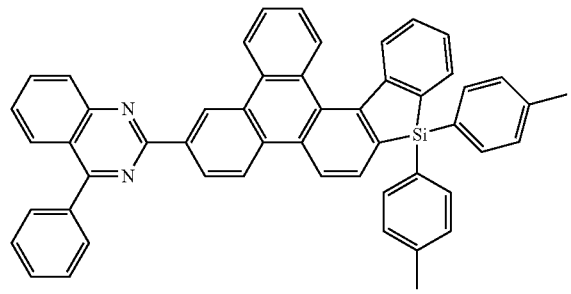
Compound 291
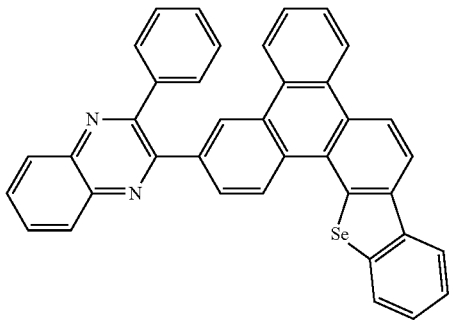
Compound 292
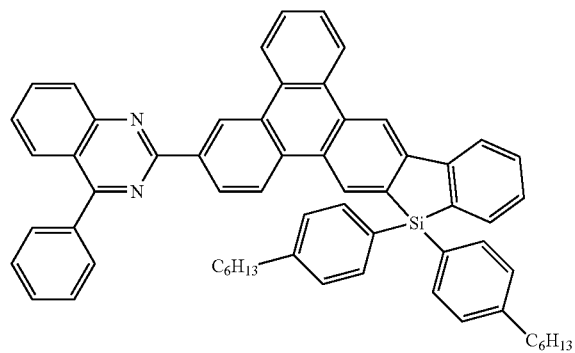
Compound 293
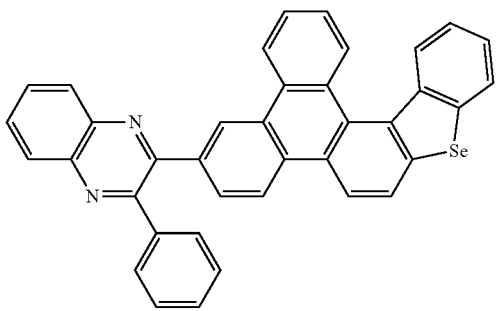

-continued
Compound 294
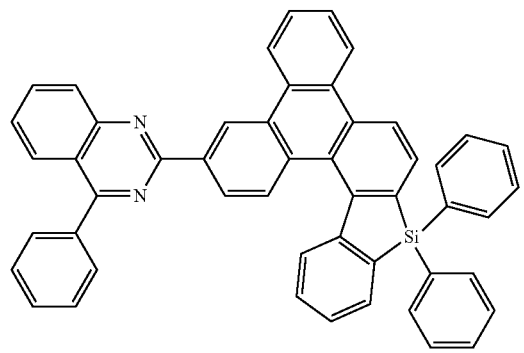
Compound 295
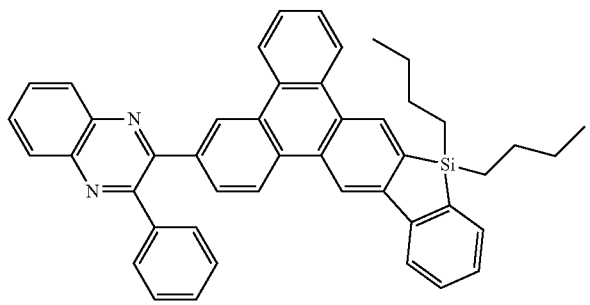
Compound 296
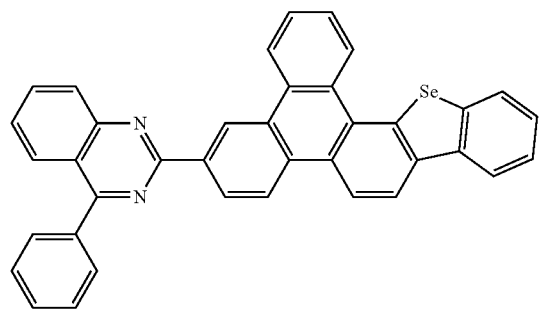
Compound 297
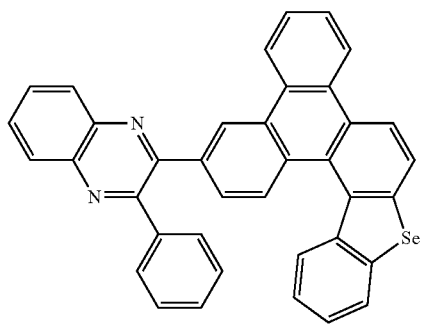
Compound 298
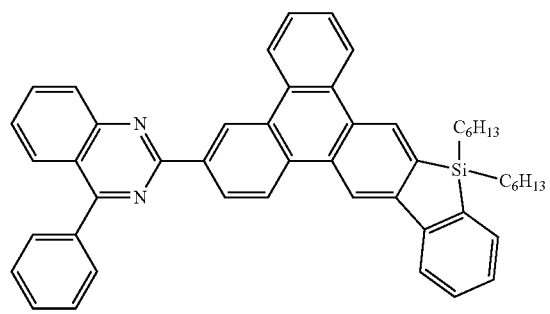
Compound 299
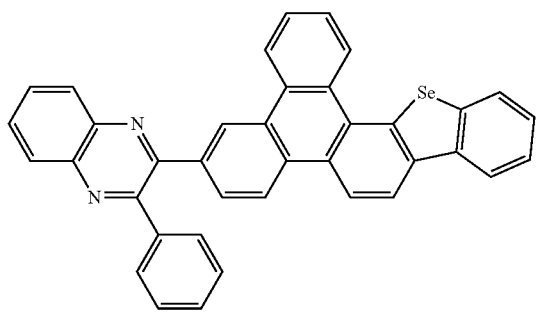
Compound 300
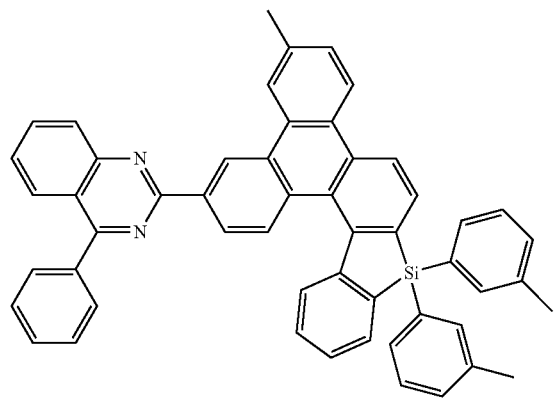
Compound 301
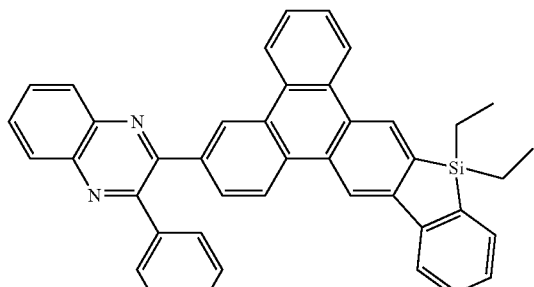

-continued
Compound 302
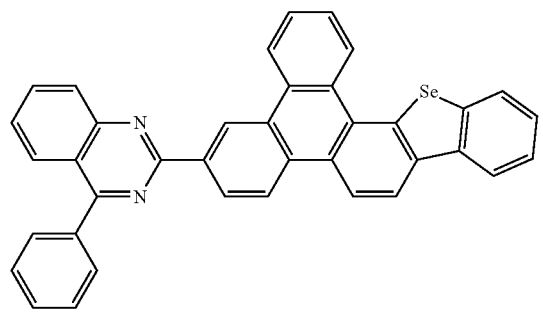
Compound 303
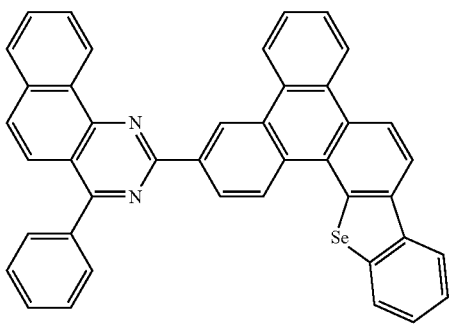
Compound 304
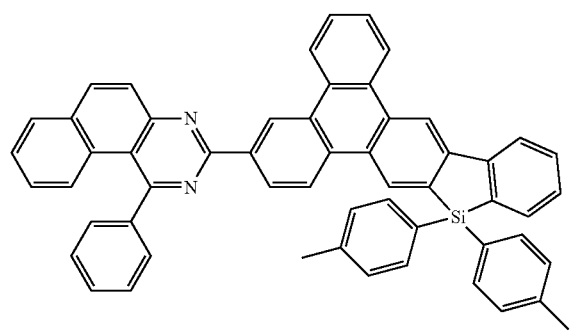
Compound 305
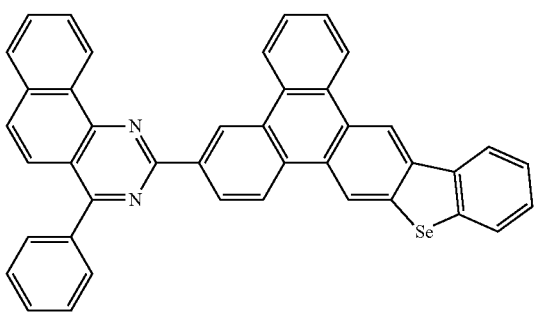
Compound 306
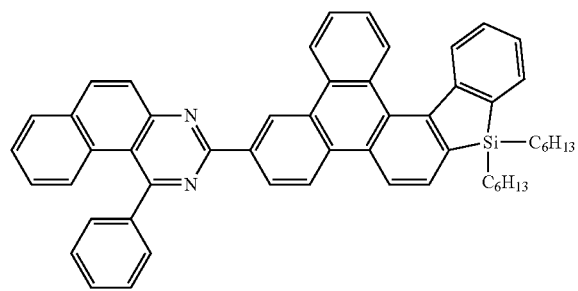
Compound 307
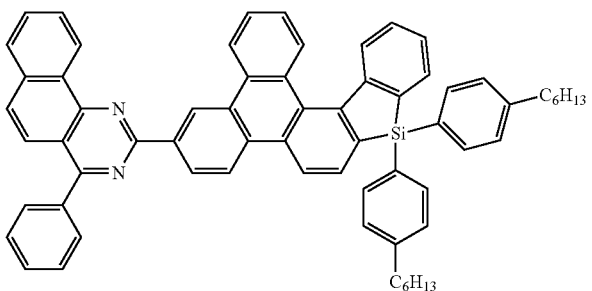
Compound 308
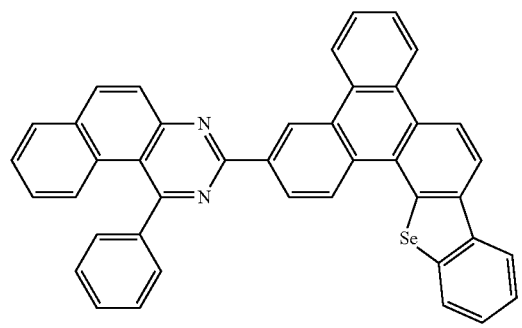
Compound 309
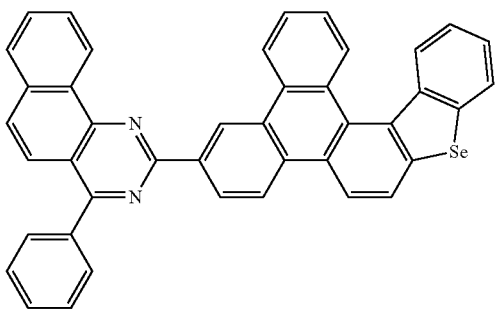

-continued
Compound 310
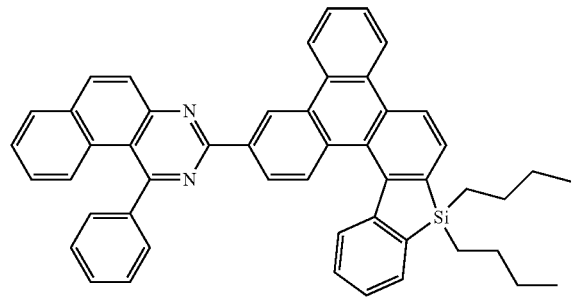
Compound 311
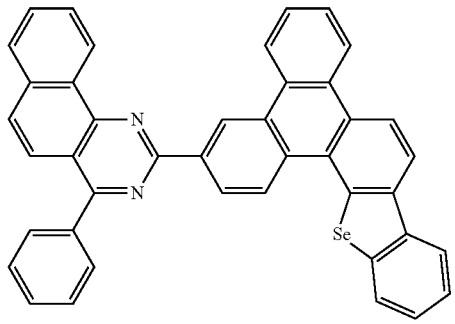
Compound 312
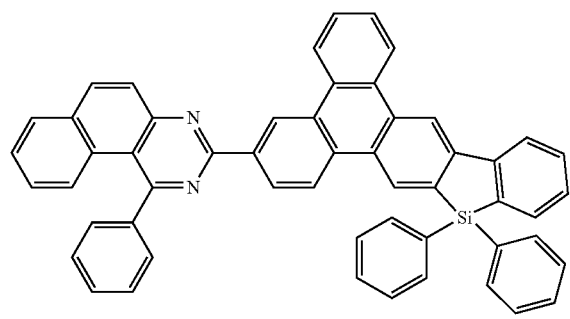
Compound 313
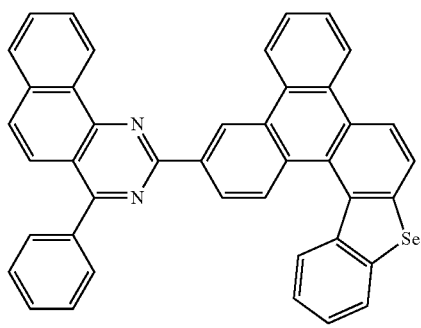
Compound 314
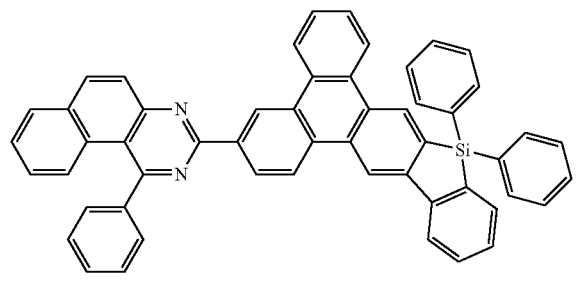
Compound 315
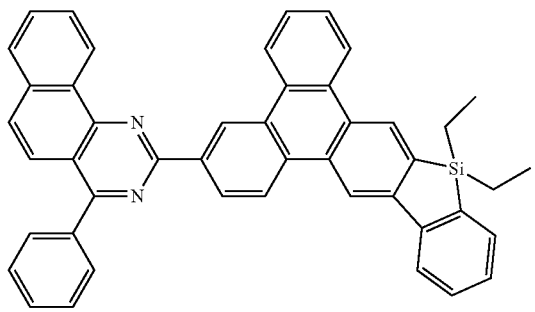
Compound 316
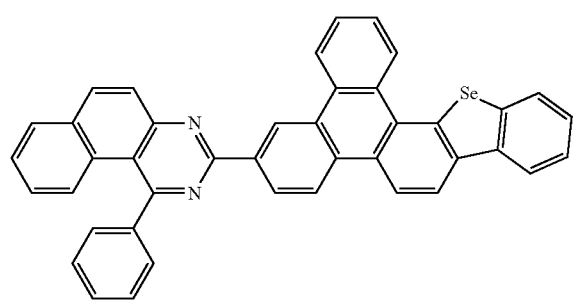
Compound 317
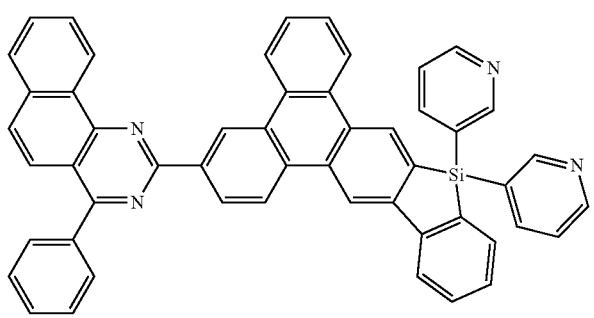

-continued
Compound 318
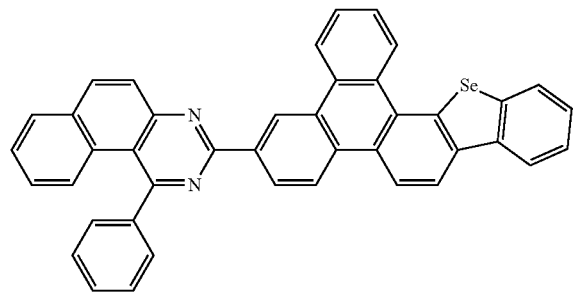
Compound 319
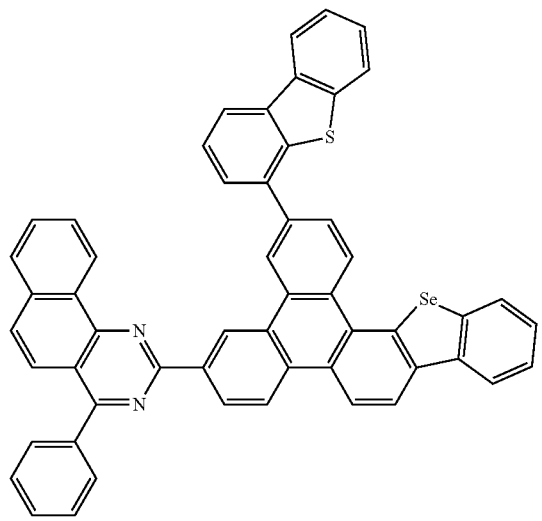
Compound 320
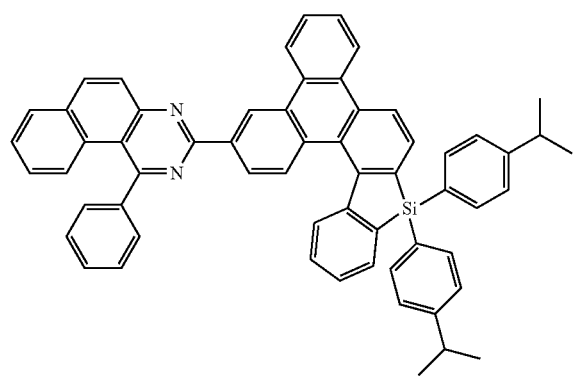
Compound 321
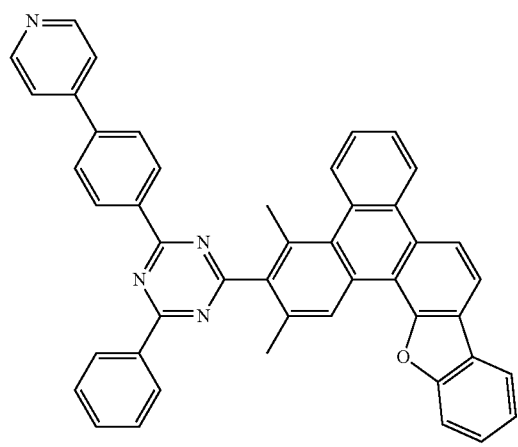
Compound 322
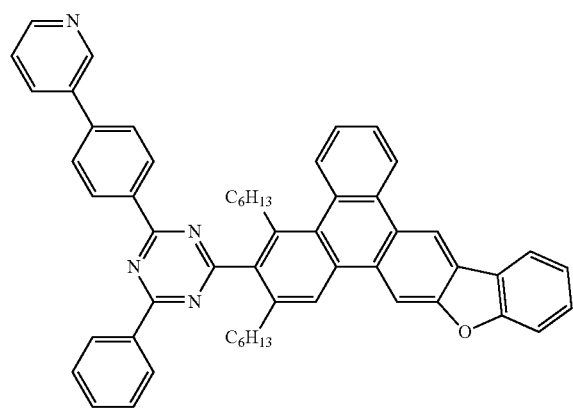
Compound 323
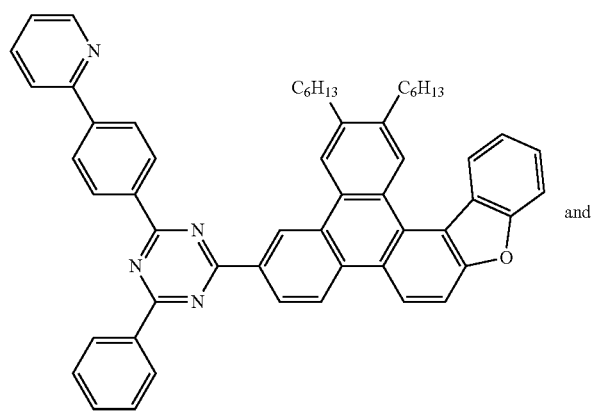
and Compound 324

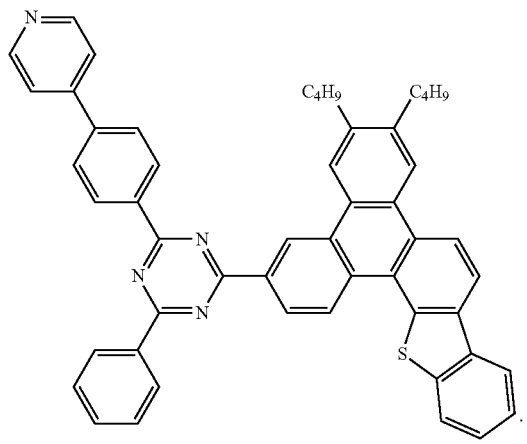

Detailed preparation of the organic compounds of the present invention will be clarified by exemplary embodiments below, but the present invention is not limited thereto. EXAMPLES 1 to 17 show the preparation of the organic compounds of the present invention, and EXAMPLE 18 and EXAMPLE 19 show the fabrication and test reports of the organic EL devices.

Example 1

Synthesis of 1-bromo-2-iodo-4-methoxybenzene

A mixture of 40 g (171 mmol) of 1-iodo-3-methoxybenzene, 32 g (179 mmol) of N-bromosuccinimide, and 600 ml of DMF was degassed and placed under nitrogen, and then heated at 80° C. for 12 hrs. After the reaction finished, the mixture was allowed to cool to room temperature. Subsequently, the solvent was removed under reduced pressure, and the crude product was purified by column chromatography, yielding 45 g of 1-bromo-2-iodo-4-methoxybenzene as yellow oil (84.1%). $^1$H NMR (CDCl$_3$, 400 MHz): chemical shift (ppm) 7.43 (dd, 1H), 7.35 (dd, 1H), 6.73 (dd, 1H), 3.74 (s, 3H).

Synthesis of 2-bromo-5-methoxy-1,1'-biphenyl

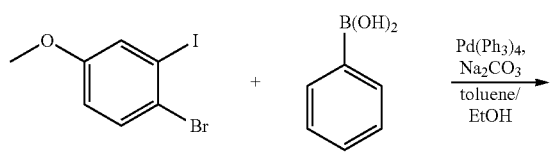

A mixture of 40 g (127.8 mmol) of 1-bromo-2-iodo-4-methoxybenzene, 15.6 g (127.8 mmol) of phenylboronic acid, 2.95 g (2.56 mmol) of Pd(Ph$_3$)$_4$, 155 ml of 2M Na$_2$CO$_3$, 100 ml of EtOH and 300 ml of toluene was degassed and placed under nitrogen, and then heated to reflux for 12 hrs. After the reaction finished, the mixture was allowed to cool to room temperature. Subsequently, the solvent was removed under reduced pressure, and the crude product was purified by column chromatography, yielding 30 g of 2-bromo-5-methoxy-1,1'-biphenyl as colorless liquid (89.2%). $^1$H NMR (CDCl$_3$, 400 MHz): chemical shift (ppm) 7.55 (d, 1H), 7.46-7.38 (m, 5H), 6.89 (d, 1H), 6.79 (dd, 1H), 3.81 (s, 3H).

Synthesis of (5-methoxy-[1,1'-biphenyl]-2-yl) boronic acid

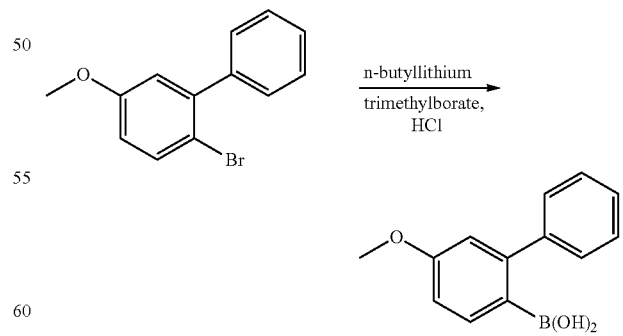

The compound 2-bromo-5-methoxy-1,1'-biphenyl (30 g, 114 mmol) was mixed with 600 nil of dry THF. To the mixture, 54.7 ml of N-butyllithium (137 mmol) was added at −60 t and the mixture was stirred for 1 hrs. After the reaction finished, 17.8 g (171 mmol) of trimethyl borate was added and the mixture was stirred overnight. 228 ml (228 mmole) of 1M HCl was added and the mixture was stirred for 1 hrs. The mixture was extracted with ethyl acetate/H$_2$O, and the organic layer was removed under reduced pressure. The crude product was washed by hexane, yielding 19.5 g of (5-methoxy-[1,1'-biphenyl]-2-yl) boronic acid as white solid (75%).

Synthesis of 3-(5-methoxy-[1,1'-biphenyl]-2-yl) dibenzo[b,d]-thiophene

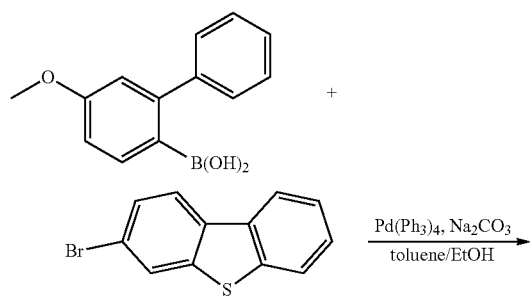

A mixture of 20 g (87.7 mmol) of (5-methoxy-[1,1'-biphenyl]-2-yl)-boronic acid, 25.4 g (96.5 mmol) of 3-bromodibenzo[b,d]thiophene, 2.03 g (1.75 mmol) of Pd(Ph$_3$)$_4$, 87.7 ml of 2M Na$_2$CO$_3$, 200 ml of EtOH and 400 ml of toluene was degassed and placed under nitrogen, and then heated to reflux for 12 hrs. After the reaction finished, the mixture was allowed to cool to room temperature. Subsequently, the solvent was removed under reduced pressure, and the crude product was purified by column chromatography, yielding 23.1 g of 3-(5-methoxy-[1,1'-biphenyl]-2-yl)-dibenzo[b,d]thiophene as white solid (71.9%). $^1$H NMR (CDCl$_3$, 400 MHz): chemical shift (ppm) 8.47 (d, 1H), 8.12-8.06 (m, 3H), 8.01 (d, 1H), 7.77-7.74 (m, 3H), 7.49-7.45 (m, 4H), 7.41-7.38 (m, 2H), 7.02 (d, 1H), 3.81 (s, 3H).

Synthesis of 6-methoxybenzo[b]triphenyleno[2,3-d] thiophene

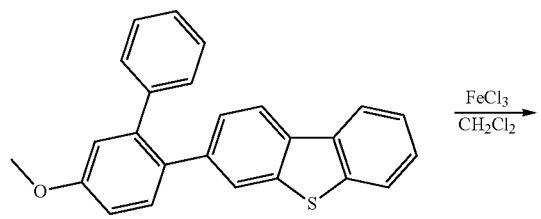

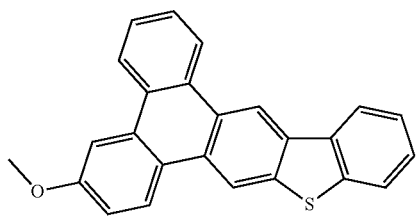

The compound 3-(5-methoxy-[1,1'-biphenyl]-2-yl) dibenzo[b,d]-thiophene (20 g, 54.6 mmol) was mixed with 700 ml of CH$_2$Cl$_2$. To the mixture, 88.5 g of FeCl$_3$ (546 mmol) was added and the mixture was stirred for 1 hrs. After the reaction finished, the solvent was removed under reduced pressure, and the crude product was purified by column chromatography, yielding 8.5 g of 6-methoxybenzo[b]triphenyleno[2,3-d]-thiophene as white solid (42.7%). $^1$H NMR (CDCl$_3$, 400 MHz): chemical shift (ppm) 8.91-8.89 (m, 2H), 8.81 (d, 1H), 8.49 (d, 1H), 8.14 (m, 2H), 7.99 (d, H), 7.89-7.85 (m, 2H), 7.62 (s, 1H), 7.54-7.51 (m, 2H), 7.36 (d, 1H), 3.82 (s, 3H).

Synthesis of benzo[b]triphenyleno[2,3-d]thiophen-6-ol

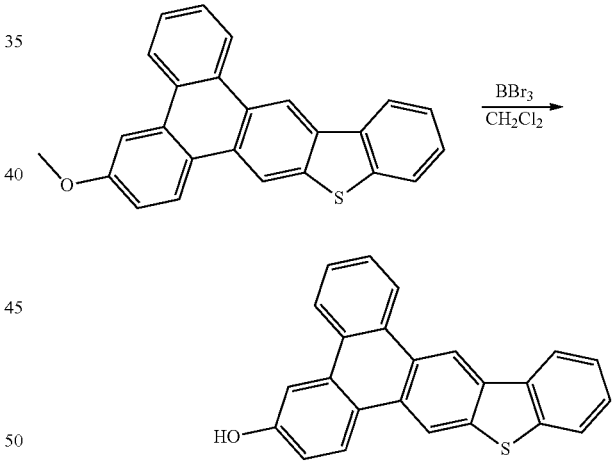

The compound 6-methoxybenzo[b]triphenyleno[2,3-d]-thiophene (10 g, 27.4 mmol) was mixed with 400 ml of CH$_2$Cl$_2$. To the mixture, 8.25 g of BBr$_3$ (32.9 mmol) was added and the mixture was stirred overnight. After the reaction finished, the solvent was removed under reduced pressure, and the crude product was purified by column chromatography, yielding 8.8 g of benzo[b]triphenyleno[2,3-d]thiophen-6-ol as white solid (91.5%). $^1$H NMR (CDCl$_3$, 400 MHz): chemical shift (ppm) 8.89-8.87 (m, 2H), 8.78 (d, 1H), 8.45 (d, 1H), 8.09 (m, 2H), 7.94 (d, H), 7.86-7.83 (m, 2H), 7.58 (s, 1H), 7.51-7.48 (m, 2H), 7.31 (d, 1H), 5.41 (s, 1H).

Synthesis of benzo[b]triphenyleno[2,3-d]thiophen-6-yl trifluoro-methanesulfonate

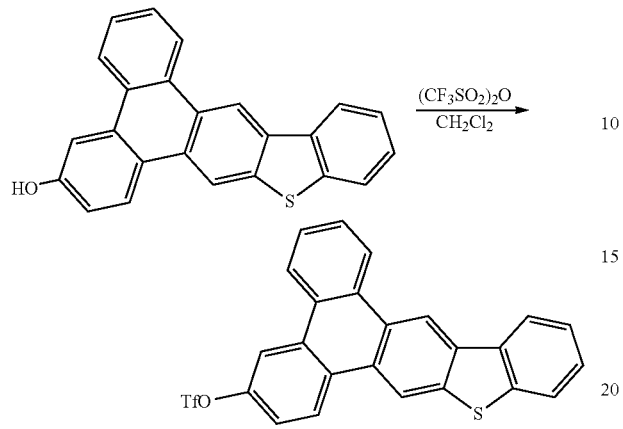

The compound benzo[b]triphenyleno[2,3-d]thiophen-6-ol (10 g, 28.5 mmol) was mixed with 450 ml of CH$_2$Cl$_2$. To the mixture, 3.4 g of pyridine (42.8 mmol) was added and the mixture was stirred for 1 hrs. To the mixture, 13.7 g of (CF$_3$SO$_2$)$_2$O (48.5 mmol) was added and the mixture was stirred for 1 hrs. After the reaction finished, the solvent was removed under reduced pressure, and the crude product was purified by column chromatography, yielding 10.5 g of benzo[b]triphenyleno[2,3-d]thiophen-6-yltrifluoro-methanesulfonate as yellow solid (55.9%). $^1$H NMR (CDCl$_3$, 400 MHz): chemical shift (ppm) 8.99-8.95 (m, 3H), 8.47 (d, 1H), 8.14-8.11 (m, 3H), 7.97 (d, H), 7.88-7.85 (m, 2H), 7.58 (s, 1H), 7.53-7.51 (m, 2H).

Synthesis of 2-(benzo[b]triphenyleno[2,3-d]thiophen-6-yl)-4,4,5,5-tetramethyl-1,3,2-dioxaborolane

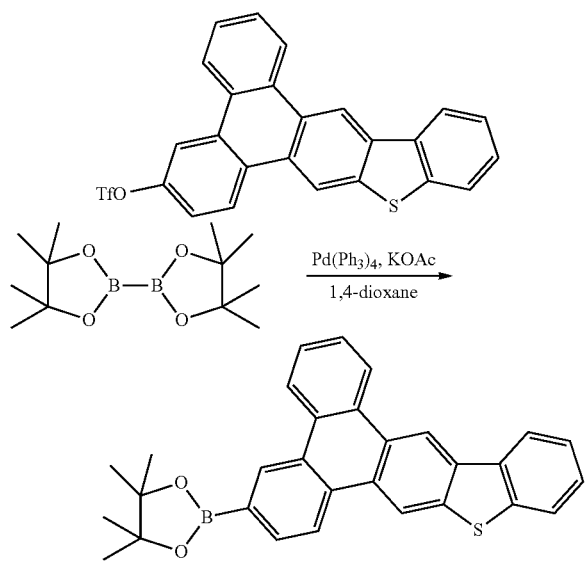

A mixture of 5 g (10.4 mmol) of benzo[b]triphenyleno[2,3-d]thiophen-6-yl trifluoromethanesulfonate, 3.16 g (12.4 mmol) of bis(pinacolato)diboron, 0.48 g (0.4 mmol) of Pd(Ph$_3$)$_4$, 2.04 g (20.8 mmol) of potassium acetate, and 60 ml of 1,4-dioxane was degassed and placed under nitrogen, and then heated to reflux for 12 hrs. After the reaction finished, the mixture was allowed to cool to room temperature. Subsequently, the solvent was removed under reduced pressure, and the crude product was purified by column chromatography, yielding 3.1 g of 2-(benzo[b]triphenyleno[2,3-d]thiophen-6-yl)-4,4,5,5-tetramethyl-1,3,2-dioxaborolane as white solid (65%). $^1$H NMR (CDCl$_3$, 400 MHz): chemical shift (ppm) 8.94-8.88 (m, 3H), 8.47 (d, 1H), 8.15-8.12 (m, 3H), 7.99 (d, 1H), 7.87-7.84 (m, 3H), 7.54-7.52 (m, 2H), 1.27 (s, 12H).

Synthesis of 2-(benzo[b]triphenyleno[2,3-d]thiophen-6-yl)-4,6-diphenyl-1,3,5-triazine (Compound 5)

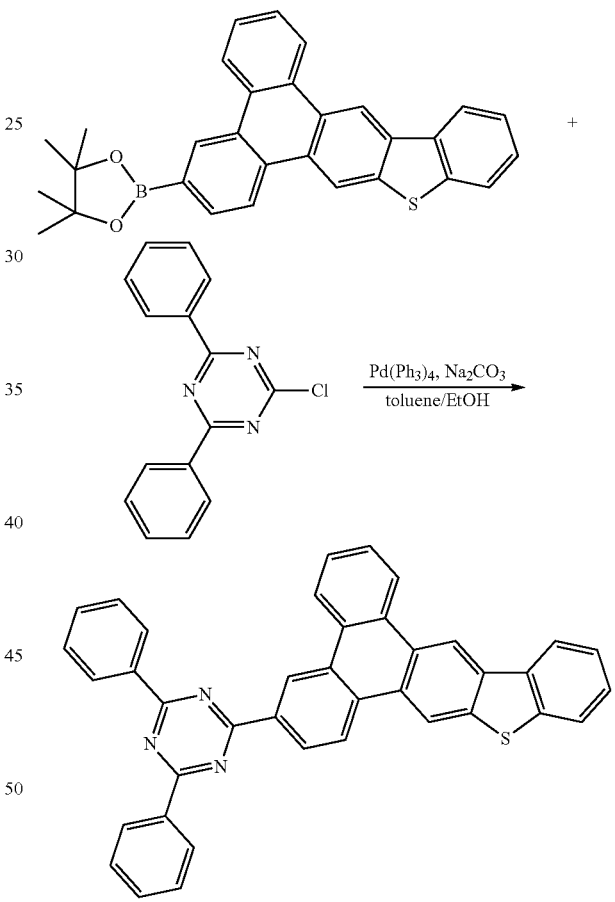

A mixture of 3 g (6.51 mmol) of 2-(benzo[b]triphenyleno[2,3-d]-thiophen-6-yl)-4,4,5,5-tetramethyl-1,3,2-dioxaborolane, 1.92 g (7.17 mmol) of 92-chloro-4,6-diphenyl-1,3,5-triazine, 0.15 g (0.13 mmol) of Pd(Ph$_3$)$_4$, 6.5 ml of 2M Na$_2$CO$_3$, 20 ml of EtOH and 40 ml of toluene was degassed and placed under nitrogen, and then heated to reflux for 12 hrs. After the reaction finished, the mixture was allowed to cool to room temperature. Subsequently, the solvent was removed under reduced pressure, and the crude product was purified by column chromatography, yielding 2.5 g of 2-(benzo[b]triphenyleno[2,3-d]thiophen-6-yl)-4,6-diphenyl-1,3,5-triazine as yellow solid (68%). ¹H NMR (CDCl$_3$, 400 MHz): chemical shift (ppm) 8.99-8.93 (m, 3H), 8.46 (d, 1H), 8.33 (s, 1H), 8.29-8.24 (m, 4H), 8.13-8.09 (m, 3H), 7.97 (d, H), 7.88-7.82 (m, 2H), 7.53-7.46 (m, 6H), 7.44-7.41 (m, 2H).

Example 2-17

We have used the same synthesis methods to get a series of intermediates and the following compounds are synthesized analogously.

| Ex. | Intermediate III | Intermediate IV | Product | Yield |
|---|---|---|---|---|
| 2 | | | Compound 2 | 63% |
| 3 | | | Compound 3 | 64% |
| 4 | | | Compound 20 | 58% |
| 5 | | | Compound 23 | 52% |

-continued

| Ex. | Intermediate III | Intermediate IV | Product | Yield |
|---|---|---|---|---|
| 6 | | | Compound 50 | 57% |
| 7 | | | Compound 65 | 54% |
| 8 | | | Compound 74 | 64% |
| 9 | | | Compound 75 | 61% |
| 10 | | | Compound 95 | 46% |

-continued
| Ex. | Intermediate III | Intermediate IV | Product | Yield |
|---|---|---|---|---|
| 11 | 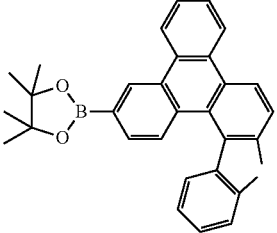 [SMILES: Cc1ccccc1-c1c(C)ccc2c3ccccc3c3cc(B4OC(C)(C)C(C)(C)O4)ccc3c12] | 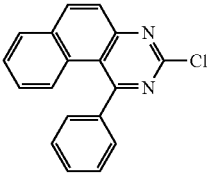 [SMILES: Clc1nc(-c2ccccc2)c2c(ccc3ccccc32)n1] | 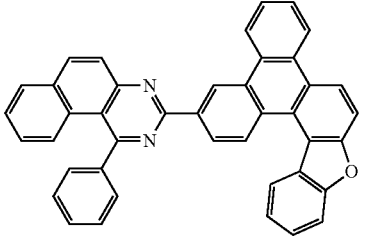 Compound 98 | 48% |
| 12 | 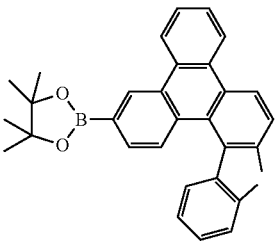 [SMILES: Cc1ccccc1-c1c(C)ccc2c3ccccc3c3cc(B4OC(C)(C)C(C)(C)O4)ccc3c12] | 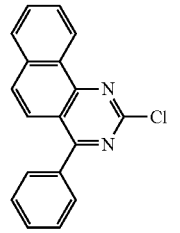 [SMILES: Clc1nc(-c2ccccc2)c2ccc3ccccc3c2n1] | 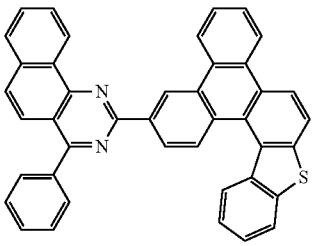 Compound 101 | 49% |
| 13 | 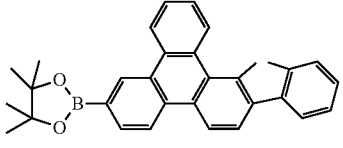 [SMILES: Cc1ccccc1-c1ccc2c3ccc(B4OC(C)(C)C(C)(C)O4)cc3c3ccccc3c2c1C] | 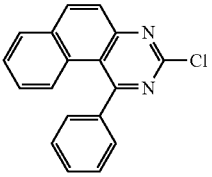 [SMILES: Clc1nc(-c2ccccc2)c2c(ccc3ccccc32)n1] | 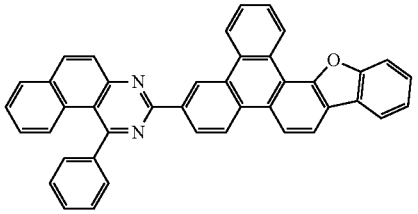 Compound 104 | 47% |
| 14 | 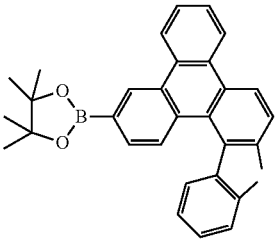 [SMILES: Cc1ccccc1-c1c(C)ccc2c3ccccc3c3cc(B4OC(C)(C)C(C)(C)O4)ccc3c12] | 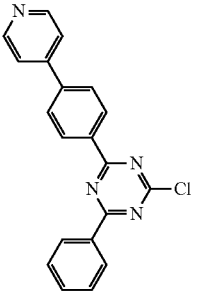 [SMILES: Clc1nc(-c2ccccc2)nc(-c2ccc(-c3ccncc3)cc2)n1] | 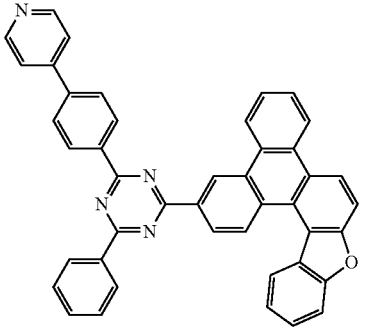 Compound 118 | 41% |
| 15 | 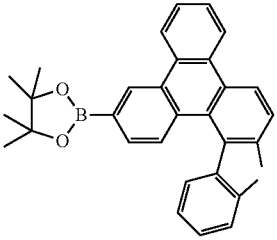 [SMILES: Cc1ccccc1-c1c(C)ccc2c3ccccc3c3cc(B4OC(C)(C)C(C)(C)O4)ccc3c12] | 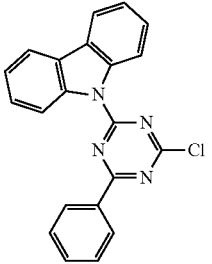 [SMILES: Clc1nc(-c2ccccc2)nc(-n2c3ccccc3c3ccccc32)n1] | 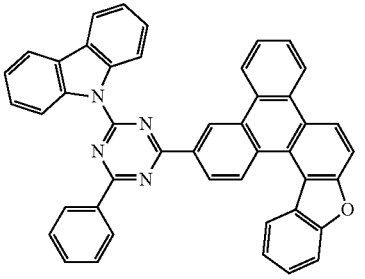 Compound 219 | 45% |

| Ex. | Intermediate III | Intermediate IV | Product | Yield |
|---|---|---|---|---|
| 16 | 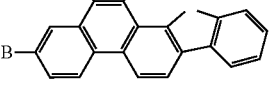 | 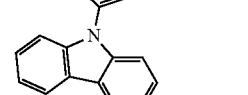 | 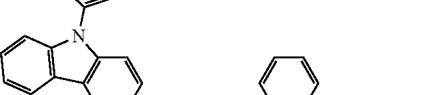  Compound 221 | 42% |
| 17 | 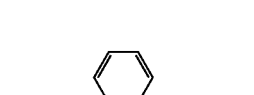 | 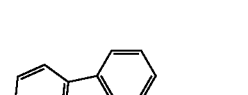 |   Compound 223 | 51% |

General Method of Producing Organic EL Device

ITO-coated glasses with 9~12 ohm/square in resistance and 120~160 nm in thickness are provided (hereinafter ITO substrate) and cleaned in a number of cleaning steps in an ultrasonic bath (e.g. detergent, deionized water). Before vapor deposition of the organic layers, cleaned ITO substrates are further treated by UV and ozone. All pre-treatment processes for ITO substrate are under clean room (class 100).

These organic layers are applied onto the ITO substrate in order by vapor deposition in a high-vacuum unit ($10^{-7}$ Torr), such as: resistively heated quartz boats. The thickness of the respective layer and the vapor deposition rate (0.1~0.3 nm/sec) are precisely monitored or set with the aid of a quartz-crystal monitor. It is also possible, as described above, for individual layers to consist of more than one compound, i.e. in general a host material doped with a dopant material and/or co-deposited with a co-host. This is successfully achieved by co-vaporization from two or more sources, which means the triphenylenobenzofuran and triphenylenobenzothiophene derivatives of the present invention are thermally stable.

Dipyrazino[2,3-f:2,3-]quinoxaline-2,3,6,7,10,11-hexacarbonitrile (HAT-CN) is used as hole injection layer in this organic EL device. N,N-Bis(naphthalene-1-yl)-N,N-bis(phenyl)-benzidine(NPB) is most widely used as the hole transporting layer. 12-(4,6-diphenyl-1,3,5-triazin-2-yl)-10,10-dimethyl-10,12-dihydrophenanthro[9',10':5,6]indeno[2,1-b]carbazole (H1) is used as emitting hosts for comparison, and bis(2-phenylpyridinato)(2,4-diphenylpyridinato)iridium (III) (D1) is used as green guest in the light emitting layer. HB1 (see the following chemical structure) is used as hole blocking material (HBM), and 2-(naphthalen-1-yl)-9-(4-(1-(4-(10-(naphthalene-2-yl)anthracen-9-yl)-phenyl)-1H-benzo[d]imidazol-2-yl)phenyl)-1,10-phenanthroline (ET1) is used as electron transporting material to co-deposit with 8-hydroxyquinolato-lithium (LiQ) in organic EL devices. The chemical structures of conventional OLED materials and the exemplary organic compounds of the present invention for producing control and exemplary organic EL devices in this invention are shown as follows:

117                                    118
HAT-CN
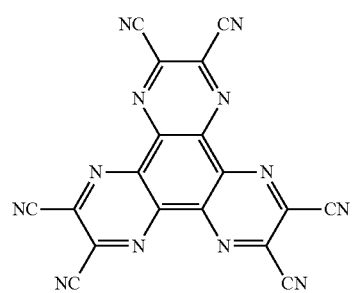            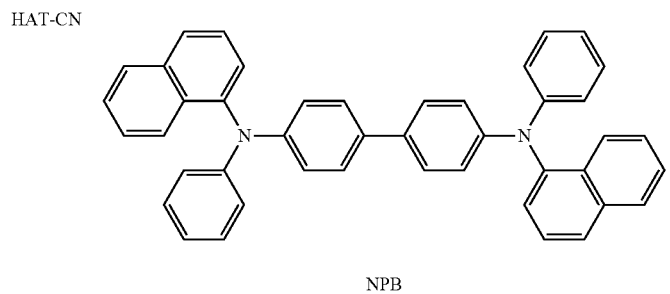
NPB
DA                                         H1
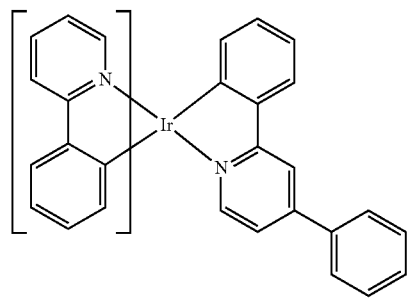            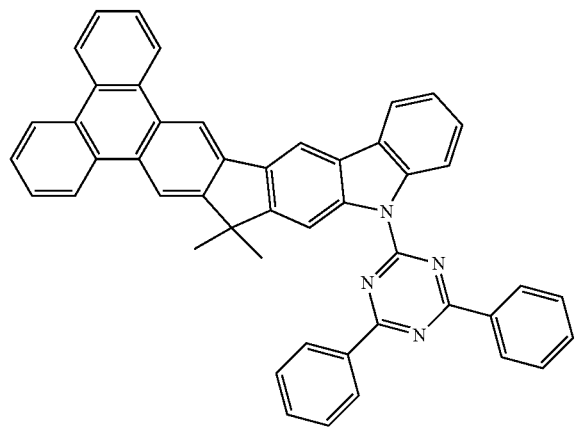
HB1
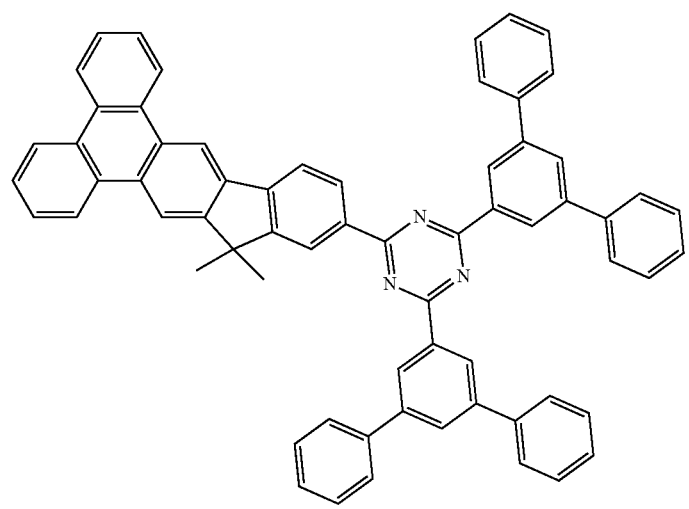

-continued
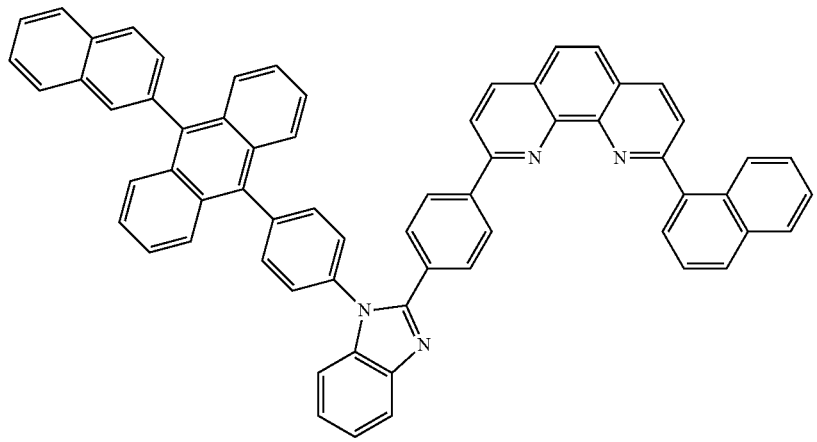
ET1
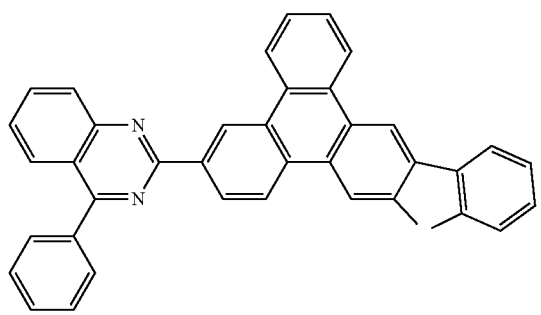
Compound 74
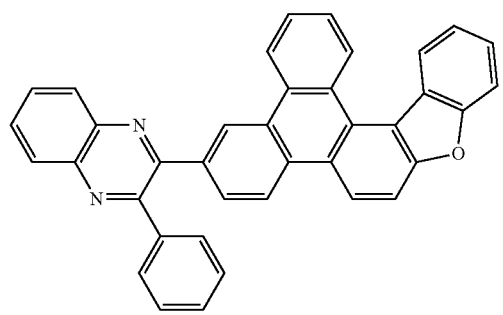
Compound 75
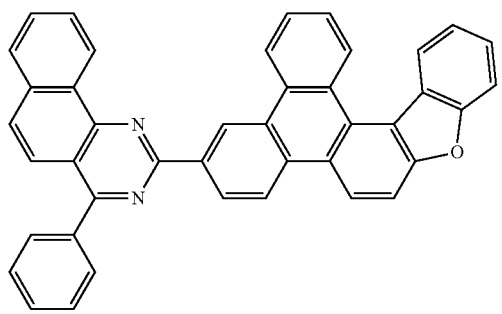
Compound 95
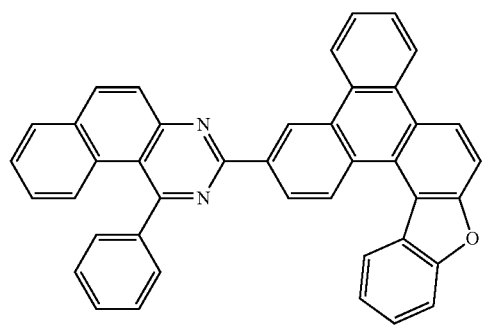
Compound 98
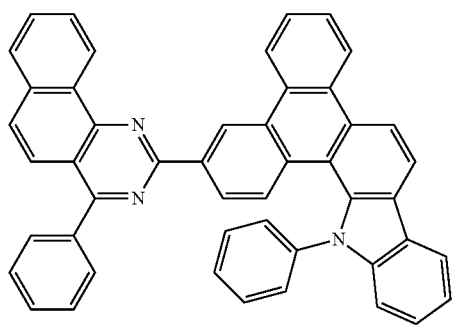
Compound 99
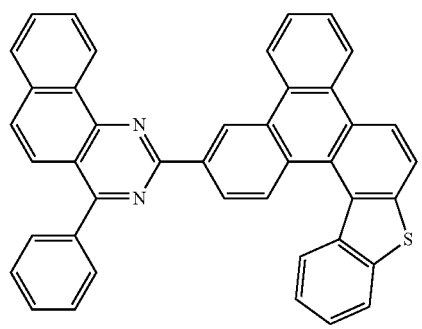
Compound 101

-continued
Compound 104
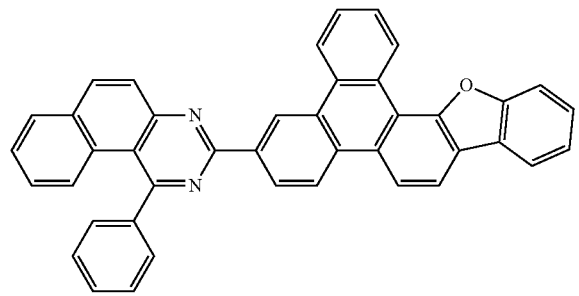
Compound 220
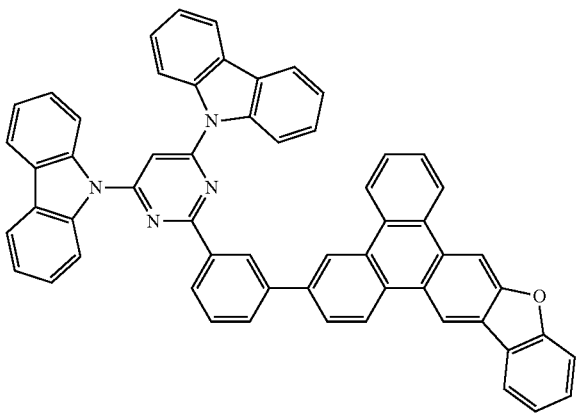
Compound 221
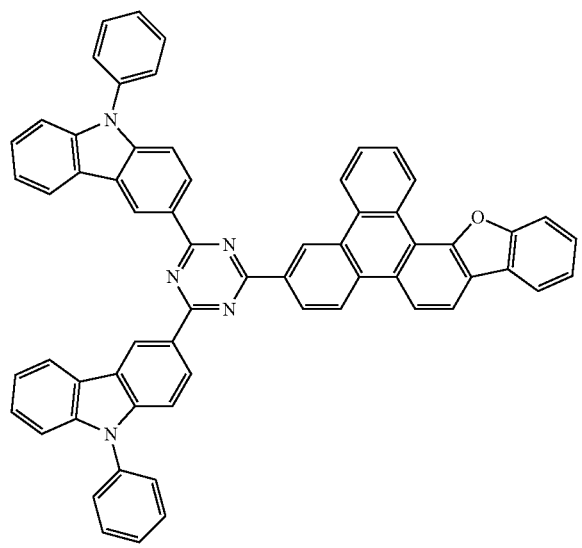
Compound 223
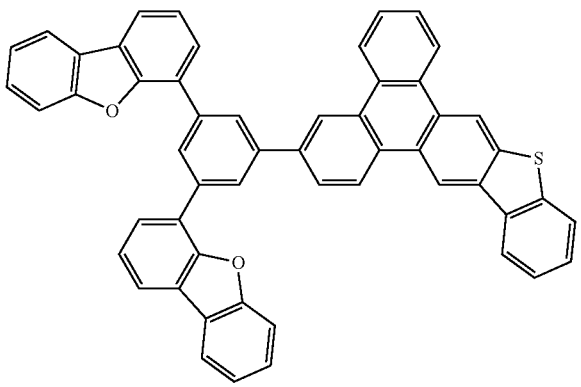
Compound 228
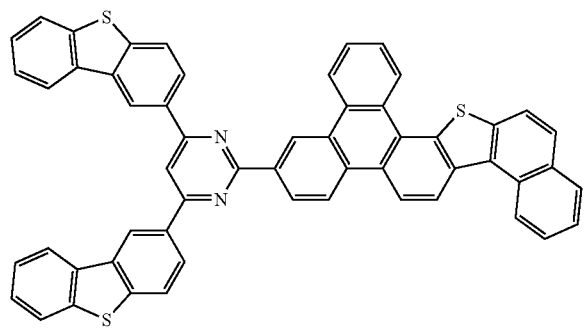
Compound 249
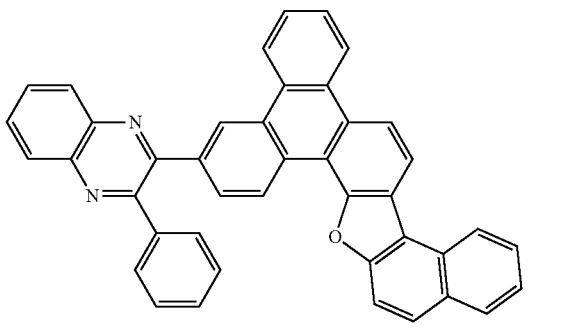

-continued
Compound 254
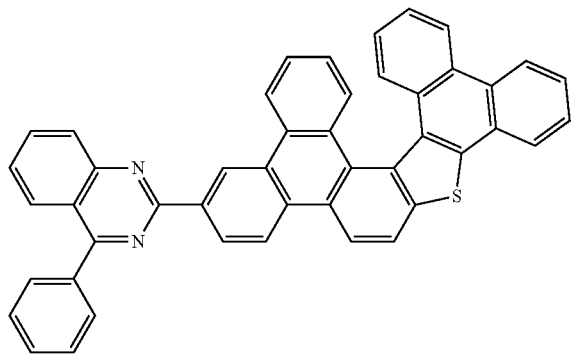
Compound 268
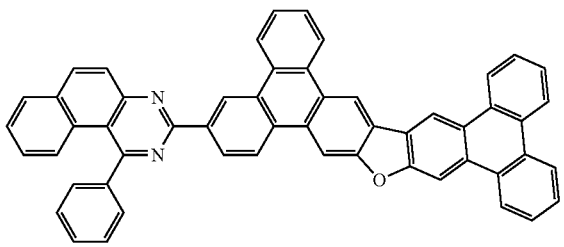
Compound 319
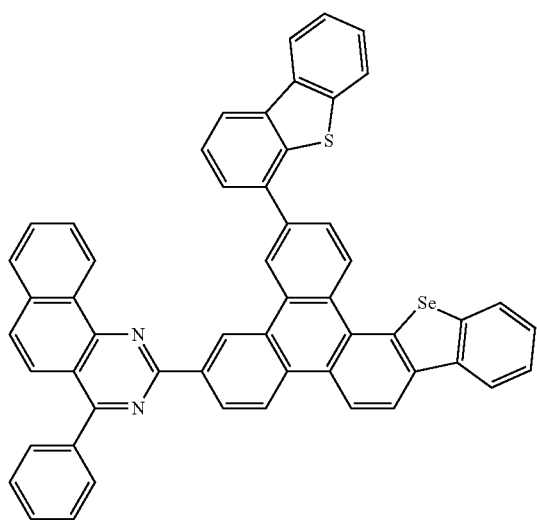
Compound 320
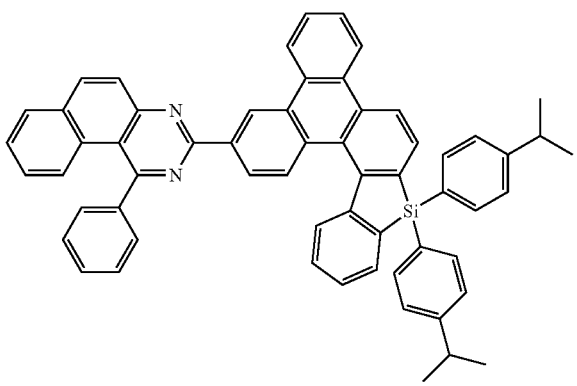
Compound 1
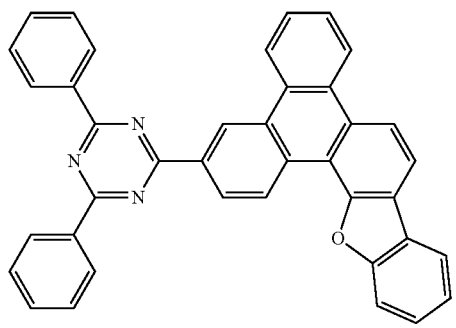
Compound 2
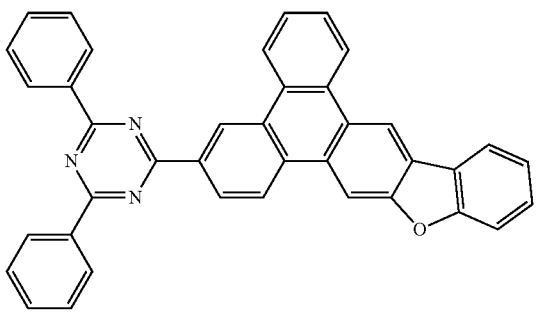
Compound 3
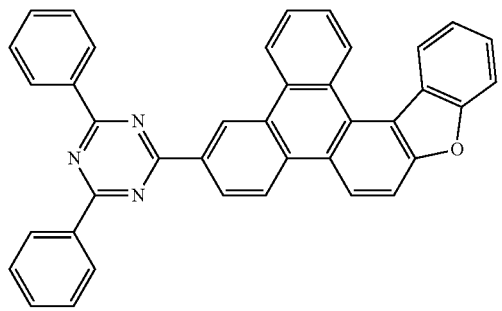
Compound 5
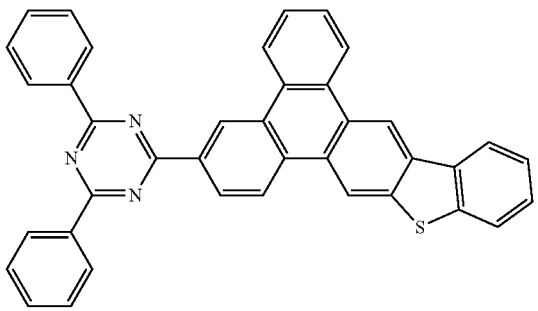

-continued
Compound 8
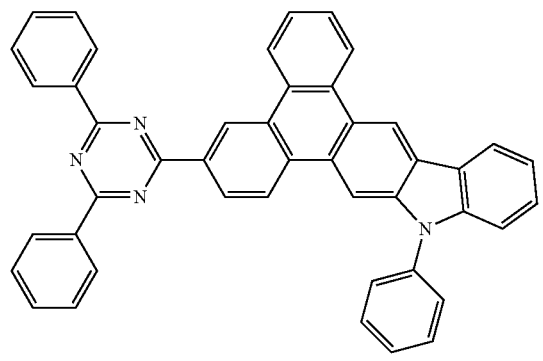
Compound 20
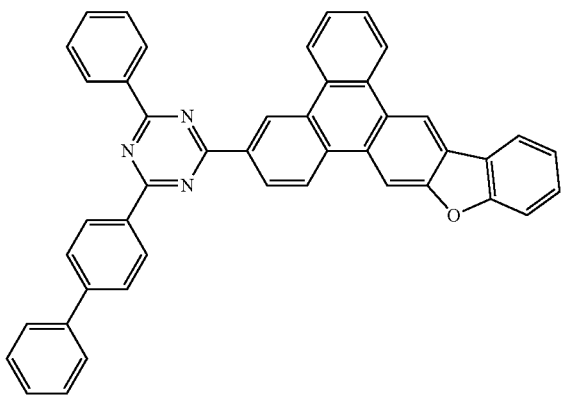
Compound 23
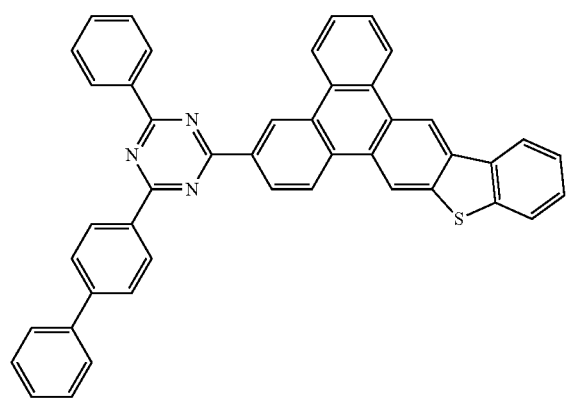
Compound 50
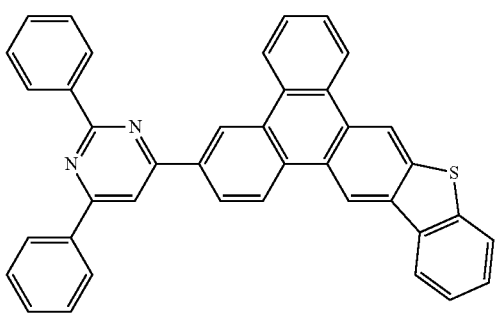
Compound 54
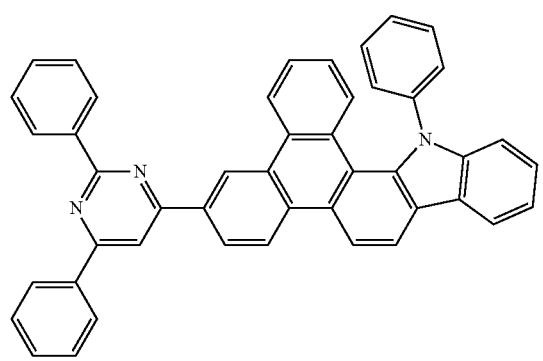
Compound 65
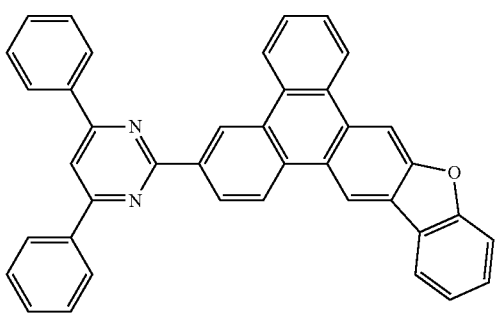

-continued
Compound 118
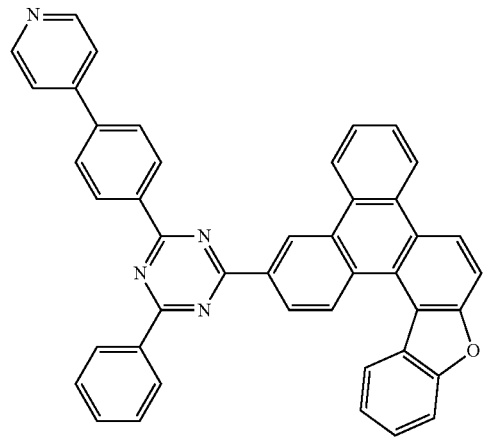
Compound 201
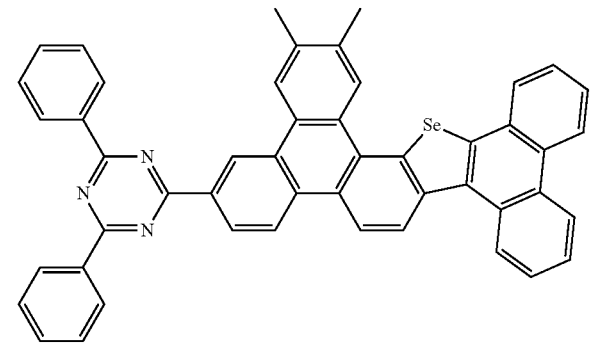
Compound 204
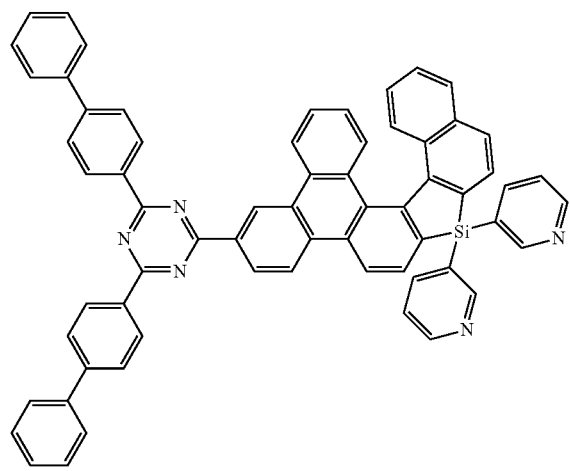
Compound 206
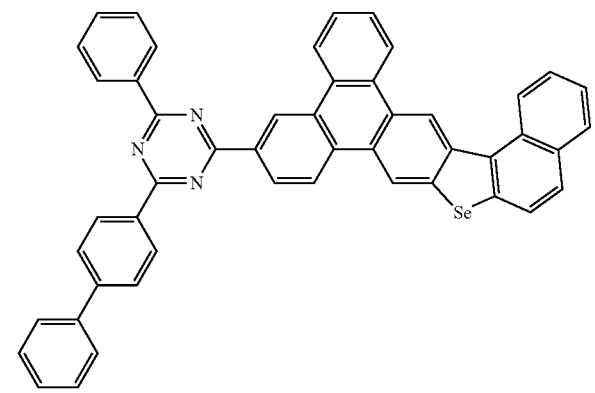
Compound 180
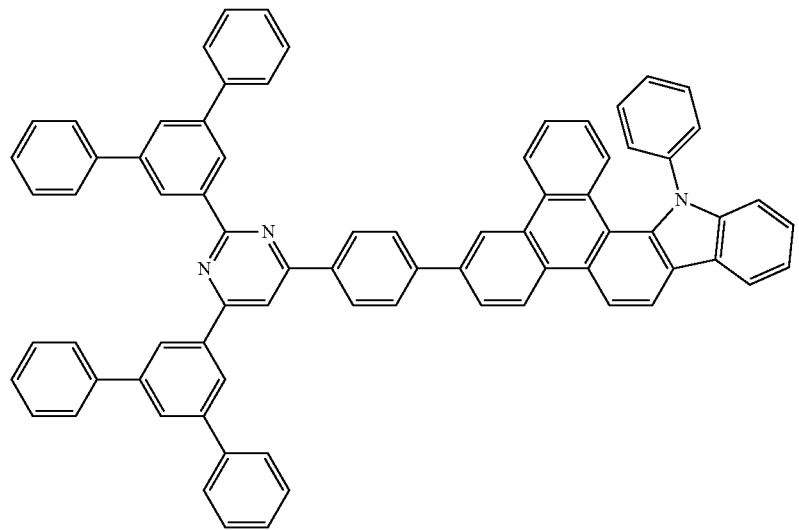

-continued

Compound 209

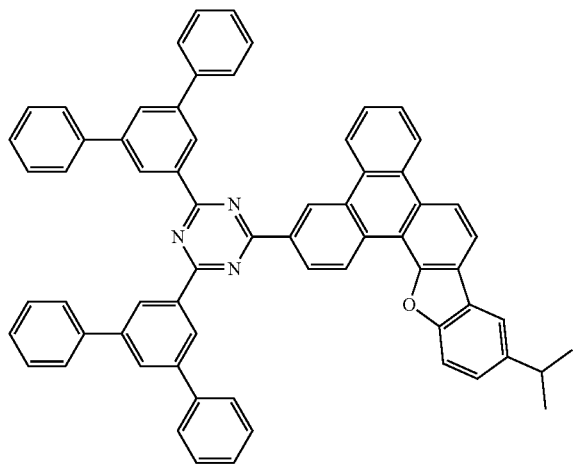

Compound 212

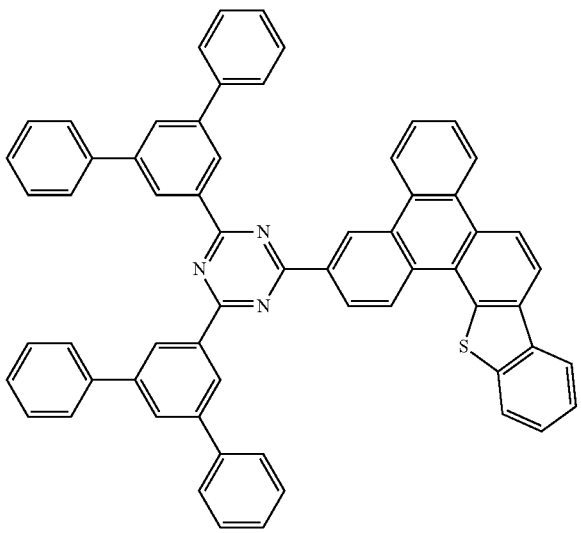

Compound 232

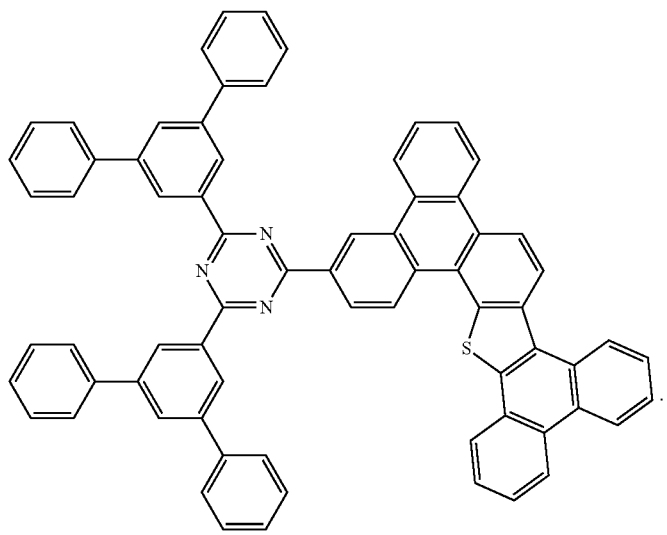

A typical organic EL device consists of low work function metals, such as Al, Mg, Ca, Li and K, as the cathode by thermal evaporation, and the low work function metals can help electrons injecting the electron transporting layer from cathode. In addition, for reducing the electron injection barrier and improving the organic EL device performance, a thin electron injecting layer is introduced between the cathode and the electron transporting layer. Conventional materials of electron injecting layer are metal halide or metal oxide with low work function, such as: LiF, LiQ, MgO, or $Li_2O$. On the other hand, after the organic EL device fabrication, EL spectra and CIE coordination are measured by using a PR650 spectra scan spectrometer. Furthermore, the current/voltage, luminescence/voltage, and yield/voltage characteristics are taken with a Keithley 2400 programmable voltage-current source. The above-mentioned apparatuses are operated at room temperature (about 25° C.) and under atmospheric pressure.

Example 18

Using a procedure analogous to the above mentioned general method, organic EL devices emitting green light and having a device structure as shown in the FIGURE were produced. The device structure, from the bottom layer 10 to the top layer 80, sequentially comprises: ITO/HAT-CN (20 nm)/NPB (110 nm)/Emitting host doped with 15% D1 (30 nm)/HB1/ET1 doped 50% LiQ (35 nm)/LiQ (1 nm)/Al (160 nm). In the device illustrated in the FIGURE, the hole injection layer (HIL) 20 is deposited onto the transparent electrode 10. The hole transport layer (HTL) 30 is deposited onto the HIL 20. The emitting layer (EML) 40, for example, an emitting host doped with 15% D1 (emitting guest material), is deposited onto the HTL 30. The hole blocking layer (HBL) 50 is deposited onto the EML 40. The electron transport layer (ETL) 60 is deposited onto the HBL 50. The electron injection layer (EIL) 70 is deposited onto the ETL 60. The metal electrode 80 is deposited onto the EIL 70. The I-V-B (at 1000 nits) test reports of these organic EL devices are summarized in Table 1 below. The half-life time is defined as the time the initial luminance of 1000 cd/m² has dropped to half.

TABLE 1

| Emitting Host Material (for EML 40) | Emitting Guest Material | Driving Voltage (V) | Current Efficiency (Yield; cd/A) | CIE(y) | Half-life time (hours) |
|---|---|---|---|---|---|
| H1 | D1 | 5.1 | 18 | 0.53 | 350 |
| Compound 74 | D1 | 3.1 | 36 | 0.54 | 740 |
| Compound 75 | D1 | 3.2 | 34 | 0.54 | 780 |
| Compound 95 | D1 | 3.3 | 33 | 0.56 | 750 |
| Compound 98 | D1 | 3.0 | 35 | 0.54 | 780 |
| Compound 99 | D1 | 3.1 | 34 | 0.54 | 770 |
| Compound 101 | D1 | 3.4 | 31 | 0.56 | 730 |
| Compound 104 | D1 | 3.3 | 33 | 0.55 | 720 |
| Compound 220 | D1 | 4.2 | 24 | 0.54 | 500 |
| Compound 221 | D1 | 4.5 | 23 | 0.53 | 510 |
| Compound 223 | D1 | 4.4 | 22 | 0.56 | 460 |
| Compound 228 | D1 | 4.2 | 25 | 0.55 | 520 |
| Compound 249 | D1 | 3.8 | 29 | 0.53 | 680 |
| Compound 254 | D1 | 3.6 | 26 | 0.56 | 660 |
| Compound 268 | D1 | 3.7 | 28 | 0.55 | 620 |
| Compound 319 | D1 | 4.9 | 21 | 0.53 | 370 |
| Compound 320 | D1 | 4.8 | 20 | 0.54 | 380 |

Example 19

Using a procedure analogous to the above mentioned general method, fluorescent green emitting organic EL device having the following device structure as shown in the FIGURE were produced. From the bottom layer 10 to the top layer 80, the structure may comprises: ITO/HAT-CN (20 nm)/NPB (130 nm)/H1 doped 15% D1 (30 nm)/HBL (10 nm)/ETL co-deposit LiQ (ETM:LiQ, ratio=1:1 (40 nm)/LiQ (1 nm)/Al (160 nm). The I-V-B (at 1000 nits) and half-life time of fluorescent blue-emitting organic EL device testing report as Table 2, The half-life time is defined that the initial luminance of 1000 cd/m$^2$ has dropped to half.

TABLE 2

(The Comp. is short for Compound)

| Material of HBL | Material of ETL | Driving Voltage (V) | Current Efficiency (Yield; cd/A) | CIE(y) | Half-life time (hours) |
|---|---|---|---|---|---|
| HB1 | ET1 | 5.1 | 18 | 0.53 | 350 |
| HB1 | Comp. 1 | 3.4 | 33 | 0.55 | 560 |
| HB1 | Comp. 2 | 3.6 | 30 | 0.56 | 500 |
| HB1 | Comp. 3 | 3.5 | 29 | 0.54 | 520 |
| HB1 | Comp. 5 | 3.7 | 30 | 0.55 | 510 |
| HB1 | Comp. 8 | 3.4 | 32 | 0.54 | 550 |
| HB1 | Comp. 20 | 3.6 | 31 | 0.55 | 540 |
| HB1 | Comp. 23 | 3.5 | 29 | 0.54 | 510 |
| HB1 | Comp. 50 | 4.2 | 27 | 0.55 | 430 |
| HB1 | Comp. 54 | 3.8 | 29 | 0.53 | 480 |
| HB1 | Comp. 65 | 4.1 | 27 | 0.56 | 450 |
| HB1 | Comp. 118 | 3.9 | 28 | 0.53 | 470 |
| HB1 | Comp. 201 | 4.5 | 24 | 0.53 | 390 |
| HB1 | Comp. 204 | 4.4 | 26 | 0.56 | 410 |
| HB1 | Comp. 206 | 4.6 | 23 | 0.54 | 380 |
| Comp. 180 | ET1 | 4.8 | 21 | 0.56 | 380 |
| Comp. 209 | ET1 | 4.7 | 24 | 0.54 | 380 |
| Comp. 212 | ET1 | 4.4 | 26 | 0.55 | 390 |
| Comp. 232 | ET1 | 4.9 | 20 | 0.53 | 370 |

In the above test reports of an organic EL device (see Table 1 and Table 2), the organic compound represented by formulas (1), (2), (3), (4), (5), (6), (7), (8), (9), (10) or (11) may be used as an emitting host material, an electron transfer or a hole blocking material for the organic EL device in the present invention displays better performance than a prior art organic EL material. More specifically, an organic compound represented by formulas (1), (2), (3), (4), (5), (6), (7), (8), (9), (10) or (11) for an organic EL device of the present invention is used as an emitting host material, an electron transfer material (ETM) or a hole blocking material (HBM) to collocate with an emitting guest material, such as D1, thereby lowering a driving voltage, or increasing a current efficiency or a half-life of the organic EL device.

Referring to Table 1 and Table 2, an organic compound, for example, compound 232, compound 212, compound 209, compound 180, compound 206, compound 204, compound 201, compound 118, compound 65, compound 54, compound 50, compound 23, compound 20, compound 8, compound 5, compound 1, compound 319, compound 320, compound 268, compound 254, compound 249, compound 228, compound 223, compound 221, compound 220, compound 104, compound 101, compound 99, compound 98, compound 95, compound 75 or compound 74, may be a emitting host material for emitting a light at a current efficiency greater than about 20 cd/A, for a half-life longer than about 370 hours, upon application of a driving voltage lower than about 4.9 V.

Referring to Table 2, being collocated with a material for HBL, such as HB1, an organic compound, for example, compound 206, compound 204, compound 201, compound 118, compound 65, compound 54, compound 50, compound 23, compound 20, compound 8, compound 5 or compound 1, may be a material of ETL for emitting a light at a current efficiency greater than about 23 cd/A, for a half-life longer than about 380 hours, upon application of a driving voltage lower than about 4.6 V.

Referring to Table 1, being collocated with an emitting guest material, such as D1, an organic compound, for example, compound 319, compound 268, compound 254, compound 249, compound 228, compound 223, compound 221, compound 220, compound 104, compound 101, compound 99, compound 98, compound 95, compound 75 or compound 74, may be an emitting host material for emitting a light for a half-life longer than about 370 hours, upon application of a driving voltage lower than about 4.9 V. Moreover, being collocated with an emitting guest material, such as D1, an organic compound, for example, compound 320, compound 319, compound 268, compound 254, compound 249, compound 228, compound 223, compound 221, compound 220, compound 104, compound 101, compound 99, compound 98, compound 95, compound 75 or compound 74, may be an emitting host material for emitting a light at a current efficiency greater than about 20 cd/A.

Referring to Table 1 and Table 2, a preferable organic compound may be, for example, compound 74. Compound 74 may be an emitting host material for emitting a light at a current efficiency of about 36 cd/A. Another preferable organic compound may be, for example, compound 98. Compound 98 may be an emitting host material for emitting a light for a half-life of about 780 hours, upon application of a driving voltage of about 3.0 V.

To sum up, the present invention discloses an organic compound, which can be used as the host, electron transfer and hole blocking material of the light emitting layer in organic EL devices. The mentioned organic compound is represented by the following formula (1):

formula (1)

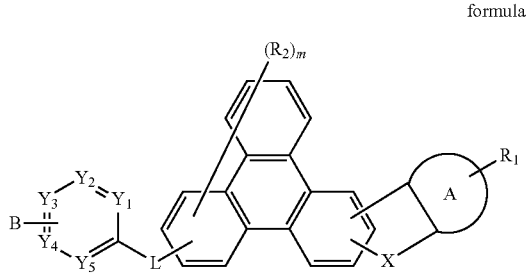

wherein X represents a divalent bridge selected from the group consisting of O, S, Se, $NR_3$ and $SiR_4R_5$; m represents an integer of 0 to 8; ring A represents a phenyl group or a fused ring hydrocarbon unit with two to four rings; L represents a single bond, a substituted or unsubstituted divalent arylene group having 6 to 30 ring carbon atoms, or a substituted or unsubstituted divalent heteroarylene group having 6 to 30 ring carbon atoms; $R_1$ to $R_5$ are independently selected from the group consisting of a hydrogen atom, a substituted or unsubstituted alkyl group having 1 to 20 carbon atoms, a substituted or unsubstituted aryl group having 6 to 30 carbon atoms, a substituted or unsubstituted aralkyl group having 6 to 30 carbon atoms and a substituted or unsubstituted heteroaryl group having 3 to 30 carbon atoms; $Y_1$ to $Y_5$ independently represent a nitrogen atom or $CR_6$; $R_6$ represents a hydrogen atom, a substituted or unsubstituted phenylene group having 6 to 30 ring carbon atoms, or a bond linked to B. B may be represented by the following formula (2):

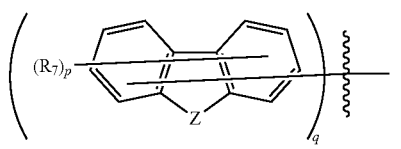

formula (2)

wherein q represents an integer of 0 to 3; p represents an integer of 0 to 7; Z represents O, S, or $NR_8$, $R_8$ represents a hydrogen atom, a substituted or unsubstituted phenyl group, a substituted or unsubstituted carbazole group, or a bond linked to formula (1), $R_7$ has the same definition as $R_1$.

Obviously, many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. An organic compound represented by the following formula (1):

formula (1)

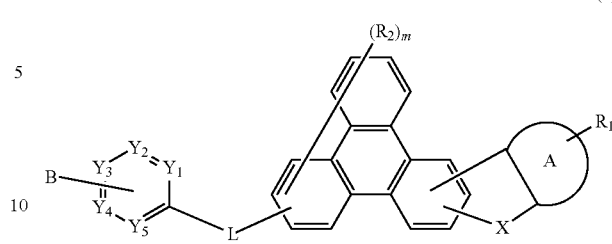

wherein X represents a divalent bridge selected from the group consisting of O, S, Se, $NR_3$ and $SiR_4R_5$; m represents an integer of 0 to 8; fused ring A selected from the group consisting of a naphthyl group, an anthracenyl group, a phenanthrenyl group, a pyrenyl group and a chrysenyl group; L represents a single bond, a substituted or unsubstituted divalent arylene group having 6 to 30 ring carbon atoms, or a substituted or unsubstituted divalent heteroarylene group having 6 to 30 ring carbon atoms; $R_1$ to $R_5$ are independently selected from the group consisting of a hydrogen atom, a substituted or unsubstituted alkyl group having 1 to 20 carbon atoms, a substituted or unsubstituted aryl group having 6 to 30 carbon atoms, a substituted or unsubstituted aralkyl group having 6 to 30 carbon atoms and a substituted or unsubstituted heteroaryl group having 3 to 30 carbon atoms; $Y_1$ to $Y_5$ independently represent a nitrogen atom or $CR_6$; $R_6$ represents a hydrogen atom, a substituted or unsubstituted phenylene group having 6 to 30 ring carbon atoms, or a bond linked to B; B is represented by the following formula (2):

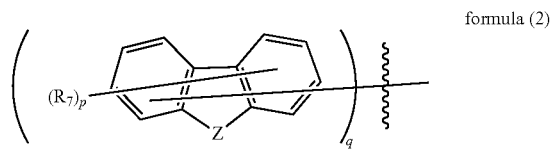

formula (2)

wherein q represents an integer of 0 to 3; p represents an integer of 0 to 7; Z represents O, S, or $NR_8$, $R_8$ represents a hydrogen atom, a substituted or unsubstituted phenyl group, a substituted or unsubstituted carbazole group, or a bond linked to formula (1), $R_7$ has the same definition as $R_1$.

2. The organic compound according to claim 1, wherein L is selected from the group consisting of the following formulas:

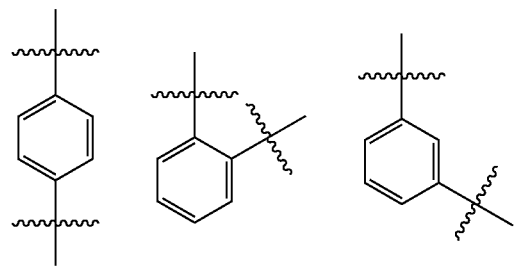

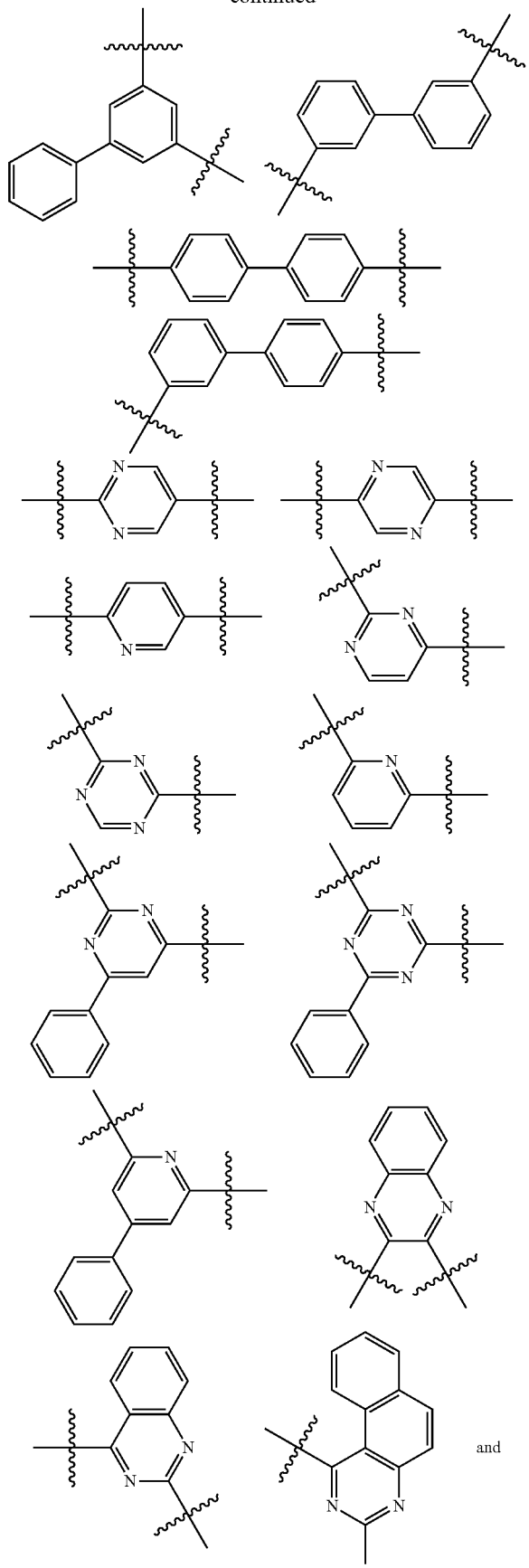

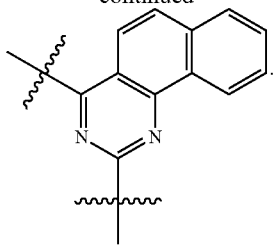

3. The organic compound according to claim 1, wherein the organic compound is represented by one of the following formula (3) to (4):

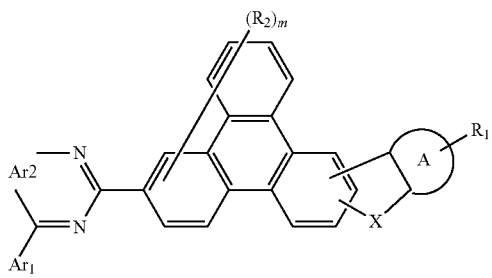

formula (3)

formula (4)

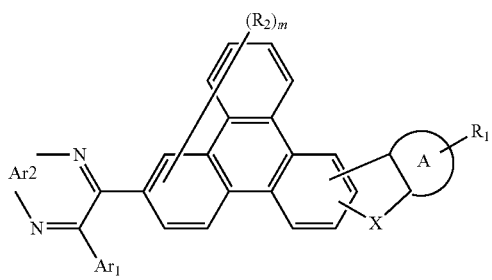

wherein Ar1 represents a phenyl group; and Ar2 represents a fused phenyl group or a fused ring hydrocarbon unit with two rings.

4. The organic compound according to claim 3, wherein the organic compound represented by the formula (3) is also represented by the following formula (6):

formula (6)

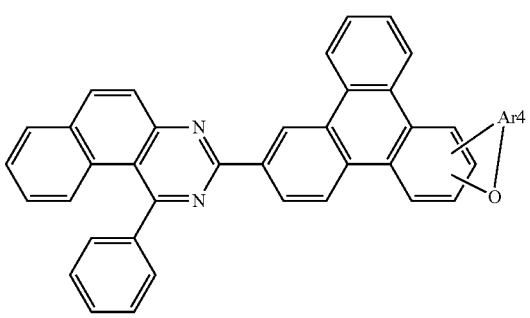

wherein Ar4 is selected from the group consisting of a naphthyl group, an anthracenyl group, a phenanthrenyl group, a pyrenyl group and a chrysenyl group.

5. The organic compound according to claim 3, wherein the organic compound represented by the formula (3) is represented by the following formula (7):

formula (7)

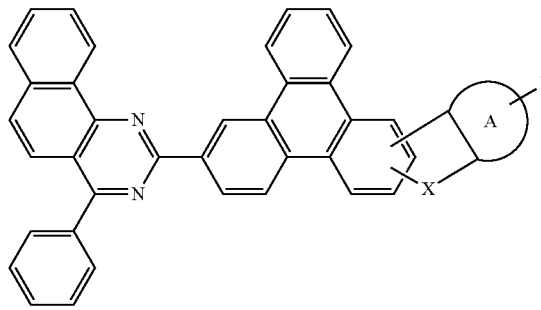

wherein X represents a divalent bridge selected from the group consisting of O, S and NR₃; and R₁ represents a hydrogen atom or an aryl group.

6. The organic compound according to claim 1, wherein the organic compound is represented by the following formula (8):

formula (8)

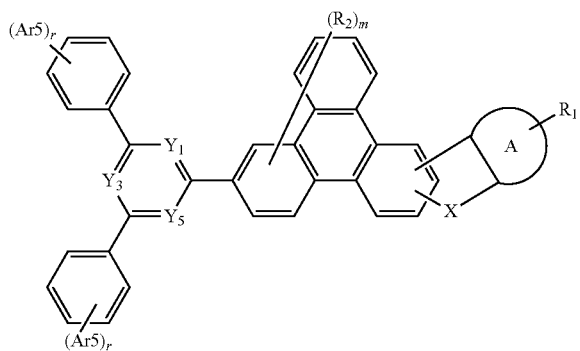

wherein Ar5 each represents a substituted or unsubstituted phenyl group; r represents an integer of 0 to 2; $Y_1$ and $Y_5$ are the same and each represents a nitrogen atom or $CR_6$; and $Y_3$ represents a nitrogen atom or $CR_6$.

7. The organic compound according to claim 6, wherein the organic compound is represented by the following formula (9):

formula (9)

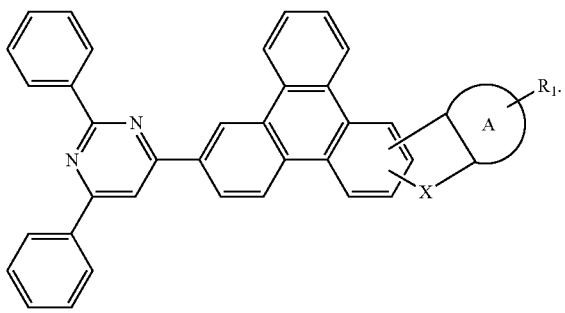

8. The organic compound according to claim 1, wherein the organic compound is represented by the following formula (11):

formula (11)

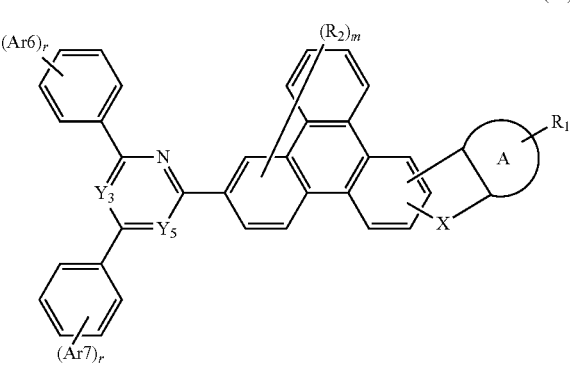

wherein Ar6 and Ar7 independently represent a nitrogen-substituted or unsubstituted phenyl group; r represents an integer of 0 to 1; $Y_3$ and $Y_5$ independently represent a nitrogen atom or $CR_6$; X represents a divalent bridge selected from the group consisting of O, S, Se, NR₃ and SiR₄R₅; R₄ and R₅ independently represent a nitrogen-substituted or unsubstituted phenyl group; and R₆ represents a hydrogen atom.

9. The organic compound according to claim 8, wherein m represents an integer of 0 or 1.

10. An organic compound represented by one of the following compounds:

Compound 2

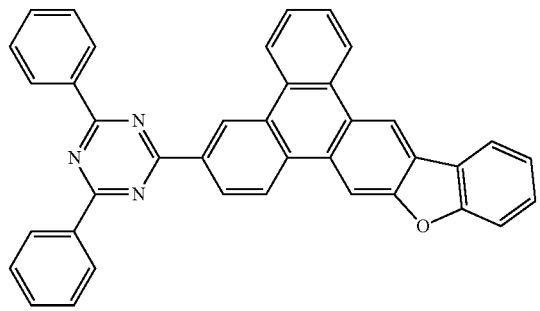

Compound 3

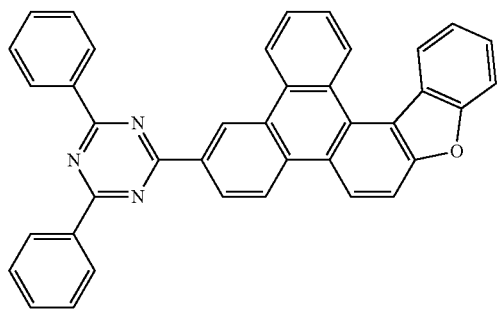

Compound 5
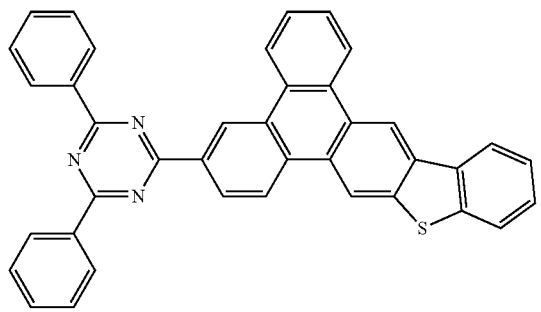
Compound 6
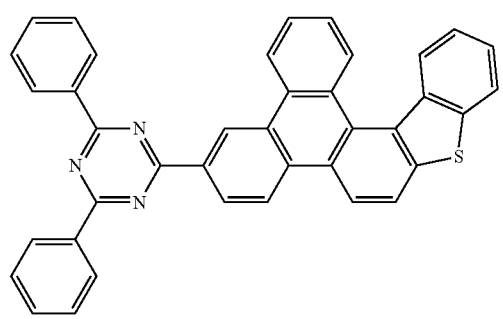
Compound 7
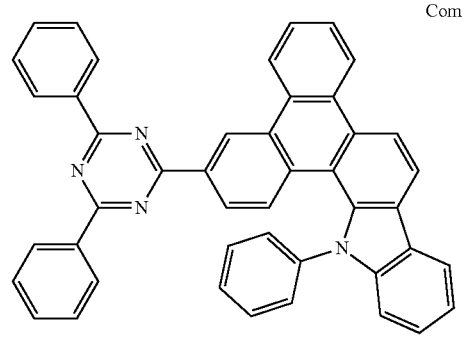
Compound 10
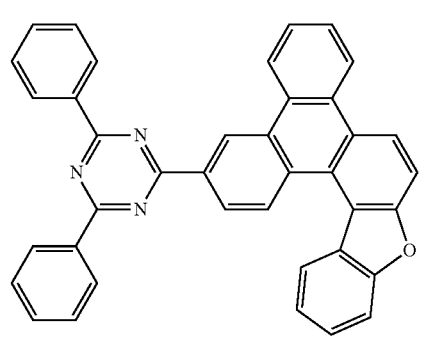
Compound 11
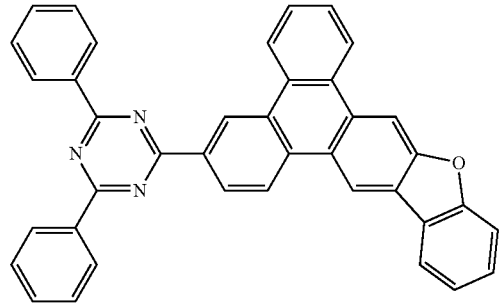
Compound 12
Compound 13
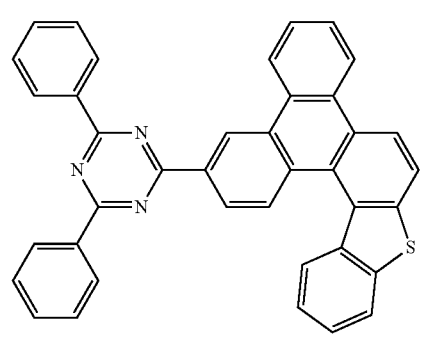
Compound 14
Compound 15
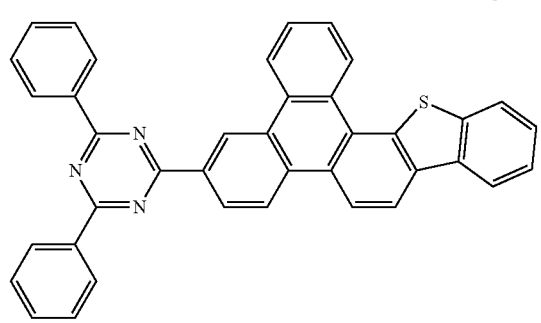

Compound 16
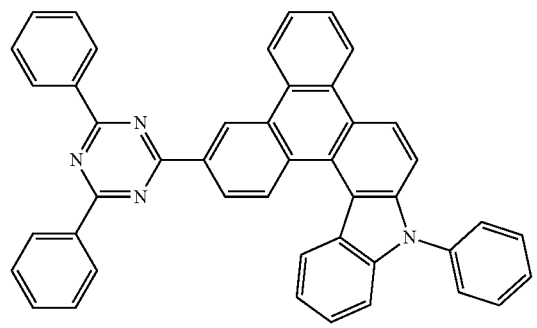
Compound 18
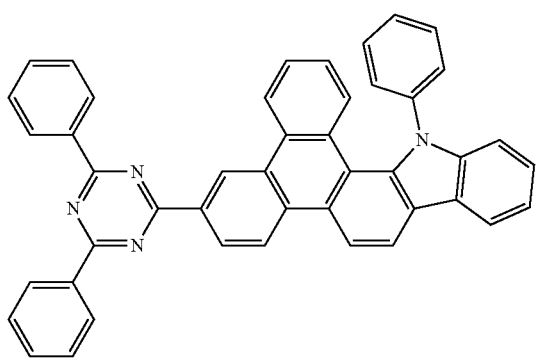
Compound 20
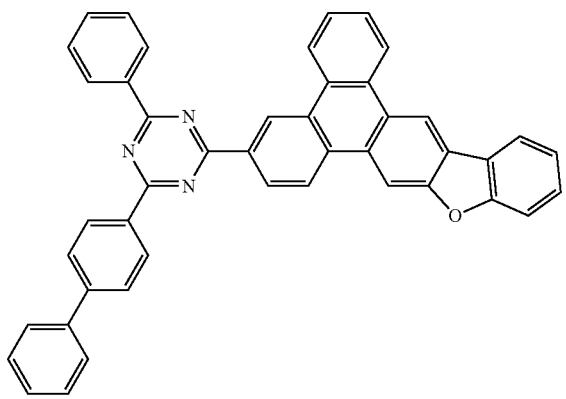
Compound 21
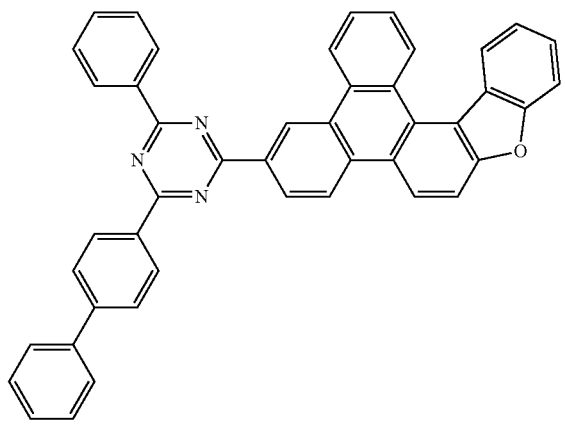
Compound 23
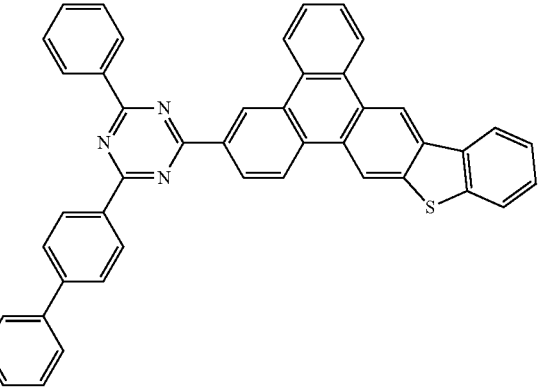
Compound 24
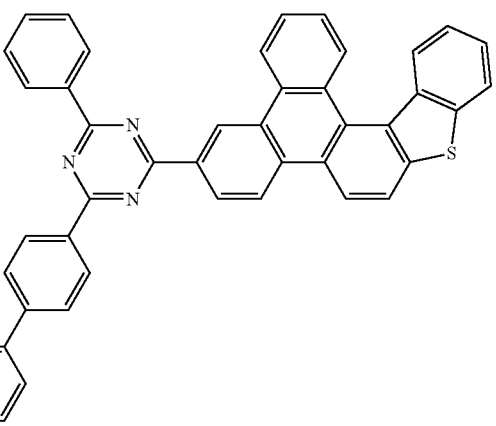
Compound 25
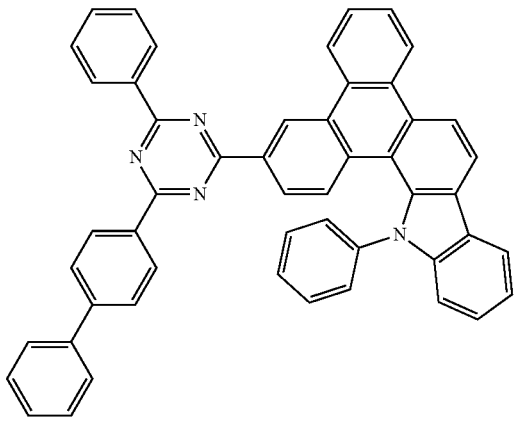

Compound 26
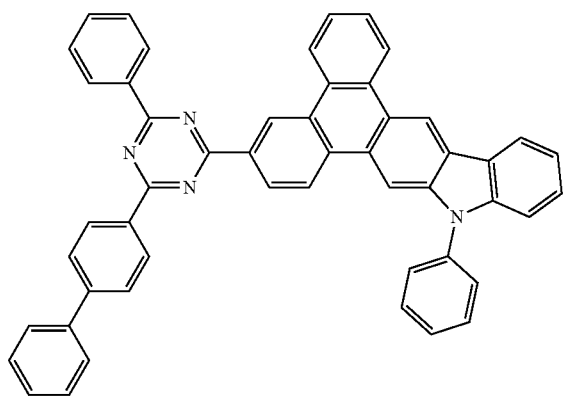
Compound 27
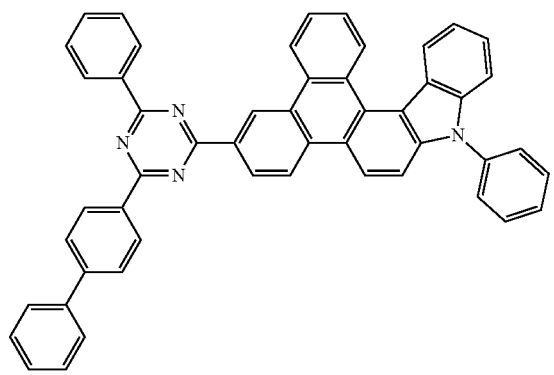
Compound 28
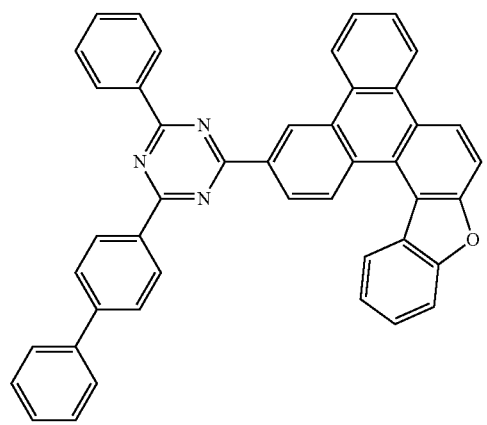
Compound 29
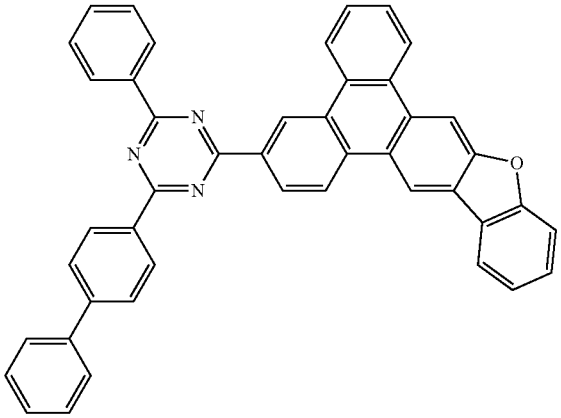
Compound 30
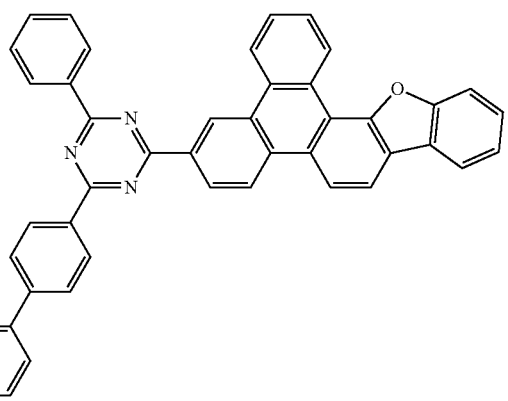
Compound 31
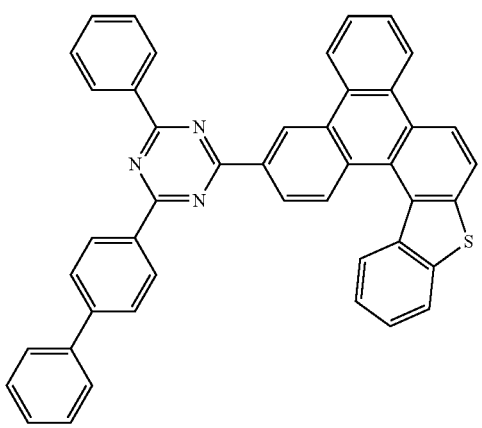

Compound 32
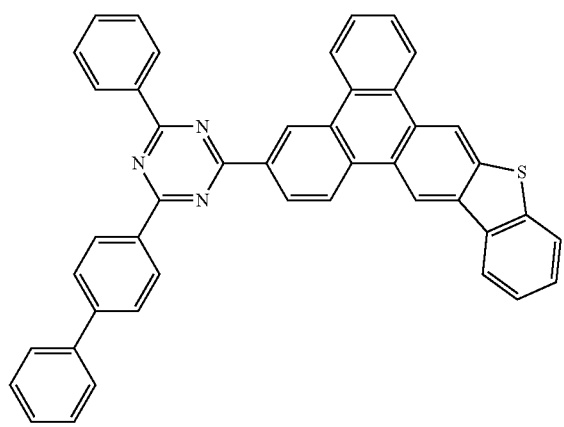
Compound 33
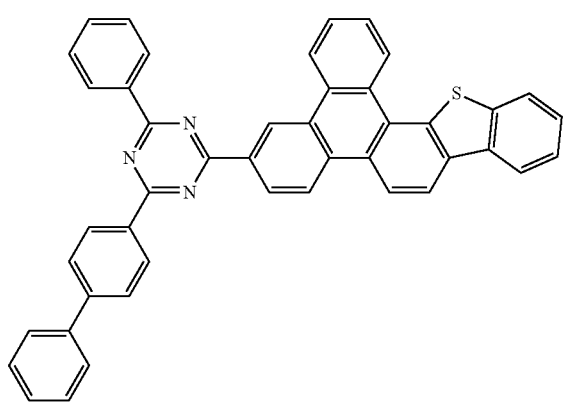
Compound 34
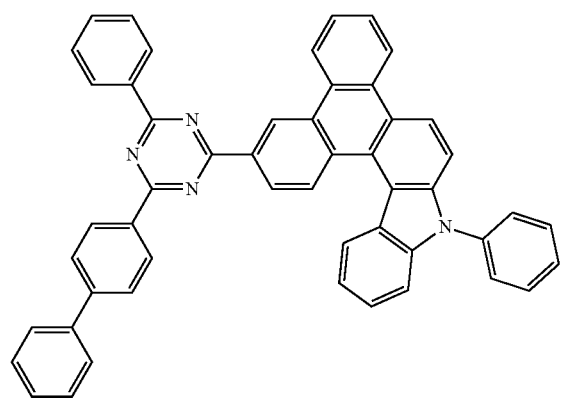
Compound 35
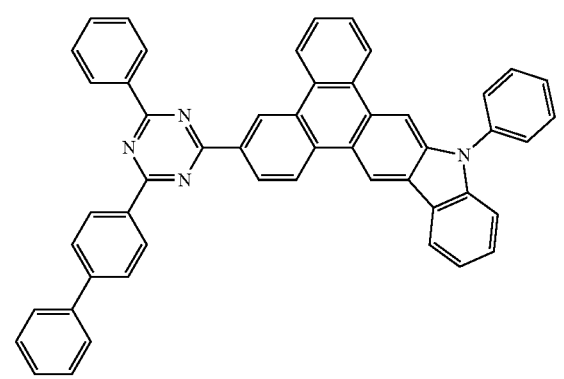
Compound 36
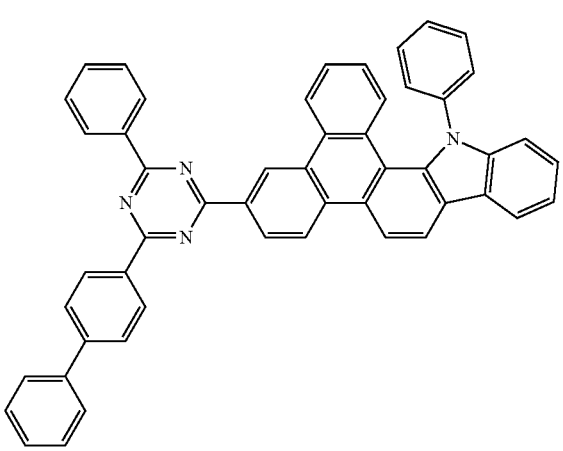
Compound 38
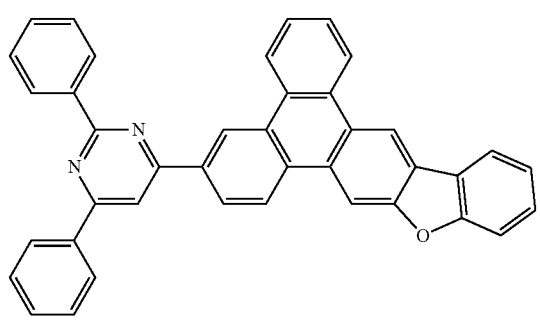
Comound 39
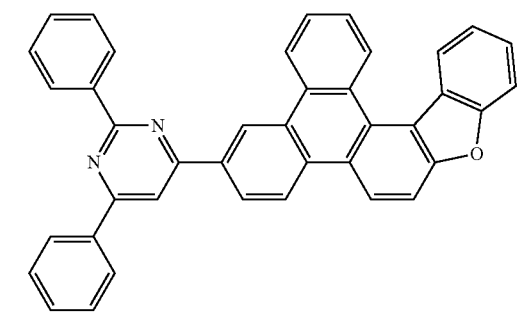
Compound 41
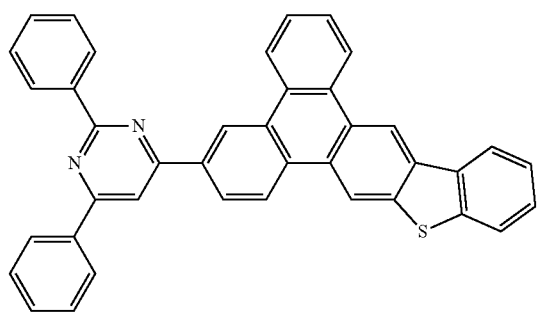

Compound 42
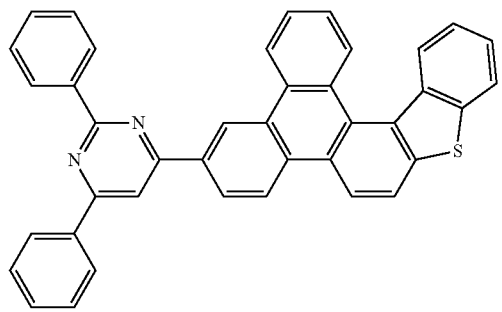
Compound 43
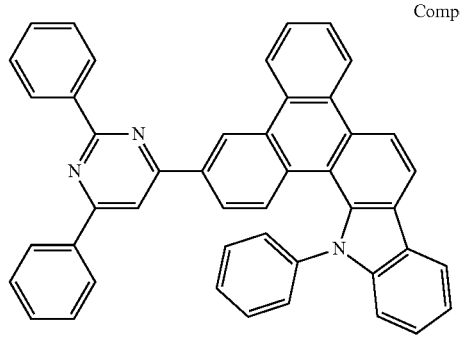
Compound 44
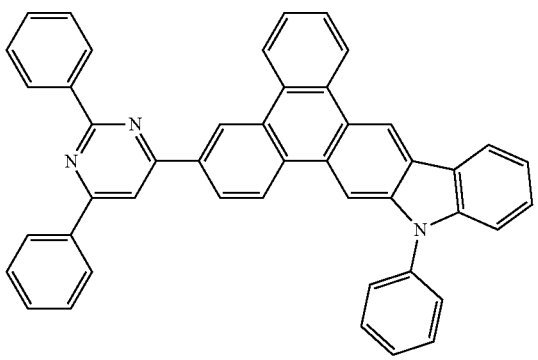
Compound 45
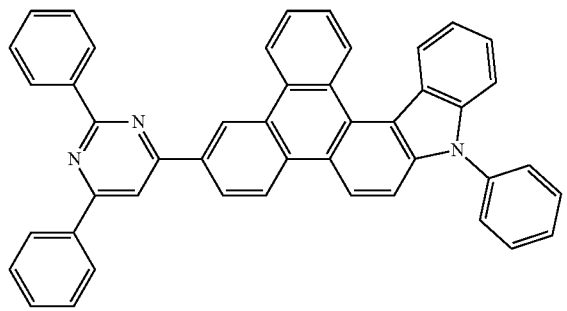
Compound 46
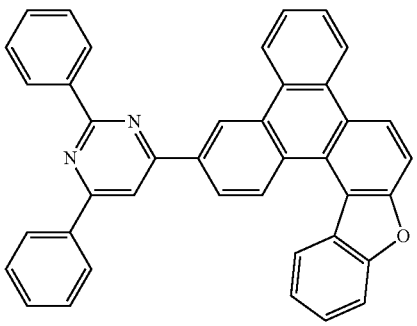
Compound 47
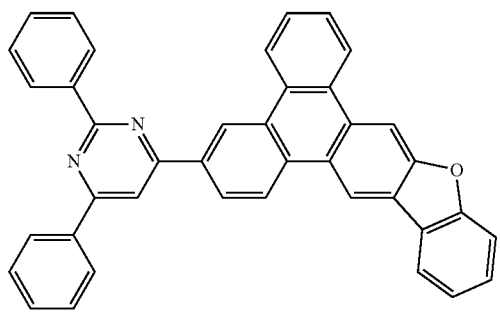
Compound 48
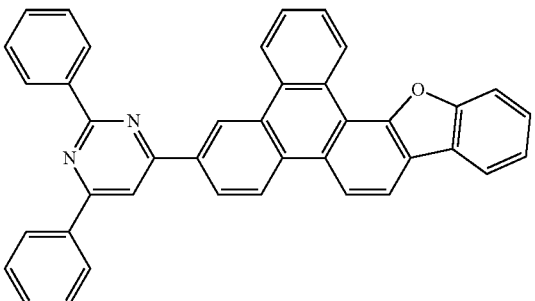
Compound 49
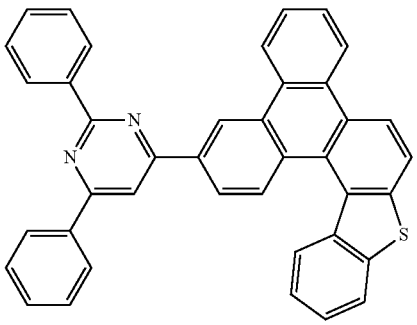
Compound 50
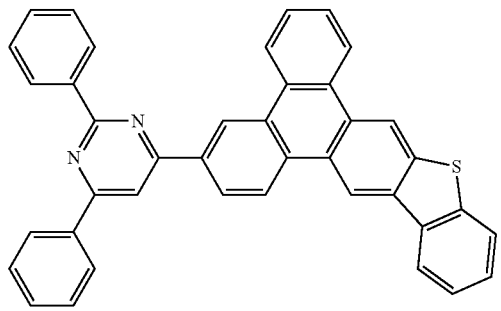

Compound 51
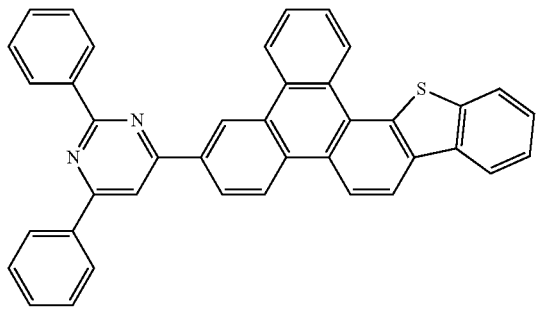
Compound 56
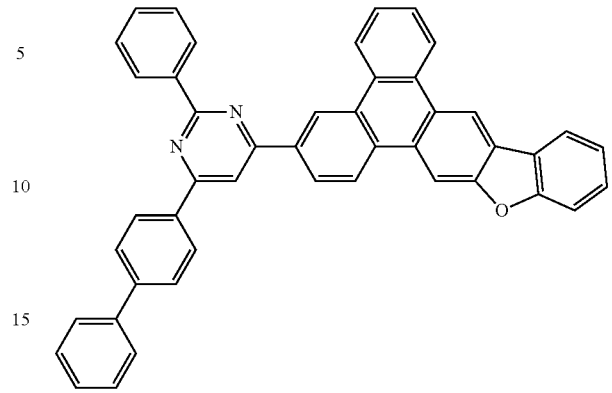
Compound 52
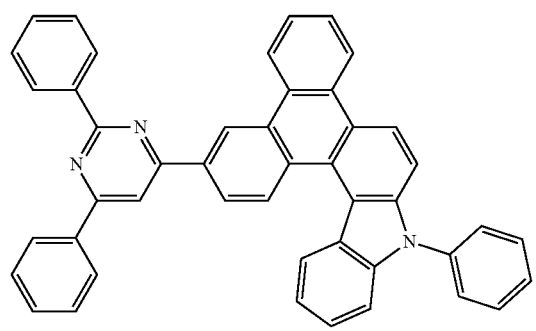
Compound 57
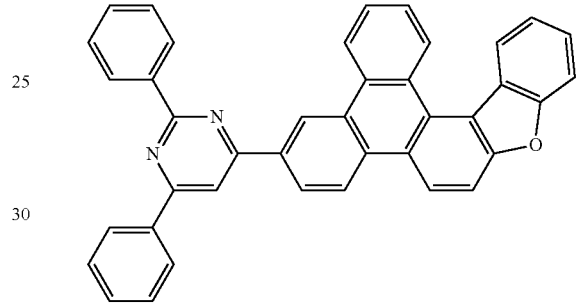
Compound 53
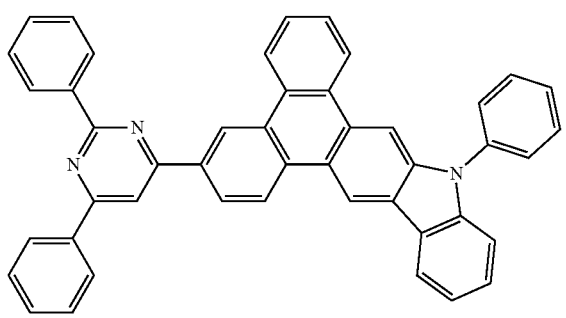
Compound 59
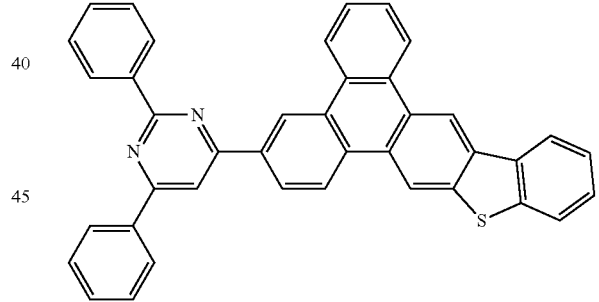
Compound 54
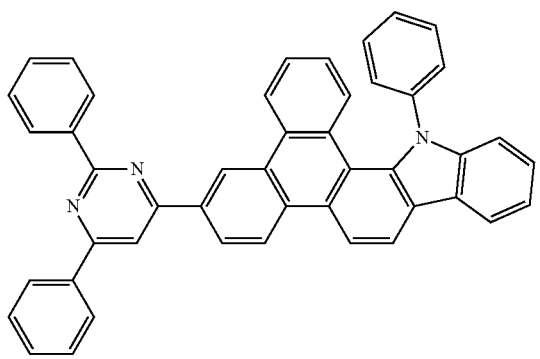
Compound 60
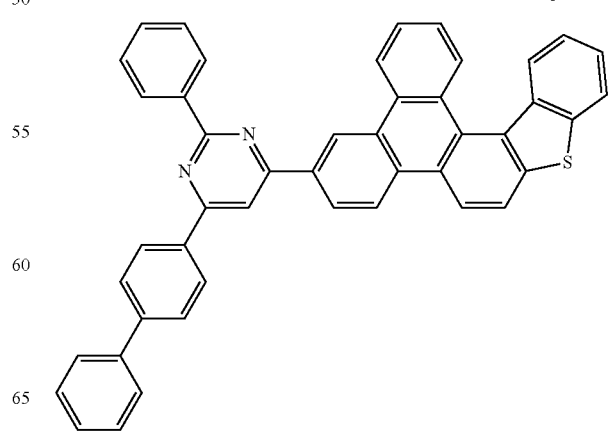

Compound 61
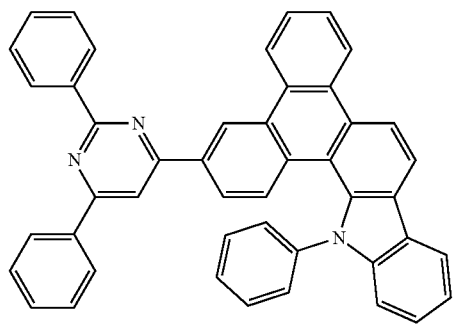
Compound 62
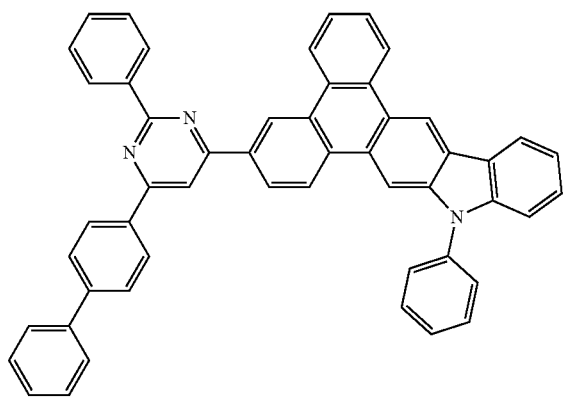
Compound 63
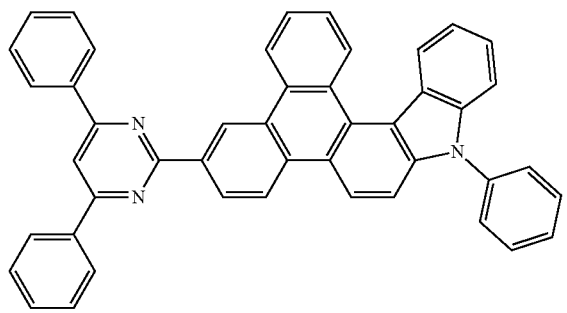
Compound 64
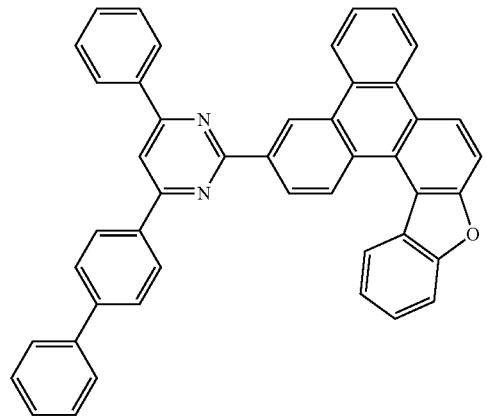
Compound 65
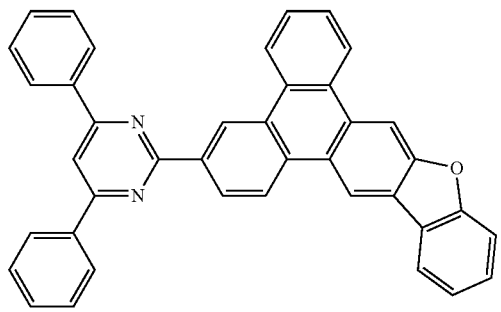
Compound 66
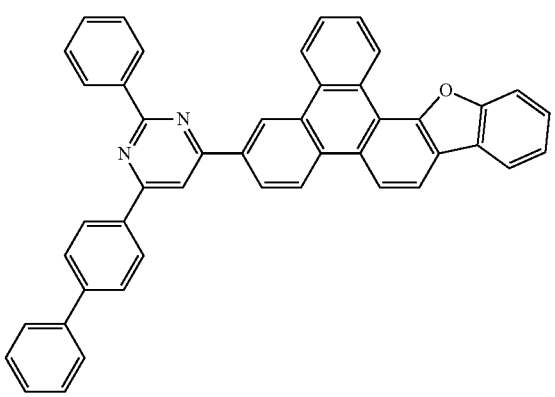
Compound 67
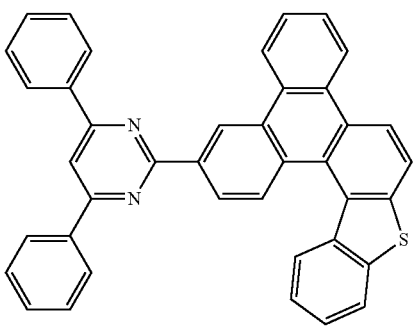
Compound 68
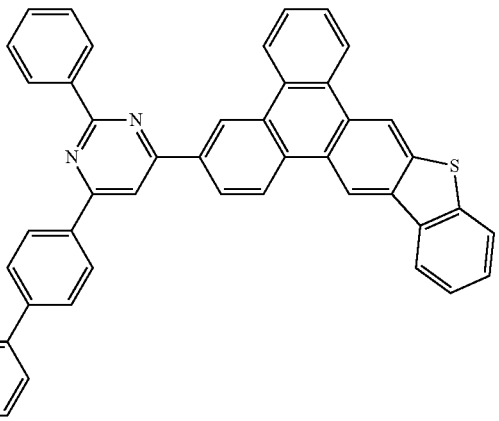

Compound 69
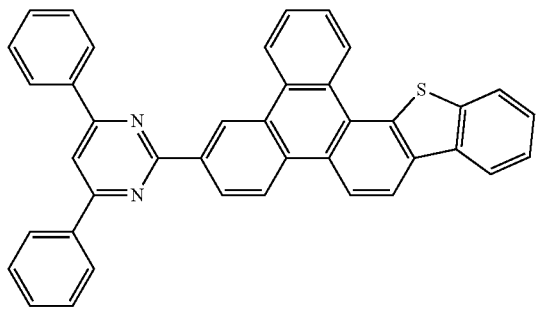
Compound 70
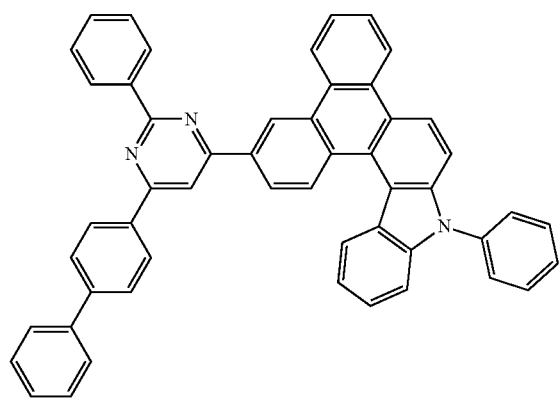
Compound 72
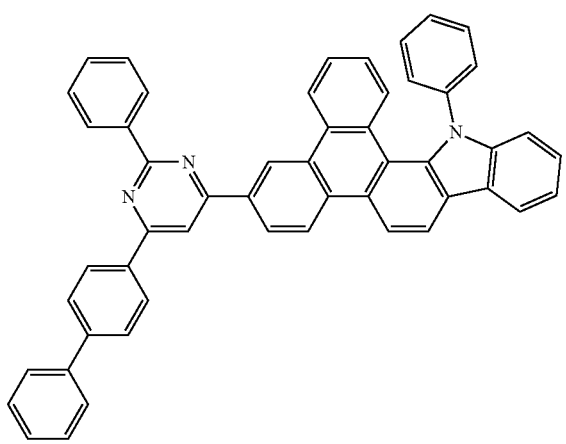
Compound 73
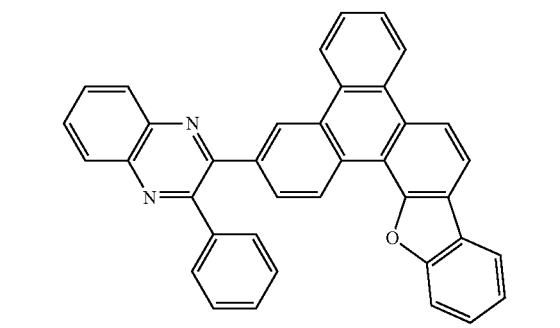
Compound 74
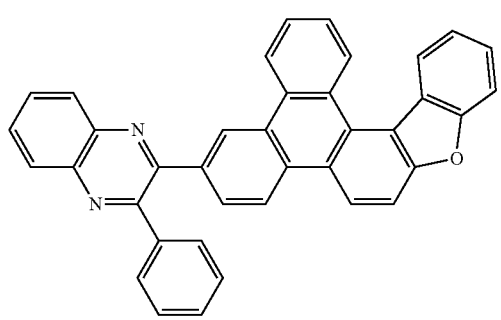
Compound 75
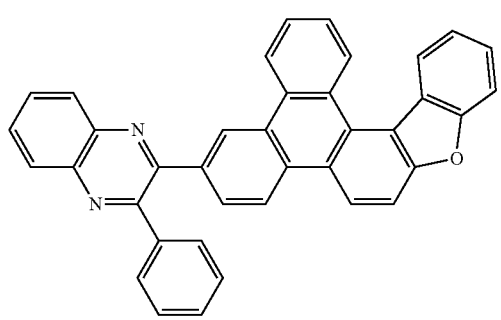
Compound 77
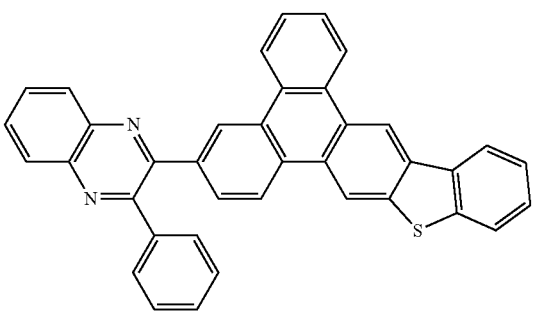
Compound 78
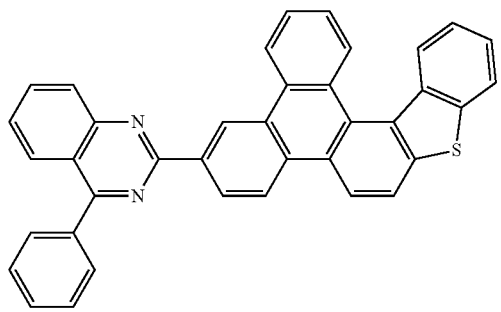

Compound 79
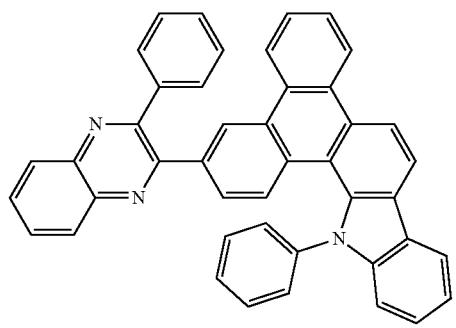
Compound 80
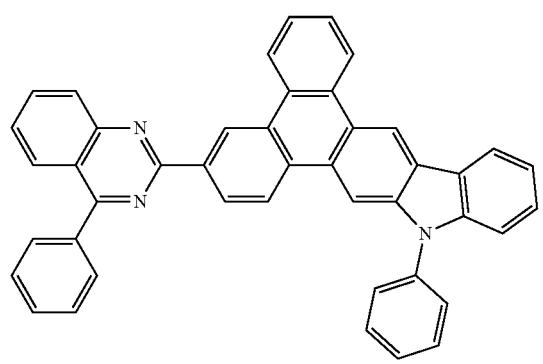
Compound 81
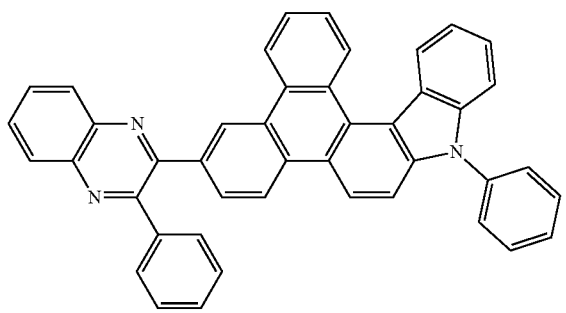
Compound 82
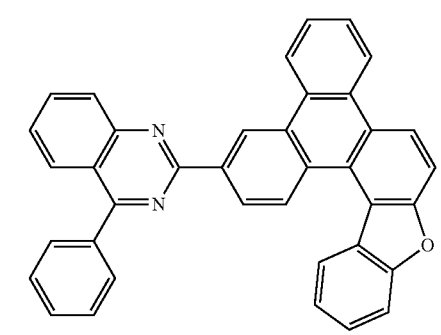
Compound 83
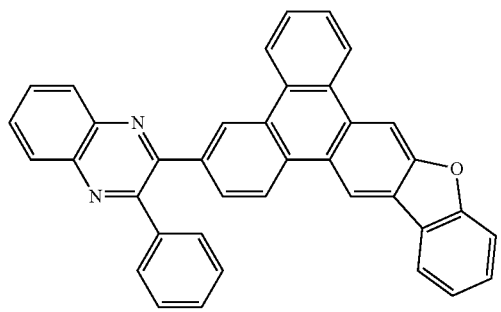
Compound 84
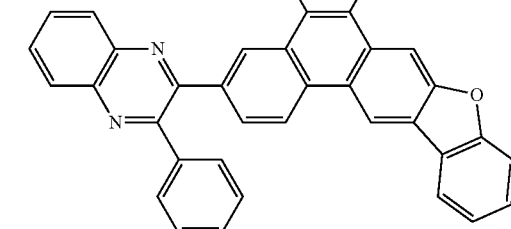
Compound 85
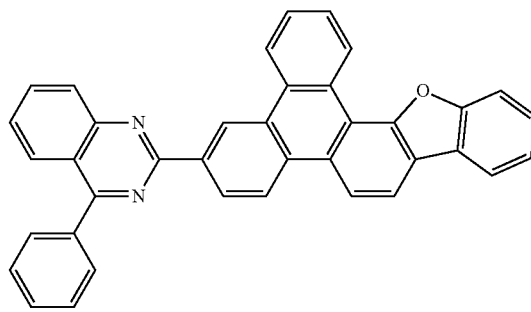
Compound 86
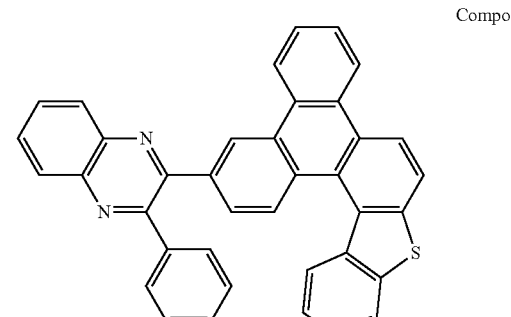
Compound 87
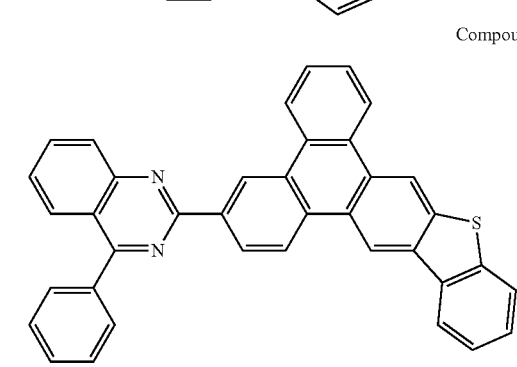

Compound 88
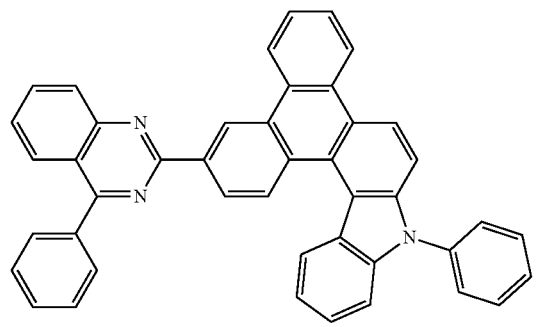
Compound 93
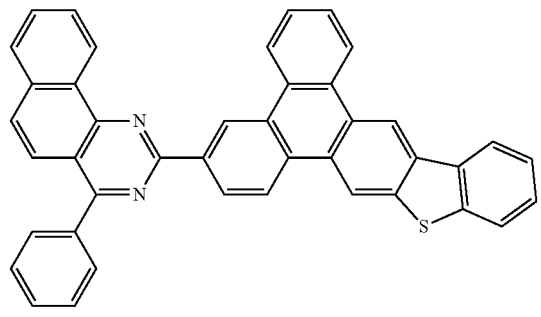
Compound 89
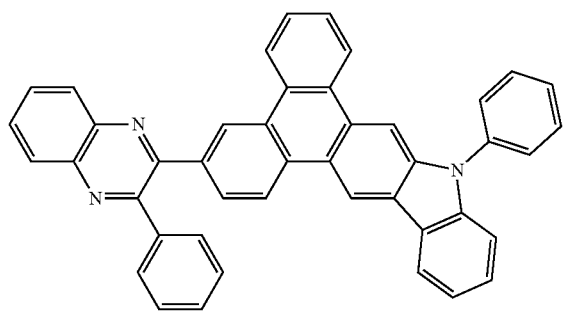
Compound 94
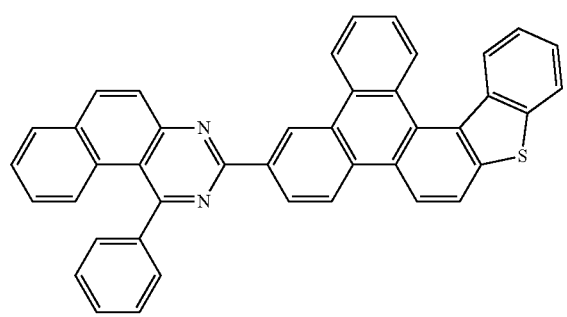
Compound 90
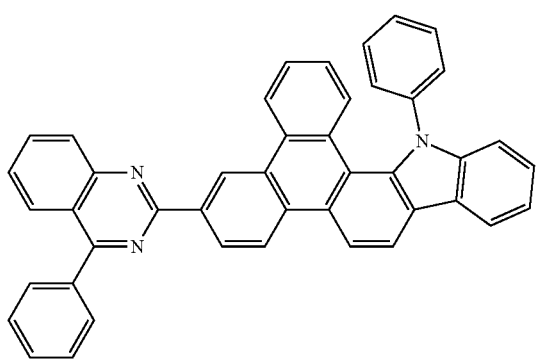
Compound 95
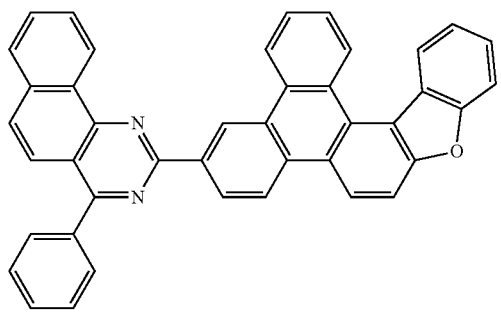
Compound 92
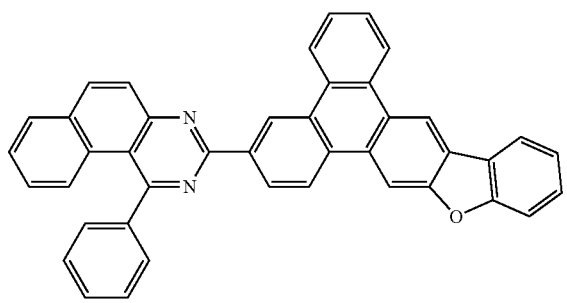
Compound 97
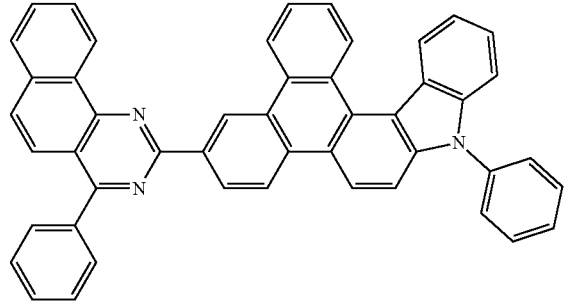

Compound 98
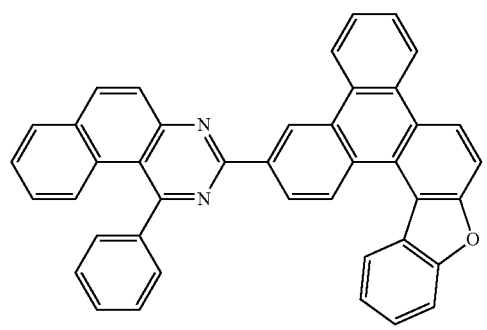
Compound 102
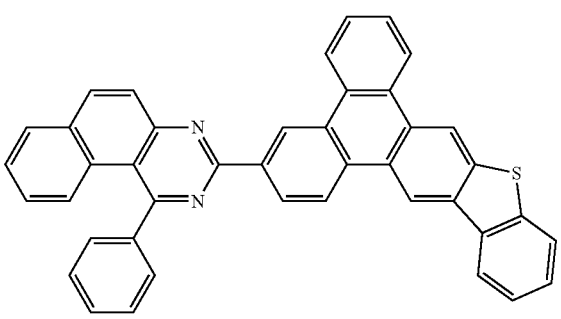
Compound 99
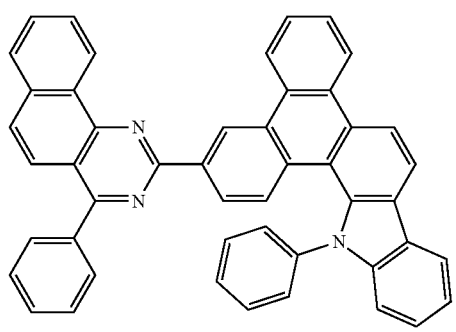
Compound 103
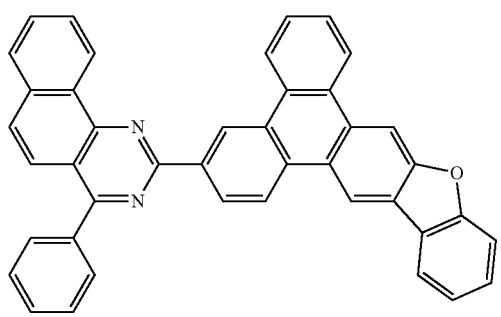
Compound 100
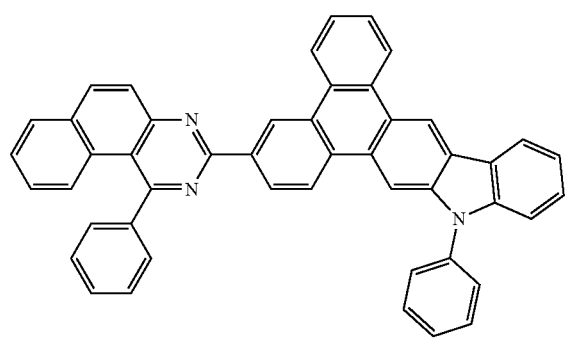
Compound 104
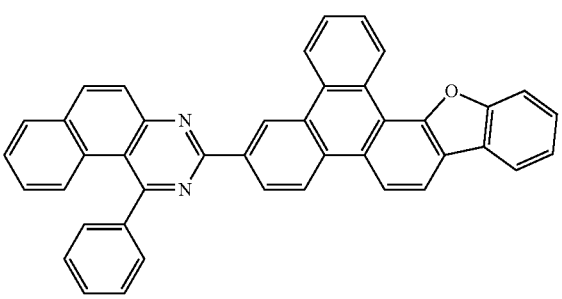
Compound 101
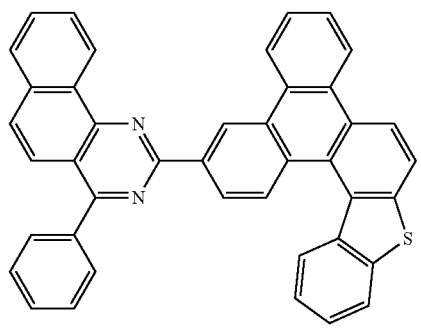
Compound 105
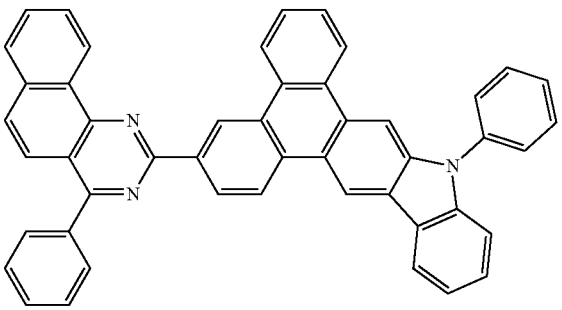

Compound 106
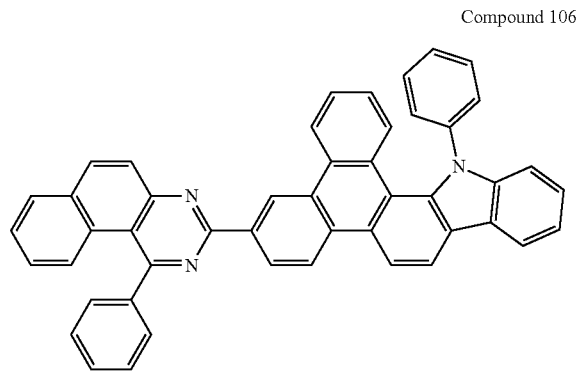
Compound 107
Compound 108
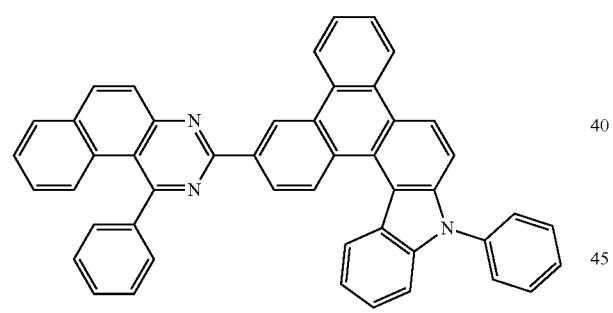
Compound 109
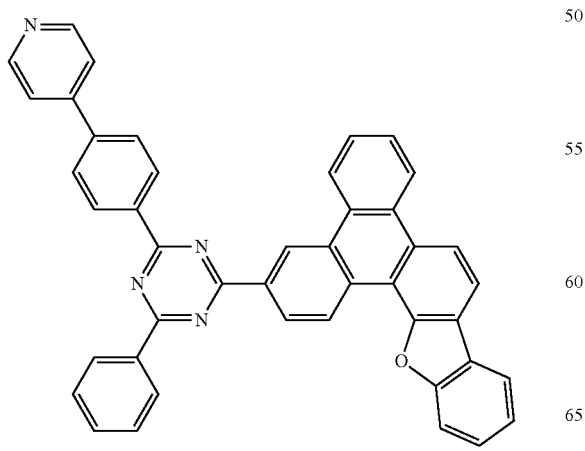
Compound 110
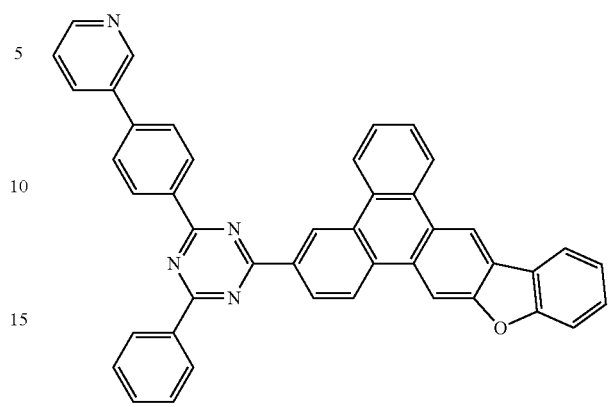
Compound 111
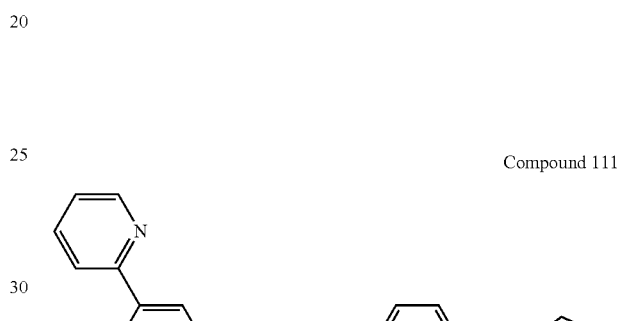
Compound 112
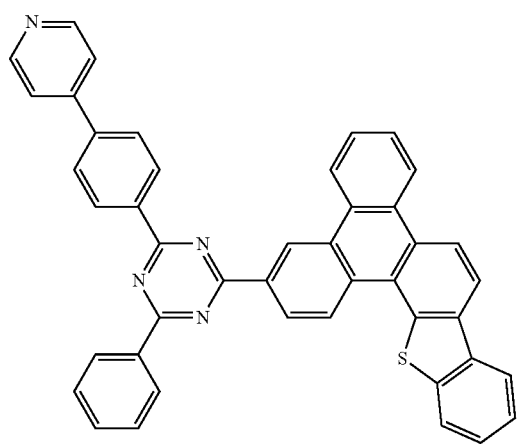

Compound 113
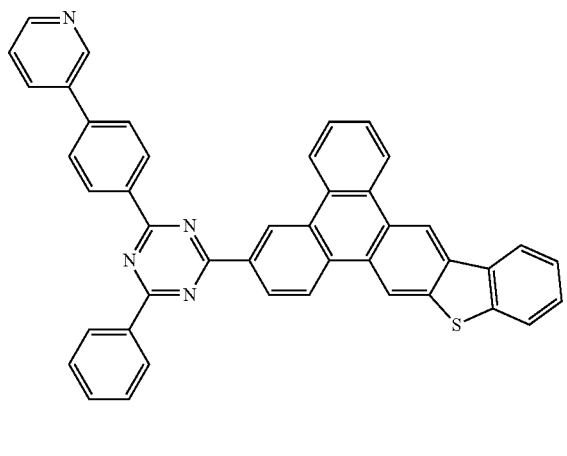
Compound 116
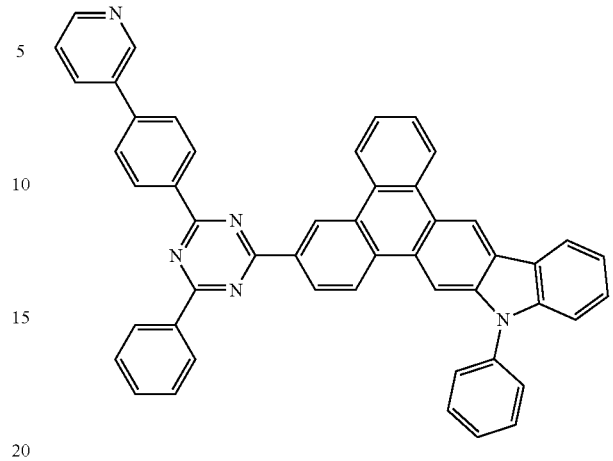
Compound 114
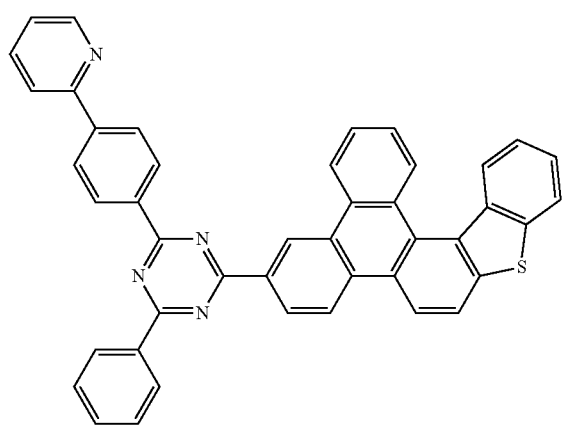
Compound 117
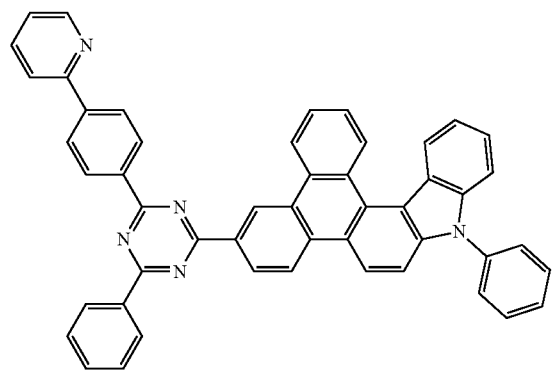
Compound 115
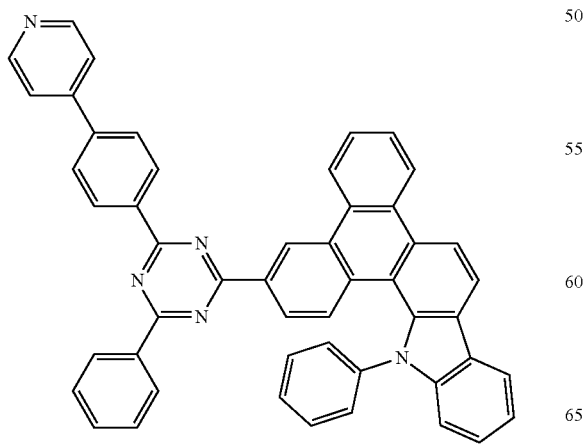
Compound 118
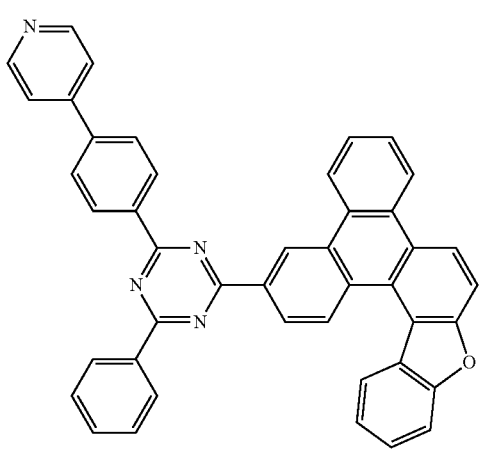

Compound 119
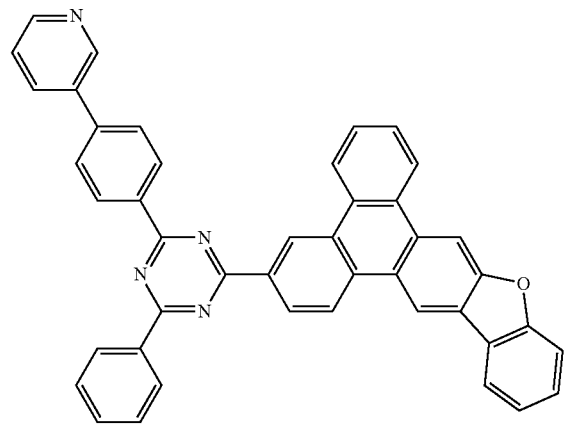
Compound 122
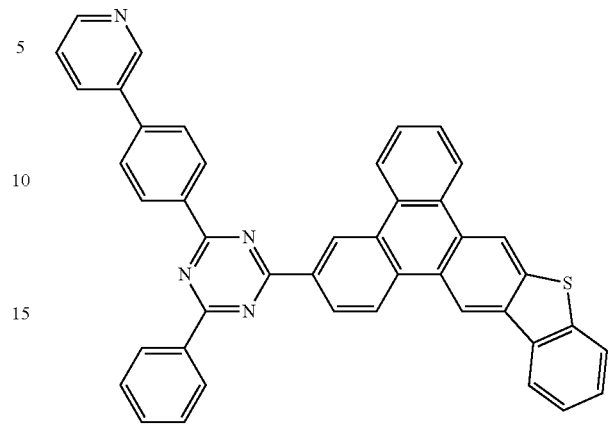
Compound 120
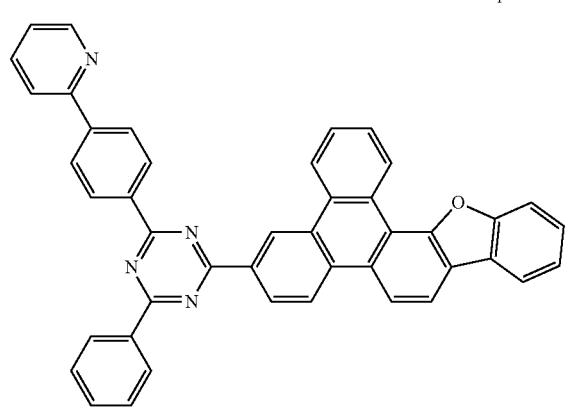
Compound 123
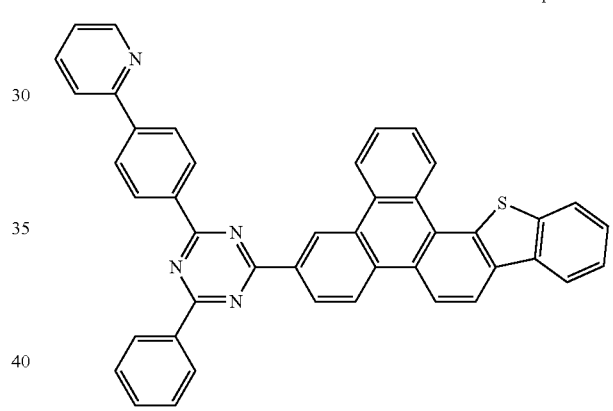
Compound 121
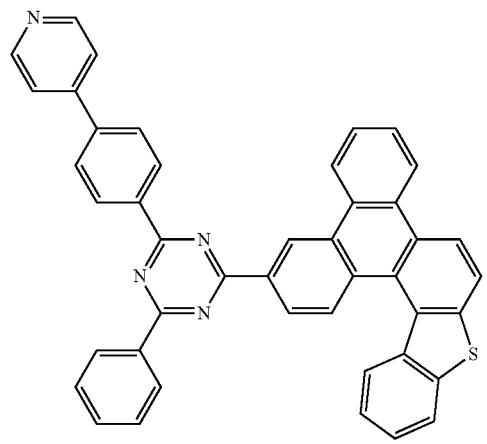
Comound 124
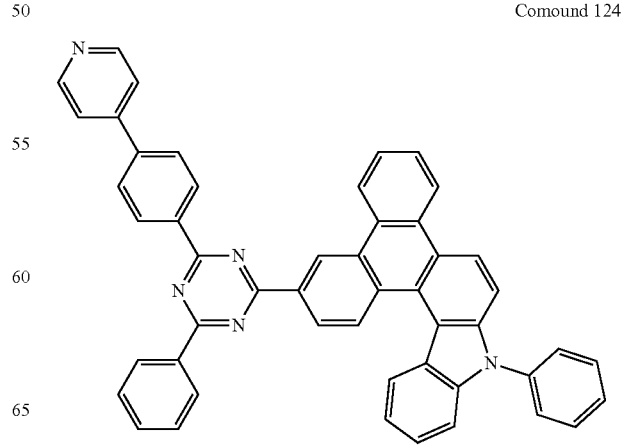

Compound 125
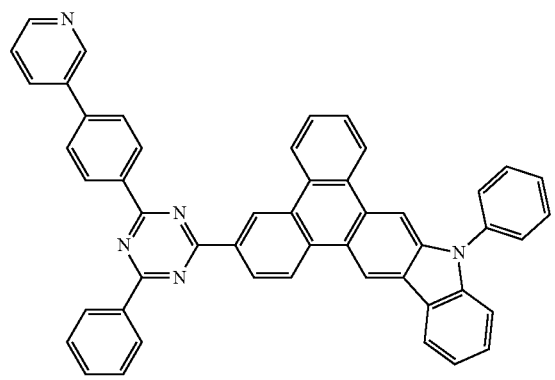
Compound 126
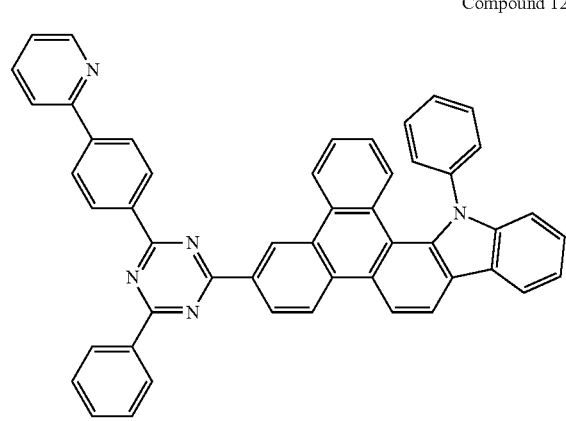
Compound 127
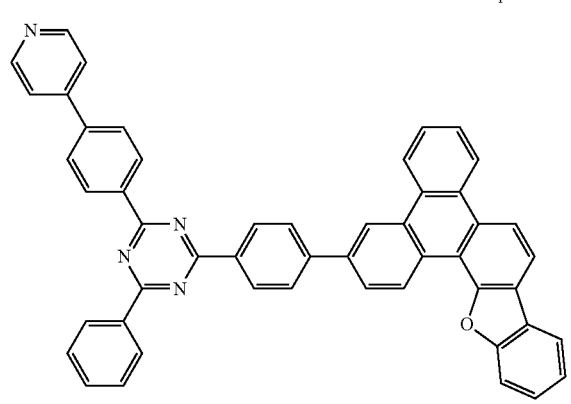
Compound 128
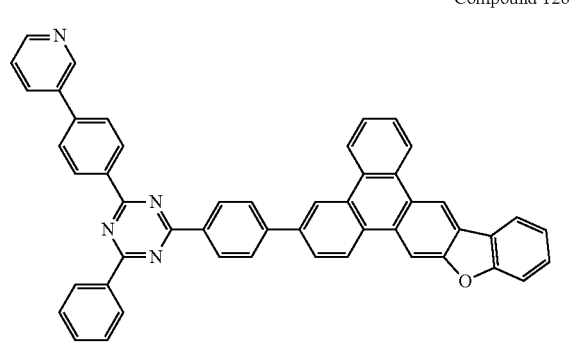
Compound 129
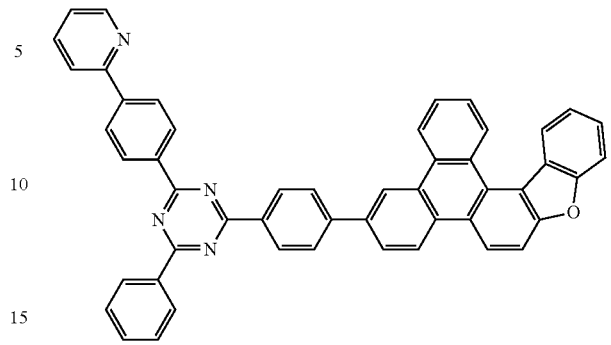
Compound 130
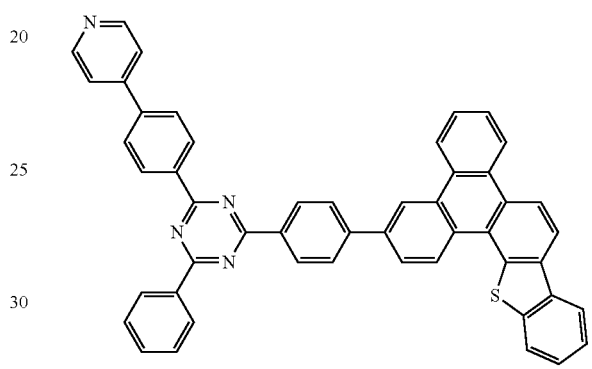
Compound 131
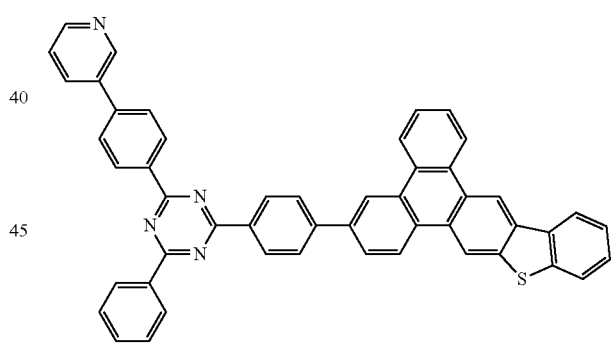
Compound 132
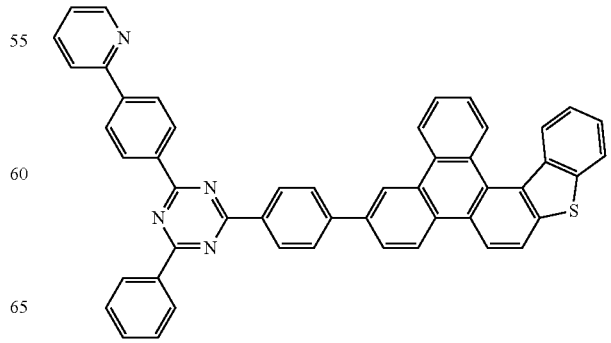

Compound 133
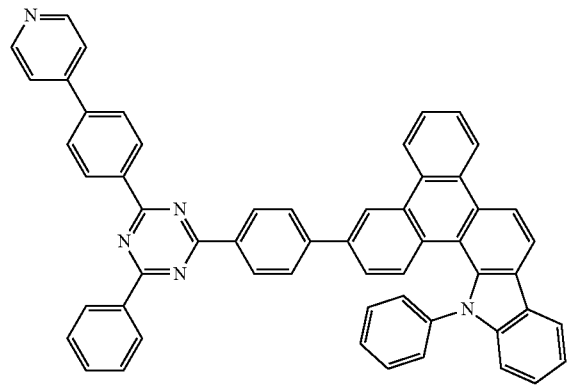
Compound 134
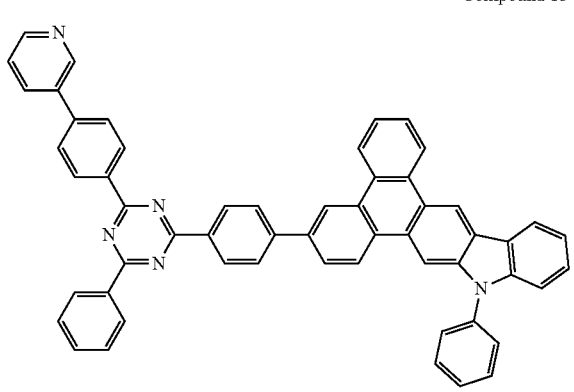
Compound 135
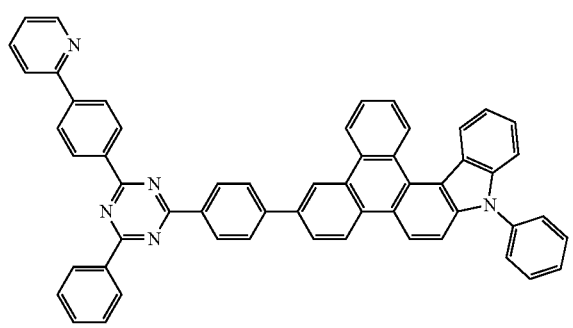
Compound 136
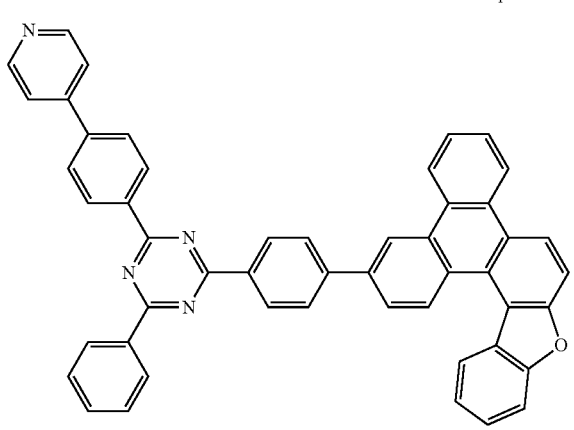
Compound 137
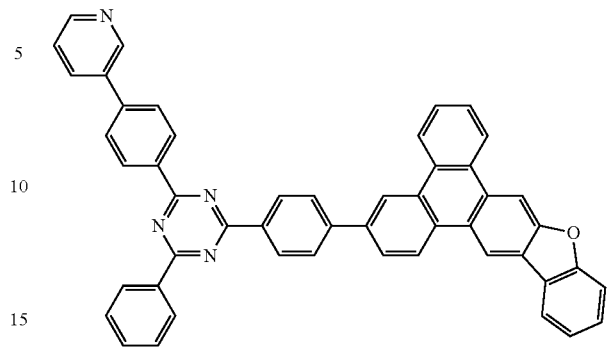
Compound 138
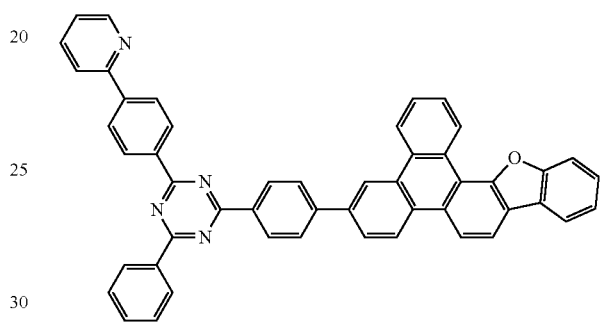
Compound 139
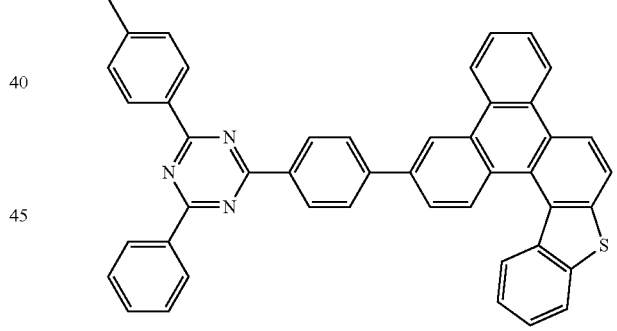
Compound 140

Compound 141
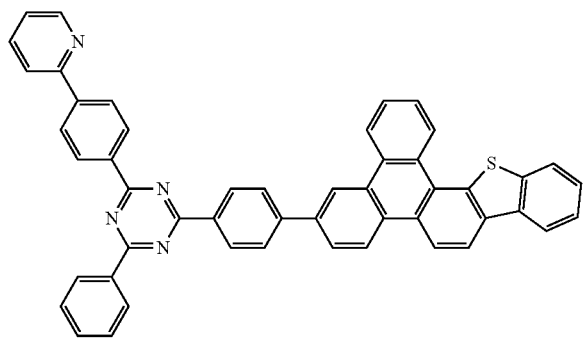
Compound 142
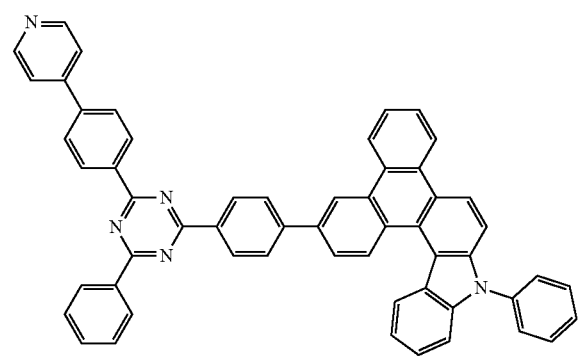
Compound 143
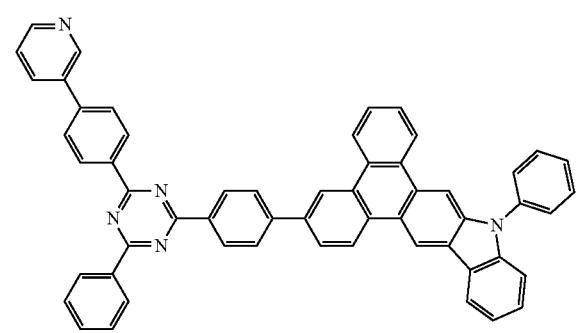
Compound 144
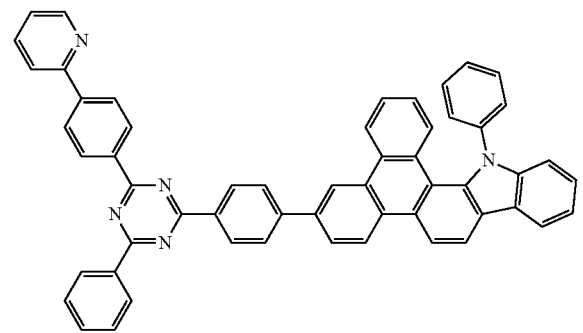
Compound 145
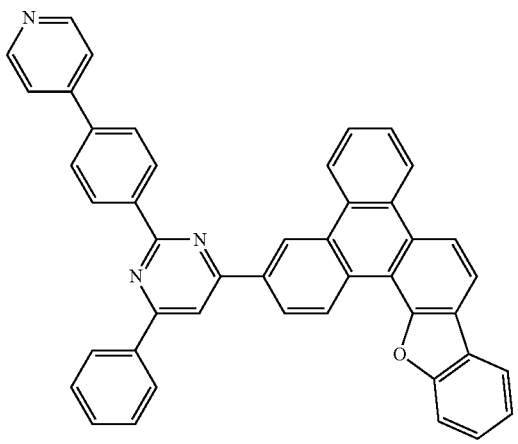
Compound 146
Compound 147
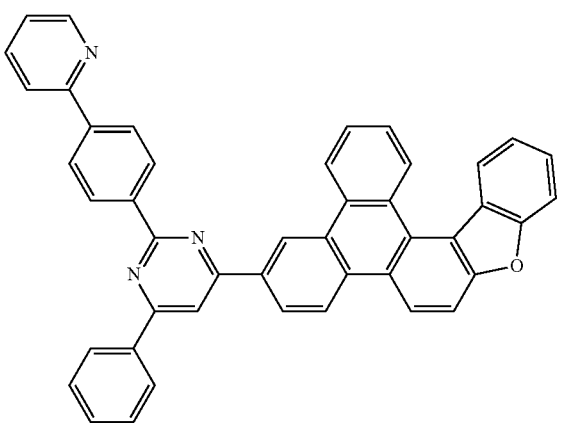

Compound 148
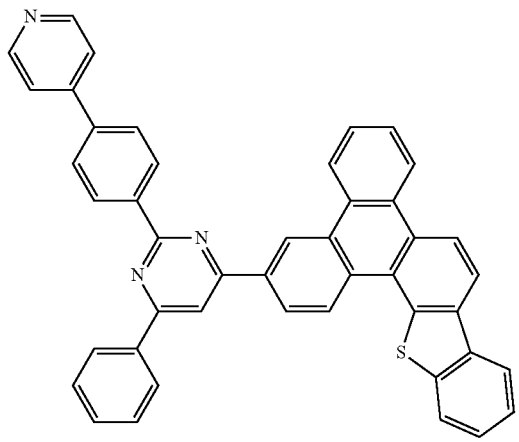
Compound 151
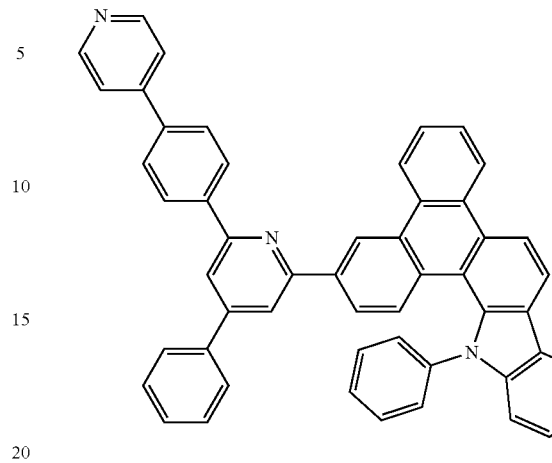
Compound 149
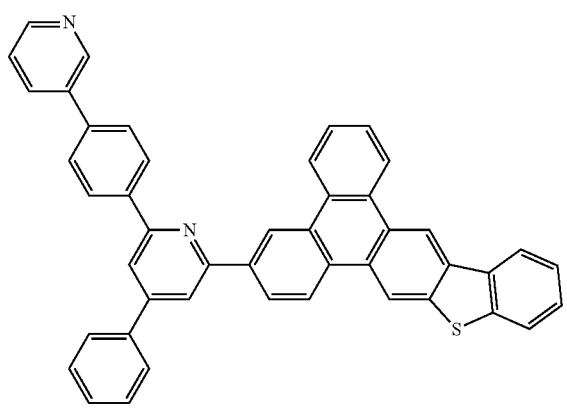
Compound 152
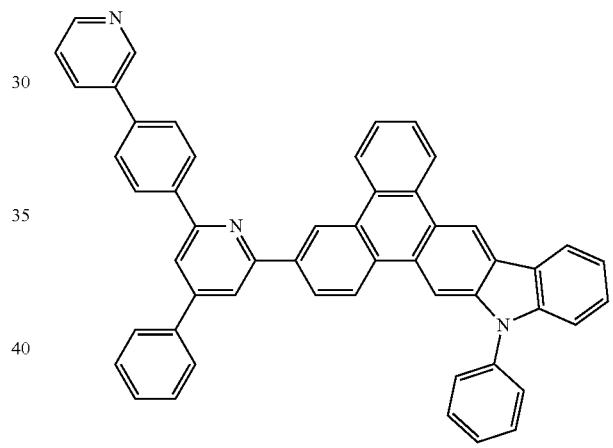
Compound 150
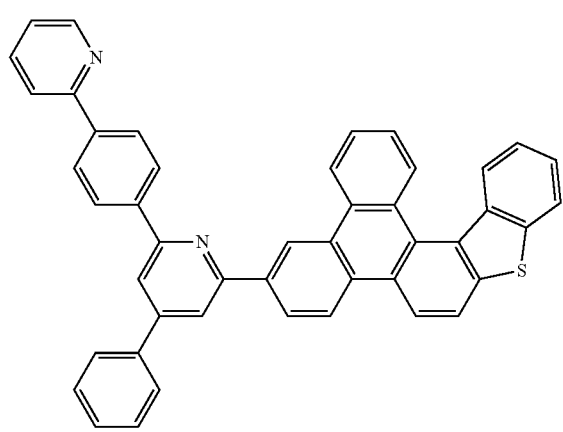
Compound 153
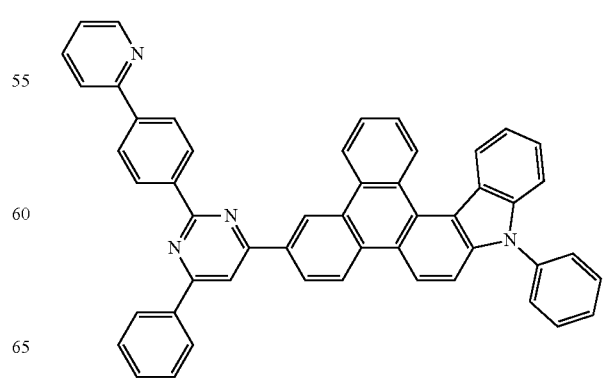

Compound 154
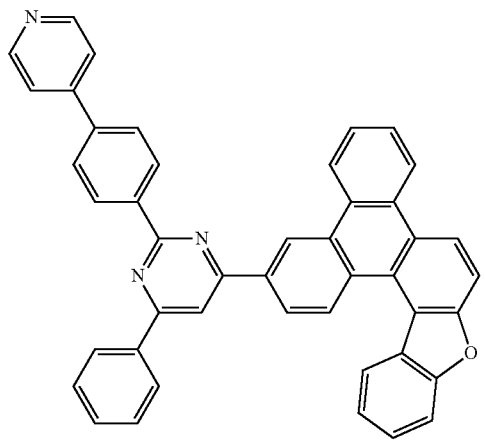
Compound 157
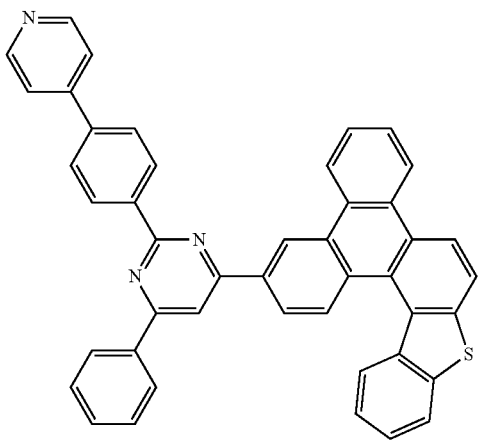
Compound 155
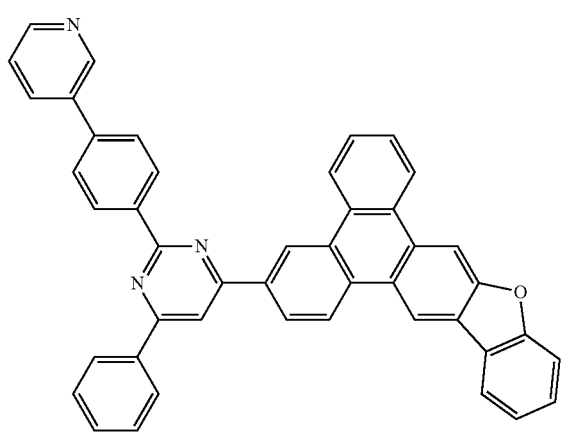
Compound 158
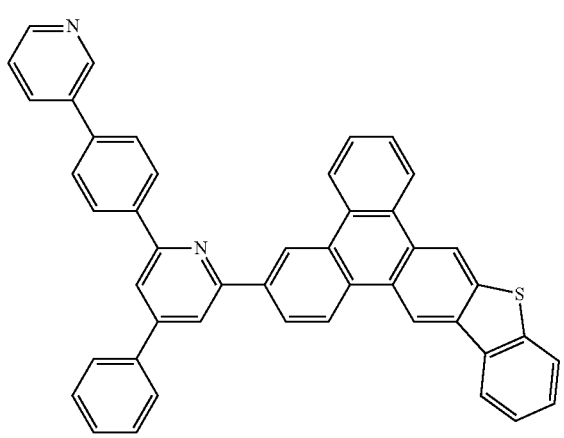
Compound 156
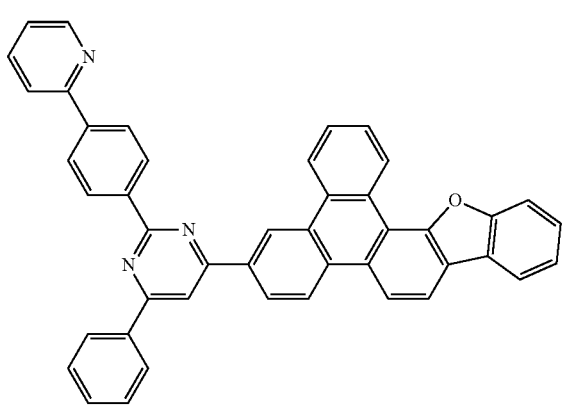
Compound 159
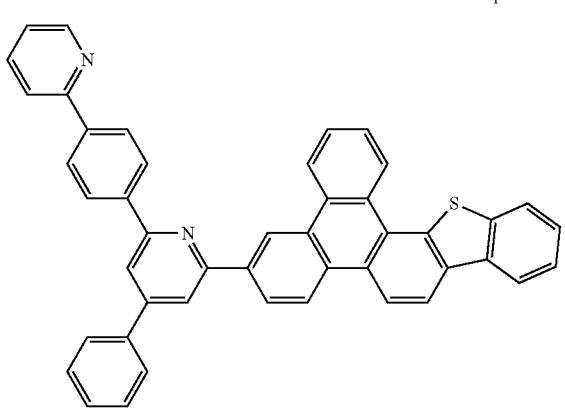

Compound 160
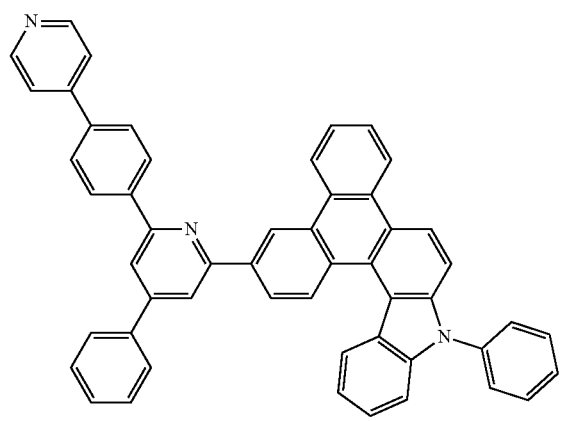
Compound 161
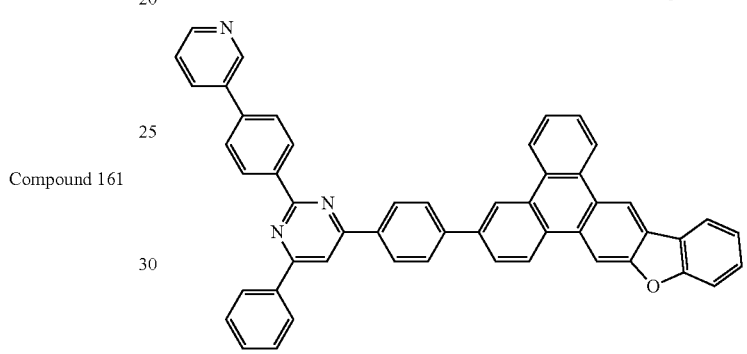
Compound 162
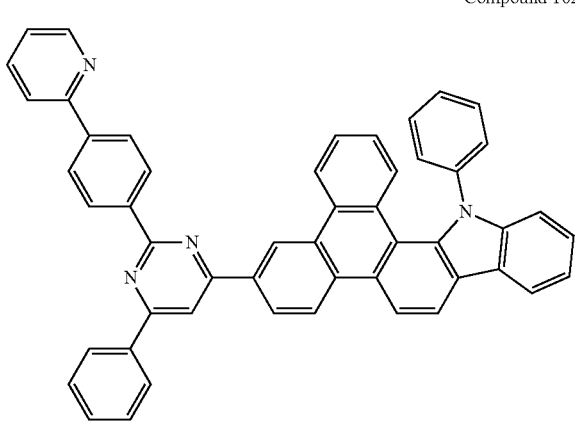
Compound 163
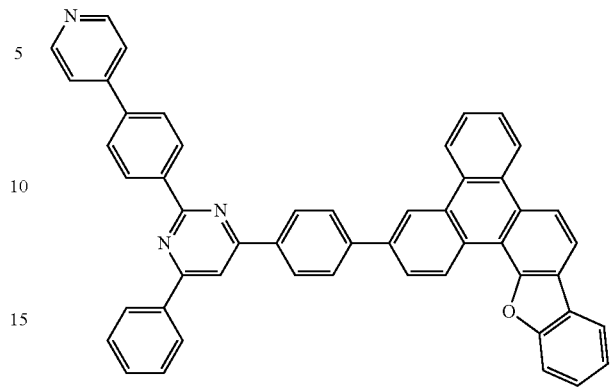
Compound 164
Compound 165
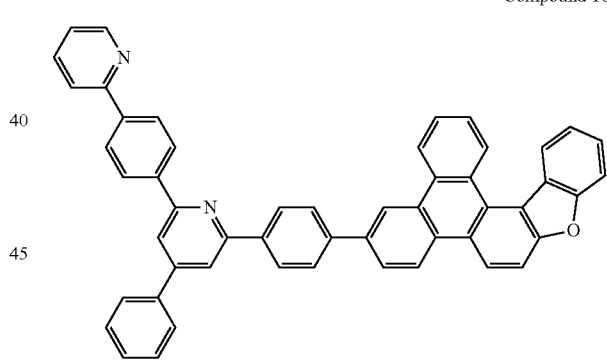
Compound 166
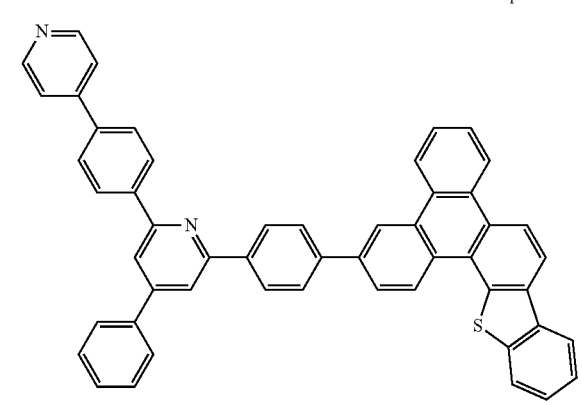

Compound 167
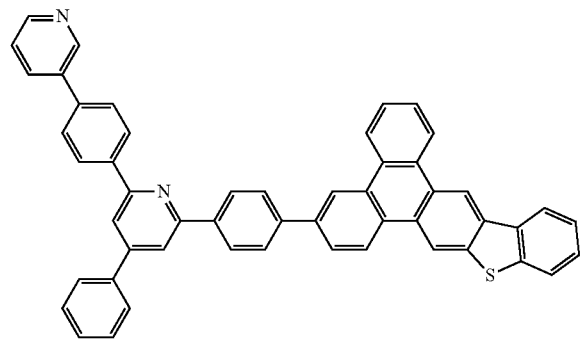
Compound 168
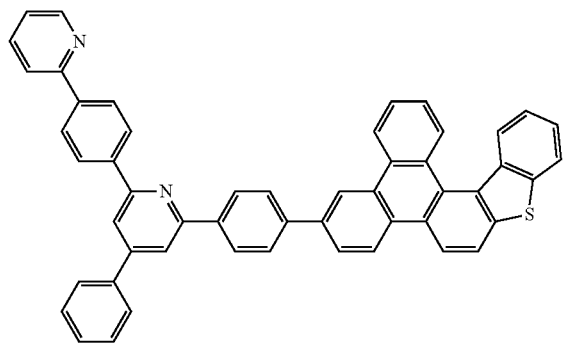
Compound 169
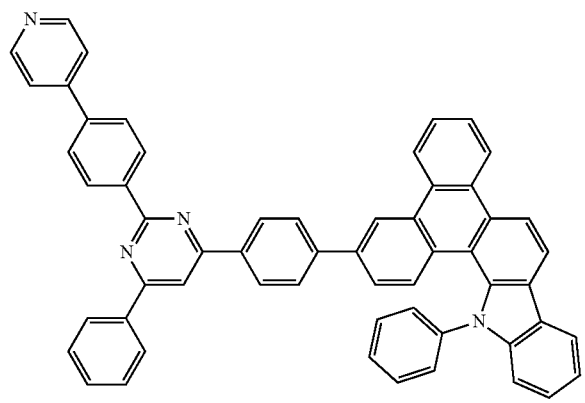
Compound 170
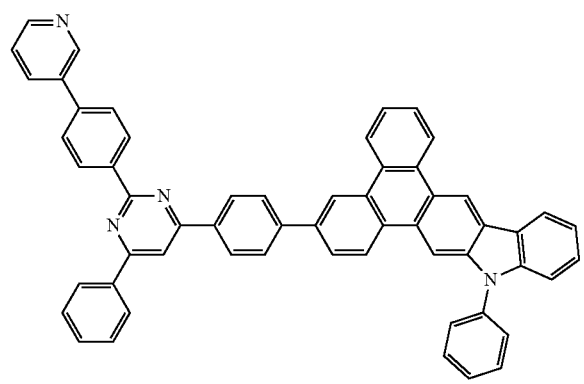
Compound 171
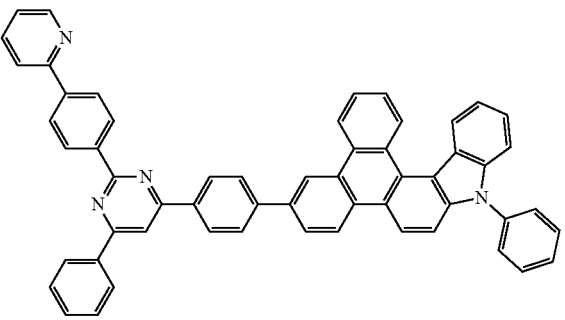
Compound 172
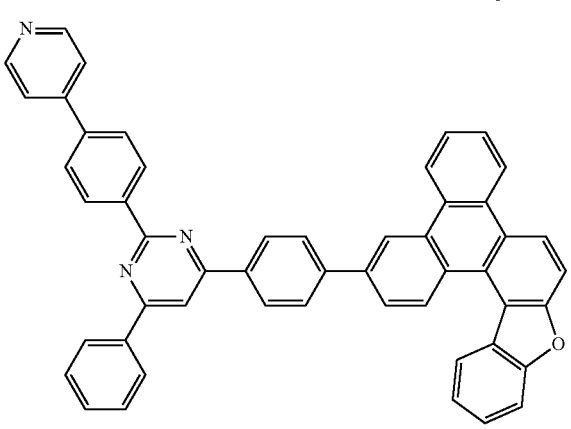
Compound 173
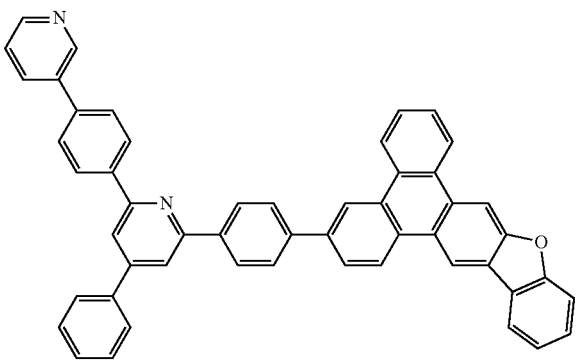
Compound 174
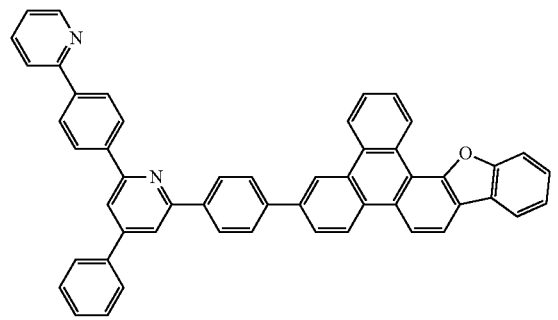

-continued
Compound 175
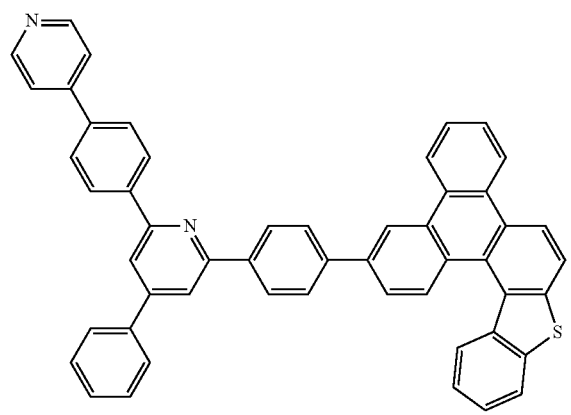
Compound 176
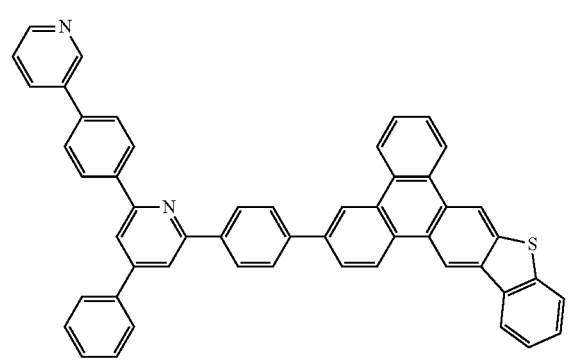
Compound 177
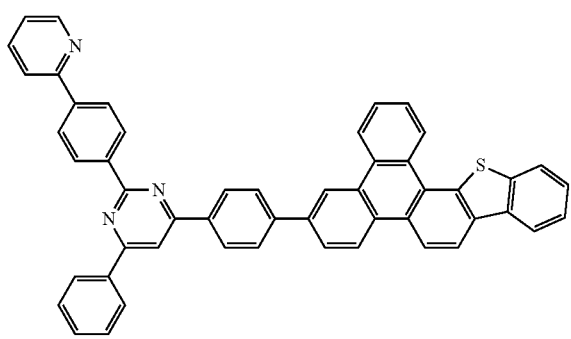
Compound 178
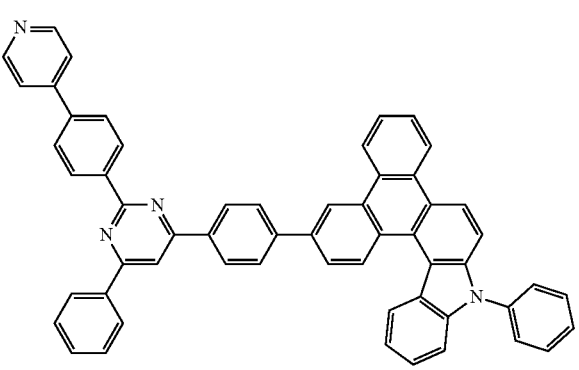
-continued
Compound 179
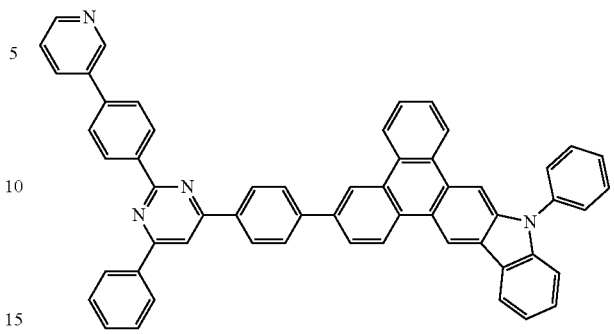
Compound 180
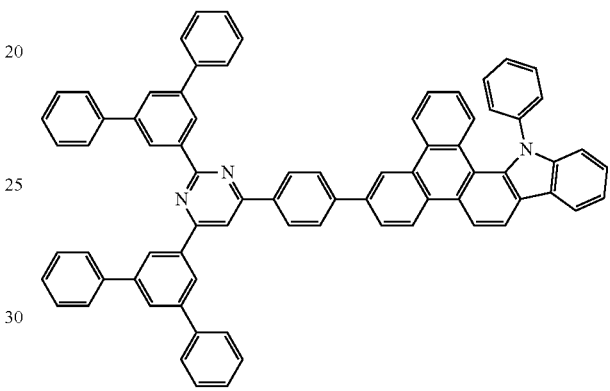
Compound 181
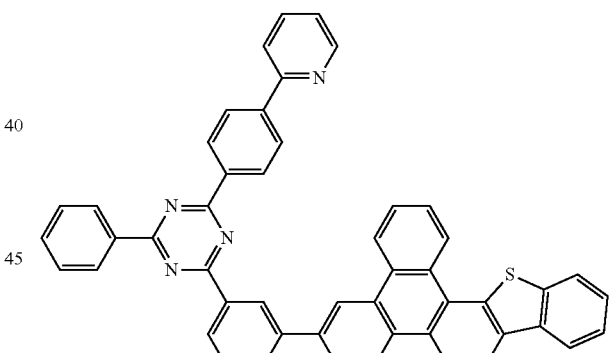
Compound 182
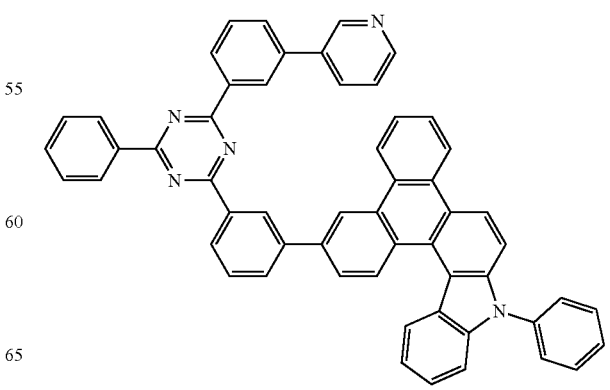

Compound 183
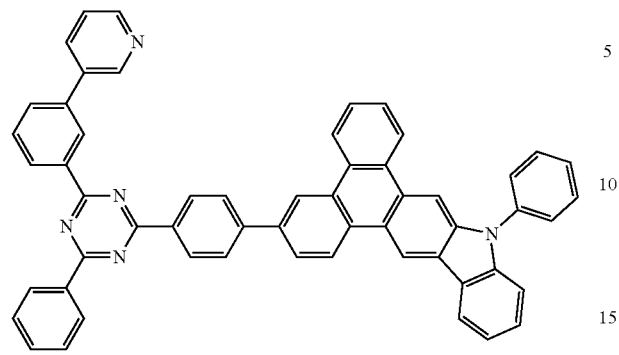
Compound 187
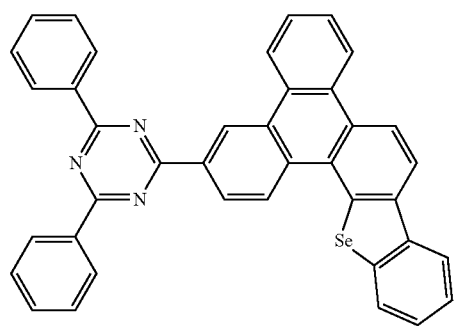
Compound 184
Compound 188
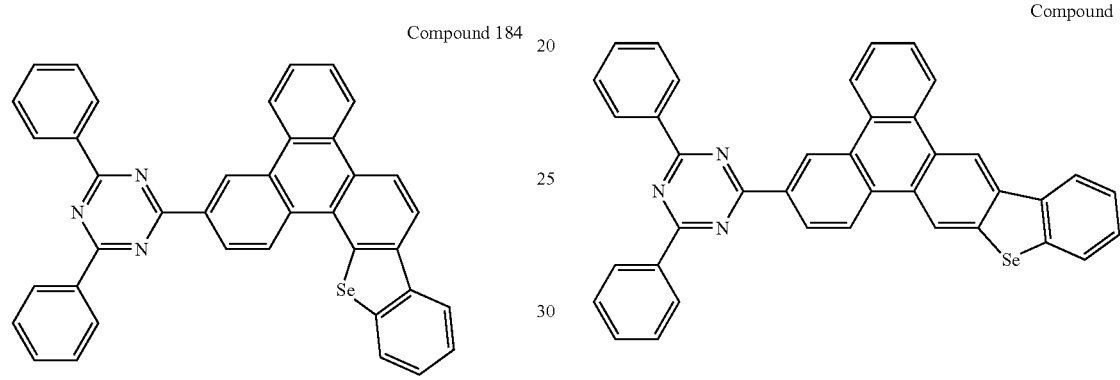
Compound 185
Compound 189
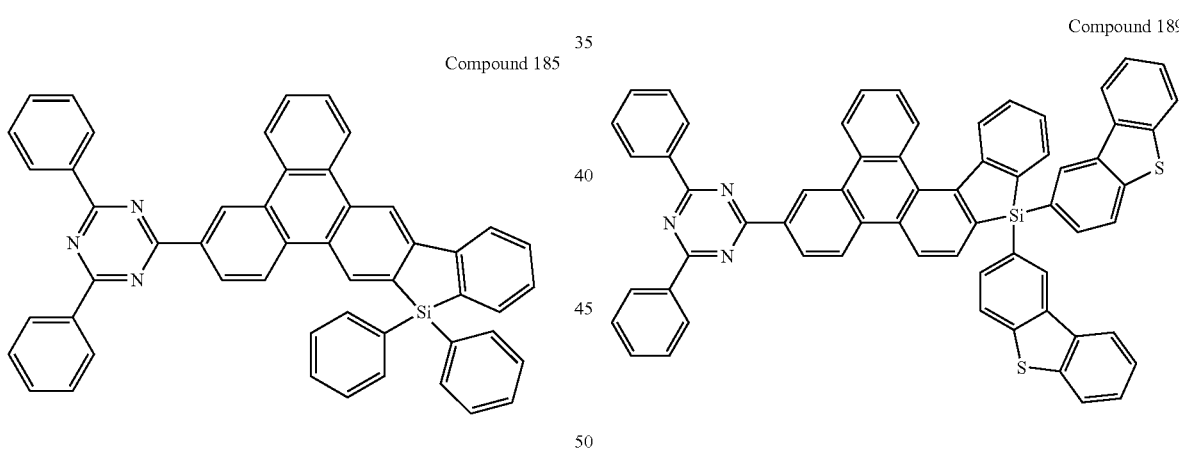
Compound 186
Compound 190
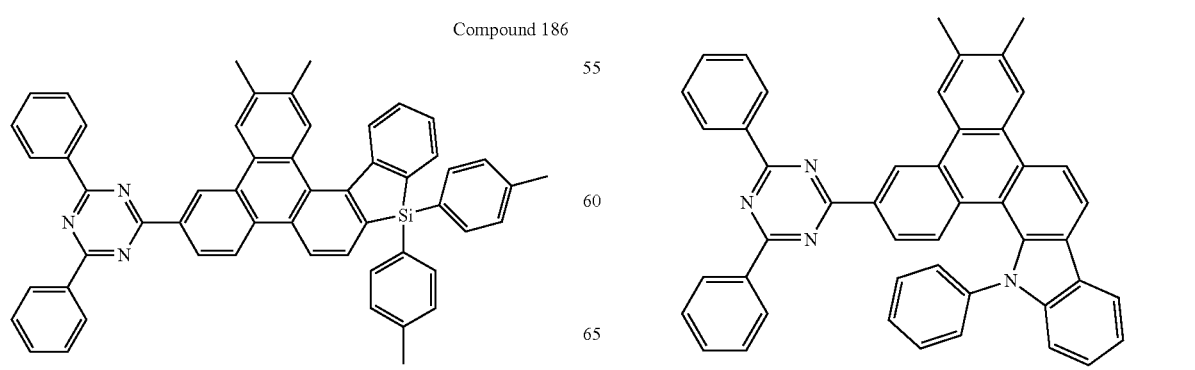

Compound 191
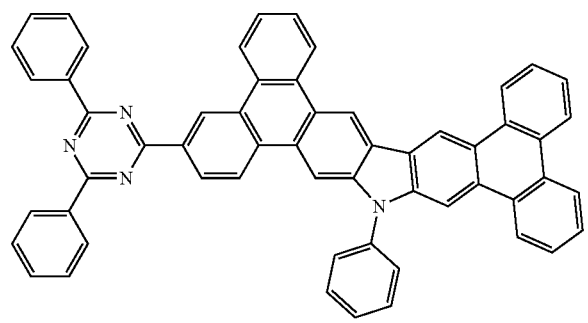
Compound 195
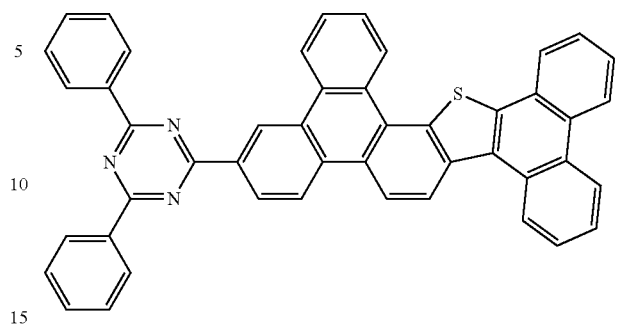
Compound 192
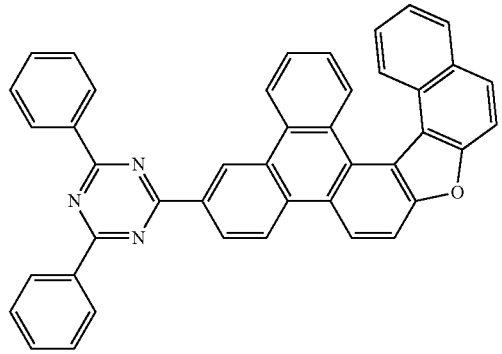
Compound 196
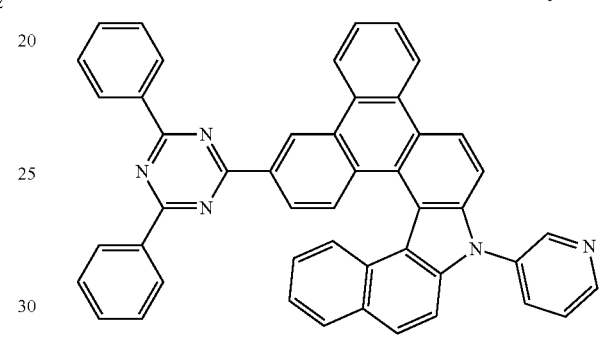
Compound 193
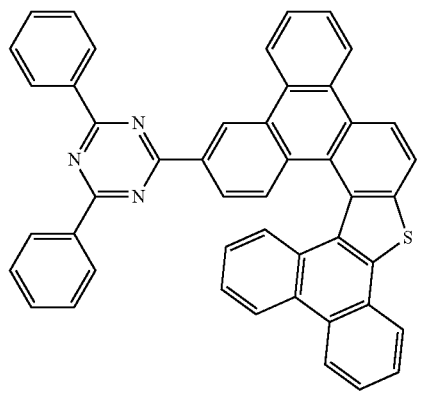
Compound 197
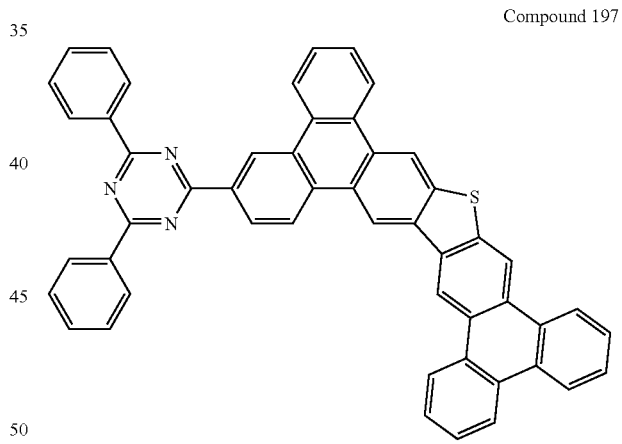
Compound 194
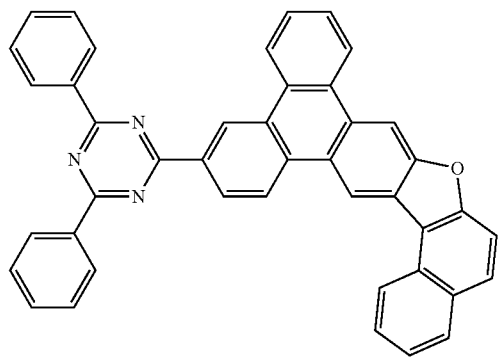
Compound 198
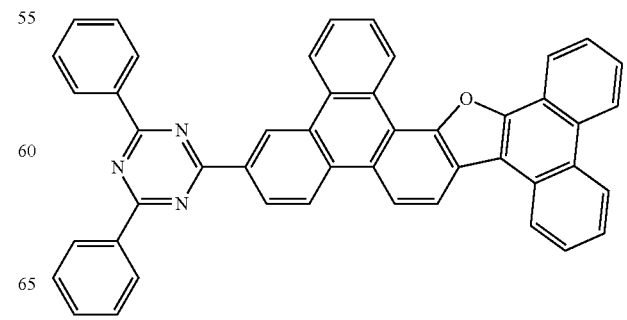

-continued
Compound 199
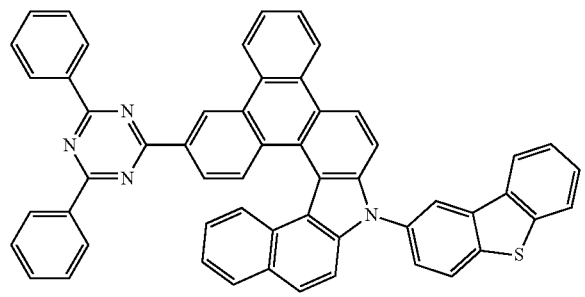
Compound 200
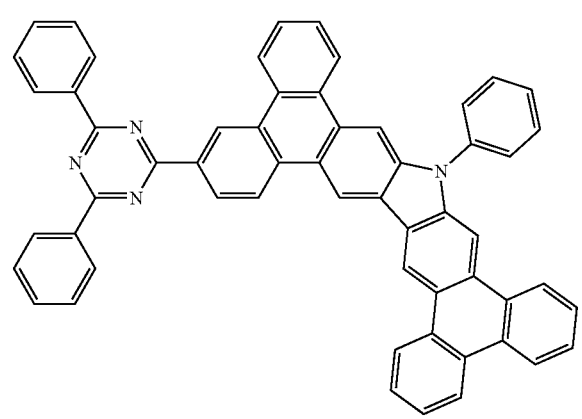
Compound 201
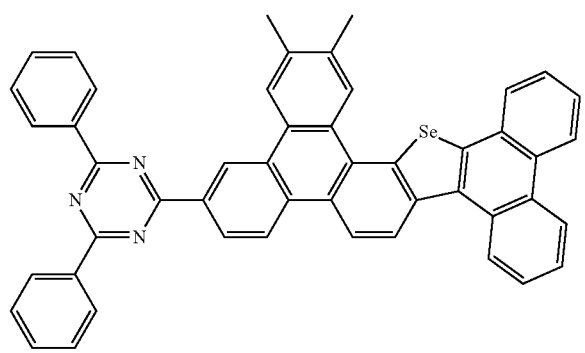
Compound 202
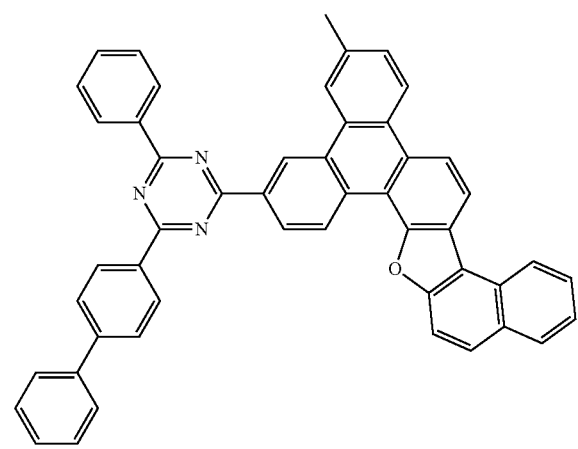
-continued
Compound 203
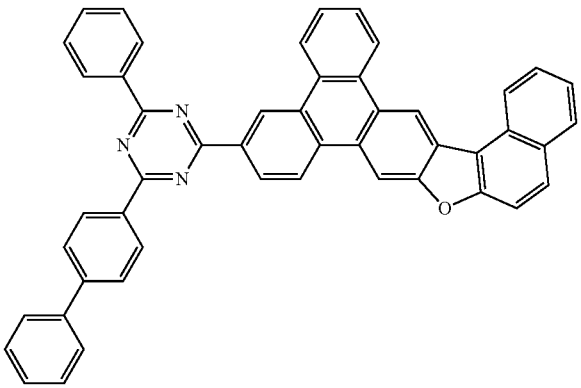
Compound 204
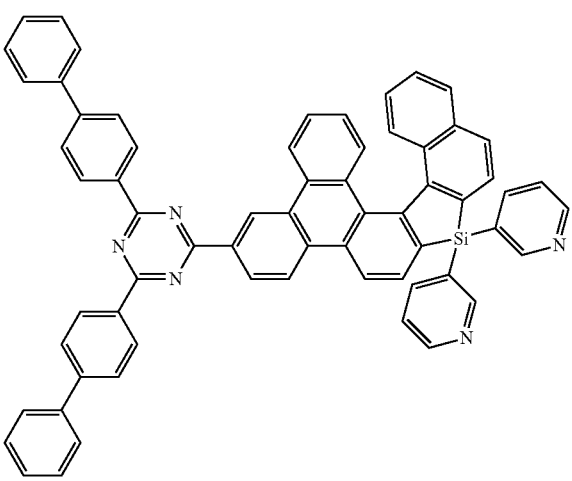
Compound 205
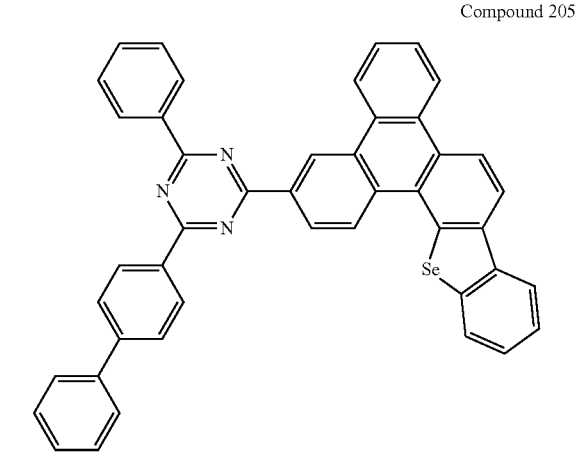

Compound 206
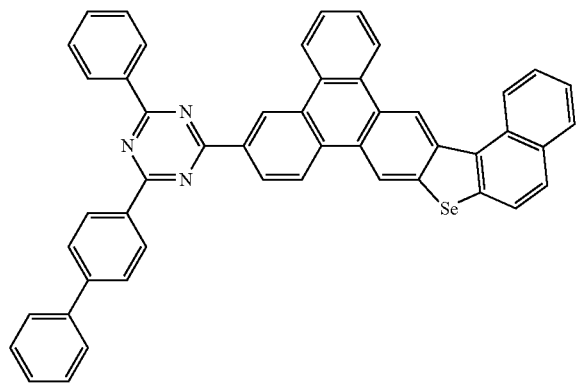
Compound 209
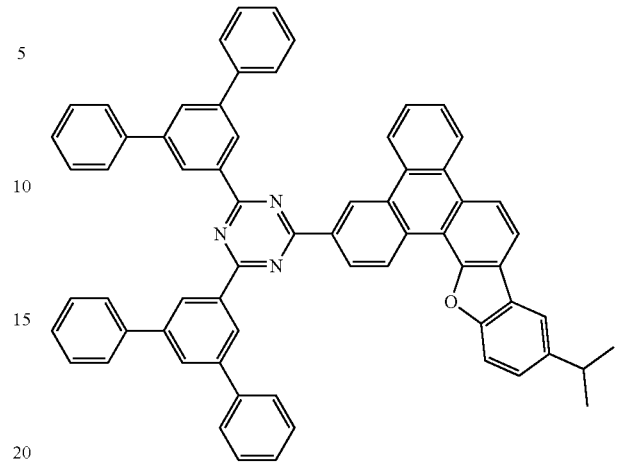
Compound 207
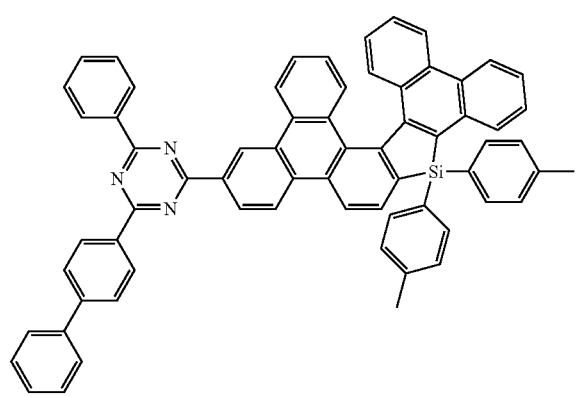
Compound 210
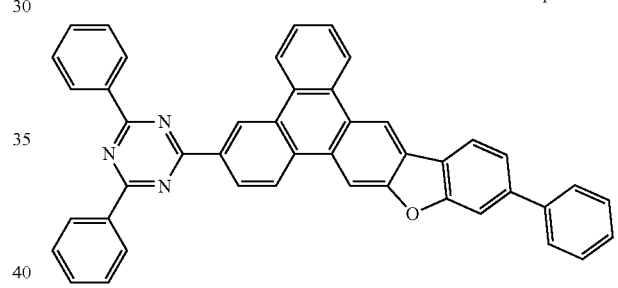
Compound 208
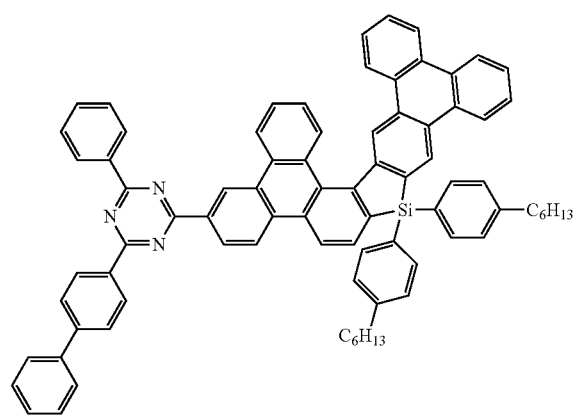
Compound 211
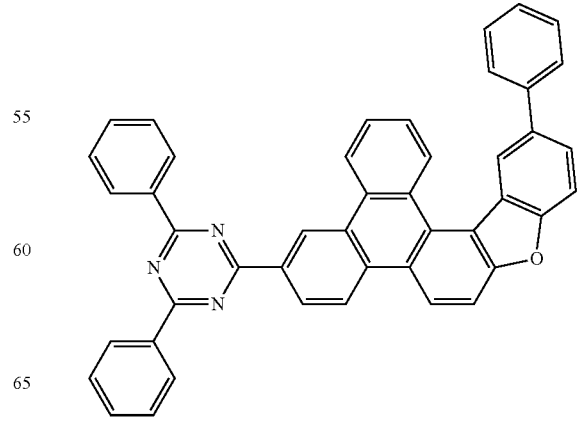

Compound 212
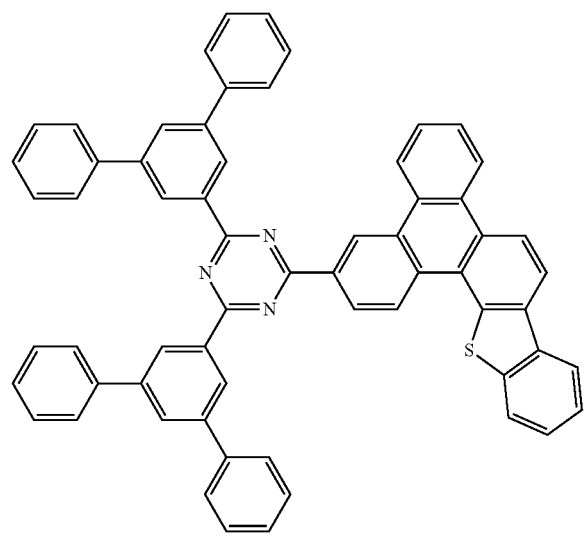
Compound 213
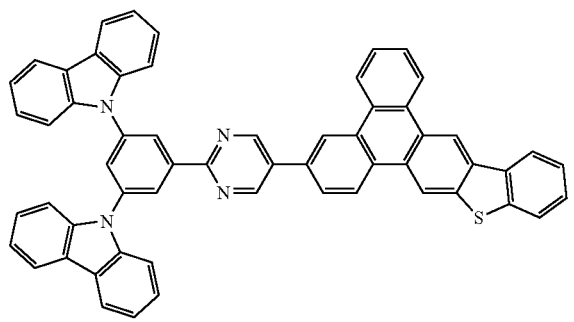
Compound 214
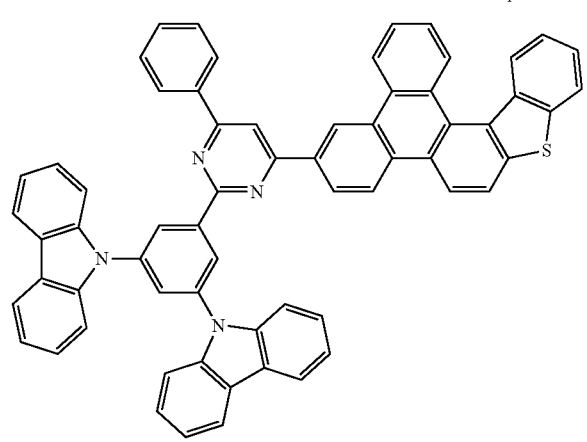
Compound 215
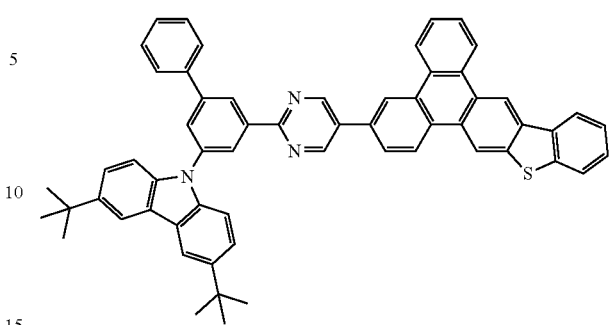
Compound 216
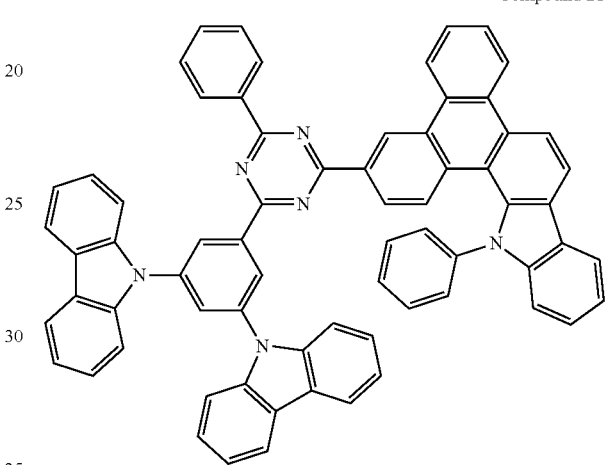
Compound 217
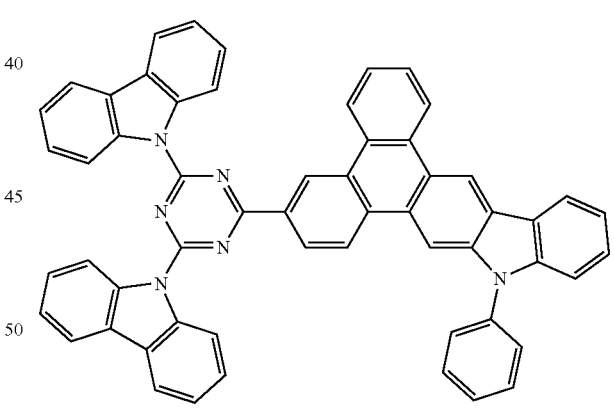
Compound 218
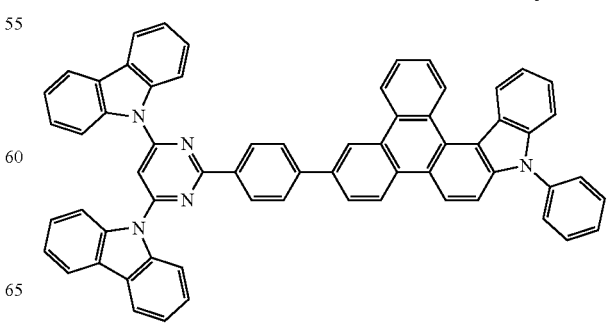

-continued
Compound 219
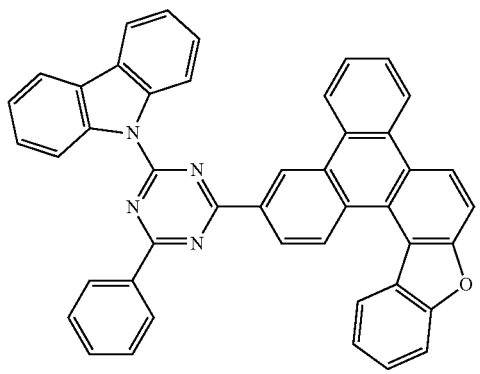
Compound 220
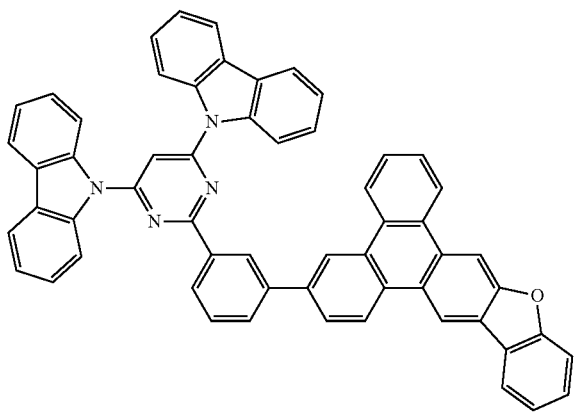
Compound 221
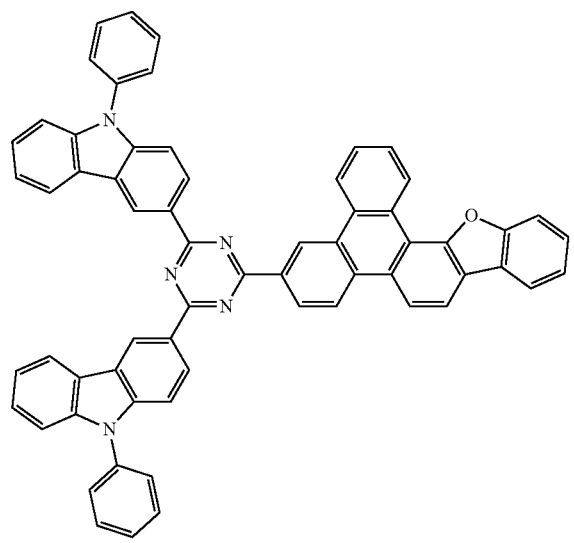
-continued
Compound 222
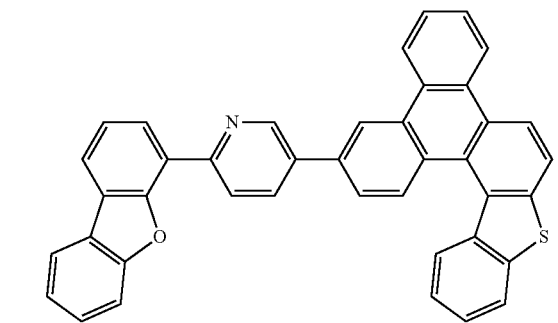
Compound 223
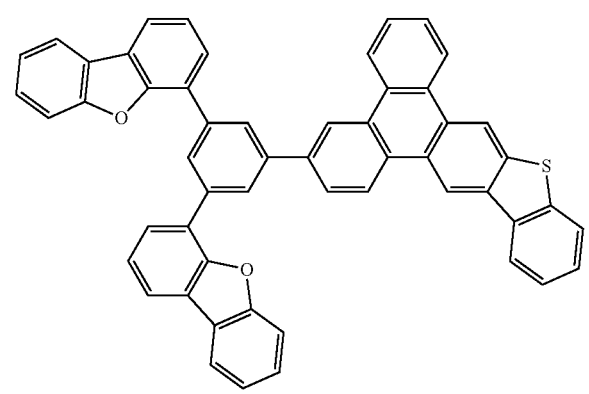
Compound 224
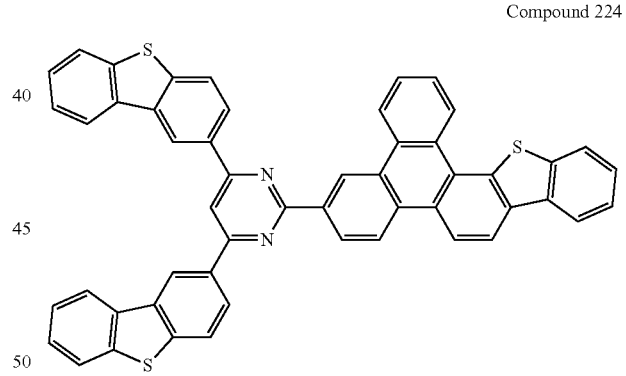
Compound 225
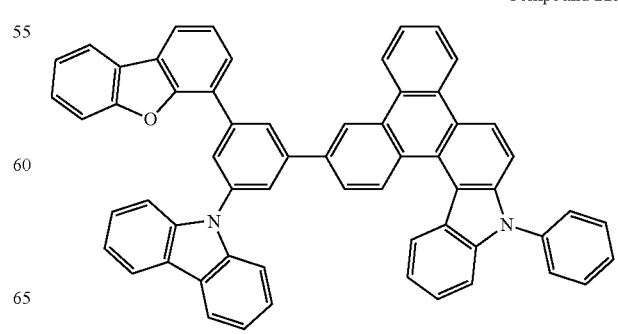

Compound 226
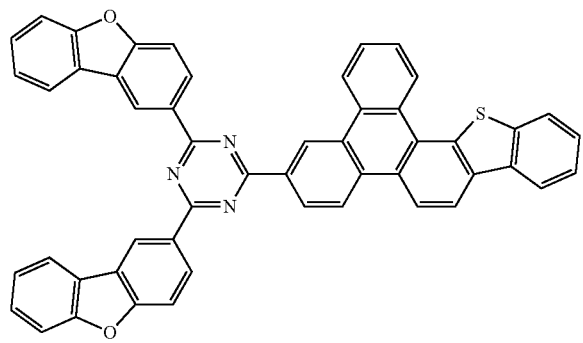
Compound 227
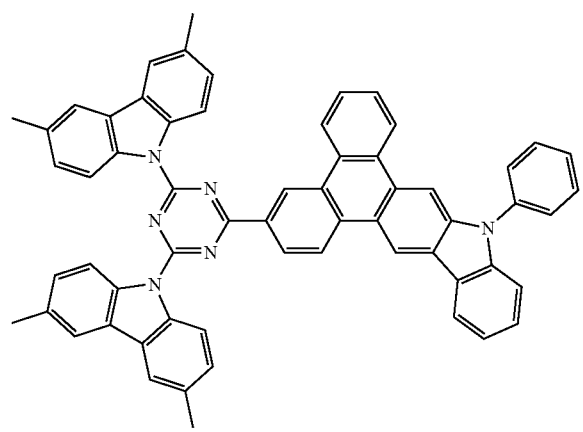
Compound 228
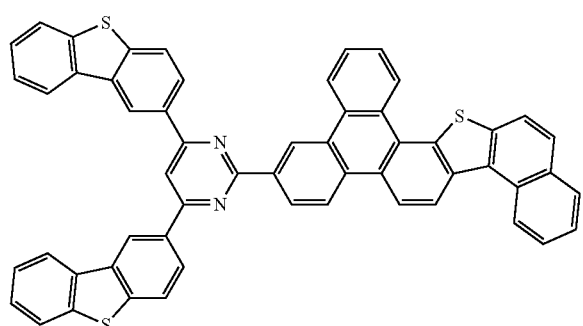
Compound 229
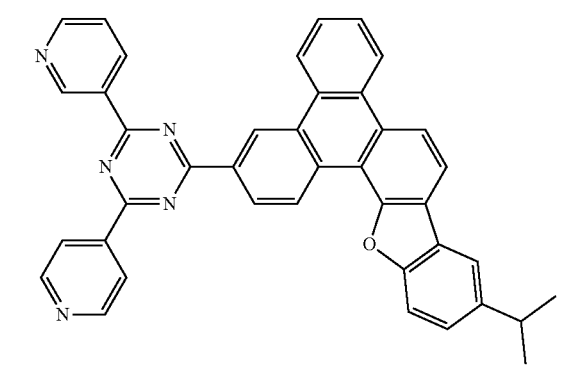
Compound 230
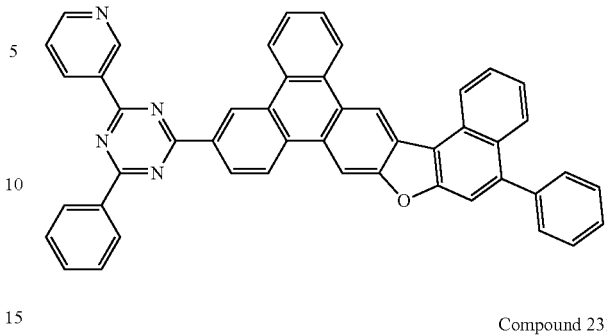
Compound 231
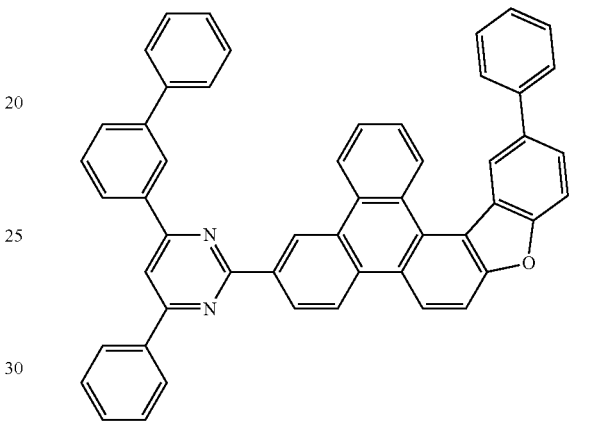
Compound 232
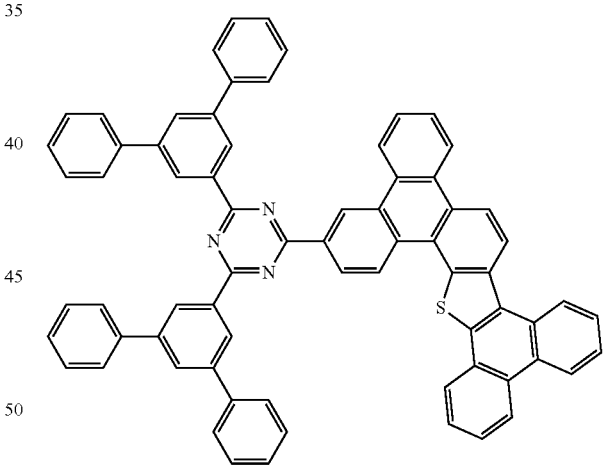
Compound 233
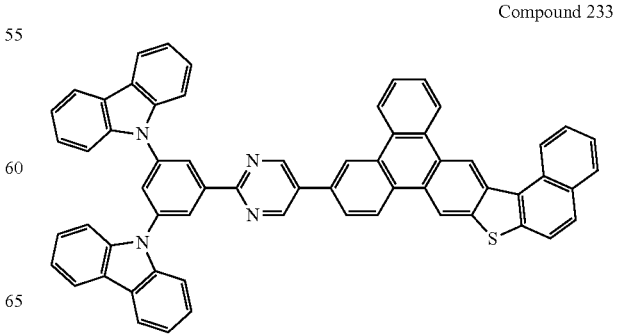

Compound 234
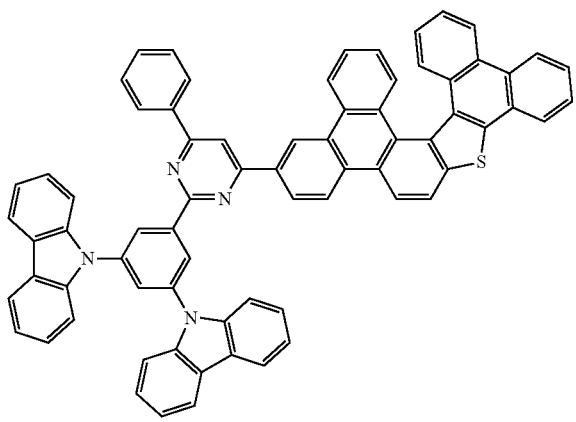
Compound 238
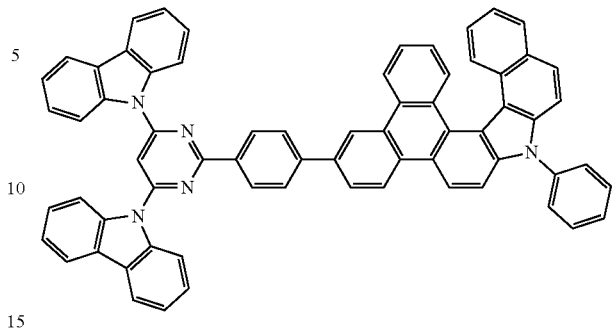
Compound 235
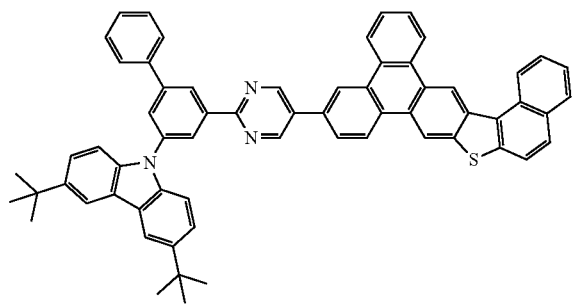
Compound 239
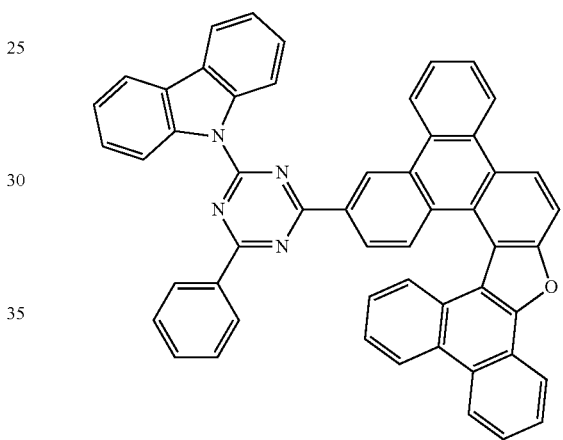
Compound 236
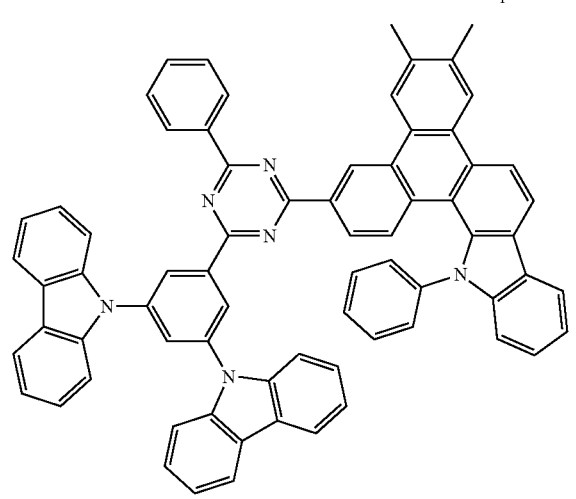
Compound 237
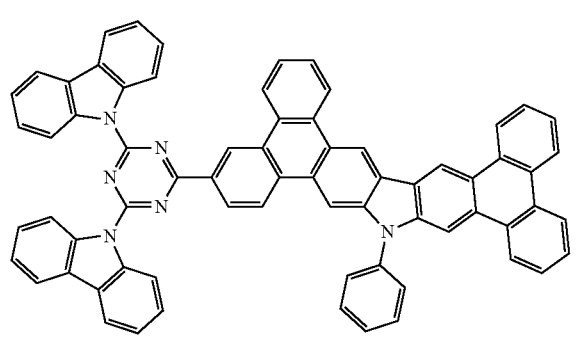
Compound 240
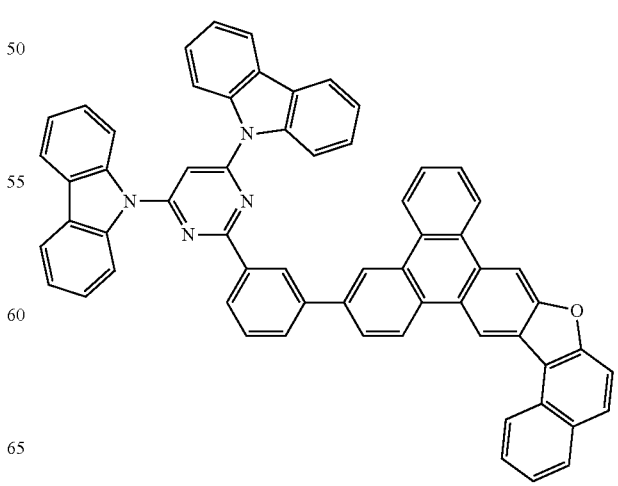

Compound 241
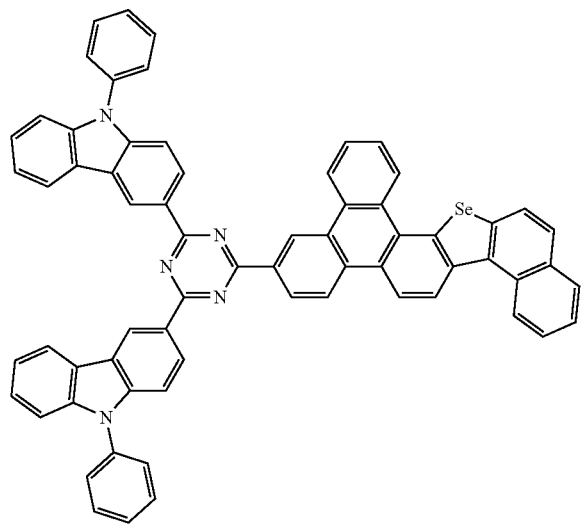
Compound 244
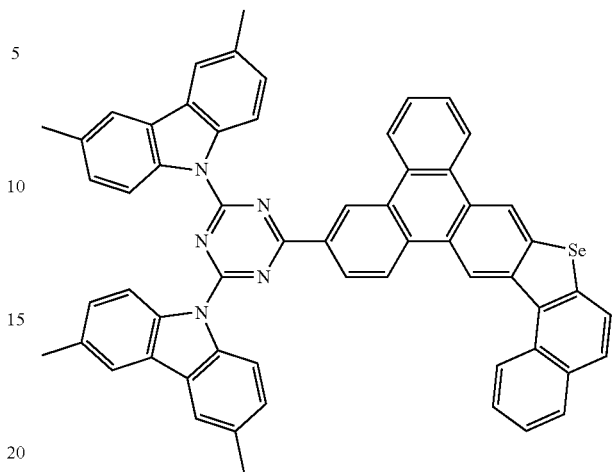
Compound 245
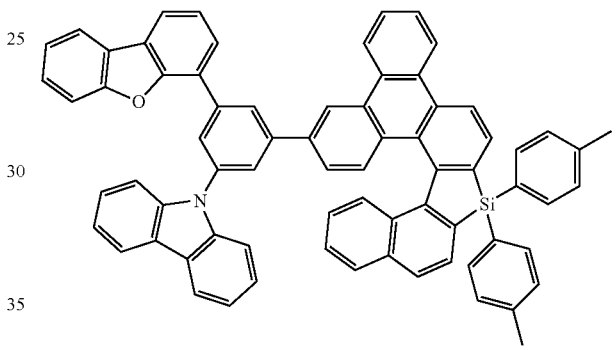
Compound 242
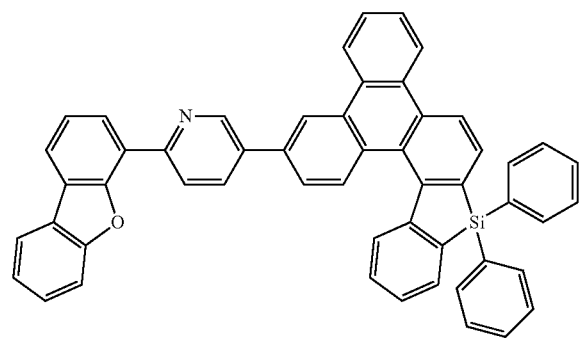
Compound 246
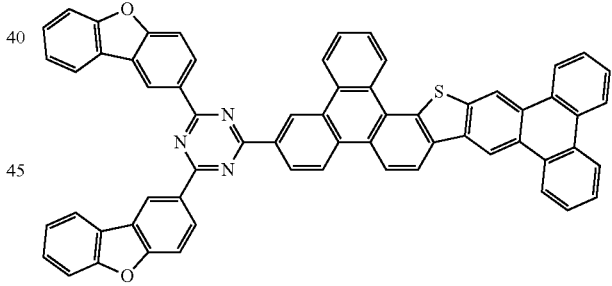
Compound 243
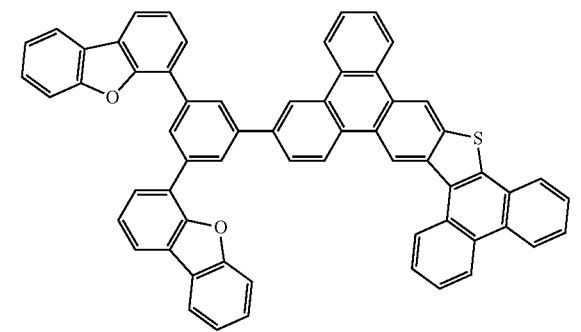
Compound 247
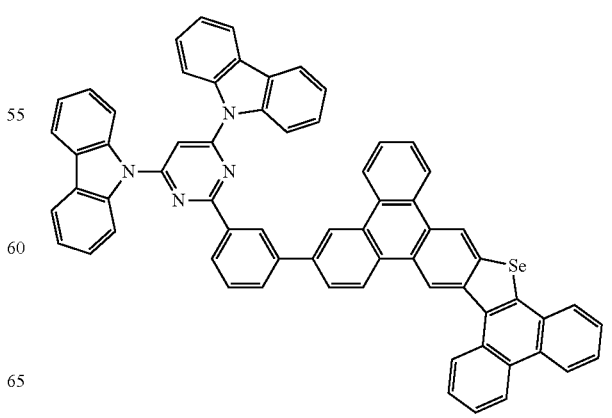

Compound 248
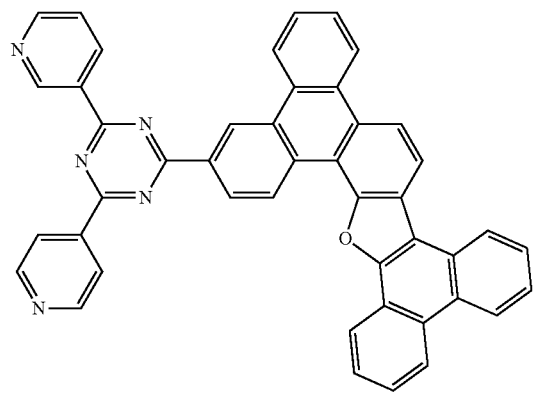
Compound 252
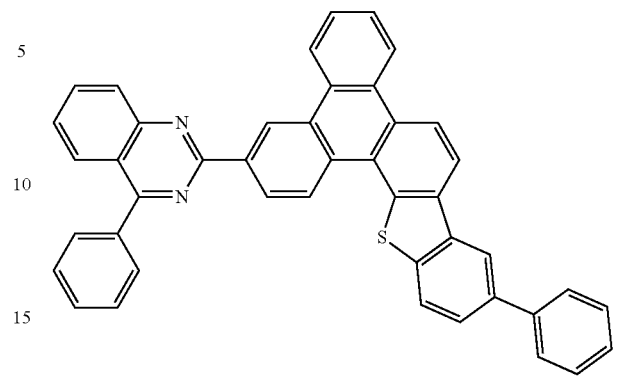
Compound 249
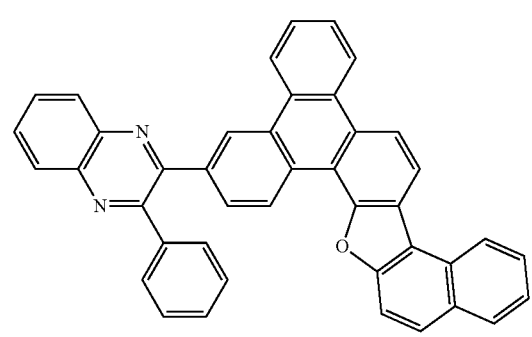
Compound 253
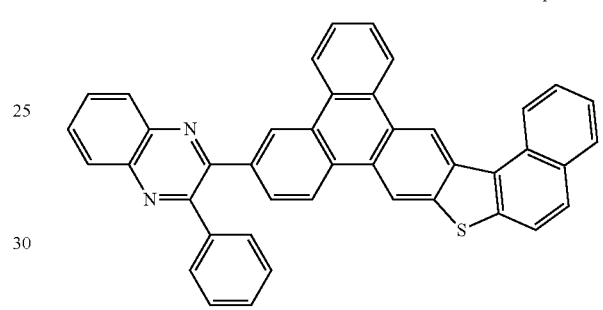
Compound 250
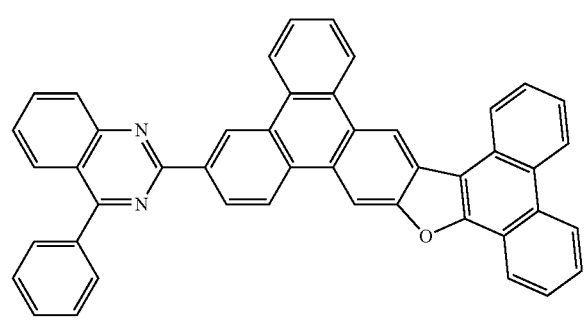
Compound 254
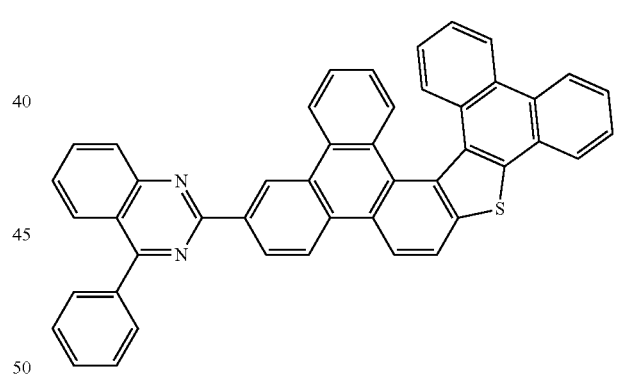
Compound 251
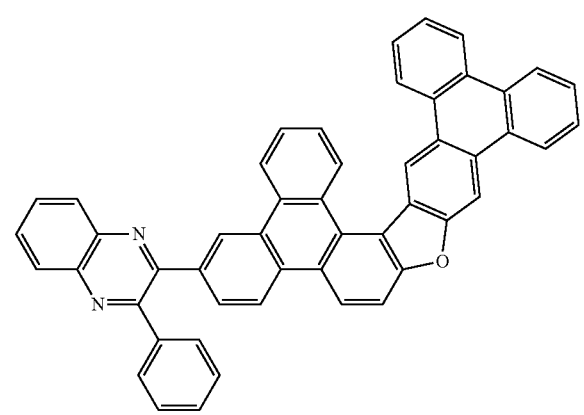
Compound 255
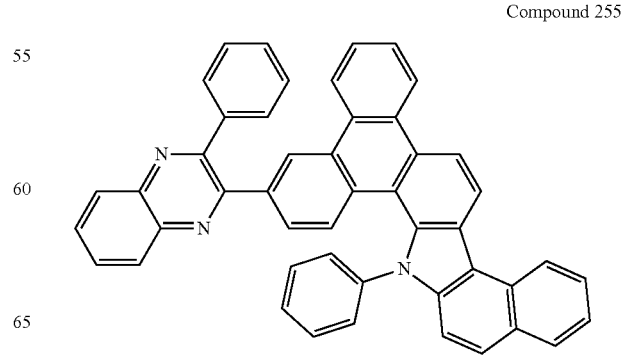

Compound 256

Compound 260

Compound 257

Compound 261

Compound 258

Compound 262

Compound 259

Compound 263

205
-continued
Compound 264
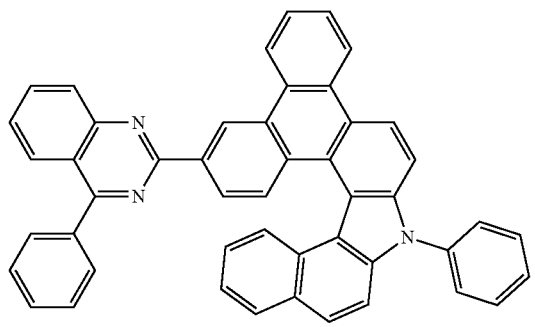
Compound 265
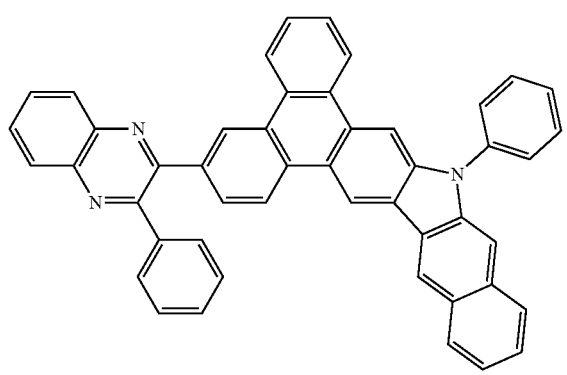
Compound 266
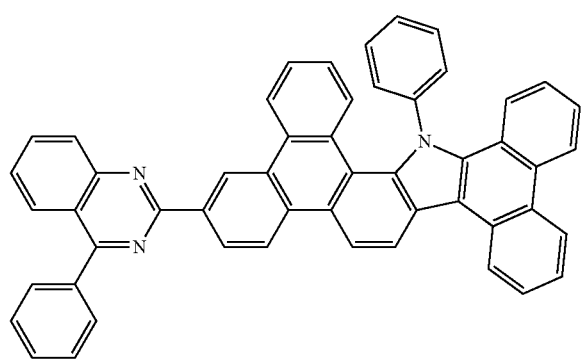
Compound 267
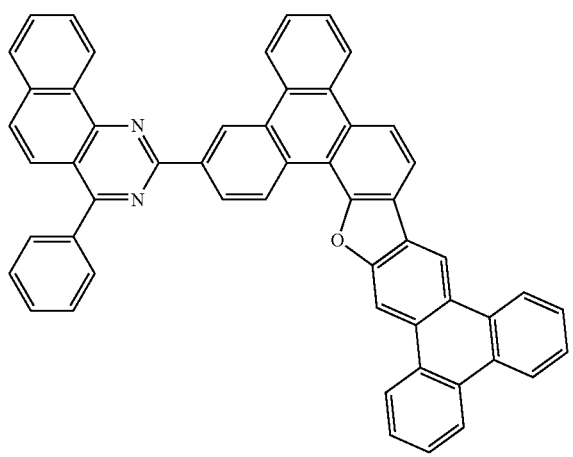
206
-continued
Compound 268
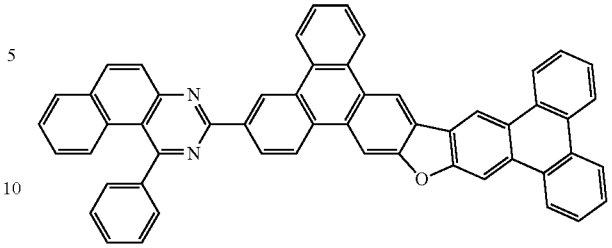
Compound 269
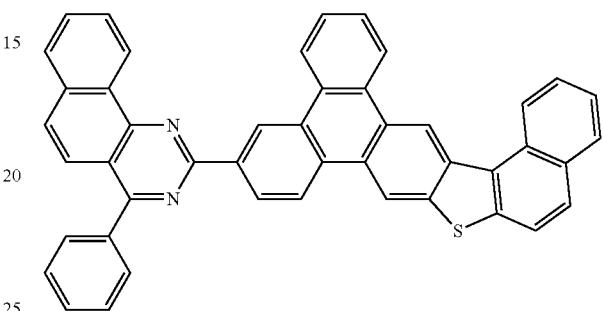
Compound 270
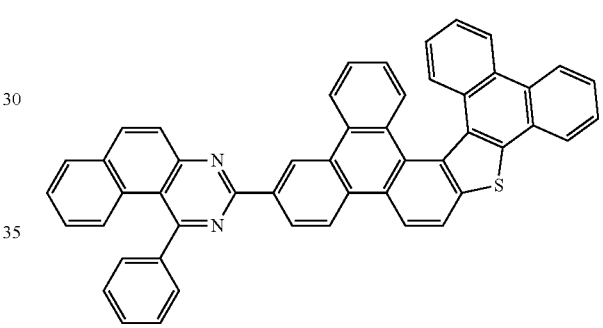
Compound 271
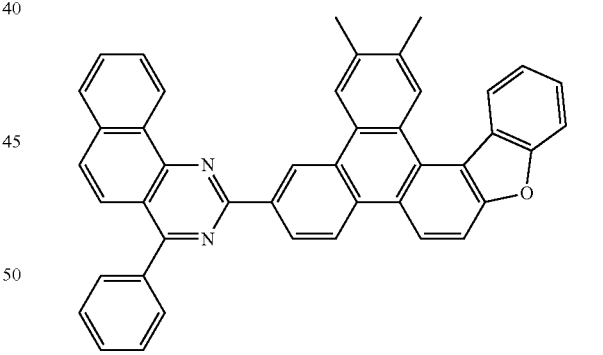
Compound 272
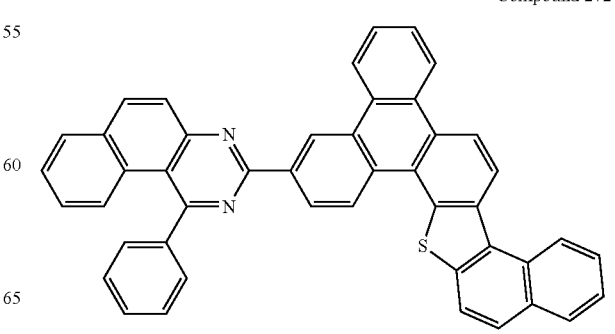

Compound 273
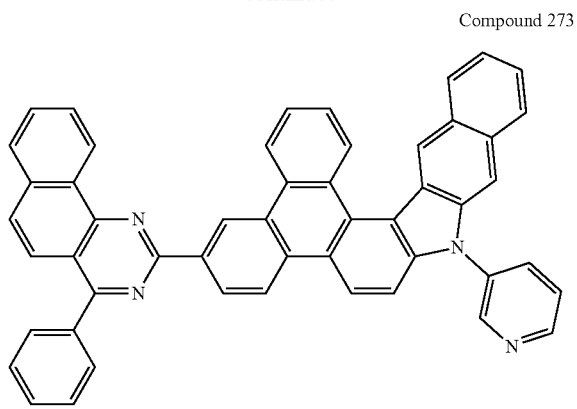
Compound 277
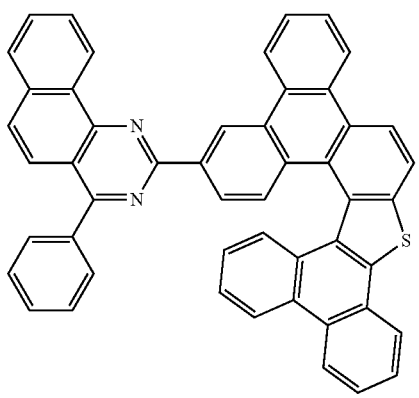
Compound 274
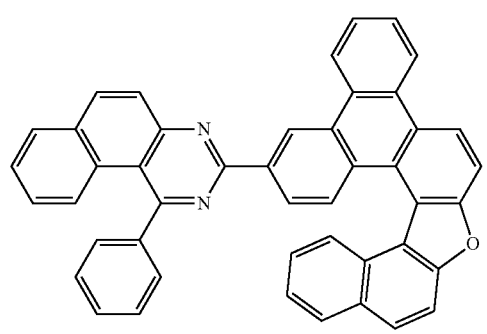
Compound 278
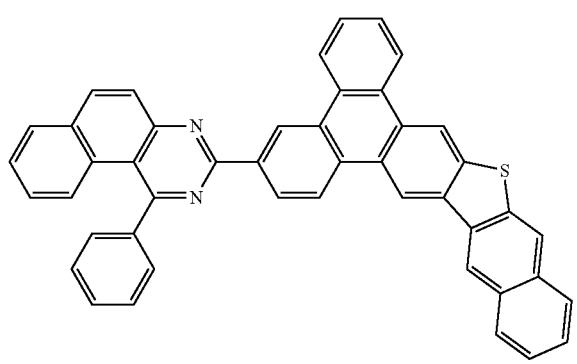
Compound 275
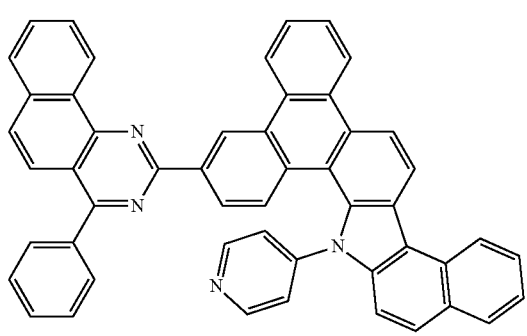
Compound 279
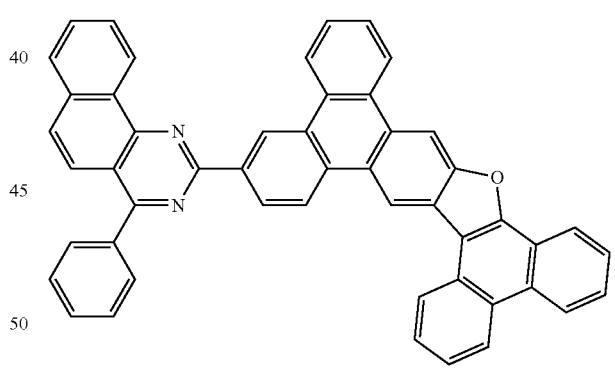
Compound 276
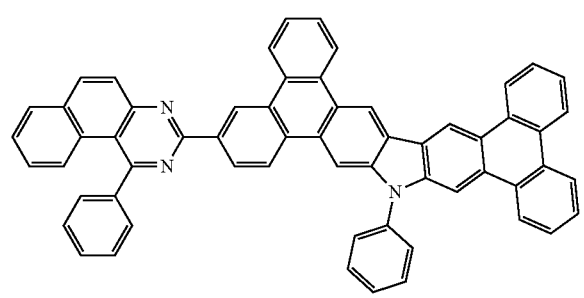
Compound 280
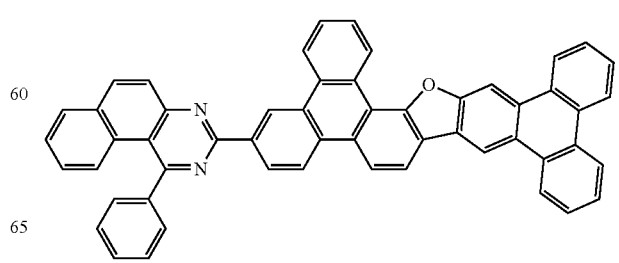

-continued
Compound 281
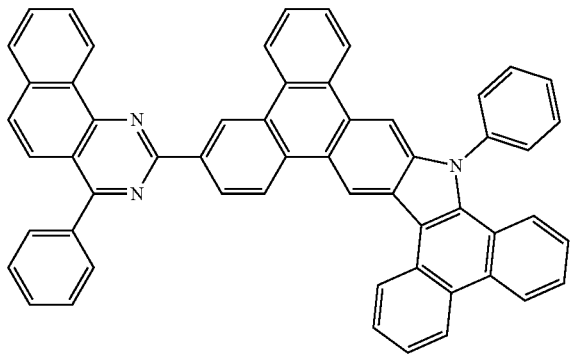
Compound 282
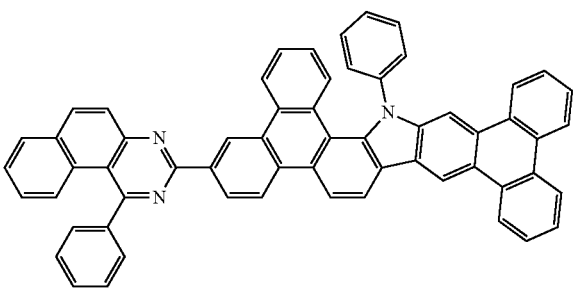
Compound 283
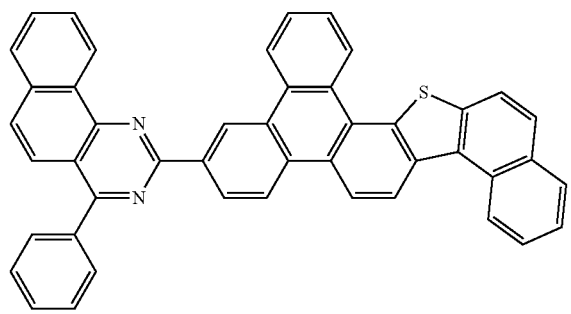
Compound 284
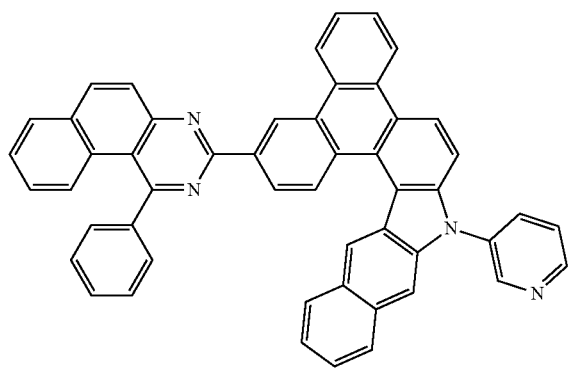
-continued
Compound 285
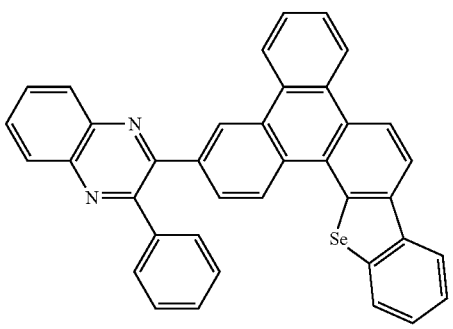
Compound 286
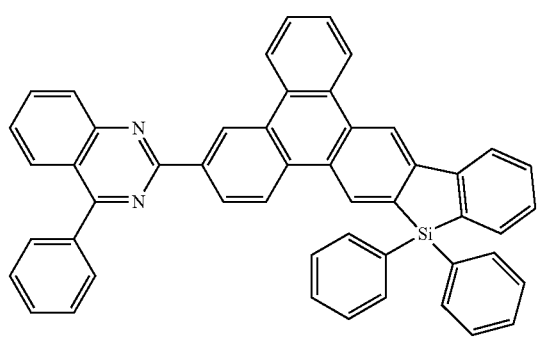
Compound 287
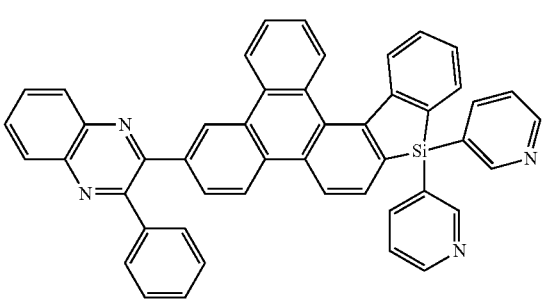
Compound 288
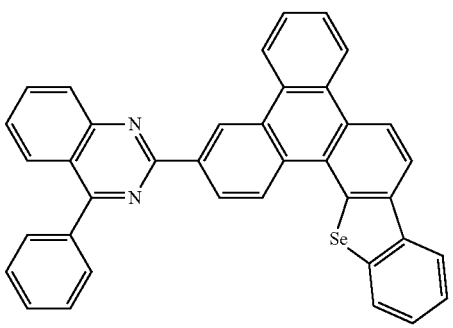

Compound 289
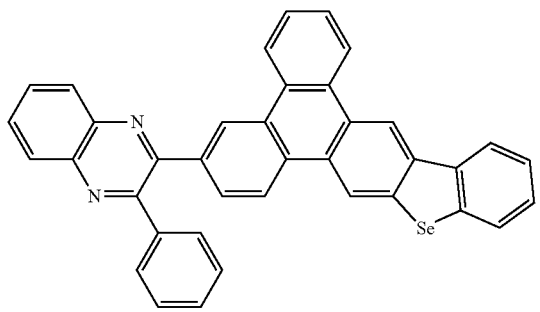
Compound 293
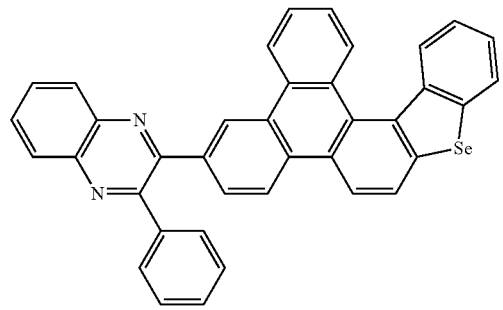
Compound 290
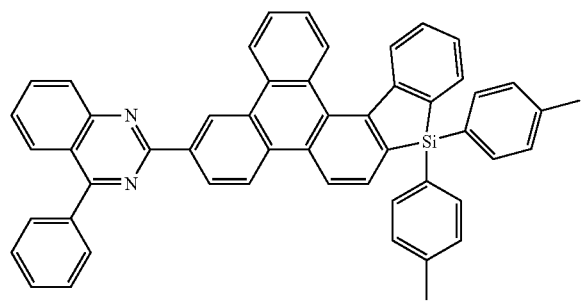
Compound 294
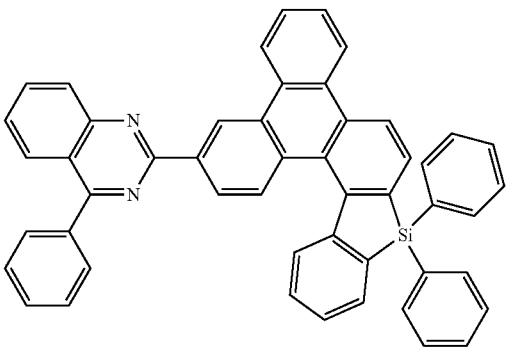
Compound 291
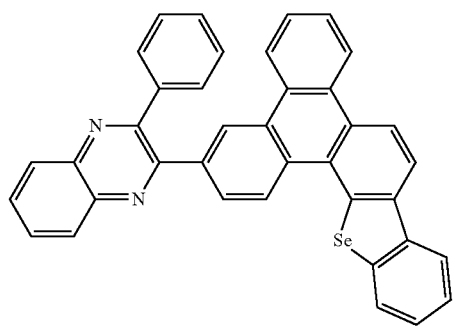
Compound 295
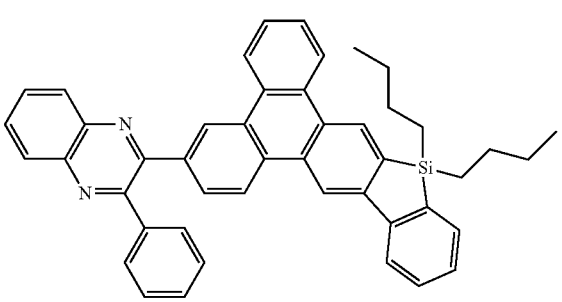
Compound 292
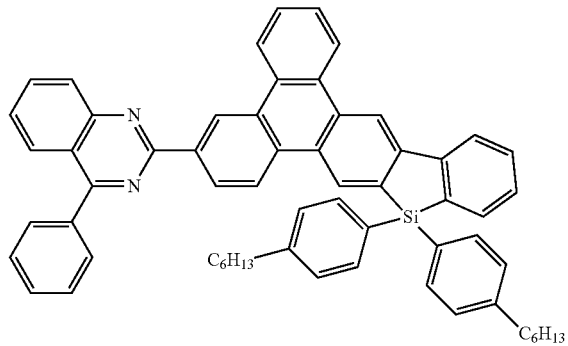
Compound 296
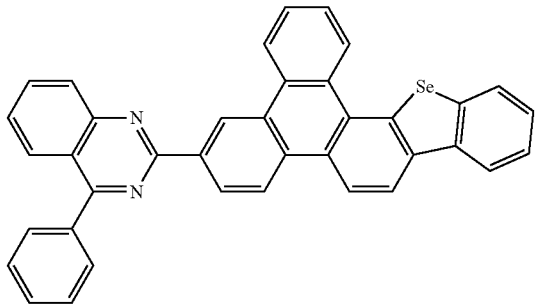

Compound 297
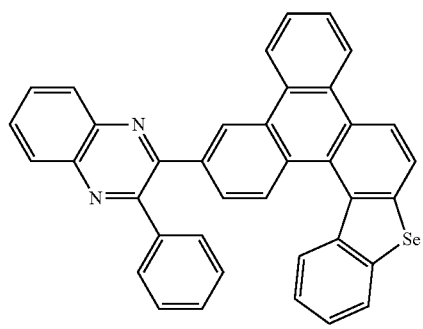
Compound 301
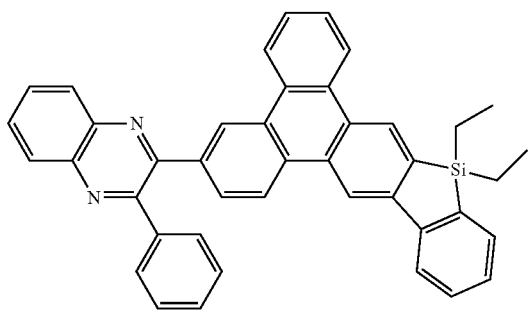
Compound 298
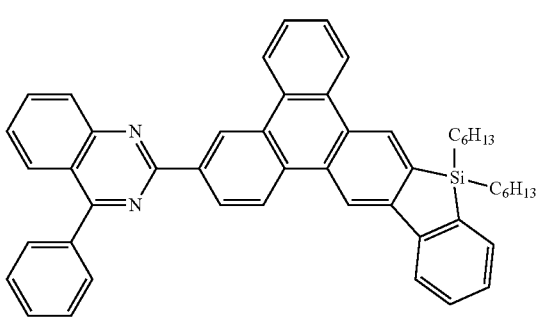
Compound 302
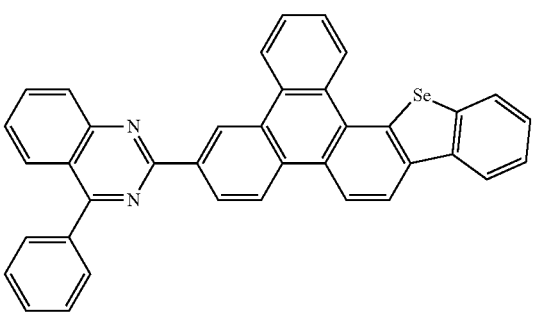
Compound 299
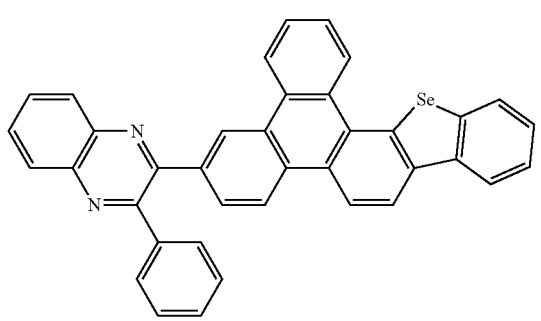
Compound 303
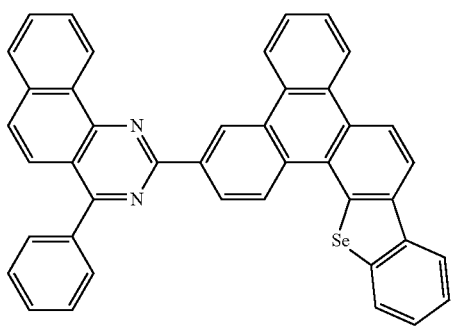
Compound 300
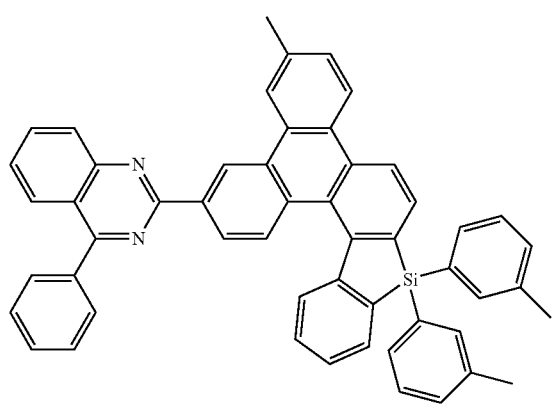
Compound 304

Compound 305
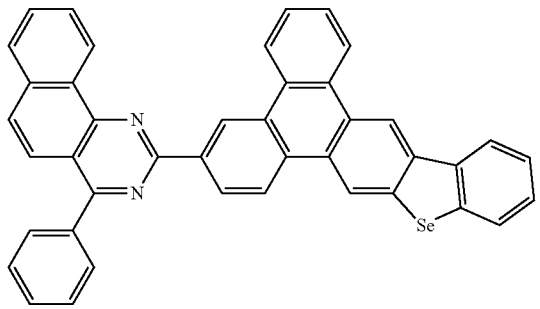
Compound 306
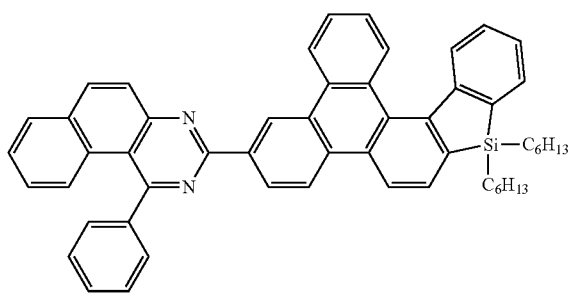
Compound 307
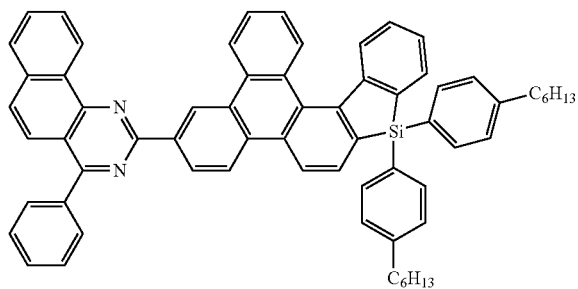
Compound 308
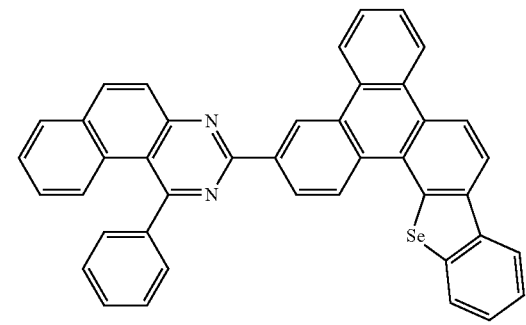
Compound 309
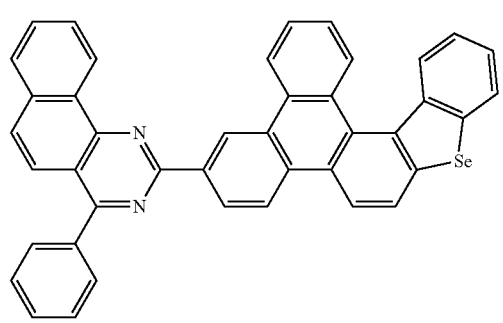
Compound 310
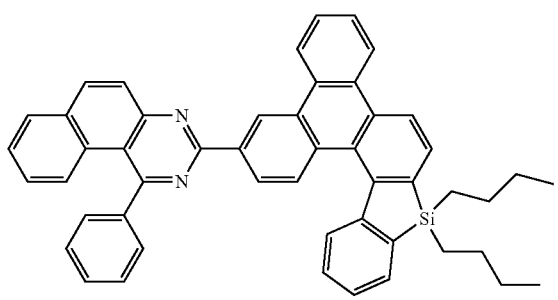
Compound 311
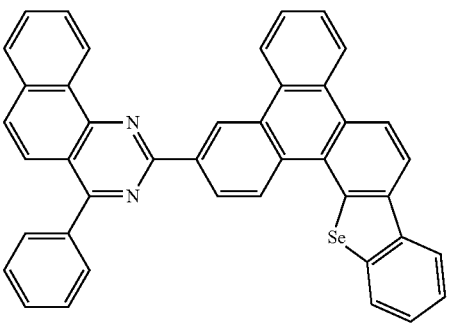
Compound 312
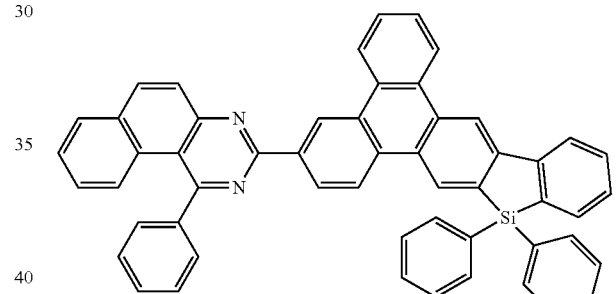
Compound 313
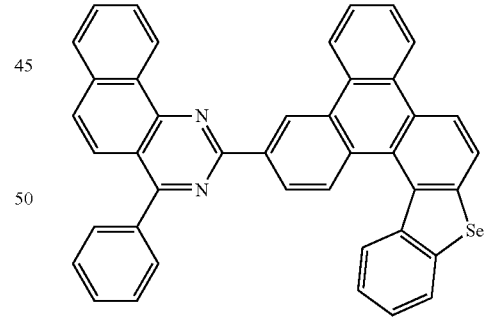
Compound 314
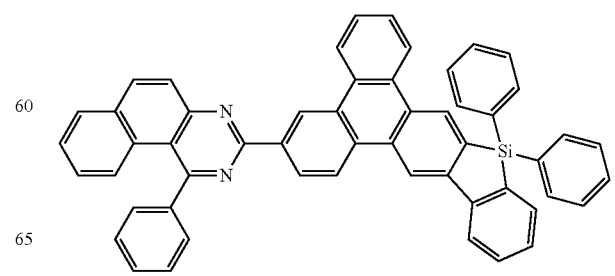

-continued
Compound 315
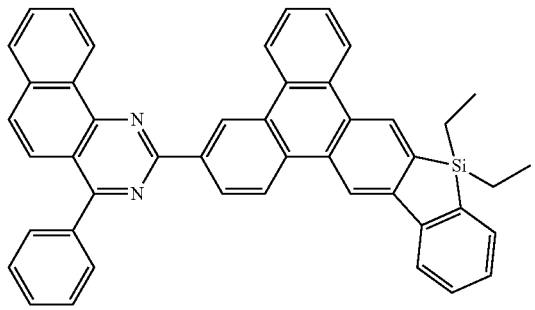
Compound 316
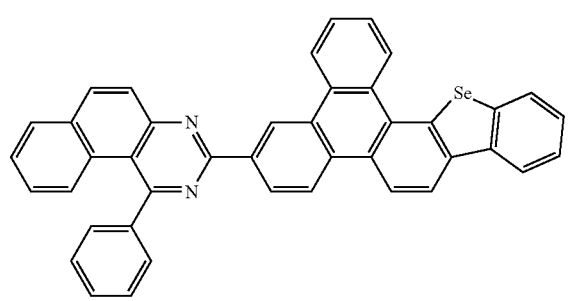
Compound 317
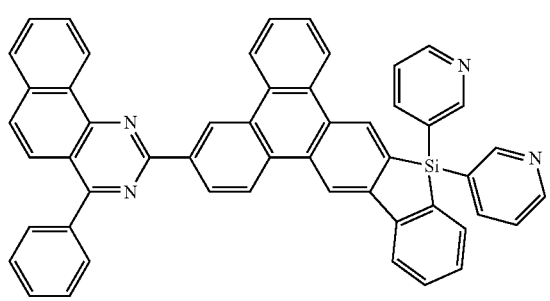
Compound 318
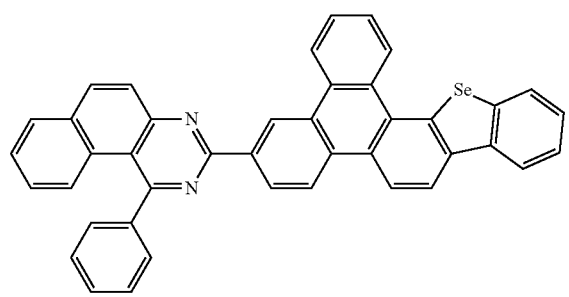
-continued
Compound 319
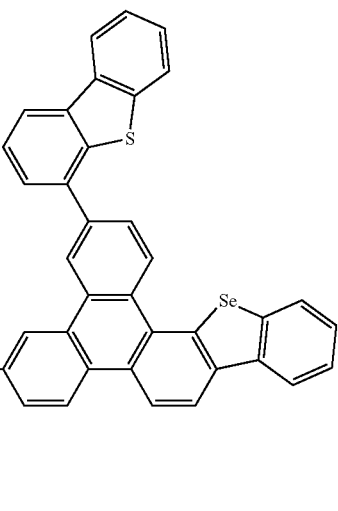
Compound 320
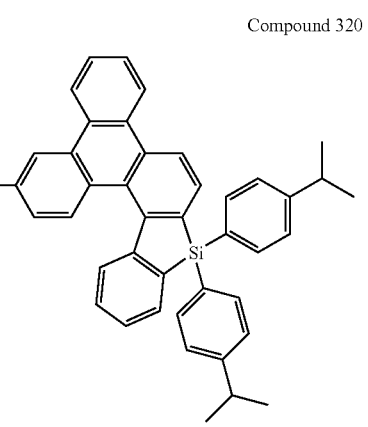
Compound 321

-continued

Compound 322

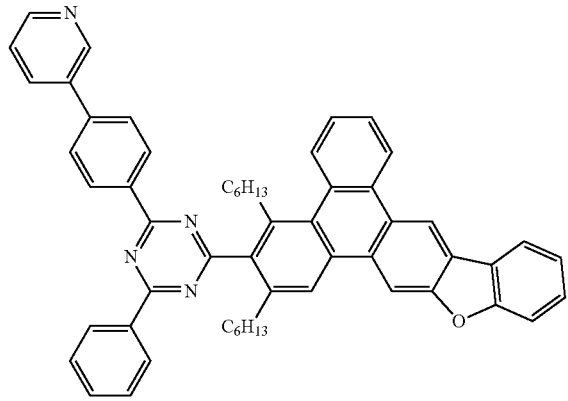

Compound 323

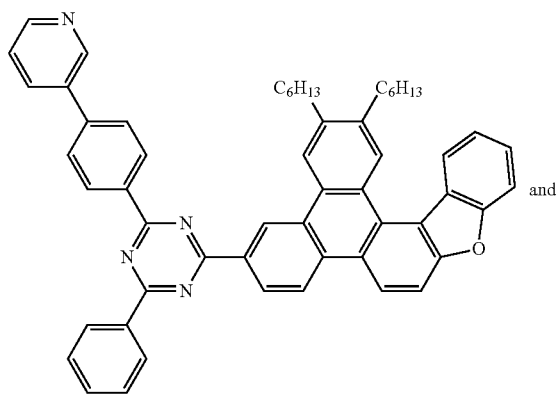

and

-continued

Compound 324

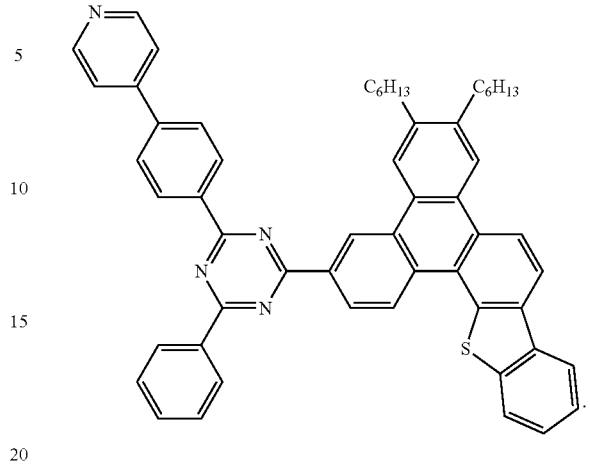

11. An organic electroluminescence device comprising a pair of electrodes composed of a cathode and an anode, and a light emitting layer between the pair of electrodes, wherein the light emitting layer comprises the organic compound according to claim 10, and wherein the organic electroluminescence device has a half-life.

12. The organic electroluminescence device according to claim 11, wherein the organic compound is host material.

13. The organic electroluminescence device according to claim 11, wherein the organic compound is an electron transfer material.

14. The organic electroluminescence device according to claim 11, wherein the organic compound is a hole blocking material.

15. The organic electroluminescence device according to claim 11, wherein the organic electroluminescence device is a lighting panel.

16. The organic electroluminescence device according to claim 11, wherein the organic electroluminescence device is a backlight panel.

17. The organic electroluminescence device according to claim 11, wherein the light emitting layer having the organic compound is capable of increasing the half-life of the organic electroluminescence device to be more than about 730 hours.

* * * * *